(12) United States Patent
Brown et al.

(10) Patent No.: US 9,056,852 B2
(45) Date of Patent: Jun. 16, 2015

(54) (ALPHA-SUBSTITUTED ARALKYLAMINO AND HETEROARYLALKYLAMINO) PYRIMIDINYL AND 1,3,5-TRIAZINYL BENZIMIDAZOLES, PHARMACEUTICAL COMPOSITIONS THEREOF, AND THEIR USE IN TREATING PROLIFERATIVE DISEASES

(75) Inventors: S. David Brown, San Carlos, CA (US); David J. Matthews, San Francisco, CA (US)

(73) Assignee: Mei Pharma, Inc., San Diego, CA (US)

(*) Notice: Subject to any disclaimer, the term of this patent is extended or adjusted under 35 U.S.C. 154(b) by 250 days.

(21) Appl. No.: 13/431,716

(22) Filed: Mar. 27, 2012

(65) Prior Publication Data

US 2012/0252802 A1    Oct. 4, 2012

Related U.S. Application Data

(60) Provisional application No. 61/468,502, filed on Mar. 28, 2011, provisional application No. 61/530,859, filed on Sep. 2, 2011, provisional application No. 61/560,699, filed on Nov. 16, 2011.

(51) Int. Cl.
| | |
|---|---|
| C07D 413/14 | (2006.01) |
| A61K 31/5377 | (2006.01) |
| C07D 403/14 | (2006.01) |
| C07D 403/04 | (2006.01) |
| C07D 401/14 | (2006.01) |
| C12N 9/12 | (2006.01) |

(52) U.S. Cl.
CPC ............ *C07D 403/04* (2013.01); *C07D 401/14* (2013.01); *C07D 403/14* (2013.01); *C07D 413/14* (2013.01); *C12N 9/1205* (2013.01)

(58) Field of Classification Search
CPC .. C07D 401/14; C07D 403/04; C07D 403/14; C07D 413/14
USPC ........................ 514/234.5; 544/113
See application file for complete search history.

(56) References Cited

U.S. PATENT DOCUMENTS

| | | | |
|---|---|---|---|
| 5,750,292 | A | 5/1998 | Sato et al. |
| 6,251,900 | B1 | 6/2001 | Kawashima et al. |
| 7,071,189 | B2 | 7/2006 | Kawashima et al. |
| 7,153,853 | B2 | 12/2006 | Kawashima et al. |
| 7,307,077 | B2 | 12/2007 | Kawashima et al. |
| 7,745,485 | B2 | 6/2010 | Durden |
| 8,486,939 | B2 | 7/2013 | Rewcastle et al. |
| 2007/0244110 | A1 | 10/2007 | Yaguchi et al. |
| 2008/0113987 | A1 | 5/2008 | Haruta et al. |
| 2008/0221103 | A1 | 9/2008 | Sharma et al. |
| 2008/0287431 | A1 | 11/2008 | Kawashima et al. |
| 2009/0181963 | A1 | 7/2009 | Dehnhardt et al. |
| 2009/0192176 | A1 | 7/2009 | Zask et al. |
| 2009/0233926 | A1 | 9/2009 | Butterworth et al. |
| 2009/0270390 | A1 | 10/2009 | Butterworth et al. |
| 2009/0312319 | A1 | 12/2009 | Ren et al. |
| 2009/0325954 | A1 | 12/2009 | Butterworth et al. |
| 2010/0022534 | A1 | 1/2010 | Butterworth et al. |
| 2010/0202963 | A1 | 8/2010 | Gallatin et al. |
| 2011/0009405 | A1* | 1/2011 | Rewcastle et al. ......... 514/234.2 |
| 2012/0165309 | A1 | 6/2012 | Takahashi et al. |

FOREIGN PATENT DOCUMENTS

| | | |
|---|---|---|
| EP | 0711804 | 5/1996 |
| EP | 1864665 | 12/2007 |
| EP | 2050749 | 4/2009 |
| EP | 2397479 | 12/2011 |
| JP | 11174638 | 2/1999 |
| WO | WO 99/05138 | 2/1999 |
| WO | WO 01/81346 | 11/2001 |
| WO | WO 02/088112 | 11/2002 |
| WO | WO 03/077921 | 9/2003 |

(Continued)

OTHER PUBLICATIONS

Rommel et al, "PI3K delta and PI3K gamma: partners in crime in inflammation in rheumatoid arthritis and beyond?" Nat. Rev. Immunol. 2007, 7:191-201.
Barber et al., "PI3Kgamma inhibition blocks glomerulonephritis and extends lifespan in a mouse model of systemic lupus," *Nat. Med.* 2005, 11, 933-935.
Berrie, "Phosphoinositide 3-kinase inhibition in cancer treatment," *Exp.Opin. Invest. Drugs* 2001, 10, 1085-1098.
Billottet et al., "A selective inhibitor of the p110delta isoform of PI 3-kinase inhibits AML cell proliferation and survival and increases the cytotoxic effects of VP16," *Oncogene* 2006, 25, 6648-6659.
Camps et al., "Blockade of PI3Kgamma suppresses joint inflammation and damage in mouse models of rheumatoid arthritis," *Nat. Med.* 2005, 11, 936-943.
Foukas & Sheperd, "Phosphoinositide 3-kinase: the protein kinase that time forgot" *Biochem. Soc. Trans.* 2004, 32, 330-331.

(Continued)

Primary Examiner — Rebecca Anderson
(74) Attorney, Agent, or Firm — Jones Day

(57) ABSTRACT

Provided herein are (alpha-substituted aralkylamino or heteroarylalkylamino) pyrimidinyl and 1,3,5-triazinyl benzimidazoles, e.g., a compound of Formula I, and their pharmaceutical compositions, preparation, and use as agents or drugs for treating proliferative diseases.

(I)

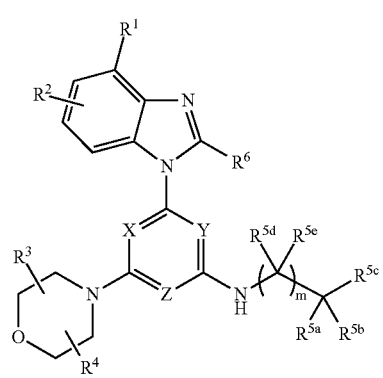

109 Claims, No Drawings

(56) References Cited

FOREIGN PATENT DOCUMENTS

| | | |
|---|---|---|
| WO | WO 03/078423 | 9/2003 |
| WO | WO 03/078426 | 9/2003 |
| WO | WO 03/078427 | 9/2003 |
| WO | WO 03/097862 | 11/2003 |
| WO | WO 2004/037812 | 5/2004 |
| WO | WO 2004/048365 | 6/2004 |
| WO | WO 2005/028467 | 3/2005 |
| WO | WO 2005/066156 | 7/2005 |
| WO | WO 2005/095389 | 10/2005 |
| WO | WO 2006/021881 | 3/2006 |
| WO | WO 2006/053109 | 5/2006 |
| WO | WO 2006/053227 | 5/2006 |
| WO | WO 2006/095906 | 9/2006 |
| WO | WO 2006/122806 | 11/2006 |
| WO | WO 2007/066099 | 6/2007 |
| WO | WO 2007/066103 | 6/2007 |
| WO | WO 2007/084786 | 7/2007 |
| WO | WO 2007/127183 | 8/2007 |
| WO | WO 2007/127175 | 11/2007 |
| WO | WO 2008/018426 | 2/2008 |
| WO | WO 2008/032027 | 3/2008 |
| WO | WO 2008/032028 | 3/2008 |
| WO | WO 2008/032033 | 3/2008 |
| WO | WO 2008/032036 | 3/2008 |
| WO | WO 2008/032041 | 3/2008 |
| WO | WO 2008/032060 | 3/2008 |
| WO | WO 2008/032064 | 3/2008 |
| WO | WO 2008/032072 | 3/2008 |
| WO | WO 2008/032077 | 3/2008 |
| WO | WO 2008/032086 | 3/2008 |
| WO | WO 2008/032089 | 3/2008 |
| WO | WO 2008/032091 | 3/2008 |
| WO | WO 2008/098058 | 8/2008 |
| WO | WO 2008/115974 | 9/2008 |
| WO | WO 2008/116129 | 9/2008 |
| WO | WO 2008/154026 | 12/2008 |
| WO | WO 2009/007751 | 1/2009 |
| WO | WO 2009/045174 | 4/2009 |
| WO | WO 2009/045175 | 4/2009 |
| WO | WO 2009/066775 | 5/2009 |
| WO | WO 2009/093981 | 7/2009 |
| WO | WO 2009/097490 | 8/2009 |
| WO | WO 2009/099163 | 8/2009 |
| WO | WO 2009/120094 | 10/2009 |
| WO | WO 2009/143313 | 11/2009 |
| WO | WO 2009/143317 | 11/2009 |
| WO | WO 2009/157880 | 12/2009 |
| WO | WO 2010/005558 | 1/2010 |
| WO | WO 2010/052569 | 5/2010 |
| WO | WO 2010/092962 | 8/2010 |
| WO | WO 2010/110685 | 9/2010 |
| WO | WO 2010/110686 | 9/2010 |
| WO | WO 2010/136491 | 12/2010 |
| WO | WO 2010/138589 | 12/2010 |
| WO | WO 2010/151735 | 12/2010 |
| WO | WO 2010/151737 | 12/2010 |
| WO | WO 2010/151740 | 12/2010 |
| WO | WO 2010/151791 | 12/2010 |
| WO | WO 2011/005119 | 1/2011 |
| WO | WO 2012/020762 | 2/2012 |
| WO | 2012135166 A1 | 10/2012 |
| WO | 2012135175 A1 | 10/2012 |

OTHER PUBLICATIONS

Fry, "Phosphoinositide 3-kinase signalling in breast cancer: how big a role might it play?" *Breast Cancer Res.* 2001, 3, 304-312.

Fry, "Structure, regulation and function of phosphoinositide 3-kinases." *Biochem. Biophys. Acta* 1994, 1226, 237-268.

Gross et al., "Design and synthesis of tricyclic corticotropin-releasing factor-1 antagonists," *J. Med Chem.* 2005, 48, 5780-5793.

Gymnopoulos et al., "Rare cancer-specific mutations in PIK3CA show gain of function," *Proc. Natl. Acad. Sci.*, 2007, 104, 5569-5574.

Hayakawa et al., "Synthesis and biological evaluation of pyrido[3',2'4,5]furo[3,2-d]pyrimidine derivatives as novel PI3 kinase p110alpha inhibitors," *Bioorg. Med. Chem. Lett.* 2007, 17, 2438-2442.

Hayakawa et al., "Synthesis and biological evaluation of imidazo[1,2-a]pyridine derivatives as novel PI3 kinase p110alpha inhibitors," *Bioorg. Med. Chem.* 2007, 15, 403-412.

Hayakawa et al., "Synthesis and biological evaluation of sulfonylhydrazone-substituted imidazo[1,2-a]pyridines as novel PI3 kinase p110alpha inhibitors," *Bioorg. Med. Chem.* 2007, 15, 5837-5844.

Horner et al., "Derivate des Chinoxalins als Isostere der Pteridine," *Justus Liebigs Annalen der Chemie* 1953, 579, 212-234.

Hu et al., "Inhibition of phosphatidylinositol 3'-kinase increases efficacy of paclitaxel in in vitro and in vivo ovarian cancer models," *Cancer Res.* 2002, 62, 1087-1092.

Huang et al., "The structure of a human p110alpha/p85alpha complex elucidates the effects of oncogenic PI3Kalpha mutations." *Science* 2007, 318, 1744-1748.

Ikenoue et al., "Functional analysis of PIK3CA gene mutations in human colorectal cancer," *Cancer Res.* 2005, 65, 4562-4567.

Ito et al., "Therapeutic potential of phosphatidylinositol 3-kinase inhibitors in inflammatory respiratory disease," *J. Pharm. Exp. Ther.* 2007, 321, 1-8.

Jackson et al., "PI 3-kinase p110beta: a new target for antithrombotic therapy," *Nat. Med.* 2005, 11, 507-514.

Kang et al., "Phosphatidylinositol 3-kinase mutations identified in human cancer are oncogenic," *Proc. Natl. Acad. Sci. USA* 2005, 102, 802-807.

Knight et al.. "A pharmacological map of the PI3-K family defines a role for p110alpha in insulin signaling," *Cell* 2006, 125, 733-747.

Kong et al., "ZSTK474 is an ATP-competitive inhibitor of class I phosphatidylinositol 3 kinase isoforms," *Cancer Sci.* 2007, 98, 1638-1642.

Lanni et al., "Design and synthesis of phenethyl benzo[1,4]oxazine-3-ones as potent inhibitors of PI3Kinasegamma,"*Bioorg. Med. Chem. Lett.* 2007, 17, 756-760.

Liew et al., "SVM model for virtual screening of Lck inhibitors," *J. Chem. Inf. Model.* 2009, 49, 877-885.

Maira et al., "Identification and characterization of NVP-BEZ235, a new orally available dual phosphatidylinositol 3-kinase/mammalian target of rapamycin inhibitor with potent in vivo antitumor activity," *Mol. Cancer Ther.* 2008, 7, 1851-1863.

Marshall et al., "Estimation of radiation-induced interphase cell death in cultures of human tumor material and in cell lines," *Oncol. Res.* 2004, 14, 297-304.

Miled et al., "Mechanism of two classes of cancer mutations in the phosphoinositide 3-kinase catalytic subunit," *Science* 2007, 317, 239-242.

Provencal et al., "Development of an efficient and scalable process of a respiratory syncytial virus inhibitor," *Org. Proc. Res. Dev.* 2004, 8, 903-908.

Pryde et al., "Novel selective inhibitors of neutral endopeptidase for the treatment of female sexual arousal disorder. Synthesis and activity of functionalized glutaramides," *J. Med. Chem.* 2006, 49, 4409-4424.

Raynaud et al., "Pharmacologic characterization of a potent inhibitor of class I phosphatidylinositide 3-kinases." *Cancer Res.* 2007, 67, 5840-5850.

Sabat et al., "The development of 2-benzimidazole substituted pyrimidine based inhibitors of lymphocyte specific kinase (Lck)," *Bioorg. Med. Che. Lett.* 2006, 16, 5973-5977.

Samuels et al., "High frequency of mutations of the PIK3CA gene in human cancers," *Science* 2004, 304, 554.

Semba et al., "The in vitro and in vivo effects of 2-(4-morpholinyl)-8-phenyl-chromone (LY294002), a specific inhibitor of phosphatidylinositol 3'-kinase, in human colon cancer cells," *Clin. Cancer Res.* 2002, 8, 1957-1963.

Shepherd, "Mechanisms regulating phosphoinositide 3-kinase signalling in insulin-sensitive tissues," *Acta Physiol. Scand.* 2005, 183, 3-12.

Stauffer et al., "Blocking the PI3K/PKB pathway in tumor cells," *Curr. Med. Chem. Anticancer Agents* 2005, 5, 449-462.

(56) References Cited

OTHER PUBLICATIONS

Stephens et al., "Phosphoinositide 3-kinases as drug targets in cancer," *Curr. Opin. Pharmacal.* 2005, 5, 357-365.
Stirdivant et al., "Cloning and mutagenesis of the p110 alpha subunit of human phosphoinositide 3'-hydroxykinase," *Bioorg. Med. Chem.* 1997, 5, 65-74.
Toshiyuki et al., "Synthesis and antitumor activity of benzimidazolyl-1,3,5-triazine and benzimidazolylpyrimidine derivatives," *Chem. Pharm. Bull.* 2000, 48, 1778-1781.
Vanhaesebroeck and Waterfield, "Signaling by distinct classes of phosphoinositide 3-kinases," *Exp. Cell. Res.* 1999, 253, 239-254.
Volina et al., "Molecular cloning, cDNA sequence, and chromosomal localization of the human phosphatidylinositol 3-kinase p110 alpha (PIK3CA) gene," *Genomics* 1994, 24, 472-477.
Walker et al., "Structural determinants of phosphoinositide 3-kinase inhibition by wortmannin,LY294002, quercetin, myricetin, and staurosporine," *Mol. Cell.* 2000, 6, 909-919.
Wipf et al., "Synthesis and biological evaluation of synthetic viridins derived from C(20)-heteroalkylation of the steroidal PI-3-kinase inhibitor wortmannin," *Org. Biomol. Chem.*, 2004, 2, 1911-1920.
Yaguchi et al., "Antitumor activity of ZSTK474, a new phosphatidylinositol 3-kinase inhibitor," *J. Natl. Cancer Inst.* 2006, 98, 545-556.
Zask et al., "Synthesis and structure-activity relationships of ring-opened 17-hydroxywortmannins: potent phosphoinositide 3-kinase inhibitors with improved properties and anticancer efficacy," *J. Med. Chem.*, 2008, 51, 1319-1323.
Zhu et al., "Pegylated wortmannin and 17-hydroxywortmannin conjugates as phosphoinositide 3-kinase inhibitors active in human tumor xenograft models," *J. Med. Chem.*, 2006, 49, 1373-1378.
Bedingfield et al., Structure activity relationaships for a series of phenylglyceine derivatives acting at mGluRs, British Journal of Pharmacology (1995) 116: 3323-3329.

* cited by examiner

(ALPHA-SUBSTITUTED ARALKYLAMINO AND HETEROARYLALKYLAMINO) PYRIMIDINYL AND 1,3,5-TRIAZINYL BENZIMIDAZOLES, PHARMACEUTICAL COMPOSITIONS THEREOF, AND THEIR USE IN TREATING PROLIFERATIVE DISEASES

CROSS REFERENCE TO RELATED APPLICATIONS

This application claims the benefit of the priority of U.S. Provisional Application Nos. 61/468,502, filed Mar. 28, 2011; 61/530,859, filed Sep. 2, 2011; and 61/560,699, filed Nov. 16, 2011; the disclosure of each of which is incorporated herein by reference in its entirety.

FIELD

Provided herein are (alpha-substituted aralkylamino or heteroarylalkylamino) pyrimidinyl and 1,3,5-triazinyl benzimidazoles, and their pharmaceutical compositions, preparation, and use as agents or drugs for treating proliferative diseases.

BACKGROUND

Phosphoinositide-3-kinases (PI3Ks) are a group of lipid kinases, which phosphorylate the 3-hydroxyl of phosphoinositides. They are classified into at least three classes (classes I, II, and III) and play an important role in cellular signaling (Stephens et al., *Curr. Opin. Pharmacol.* 2005, 5, 357). Class I enzymes are further classified into classes Ia and Ib based on their mechanism of activation. Class Ia PI3Ks are heterodimeric structures consisting of a catalytic subunit (p110α, p110β, or p110δ) in complex with a regulatory p85 subunit, while class-Ib PI3K (p110γ) is structurally similar but lacks the p85 regulatory subunit, and instead is activated by βγ subunits of heterotrimeric G-proteins (Walker et al., *Mol. Cell.* 2000, 6, 909).

PI3Ks play a variety of roles in normal tissue physiology (Foukas & Shepherd, *Biochem. Soc. Trans.* 2004, 32, 330; Shepherd, *Acta Physiol. Scand.* 2005, 183, 3), with p110α having a specific role in cancer growth, p110β in thrombus formation mediated by integrin $\alpha_{IIb}\beta_3$ (Jackson et al., *Nat. Med.* 2005, 11, 507), and p110γ in inflammation, rheumatoid arthritis, and other chronic inflammation states (Barber et al., *Nat. Med.* 2005, 11, 933; Camps et al., *Nat. Med.* 2005, 11, 936; Rommel et al., *Nat. Rev.* 2007, 7, 191; and Ito, et al., *J. Pharm. Exp. Therap.* 2007, 321, 1). Therefore, there is a need for PI3K inhibitors for treating cancer and/or inflammatory diseases.

SUMMARY OF THE DISCLOSURE

Provided herein is a compound of Formula I:

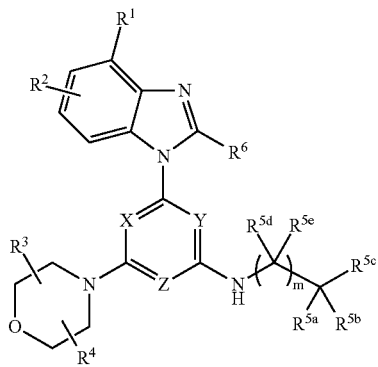

(I)

or an enantiomer, a mixture of enantiomers, a mixture of two or more diastereomers, or an isotopic variant thereof; or a pharmaceutically acceptable salt, solvate, hydrate, or prodrug thereof; wherein:

X, Y, and Z are each independently N or $CR^X$, with the proviso that at least two of X, Y, and Z are nitrogen atoms; where $R^X$ is hydrogen or $C_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$;

$R^{5c}$ is —$(CR^{5f}R^{5g})_n$—$(C_{6-14}$ aryl) or —$(CR^{5f}R^{5g})_n$-heteroaryl;

$R^{5d}$ and $R^{5e}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$;

$R^{5f}$ and $R^{5g}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$; or —S(O)$_2$NR$^{1b}$R$^{1c}$; or (d) when one occurrence of R$^{5f}$ and one occurrence of R$^{5g}$ are attached to the same carbon atom, the R$^{5f}$ and R$^{5g}$ together with the carbon atom to which they are attached form a $C_{3-10}$ cycloalkyl or heterocyclyl;

$R^6$ is hydrogen, $C_{1-6}$ alkyl, —S—$C_{1-6}$ alkyl, —S(O)—$C_{1-6}$ alkyl, or —SO$_2$—$C_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl in R$^1$, R$^2$, R$^3$, R$^4$, R$^6$, R$^X$, R$^{1a}$, R$^{1b}$, R$^{1c}$, R$^{1d}$, R$^{5a}$, R$^{5b}$, R$^{5c}$, R$^{5d}$, R$^{5e}$, R$^{5f}$ and R$^{5g}$ is optionally substituted with one or more, in one embodiment, one, two, three, or four, substituents Q, wherein each substituent Q is independently selected from (a) oxo, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is further optionally substituted with one or more, in one embodiment, one, two, three, or four, substituents $Q^a$; or (iii) R$^b$ and R$^c$ together with the N atom to which they are attached form heterocyclyl, which is further optionally substituted with one or more, in one embodiment, one, two, three, or four, substituents $Q^a$;

wherein each $Q^a$ is independently selected from the group consisting of (a) oxo, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

In one embodiment, m is 0; and R$^{5a}$ and R$^{5b}$ are each independently (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, OC(NR$^{1a}$)NR$^{1b}$R$^{1c}$, —OS(O)R$^{1a}$, —OS(O)$_2$R$^{1a}$, —OS(O)$_2$NR$^{1b}$R$^{1c}$, —OS(O)NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$.

Also provided herein are pharmaceutical compositions comprising a compound disclosed herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof and one or more pharmaceutically acceptable excipients.

Furthermore, provided herein is a method for treating, preventing, or ameliorating one or more symptoms of a PI3K-mediated disorder, disease, or condition in a subject, comprising administering to the subject a therapeutically effective amount of a compound disclosed herein, e.g., a compound of Formula I, or an enantiomer, a mixture of enantiomers, a mixture of two or more diastereomers, or an isotopic variant thereof or a pharmaceutically acceptable salt, solvate, hydrate, or prodrug thereof.

Provided herein is a method for treating, preventing, or ameliorating one or more symptoms of a PI3Kδ-mediated disorder, disease, or condition in a subject, comprising administering to the subject a therapeutically effective amount of a compound disclosed herein, e.g., a compound of Formula I, or an enantiomer, a mixture of enantiomers, a mixture of two or more diastereomers, or an isotopic variant thereof or a pharmaceutically acceptable salt, solvate, hydrate, or prodrug thereof.

Provided herein is a method for treating, preventing, or ameliorating one or more symptoms of a proliferative disease in a subject, comprising administering to the subject a therapeutically effective amount of a compound disclosed herein, e.g., a compound of Formula I, or an enantiomer, a mixture of enantiomers, a mixture of two or more diastereomers, or an isotopic variant thereof or a pharmaceutically acceptable salt, solvate, hydrate, or prodrug thereof.

Provided herein is a method for modulating PI3K activity, comprising contacting a PI3K with an effective amount of a compound disclosed herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof.

Provided herein is a method for modulating PI3Kδ activity, comprising contacting PI3Kδ with an effective amount of a compound disclosed herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof.

Provided herein is a method for selectively modulating PI3Kδ activity, comprising contacting PI3Kδ with an effective amount of a compound disclosed herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof.

DETAILED DESCRIPTION

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, 21st Edition, Lippincott Williams & Wilkins: Philadelphia, Pa., 2005; Handbook of Pharmaceutical Excipients, 5th Edition, Rowe et al., Eds., The Pharmaceutical Press and the American Pharmaceutical Association: 2005; and Handbook of Pharmaceutical Additives, 3rd Edition, Ash and Ash Eds., Gower Publishing Company: 2007; Pharmaceutical Preformulation and Formulation, 2nd Edition, Gibson Ed., CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a disorder, disease, or condition. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a disorder, disease, or condition.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "PI3K" refers to a phosphoinositide 3-kinase or variant thereof, which is capable of phosphorylating the inositol ring of PI in the D-3 position. The term "PI3K variant" is intended to include proteins substantially homologous to a native PI3K, i.e., proteins having one or more naturally or non-naturally occurring amino acid deletions, insertions, or substitutions (e.g., PI3K derivatives, homologs, and fragments), as compared to the amino acid sequence of a native PI3K. The amino acid sequence of a PI3K variant is at least about 80% identical, at least about 90% identical, or at least about 95% identical to a native PI3K. Examples of PI3K include, but are not limited to, p110α, p110β, p110δ, p110γ, PI3K-C2α, PI3K-C2β, PI3K-C2γ, Vps34, mTOR, ATM, ATR, and DNA-PK. See, Fry, Biochem. Biophys. Acta 1994, 1226, 237-268; Vanhaesebroeck and Waterfield, Exp. Cell. Res. 1999, 253, 239-254; and Fry, Breast Cancer Res. 2001, 3, 304-312. PI3Ks are classified into at least four classes. Class I includes p110α, p110β, p110δ, and p110γ. Class II includes PI3K-C2α, PI3K-C2β, and PI3K-C2γ. Class III includes Vps34. Class IV includes mTOR, ATM, ATR, and DNA-PK. In certain embodiments, the PI3K is a Class I kinase. In certain embodiments, the PI3K is p110α, p110β, p110δ, or p110γ. In certain embodiments, the PI3K is a variant of a Class I kinase. In certain embodiments, the PI3K is a p110α mutant. Examples of p110α mutants include, but are not limited to, R38H, G106V, K111N, K227E, N345K, C420R, P539R, E542K, E545A, E545G, E545K, Q546K, Q546P, E453Q, H710P, I800L, T1025S, M1043I, M1043V, H1047L, H1047R, and H1047Y (Ikenoue et al., Cancer Res. 2005, 65, 4562-4567; Gymnopoulos et al., Proc. Natl. Acad. Sci., 2007, 104, 5569-5574). In certain embodiments, the PI3K is a Class II kinase. In certain embodiments, the PI3K is PI3K-C2α, PI3K-C2β, or PI3K-C2γ. In certain embodiments, the PI3K is a Class III kinase. In certain embodiments, the PI3K is Vps34. In certain embodiments, the PI3K is a Class IV kinase. In certain embodiments, the PI3K is mTOR, ATM, ATR, or DNA-PK.

The terms "PI3K-mediated disorder, disease, or condition" and "a disorder, disease, or condition mediated by PI3K" refer to a disorder, disease, or condition characterized by abnormal or dysregulated, e.g., less than or greater than normal, PI3K activity. Abnormal PI3K functional activity might arise as the result of PI3K overexpression in cells, expression of PI3K in cells which normally do not express PI3K, or dysregulation due to constitutive activation, caused, for example, by a mutation in PI3K. A PI3K-mediated disorder, disease, or condition may be completely or partially mediated by abnormal PI3K activity. In particular, PI3K-mediated disorder, disease, or condition is one in which modulation of a PI3K activity results in some effect on the underlying disorder, disease, or condition, e.g., a PI3K inhibitor results in some improvement in at least some of patients being treated.

The terms "p110δ-mediated disorder, disease, or condition," "a disorder, disease, or condition mediated by p110δ," "PI3Kδ-mediated disorder, disease, or condition," and "a disorder, disease, or condition mediated by PI3Kδ" refer to a disorder, disease, or condition characterized by abnormal or dysregulated, e.g., less than or greater than normal, p110δ activity. Abnormal p110δ functional activity might arise as the result of p110δ overexpression in cells, expression of p110δ in cells which normally do not express p110δ, or dysregulation due to constitutive activation, caused, for example, by a mutation in p110δ. A p110δ-mediated disorder, disease, or condition may be completely or partially mediated by abnormal p110δ activity. In particular, p110δ-mediated disorder, disease, or condition is one in which modulation of a p110δ activity results in some effect on the underlying disorder, disease, or condition, e.g., a p110δ inhibitor results in some improvement in at least some of patients being treated.

The term "alkyl" refers to a linear or branched saturated monovalent hydrocarbon radical, wherein the alkylene may optionally be substituted with one or more substituents Q as described herein. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkylene" refers to a linear or branched saturated divalent hydrocarbon radical, wherein the alkylene may optionally be substituted with one or more substituents Q as described herein. The term "alkylene" encompasses both linear and branched alkylene, unless otherwise specified. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms). For example, $C_{1-6}$ alkylene refers to a linear saturated divalent hydrocarbon radical of 1 to 6 carbon atoms or a branched saturated divalent hydrocarbon radical of 3 to 6 carbon atoms.

The term "heteroalkylene" refers to a linear or branched saturated divalent hydrocarbon radical that contains one or more heteroatoms each independently selected from O, S, and N in the hydrocarbon chain. For example, $C_{1-6}$ heteroalkylene refers to a linear saturated divalent hydrocarbon radical of 1 to 6 carbon atoms or a branched saturated divalent hydrocarbon radical of 3 to 6 carbon atoms. In certain embodiments, the heteroalkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ heteroalkylene groups are also referred as "lower heteroalkylene." Examples of heteroalkylene groups include, but are not limited to, —CH$_2$O—, —CH$_2$OCH$_2$—, —CH$_2$CH$_2$O—, —CH$_2$NH—, —CH$_2$NHCH$_2$—, —CH$_2$CH$_2$NH—, —CH$_2$S—, —CH$_2$SCH$_2$—, and —CH$_2$CH$_2$S—. In certain embodiments, heteroalkylene may also be optionally substituted with one or more substituents Q as described herein.

The term "alkenyl" refers to a linear or branched monovalent hydrocarbon radical, which contains one or more, in one embodiment, one, two, three, four, or five, in another embodiment, one, carbon-carbon double bond(s). The alkenyl may be optionally substituted with one or more substituents Q as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkenylene" refers to a linear or branched divalent hydrocarbon radical, which contains one or more, in one embodiment, one, two, three, four, or five, in another embodiment, one, carbon-carbon double bond(s). The alkenylene may be optionally substituted with one or more substituents Q as described herein. Similarly, the term "alkenylene" also embraces radicals having "cis" and "trans" configurations, or alternatively, "E" and "Z" configurations. As used herein, the term "alkenylene" encompasses both linear and branched alkenylene, unless otherwise specified. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene, allylene, propenylene, butenylene, and 4-methylbutenylene.

The term "heteroalkenylene" refers to a linear or branched divalent hydrocarbon radical, which contains one or more, in one embodiment, one, two, three, four, or five, in another embodiment, one, carbon-carbon double bond(s), and which contains one or more heteroatoms each independently selected from O, S, and N in the hydrocarbon chain. The heteroalkenylene may be optionally substituted with one or more substituents Q as described herein. The term "heteroalkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ heteroalkenylene refers to a linear unsaturated divalent hydrocarbon radical of 2 to 6 carbon atoms or a branched unsaturated divalent hydrocarbon radical of 3 to 6 carbon atoms. In certain embodiments, the heteroalkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of heteroalkenylene groups include, but are not limited to, —CH=CHO—, —CH=CHOCH$_2$—, —CH=CHCH$_2$O—, —CH=CHS—, —CH=CHSCH$_2$—, —CH=CHCH$_2$S—, or —CH=CHCH$_2$NH—.

The term "alkynyl" refers to a linear or branched monovalent hydrocarbon radical, which contains one or more, in one embodiment, one, two, three, four, or five, in another embodiment, one, carbon-carbon triple bond(s). The alkynyl may be optionally substituted with one or more substituents Q as described herein. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "cycloalkyl" refers to a cyclic saturated bridged and/or non-bridged monovalent hydrocarbon radical, which may be optionally substituted with one or more substituents Q as described herein. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, bicyclo[2.1.1]hexyl, bicyclo[2.2.1]heptyl, decalinyl, and adamantyl.

The term "cycloalkenyl" refers to a cyclic unsaturated, nonaromatic bridged and/or non-bridged monovalent hydrocarbon radical, which may be optionally substituted with one or more substituents Q as described herein. In certain embodiments, the cycloalkenyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclobutenyl, cyclopentenyl, cyclohexenyl, or cycloheptenyl, The term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, the aralkyl are optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms independently selected from O, S, N, and P in the ring. A heteroaryl group is bonded to the rest of a molecule through its aromatic ring. Each ring of a heteroaryl group can contain one or two O atoms, one or two S atoms, one to four N atoms, and/or one or two P atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl may also be optionally substituted with one or more substituents Q as described herein as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms independently selected from O, S, N, and P; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. A heterocyclyl group is bonded to the rest of a molecule through its non-aromatic ring. In certain embodiments, the heterocyclyl is a monocyclic, bicyclic, tricyclic, or tetracyclic ring system, which may be spiro, fused, or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl may also be optionally substituted with one or more substituents Q as described herein.

The term "halogen", "halide" or "halo" refers to fluorine, chlorine, bromine, and/or iodine.

The term "optionally substituted" is intended to mean that a group or substituent, such as an alkyl, alkylene, heteroalkylene, alkenyl, alkenylene, heteroalkenylene, alkynyl, cycloalkyl, cycloalkenyl, aryl, aralkyl, heteroaryl, heteroaryl-$C_{1-6}$ alkyl, and heterocyclyl group, may be substituted with one or more substituents Q, each of which is independently selected from, e.g., (a) oxo (=O), halo, cyano (—CN), and nitro (—$NO_2$); (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, four, or five, substituents $Q^a$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^aC$(O)$R^d$, —N$R^aC$(O)O$R^d$, —N$R^aC$(O)N$R^bR^c$, —N$R^aC$(=N$R^d$)N$R^bR^c$, —N$R^aS$(O)$R^d$, —N$R^aS$(O)$_2R^d$, —N$R^aS$(O)N$R^bR^c$, —N$R^aS$(O)$_2$N$R^bR^c$, —P(O)$R^aR^d$, —P(O)(O$R^a$)$R^d$, —P(O)(O$R^a$)(O$R^d$), —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heteroaryl or heterocyclyl, optionally substituted with one or more, in one embodiment, one, two, three, or four, substituents $Q^a$. As used herein, all groups that can be substituted are "optionally substituted," unless otherwise specified.

In one embodiment, each substituent $Q^a$ is independently selected from the group consisting of (a) oxo, cyano, halo, and nitro; and (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^eC$(O)$R^h$, —N$R^eC$(O)O$R^h$, —N$R^eC$(O)N$R^fR^g$, —N$R^eC$(=N$R^h$)N$R^fR^g$, —N$R^eS$(O)$R^h$, —N$R^eS$(O)$_2R^h$, —N$R^eS$(O)N$R^fR^g$, —N$R^eS$(O)$_2$N$R^fR^g$, —P(O)$R^eR^h$, —P(O)(O$R^e$)$R^h$, —P(O)(O$R^e$)(O$R^h$), —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (ii) $R^f$ and $R^g$ together with the N atom to which they are attached form heteroaryl or heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "isotopic variant" refers to a compound that contains an unnatural proportion of an isotope at one or more of the atoms that constitute such a compound. In certain embodiments, an "isotopic variant" of a compound contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C) nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I) iodine-125 ($^{125}$I), iodine-127 ($^{127}$I), iodine-129 ($^{129}$I), and iodine-131 ($^{131}$I). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O) oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^2$H, for example, or any carbon can be $^{13}$C, for example, or any nitrogen can be $^{15}$N, for example, or any oxygen can be $^{18}$O, for example, where feasible according to the judgment of one of skill. In certain embodiments, an "isotopic variant" of a compound contains unnatural proportions of deuterium (D).

The term "solvate" refers to a complex or aggregate formed by one or more molecules of a solute, e.g., a compound provided herein, and one or more molecules of a solvent, which present in a stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "an enantiomer, a mixture of enantiomers, a mixture of two or more diastereomers, or an isotopic variant thereof; or a pharmaceutically acceptable salt, solvate, hydrate, or prodrug thereof" has the same meaning as the phrase "an enantiomer, a mixture of enantiomers, a mixture of two or more diastereomers, or an isotopic variant of the compound referenced therein; or a pharmaceutically acceptable salt, solvate, hydrate, or prodrug of the compound referenced therein; or a pharmaceutically acceptable salt, solvate, hydrate, or prodrug of an enantiomer, a mixture of enantiomers, a mixture of two or more diastereomers, or an isotopic variant of the compound referenced therein."

Compounds

In one embodiment, provided herein is a compound of Formula I:

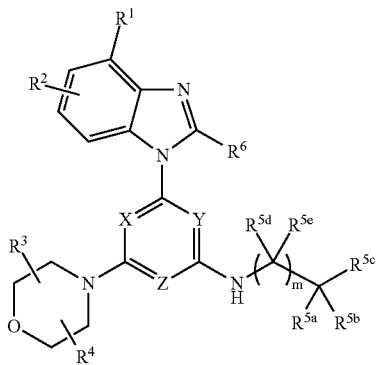

(I)

or an enantiomer, a mixture of enantiomers, a mixture of two or more diastereomers, or an isotopic variant thereof; or a pharmaceutically acceptable salt, solvate, hydrate, or prodrug thereof; wherein:

X, Y, and Z are each independently N or $CR^X$, with the proviso that at least two of X, Y, and Z are nitrogen atoms; where $R^X$ is hydrogen or $C_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O) $R^{1a}$, —OC(O)O$R^{1a}$, —C(O)N$R^{1b}R^{1c}$, —OC(=N$R^{1a}$) N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$) N$R^{1b}R^{1c}$, —N$R^{1a}$S(O)$R^{1d}$, —N$R^{1a}$S(O)$_2R^{1d}$, —N$R^{1a}$S(O) N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5c}$ is —(C$R^{5f}R^{5g}$)$_n$—(C$_{6-14}$ aryl) or —(C$R^{5f}R^{5g}$)$_n$-heteroaryl;

$R^{5d}$ and $R^{5e}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5f}$ and $R^{5g}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$; or —S(O)$_2$N$R^{1b}R^{1c}$; or (d) when one occurrence of $R^{5f}$ and one occurrence of $R^{5g}$ are attached to the same carbon atom, the $R^{5f}$ and $R^{5g}$ together with the carbon atom to which they are attached form a $C_{3-10}$ cycloalkyl or heterocyclyl;

$R^6$ is hydrogen, $C_{1-6}$ alkyl, —S—$C_{1-6}$ alkyl, —S(O)—$C_{1-6}$ alkyl, or —SO$_2$—$C_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl in $R^1$, $R^2$, $R^3$, $R^4$, $R^6$, $R^X$, $R^{1a}$, $R^{1b}$, $R^{1c}$, $R^{1d}$, $R^{5a}$, $R^{5b}$, $R^{5c}$, $R^{5d}$, $R^{5e}$, $R^{5f}$, and $R^{5g}$ is optionally substituted with one or more, in one embodiment, one, two, three, or four, substituents Q, wherein each substituent Q is independently selected from (a) oxo, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(N$R^a$)

$NR^bR^c$, $-OR^a$, $-OC(O)R^a$, $-OC(O)OR^a$, $-OC(O)NR^bR^c$, $-OC(=NR^a)NR^bR^c$, $-OS(O)R^a$, $-OS(O)_2R^a$, $-OS(O)NR^bR^c$, $-OS(O)_2NR^bR^c$, $-NR^bR^c$, $-NR^aC(O)R^d$, $-NR^aC(O)OR^d$, $-NR^aC(O)NR^bR^c$, $-NR^aC(=NR^d)NR^bR^c$, $-NR^aS(O)R^d$, $-NR^aS(O)_2R^d$, $-NR^aS(O)NR^bR^c$, $-NR^aS(O)_2NR^bR^c$, $-SR^a$, $-S(O)R^a$, $-S(O)_2R^a$, $-S(O)NR^bR^c$, and $-S(O)_2NR^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is further optionally substituted with one or more, in one embodiment, one, two, three, or four, substituents $Q^a$; or (iii) $R^b$ and $R^c$ together with the N atom to which they are attached form heterocyclyl, which is further optionally substituted with one or more, in one embodiment, one, two, three, or four, substituents $Q^a$;

wherein each $Q^a$ is independently selected from the group consisting of (a) oxo, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) $-C(O)R^e$, $-C(O)OR^e$, $-C(O)NR^fR^g$, $-C(NR^e)NR^fR^g$, $-OR^e$, $-OC(O)R^e$, $-OC(O)OR^e$, $-OC(O)NR^fR^g$, $-OC(=NR^e)NR^fR^g$, $-OS(O)R^e$, $-OS(O)_2R^e$, $-OS(O)NR^fR^g$, $-OS(O)_2NR^fR^g$, $-NR^fR^g$, $-NR^eC(O)R^h$, $-NR^eC(O)OR^h$, $-NR^eC(O)NR^fR^g$, $-NR^eC(=NR^h)NR^fR^g$, $-NR^eS(O)R^h$, $-NR^eS(O)_2R^h$, $-NR^eS(O)NR^fR^g$, $-NR^eS(O)_2NR^fR^g$, $-SR^e$, $-S(O)R^e$, $-S(O)_2R^e$, $-S(O)NR^fR^g$, and $-S(O)_2NR^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In one embodiment, in Formula I,

X, Y, and Z are each independently N or $CR^X$, with the proviso that at least two of X, Y, and Z are nitrogen atoms; where $R^X$ is hydrogen or $C_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(NR^{1a})NR^{1b}R^{1c}$, $-OR^{1a}$, $-OC(O)R^{1a}$, $-OC(O)OR^{1a}$, $-OC(O)NR^{1b}R^{1c}$, $-OC(=NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(=NR^{1d})NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-SR^{1a}$, $-S(O)R^{1a}$, $-S(O)_2R^{1a}$, $-S(O)NR^{1b}R^{1c}$, or $-S(O)_2NR^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(NR^{1a})NR^{1b}R^{1c}$, $-OR^{1a}$, $-OC(O)R^{1a}$, $-OC(O)OR^{1a}$, $-OC(O)NR^{1b}R^{1c}$, $-OC(=NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}S(O)NR^{1b}R^{1c}$, $-NR^{1a}S(O)_2NR^{1b}R^{1c}$, $-SR^{1a}$, $-S(O)R^{1a}$, $-S(O)_2R^{1a}$, $-S(O)NR^{1b}R^{1c}$, or $-S(O)_2NR^{1b}R^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(NR^{1a})NR^{1b}R^{1c}$, $-OR^{1a}$, $-OC(O)R^{1a}$, $-OC(O)OR^{1a}$, $-OC(O)NR^{1b}R^{1c}$, $-OC(=NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(=NR^{1d})NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-SR^{1a}$, $-S(O)R^{1a}$, $-S(O)_2R^{1a}$, $-S(O)NR^{1b}R^{1c}$, or $-S(O)_2NR^{1b}R^{1c}$;

$R^{5c}$ is $-(CR^{5f}R^{5g})_n-(C_{6-14}$ aryl) or $-(CR^{5f}R^{5g})_n$-heteroaryl;

$R^{5d}$ and $R^{5e}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(NR^{1a})NR^{1b}R^{1c}$, $-OR^{1a}$, $-OC(O)R^{1a}$, $-OC(O)OR^{1a}$, $-OC(O)NR^{1b}R^{1c}$, $-OC(=NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(=NR^{1d})NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-SR^{1a}$, $-S(O)R^{1a}$, $-S(O)_2R^{1a}$, $-S(O)NR^{1b}R^{1c}$, or $-S(O)_2NR^{1b}R^{1c}$;

$R^{5f}$ and $R^{5g}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(NR^{1a})NR^{1b}R^{1c}$, $-OR^{1a}$, $-OC(O)R^{1a}$, $-OC(O)OR^{1a}$, $-OC(O)NR^{1b}R^{1c}$, $-OC(=NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(=NR^{1d})NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-SR^{1a}$, $-S(O)R^{1a}$, $-S(O)_2R^{1a}$, $-S(O)NR^{1b}R^{1c}$; or $-S(O)_2NR^{1b}R^{1c}$; or (d) when one occurrence of $R^{5f}$ and one occurrence of $R^{5g}$ are attached to the same carbon atom, the $R^{5f}$ and $R^{5g}$ together with the carbon atom to which they are attached form a $C_{3-10}$ cycloalkyl or heterocyclyl;

$R^6$ is hydrogen, $C_{1-6}$ alkyl, $-S-C_{1-6}$ alkyl, $-S(O)-C_{1-6}$ alkyl, or $-SO_2-C_{1-6}$ alkyl;

m is 0 or 1; and n is 0, 1, 2, 3, or 4;

with the proviso that the compound is neither 4-(2-(difluoromethyl)-1H-benzo[c]imidazol-1-yl)-6-morpholino-N-(2-phenyl-2-(pyrrolidin-1-yl)ethyl)-1,3,5-triazin-2-amine nor 6-(2-(difluoromethyl)-1H-benzo[d]imidazol-1-yl)-N-(1-(4-((R)-3-(methoxymethyl)morpholino)phenyl)ethyl)-2-morpholinopyrimidin-4-amine;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more, in one embodiment, one, two, three, or four, substituents Q as defined herein.

In another embodiment, in Formula I,

X, Y, and Z are each independently N or $CR^X$, with the proviso that at least two of X, Y, and Z are nitrogen atoms; where $R^X$ is hydrogen or $C_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(NR^{1a})NR^{1b}R^{1c}$, $-OR^{1a}$, $-OC(O)R^{1a}$, $-OC(O)OR^{1a}$, $-OC(O)NR^{1b}R^{1c}$, $-OC(=NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C$ (O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; wherein each R$^{1a}$, R$^{1b}$, R$^{1c}$, and R$^{1d}$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^{1b}$ and R$^{1c}$ together with the N atom to which they are attached form heterocyclyl;

R$^3$ and R$^4$ are each independently hydrogen or C$_{1-6}$ alkyl; or R$^3$ and R$^4$ are linked together to form a bond, C$_{1-6}$ alkylene, C$_{1-6}$ heteroalkylene, C$_{2-6}$ alkenylene, or C$_{2-6}$ heteroalkenylene;

R$^{5a}$ is (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5b}$ is (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5c}$ is —(CR$^{5f}$R$^{5g}$)$_n$—(C$_{6-14}$ aryl) or —(CR$^{5f}$R$^{5g}$)$_n$-heteroaryl;

R$^{5d}$ and R$^{5e}$ are each independently (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5f}$ and R$^{5g}$ are each independently (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$; or —S(O)$_2$NR$^{1b}$R$^{1c}$; or (d) when one occurrence of R$^{5f}$ and one occurrence of R$^{5g}$ are attached to the same carbon atom, the R$^{5f}$ and R$^{5g}$ together with the carbon atom to which they are attached form a C$_{3-10}$ cycloalkyl or heterocyclyl;

R$^6$ is hydrogen, C$_{1-6}$ alkyl, —S—C$_{1-6}$ alkyl, —S(O)—C$_{1-6}$ alkyl, or —SO$_2$—C$_{1-6}$ alkyl;

m is 0 or 1; and n is 0, 1, 2, 3, or 4;

with the proviso that, when X, Y, and Z are N, and R$^{5a}$ is hydrogen, R$^{5b}$ is not pyrrolidinyl; and when X and Z are N, Y is CH, and R$^{5a}$ is hydrogen, R$^{5b}$ is not 4-((R)-3-(methoxymethyl)morpholino)phenyl;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more, in one embodiment, one, two, three, or four, substituents Q as defined herein.

In yet another embodiment, in Formula I,

X, Y, and Z are each independently N or CR$^X$, with the proviso that at least two of X, Y, and Z are nitrogen atoms; where R$^X$ is hydrogen or C$_{1-6}$ alkyl;

R$^1$ and R$^2$ are each independently (a) hydrogen, cyano, halo, or nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; wherein each R$^{1a}$, R$^{1b}$, R$^{1c}$, and R$^{1d}$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^{1b}$ and R$^{1c}$ together with the N atom to which they are attached form heterocyclyl;

R$^3$ and R$^4$ are each independently hydrogen or C$_{1-6}$ alkyl; or R$^3$ and R$^4$ are linked together to form a bond, C$_{1-6}$ alkylene, C$_{1-6}$ heteroalkylene, C$_{2-6}$ alkenylene, or C$_{2-6}$ heteroalkenylene;

R$^{5a}$ is (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5b}$ is (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5c}$ is —(CR$^{5f}$R$^{5g}$)$_n$—(C$_{6-14}$ aryl) or —(CR$^{5f}$R$^{5g}$)$_n$-heteroaryl;

R$^{5d}$ and R$^{5e}$ are each independently (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)

NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5f}$ and R$^{5g}$ are each independently (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; or (d) when one occurrence of R$^{5f}$ and one occurrence of R$^{5g}$ are attached to the same carbon atom, the R$^{5f}$ and R$^{5g}$ together with the carbon atom to which they are attached form a C$_{3-10}$ cycloalkyl or heterocyclyl;

R$^6$ is hydrogen, C$_{1-6}$ alkyl, —S—C$_{1-6}$ alkyl, —S(O)—C$_{1-6}$ alkyl, or —SO$_2$—C$_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more, in one embodiment, one, two, three, or four, substituents Q as defined herein.

In still another embodiment, in Formula I,

X, Y, and Z are N;

R$^1$ and R$^2$ are each independently (a) hydrogen, cyano, halo, or nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; wherein each R$^{1a}$, R$^{1b}$, R$^{1c}$ and R$^{1d}$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^{1b}$ and R$^{1c}$ together with the N atom to which they are attached form heterocyclyl;

R$^3$ and R$^4$ are each independently hydrogen or C$_{1-6}$ alkyl; or R$^3$ and R$^4$ are linked together to form a bond, C$_{1-6}$ alkylene, C$_{1-6}$ heteroalkylene, C$_{2-6}$ alkenylene, or C$_{2-6}$ heteroalkenylene;

R$^{5a}$ is (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5b}$ is (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, or heteroaryl; or (c) —C(O)R$^{1a}$, —C(O)OR$^{1a}$, —C(O)NR$^{1b}$R$^{1c}$, —C(NR$^{1a}$) NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5c}$ is —(CR$^{5f}$R$^{5g}$)$_n$—(C$_{6-14}$ aryl) or —(CR$^{5f}$R$^{5g}$)$_n$-heteroaryl;

R$^{5d}$ and R$^{5e}$ are each independently (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5f}$ and R$^{5g}$ are each independently (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$; or —S(O)$_2$NR$^{1b}$R$^{1c}$; or (d) when one occurrence of R$^{5f}$ and one occurrence of R$^{5g}$ are attached to the same carbon atom, the R$^{5f}$ and R$^{5g}$ together with the carbon atom to which they are attached form a C$_{3-10}$ cycloalkyl or heterocyclyl;

R$^6$ is hydrogen, C$_{1-6}$ alkyl, —S—C$_{1-6}$ alkyl, —S(O)—C$_{1-6}$ alkyl, or —SO$_2$—C$_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more, in one embodiment, one, two, three, or four, substituents Q as defined herein.

In one embodiment, the compound of Formula I has the structure of Formula Ia:

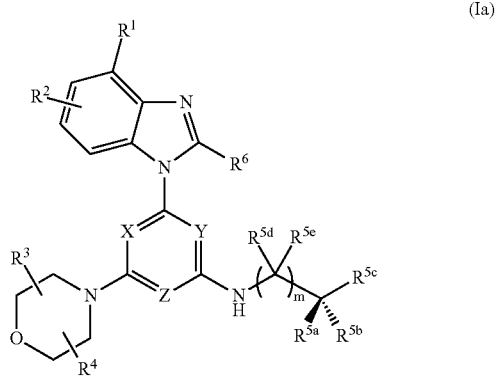

(Ia)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{5c}$, $R^{5d}$, $R^{5e}$, m, X, Y, and Z are each as defined herein. In one embodiment, m is 0. In another embodiment, m is 1.

In another embodiment, the compound of Formula I has the structure of Formula Ib:

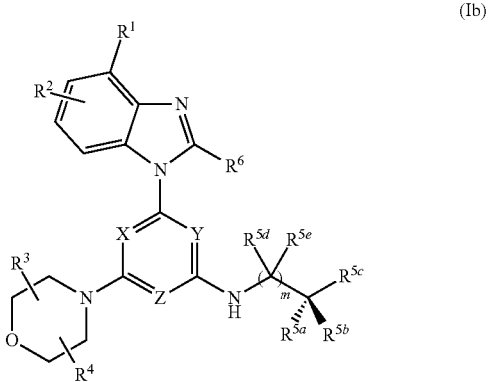

(Ib)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{5c}$, $R^{5d}$, $R^{5e}$, m, X, Y, and Z are each as defined herein. In one embodiment, m is 0. In another embodiment, m is 1.

In one embodiment, provided herein is a compound of Formula I, Ia, or Ib as described herein, or an enantiomer, a mixture of enantiomers, a mixture of two or more diastereomers, or an isotopic variant thereof; or a pharmaceutically acceptable salt, solvate, hydrate, or prodrug thereof; wherein m is 0; $R^{5a}$ and $R^{5b}$ are each independently (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; and $R^1$, $R^2$, $R^3$, $R^4$, $R^{5c}$, $R^6$, X, Y, Z, $R^{1a}$, $R^{1b}$, $R^{1c}$, and $R^{1d}$ are defined herein elsewhere.

In yet another embodiment, provided herein is a compound of Formula II:

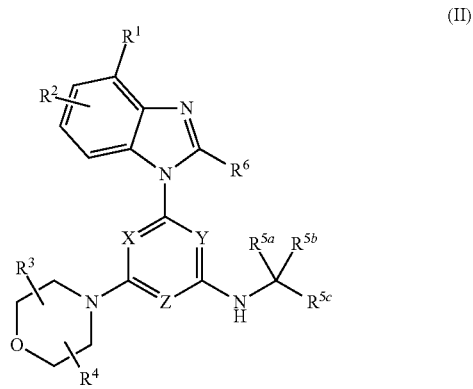

(II)

or an enantiomer, a mixture of enantiomers, a mixture of two or more diastereomers, or an isotopic variant thereof; or a pharmaceutically acceptable salt, solvate, hydrate, or prodrug thereof; wherein:

X, Y, and Z are each independently N or CR$^X$, with the proviso that at least two of X, Y, and Z are nitrogen atoms; where R$^X$ is hydrogen or $C_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5c}$ is —(C$R^{5f}R^{5g}$)$_n$—(C$_{6-14}$ aryl) or —(C$R^{5f}R^{5g}$)$_n$-heteroaryl;

$R^{5f}$ and $R^{5g}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; or (d) when one occurrence of $R^{5f}$ and one occurrence of $R^{5g}$ are attached to the same carbon atom, the $R^{5f}$ and $R^{5g}$ together with the carbon atom to which they are attached form a $C_{3-10}$ cycloalkyl or heterocyclyl;

R⁶ is hydrogen, C₁₋₆ alkyl, —S—C₁₋₆ alkyl, —S(O)—C₁₋₆ alkyl, or —SO₂—C₁₋₆ alkyl; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl in R¹, R², R³, R⁴, R⁶, Rˣ, R¹ᵃ, R¹ᵇ, R¹ᶜ, R¹ᵈ, R⁵ᵃ, R⁵ᵇ, R⁵ᶜ, R⁵ᶠ, and R⁵ᵍ is optionally substituted with one or more, in one embodiment, one, two, three, or four, substituents Q, wherein each substituent Q is independently selected from (a) oxo, cyano, halo, and nitro; (b) C₁₋₆ alkyl, C₂₋₆ alkenyl, C₂₋₆ alkynyl, C₃₋₁₀ cycloalkyl, C₆₋₁₄ aryl, C₇₋₁₅ aralkyl, heteroaryl, and heterocyclyl, each of which is further optionally substituted with one or more, in one embodiment, one, two, three, or four, substituents Qᵃ; and (c) —C(O)Rᵃ, —C(O)ORᵃ, —C(O)NRᵇRᶜ, —C(NRᵃ)NRᵇRᶜ, —ORᵃ, —OC(O)Rᵃ, —OC(O)ORᵃ, —OC(O)NRᵇRᶜ, —OC(=NRᵃ)NRᵇRᶜ, —OS(O)Rᵃ, —OS(O)₂Rᵃ, —OS(O)NRᵇRᶜ, —OS(O)₂NRᵇRᶜ, —NRᵇRᶜ, —NRᵃC(O)Rᵈ, —NRᵃC(O)ORᵈ, —NRᵃC(O)NRᵇRᶜ, —NRᵃC(=NRᵈ)NRᵇRᶜ, —NRᵃS(O)Rᵈ, —NRᵃS(O)₂Rᵈ, —NRᵃS(O)NRᵇRᶜ, —NRᵃS(O)₂NRᵇRᶜ, —SRᵃ, —S(O)Rᵃ, —S(O)₂Rᵃ, —S(O)NRᵇRᶜ, and —S(O)₂NRᵇRᶜ, wherein each Rᵃ, Rᵇ, Rᶜ, and Rᵈ is independently (i) hydrogen; (ii) C₁₋₆ alkyl, C₂₋₆ alkenyl, C₂₋₆ alkynyl, C₃₋₁₀ cycloalkyl, C₆₋₁₄ aryl, C₇₋₁₅ aralkyl, heteroaryl, or heterocyclyl, each of which is further optionally substituted with one or more, in one embodiment, one, two, three, or four, substituents Qᵃ; or (iii) Rᵇ and Rᶜ together with the N atom to which they are attached form heterocyclyl, which is further optionally substituted with one or more, in one embodiment, one, two, three, or four, substituents Qᵃ;

wherein each Qᵃ is independently selected from the group consisting of (a) oxo, cyano, halo, and nitro; (b) C₁₋₆ alkyl, C₂₋₆ alkenyl, C₂₋₆ alkynyl, C₃₋₁₀ cycloalkyl, C₆₋₁₄ aryl, C₇₋₁₅ aralkyl, heteroaryl, and heterocyclyl; and (c) —C(O)Rᵉ, —C(O)ORᵉ, —C(O)NRᶠRᵍ, —C(NRᵉ)NRᶠRᵍ, —ORᵉ, —OC(O)Rᵉ, —OC(O)ORᵉ, —OC(O)NRᶠRᵍ, —OC(=NRᵉ)NRᶠRᵍ, —OS(O)Rᵉ, —OS(O)₂Rᵉ, —OS(O)NRᶠRᵍ, —OS(O)₂NRᶠRᵍ, —NRᶠRᵍ, —NRᵉC(O)Rʰ, —NRᵉC(O)ORʰ, —NRᵉC(O)NRᶠRᵍ, —NRᵉC(=NRʰ)NRᶠRᵍ, —NRᵉS(O)Rʰ, —NRᵉS(O)₂Rʰ, —NRᵉS(O)NRᶠRᵍ, —NRᵉS(O)₂NRᶠRᵍ, —SRᵉ, —S(O)Rᵉ, —S(O)₂Rᵉ, —S(O)NRᶠRᵍ, and —S(O)₂NRᶠRᵍ; wherein each Rᵉ, Rᶠ, Rᵍ, and Rʰ is independently (i) hydrogen; (ii) C₁₋₆ alkyl, C₂₋₆ alkenyl, C₂₋₆ alkynyl, C₃₋₁₀ cycloalkyl, C₆₋₁₄ aryl, C₇₋₁₅ aralkyl, heteroaryl, or heterocyclyl; or (iii) Rᶠ and Rᵍ together with the N atom to which they are attached form heterocyclyl.

In yet another embodiment, provided herein is a compound of Formula II:

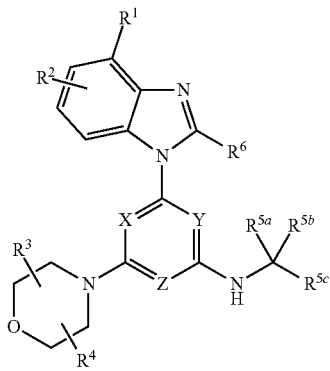

(II)

or an enantiomer, a mixture of enantiomers, a mixture of two or more diastereomers, or an isotopic variant thereof; or a pharmaceutically acceptable salt, solvate, hydrate, or prodrug thereof; wherein:

X, Y, and Z are each independently N or CRˣ, with the proviso that at least two of X, Y, and Z are nitrogen atoms; where Rˣ is hydrogen or C₁₋₆ alkyl;

R¹ and R² are each independently (a) hydrogen, cyano, halo, or nitro; (b) C₁₋₆ alkyl, C₂₋₆ alkenyl, C₂₋₆ alkynyl, C₃₋₁₀ cycloalkyl, C₆₋₁₄ aryl, C₇₋₁₅ aralkyl, heteroaryl, or heterocyclyl; or (c) —C(O)R¹ᵃ, —C(O)OR¹ᵃ, —C(O)NR¹ᵇR¹ᶜ, —C(NR¹ᵃ)NR¹ᵇR¹ᶜ, —OR¹ᵃ, —OC(O)R¹ᵃ, —OC(O)OR¹ᵃ, —OC(O)NR¹ᵇR¹ᶜ, —OC(=NR¹ᵃ)NR¹ᵇR¹ᶜ, —OS(O)R¹ᵃ, —OS(O)₂R¹ᵃ, —OS(O)NR¹ᵇR¹ᶜ, —OS(O)₂NR¹ᵇR¹ᶜ, —NR¹ᵇR¹ᶜ, —NR¹ᵃC(O)R¹ᵈ, —NR¹ᵃC(O)OR¹ᵈ, —NR¹ᵃC(O)NR¹ᵇR¹ᶜ, —NR¹ᵃC(=NR¹ᵈ)NR¹ᵇR¹ᶜ, —NR¹ᵃS(O)R¹ᵈ, —NR¹ᵃS(O)₂R¹ᵈ, —NR¹ᵃS(O)NR¹ᵇR¹ᶜ, —NR¹ᵃS(O)₂NR¹ᵇR¹ᶜ, —SR¹ᵃ, —S(O)R¹ᵃ, —S(O)₂R¹ᵃ, —S(O)NR¹ᵇR¹ᶜ, or —S(O)₂NR¹ᵇR¹ᶜ; wherein each R¹ᵃ, R¹ᵇ, R¹ᶜ, and R¹ᵈ is independently (i) hydrogen; (ii) C₁₋₆ alkyl, C₂₋₆ alkenyl, C₂₋₆ alkynyl, C₃₋₁₀ cycloalkyl, C₆₋₁₄ aryl, C₇₋₁₅ aralkyl, heteroaryl, or heterocyclyl; or (iii) R¹ᵇ and R¹ᶜ together with the N atom to which they are attached form heterocyclyl;

R³ and R⁴ are each independently hydrogen or C₁₋₆ alkyl; or R³ and R⁴ are linked together to form a bond, C₁₋₆ alkylene, C₁₋₆ heteroalkylene, C₂₋₆ alkenylene, or C₂₋₆ heteroalkenylene;

R⁵ᵃ is (a) hydrogen or halo; (b) C₁₋₆ alkyl, C₂₋₆ alkenyl, C₂₋₆ alkynyl, C₃₋₁₀ cycloalkyl, C₆₋₁₄ aryl, C₇₋₁₅ aralkyl, heteroaryl, or heterocyclyl; or (c) —C(O)R¹ᵃ, —C(O)OR¹ᵃ, —C(O)NR¹ᵇR¹ᶜ, —C(NR¹ᵃ)NR¹ᵇR¹ᶜ, —OR¹ᵃ, —OC(O)R¹ᵃ, —OC(O)OR¹ᵃ, —OC(O)NR¹ᵇR¹ᶜ, —OC(=NR¹ᵃ)NR¹ᵇR¹ᶜ, —OS(O)R¹ᵃ, —OS(O)₂R¹ᵃ, —OS(O)NR¹ᵇR¹ᶜ, —OS(O)₂NR¹ᵇR¹ᶜ, —NR¹ᵇR¹ᶜ, —NR¹ᵃC(O)R¹ᵈ, —NR¹ᵃC(O)OR¹ᵈ, —NR¹ᵃC(O)NR¹ᵇR¹ᶜ, —NR¹ᵃC(=NR¹ᵈ)NR¹ᵇR¹ᶜ, —NR¹ᵃS(O)R¹ᵈ, —NR¹ᵃS(O)₂R¹ᵈ, —NR¹ᵃS(O)NR¹ᵇR¹ᶜ, —NR¹ᵃS(O)₂NR¹ᵇR¹ᶜ, —SR¹ᵃ, —S(O)R¹ᵃ, —S(O)₂R¹ᵃ, —S(O)NR¹ᵇR¹ᶜ, or —S(O)₂NR¹ᵇR¹ᶜ;

R⁵ᵇ is (a) halo; (b) C₁₋₆ alkyl, C₂₋₆ alkenyl, C₂₋₆ alkynyl, C₃₋₁₀ cycloalkyl, C₆₋₁₄ aryl, C₇₋₁₅ aralkyl, heteroaryl, or heterocyclyl; or (c) —C(O)R¹ᵃ, —C(O)OR¹ᵃ, —C(O)NR¹ᵇR¹ᶜ, —C(NR¹ᵃ)NR¹ᵇR¹ᶜ, —OR¹ᵃ, —OC(O)R¹ᵃ, —OC(O)OR¹ᵃ, —OC(O)NR¹ᵇR¹ᶜ, —OC(=NR¹ᵃ)NR¹ᵇR¹ᶜ, —OS(O)R¹ᵃ, —OS(O)₂R¹ᵃ, —OS(O)NR¹ᵇR¹ᶜ, —OS(O)₂NR¹ᵇR¹ᶜ, —NR¹ᵇR¹ᶜ, —NR¹ᵃC(O)R¹ᵈ, —NR¹ᵃC(O)OR¹ᵈ, —NR¹ᵃC(O)NR¹ᵇR¹ᶜ, —NR¹ᵃC(=NR¹ᵈ)NR¹ᵇR¹ᶜ, —NR¹ᵃS(O)R¹ᵈ, —NR¹ᵃS(O)₂R¹ᵈ, —NR¹ᵃS(O)NR¹ᵇR¹ᶜ, —NR¹ᵃS(O)₂NR¹ᵇR¹ᶜ, —SR¹ᵃ, —S(O)R¹ᵃ, —S(O)₂R¹ᵃ, —S(O)NR¹ᵇR¹ᶜ, or —S(O)₂NR¹ᵇR¹ᶜ;

R⁵ᶜ is C₆₋₁₄ aryl or heteroaryl; and

R⁶ is hydrogen, C₁₋₆ alkyl, —S—C₁₋₆ alkyl, —S(O)—C₁₋₆ alkyl, or —SO₂—C₁₋₆ alkyl;

wherein each alkyl, alkylene, heteroalkylene, alkenyl, alkenylene, heteroalkenylene, alkynyl, cycloalkyl, aryl, aralkyl, heteroaryl, and heterocyclyl in R¹, R², R³, R⁴, R⁶, Rˣ, R¹ᵃ, R¹ᵇ, R¹ᶜ, R¹ᵈ, R⁵ᵃ, R⁵ᵇ, and R⁵ᶜ is optionally substituted with one or more, in one embodiment, one, two, three, or four, substituents Q, wherein each substituent Q is independently selected from (a) oxo, cyano, halo, and nitro; (b) C₁₋₆ alkyl, C₂₋₆ alkenyl, C₂₋₆ alkynyl, C₃₋₁₀ cycloalkyl, C₆₋₁₄ aryl, C₇₋₁₅ aralkyl, heteroaryl, and heterocyclyl, each of which is further optionally substituted with one or more, in one embodiment, one, two, three, or four, substituents Qᵃ; and (c) —C(O)Rᵃ, —C(O)ORᵃ, —C(O)NRᵇRᶜ, —C(NRᵃ)NRᵇRᶜ, —ORᵃ, —OC(O)Rᵃ, —OC(O)ORᵃ, —OC(O)NRᵇRᶜ, —OC(=NRᵃ)NRᵇRᶜ, —OS(O)Rᵃ, —OS(O)₂Rᵃ, —OS(O)NRᵇRᶜ, —OS (O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl, each of which is further optionally substituted with one or more, in one embodiment, one, two, three, or four, substituents Q$^a$; or (iii) R$^b$ and R$^c$ together with the N atom to which they are attached form heterocyclyl, which is further optionally substituted with one or more, in one embodiment, one, two, three, or four, substituents Q$^a$;

wherein each Q$^a$ is independently selected from the group consisting of (a) oxo, cyano, halo, and nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In one embodiment, the compound of Formula II has the structure of Formula IIa:

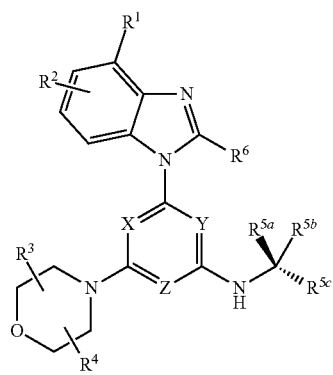

(IIa)

or an isotopic variant thereof; or a pharmaceutically acceptable salt, solvate, hydrate, or prodrug thereof; wherein R$^1$, R$^2$, R$^3$, R$^4$, R$^6$, R$^{5a}$, R$^{5b}$, R$^{5c}$, X, Y, and Z are each as defined herein.

In another embodiment, the compound of Formula II has the structure of Formula IIb:

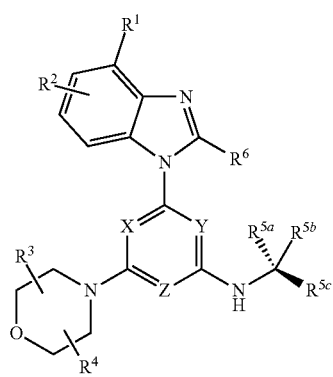

(IIb)

or an isotopic variant thereof; or a pharmaceutically acceptable salt, solvate, hydrate, or prodrug thereof; wherein R$^1$, R$^2$, R$^3$, R$^4$, R$^6$, R$^{5a}$, R$^{5b}$, R$^{5c}$, X, Y, and Z are each as defined herein.

In one embodiment, provided herein is a compound of Formula II, IIa, or IIb as described herein, or an enantiomer, a mixture of enantiomers, a mixture of two or more diastereomers, or an isotopic variant thereof; or a pharmaceutically acceptable salt, solvate, hydrate, or prodrug thereof; wherein R$^{5a}$ and R$^{5b}$ are each independently (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; and R$^1$, R$^2$, R$^3$, R$^4$, R$^{5c}$, R$^6$, X, Y, Z, R$^{1a}$, R$^{1b}$, R$^{1c}$, and R$^{1d}$ are defined herein elsewhere.

In yet another embodiment, provided herein is a compound of Formula III:

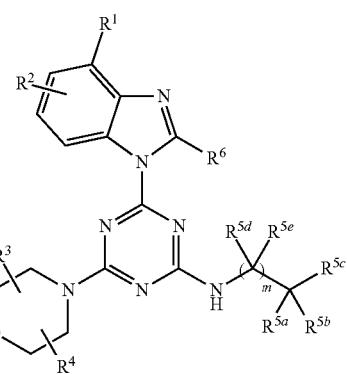

(III)

or an enantiomer, a mixture of enantiomers, a mixture of two or more diastereomers, or an isotopic variant thereof; or a pharmaceutically acceptable salt, solvate, hydrate, or prodrug thereof; wherein R$^1$, R$^2$, R$^3$, R$^4$, R$^6$, R$^{5a}$, R$^{5b}$, R$^{5c}$, R$^{5d}$, R$^{5e}$, and m are each as defined herein. In one embodiment, m is 0. In another embodiment, m is 1.

In one embodiment, the compound of Formula III has the structure of Formula IIIa:

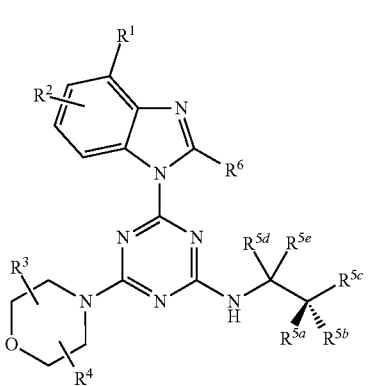

(IIIa)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{5c}$, $R^{5d}$, $R^{5e}$, and m are each as defined herein. In one embodiment, m is 0. In another embodiment, m is 1.

In another embodiment, the compound of Formula III has the structure of Formula IIIb:

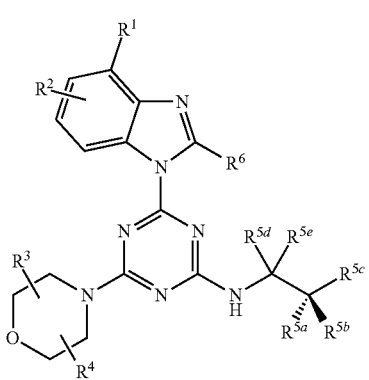

(IIIb)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{5c}$, $R^{5d}$, $R^{5e}$, and m are each as defined herein. In one embodiment, m is 0. In another embodiment, m is 1.

In one embodiment, provided herein is a compound of Formula III, IIIa, or IIIb as described herein, or an enantiomer, a mixture of enantiomers, a mixture of two or more diastereomers, or an isotopic variant thereof; or a pharmaceutically acceptable salt, solvate, hydrate, or prodrug thereof; wherein m is 0; $R^{5a}$ and $R^{5b}$ are each independently (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)O$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; and $R^1$, $R^2$, $R^3$, $R^4$, $R^{5c}$, $R^6$, $R^{1a}$, $R^{1b}$, $R^{1c}$, and $R^{1d}$ are defined herein elsewhere.

In yet another embodiment, provided herein is a compound of Formula IV:

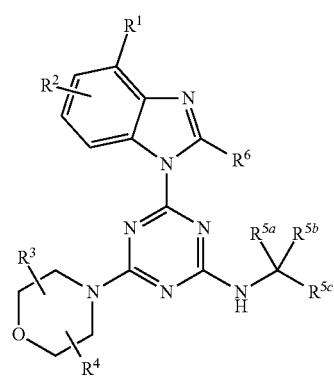

(IV)

or an enantiomer, a mixture of enantiomers, a mixture of two or more diastereomers, or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, and $R^{5c}$ are each as defined herein.

In one embodiment, the compound of Formula IV has the structure of Formula IVa:

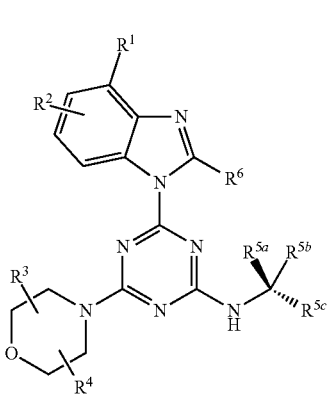

(IVa)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, and $R^{5c}$ are each as defined herein.

In another embodiment, the compound of Formula IV has the structure of Formula IVb:

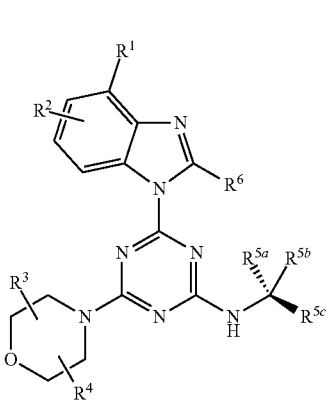

(IVb)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, and $R^{5c}$ are each as defined herein.

In one embodiment, provided herein is a compound of Formula IV, IVa, or IVb as described herein, or an enantiomer, a mixture of enantiomers, a mixture of two or more diastereomers, or an isotopic variant thereof; or a pharmaceutically acceptable salt, solvate, hydrate, or prodrug thereof; wherein $R^{5a}$ and $R^{5b}$ are each independently (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; and $R^1$, $R^2$, $R^3$, $R^4$, $R^{5c}$, $R^6$, $R^{1a}$, $R^{1b}$, $R^{1c}$, and $R^{1d}$ are defined herein elsewhere.

In yet another embodiment, provided herein is a compound of Formula V:

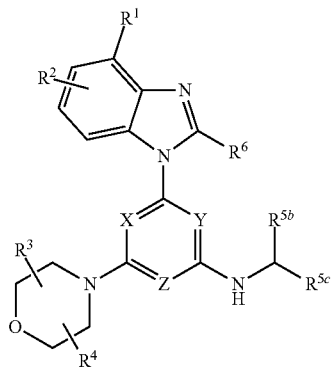

(V)

or an enantiomer, a mixture of enantiomers, a mixture of two or more diastereomers, or an isotopic variant thereof; or a pharmaceutically acceptable salt, solvate, hydrate, or prodrug thereof; wherein $R^1$, $R^2$, $R^3$, $R^4$, $R^6$, $R^{5b}$, $R^{5c}$, X, Y, and Z are each as defined herein.

In one embodiment, the compound of Formula V has the structure of Formula Va:

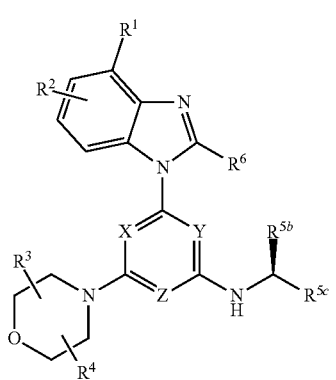

(Va)

or an isotopic variant thereof; or a pharmaceutically acceptable salt, solvate, hydrate, or prodrug thereof; wherein $R^1$, $R^2$, $R^3$, $R^4$, $R^6$, $R^{5b}$, $R^{5c}$, X, Y, and Z are each as defined herein.

In another embodiment, the compound of Formula V has the structure of Formula Vb:

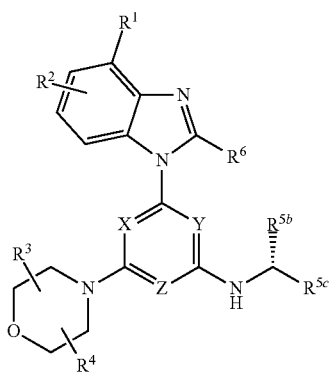

(Vb)

or an isotopic variant thereof; or a pharmaceutically acceptable salt, solvate, hydrate, or prodrug thereof; wherein $R^1$, $R^2$, $R^3$, $R^4$, $R^6$, $R^{5b}$, $R^{5c}$, X, Y, and Z are each as defined herein.

In yet another embodiment, provided herein is a compound of Formula VI:

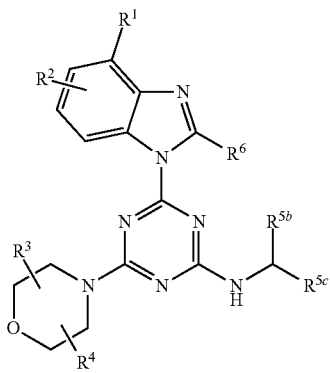

(VI)

or an enantiomer, a mixture of enantiomers, a mixture of two or more diastereomers, or an isotopic variant thereof; or a pharmaceutically acceptable salt, solvate, hydrate, or prodrug thereof; wherein $R^1$, $R^2$, $R^3$, $R^4$, $R^6$, $R^{5b}$, and $R^{5c}$ are each as defined herein.

In one embodiment, the compound of Formula VI has the structure of Formula VIa:

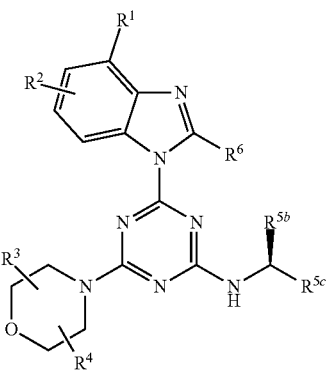

(VIa)

or an isotopic variant thereof; or a pharmaceutically acceptable salt, solvate, hydrate, or prodrug thereof; wherein $R^1$, $R^2$, $R^3$, $R^4$, $R^6$, $R^{5b}$, and $R^{5c}$ are each as defined herein.

In another embodiment, the compound of Formula VI has the structure of Formula VIb:

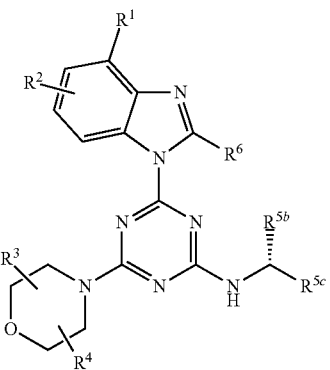

(VIb)

or an isotopic variant thereof; or a pharmaceutically acceptable salt, solvate, hydrate, or prodrug thereof; wherein $R^1$, $R^2$, $R^3$, $R^4$, $R^6$, $R^{5b}$, and $R^{5c}$ are each as defined herein.

In yet another embodiment, provided herein is a compound of Formula VII:

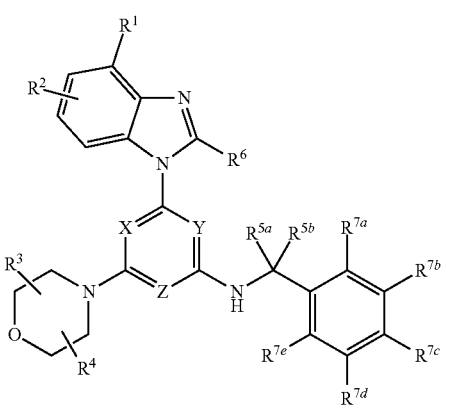

(VII)

or an enantiomer, a mixture of enantiomers, a mixture of two or more diastereomers, or an isotopic variant thereof; or a pharmaceutically acceptable salt, solvate, hydrate, or prodrug thereof; wherein:

$R^{7a}$, $R^{7b}$, $R^{7c}$, $R^{7d}$, and $R^{7e}$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

two of $R^{7a}$, $R^{7b}$, $R^{7c}$, $R^{7d}$, and $R^{7e}$ that are adjacent to each other form $C_{3-10}$ cycloalkenyl, $C_{6-14}$ aryl, heteroaryl, or heterocyclyl, each optionally substituted with one or more substituents Q; and $R^1$, $R^2$, $R^3$, $R^4$, $R^6$, $R^{1a}$, $R^{1b}$, $R^{1c}$, $R^{1d}$, $R^{5a}$, $R^{5b}$, X, Y and Z are each as defined herein.

In one embodiment, the compound of Formula VII has the structure of Formula VIIa:

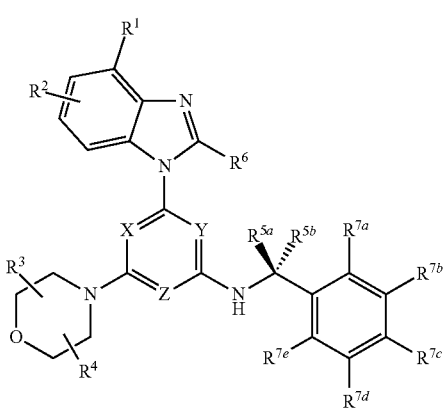

(VIIa)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{7a}$, $R^{7b}$, $R^{7c}$, $R^{7d}$, $R^{7e}$, X, Y, and Z are each as defined herein.

In another embodiment, the compound of Formula VII has the structure of Formula VIIb:

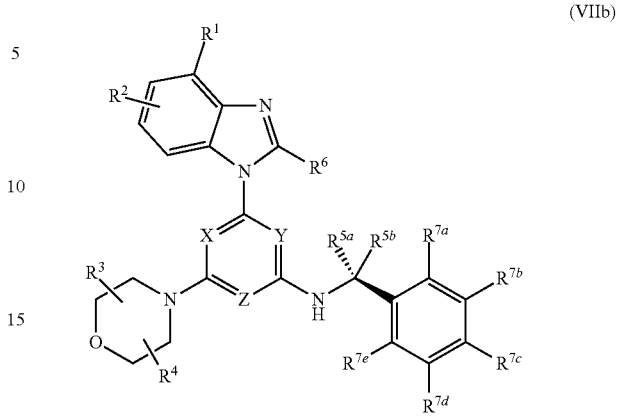

(VIIb)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{7a}$, $R^{7b}$, $R^{7c}$, $R^{7d}$, $R^{7e}$, X, Y, and Z are each as defined herein.

In yet another embodiment, provided herein is a compound of Formula VIII:

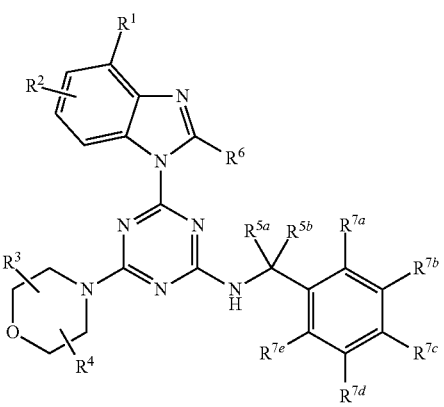

(VIII)

or an enantiomer, a mixture of enantiomers, a mixture of two or more diastereomers, or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{7a}$, $R^{7b}$, $R^{7c}$, $R^{7d}$, and $R^{7e}$ are each as defined herein.

In one embodiment, the compound of Formula VIII has the structure of Formula VIIIa:

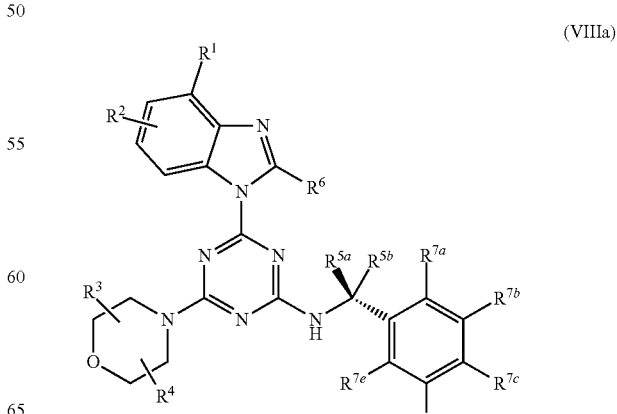

(VIIIa)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{7a}$, $R^{7b}$, $R^{7c}$, $R^{7d}$, and, $R^{7e}$ are each as defined herein.

In another embodiment, the compound of Formula VIII has the structure of Formula VIIIb:

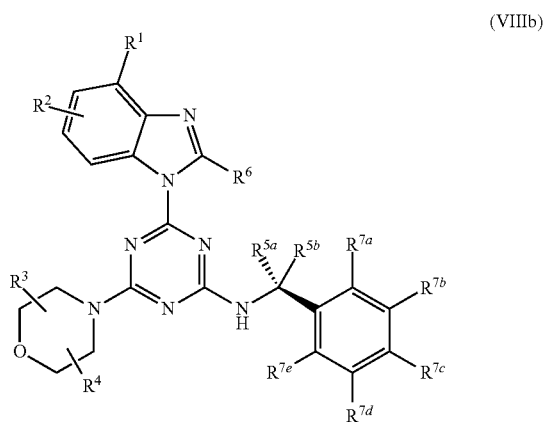

(VIIIb)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{7a}$, $R^{7b}$, $R^{7c}$, $R^{7d}$, and, $R^{7e}$ are each as defined herein.

In yet another embodiment, provided herein is a compound of Formula IX:

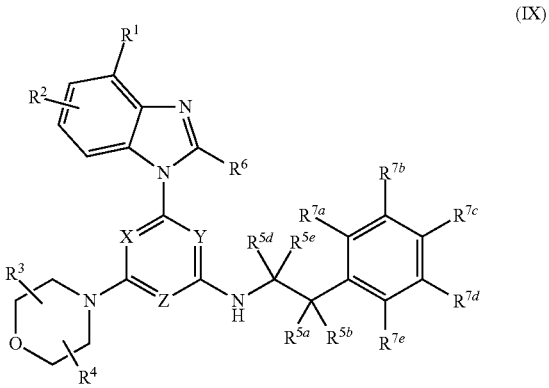

(IX)

or an enantiomer, a mixture of enantiomers, a mixture of two or more diastereomers, or an isotopic variant thereof; or a pharmaceutically acceptable salt, solvate, hydrate, or prodrug thereof; wherein:

$R^{7a}$, $R^{7b}$, $R^{7c}$, $R^{7d}$, and $R^{7e}$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

two of $R^{7a}$, $R^{7b}$, $R^{7c}$, $R^{7d}$, and $R^{7e}$ that are adjacent to each other form $C_{3-10}$ cycloalkenyl, $C_{6-14}$ aryl, heteroaryl, or heterocyclyl, each optionally substituted with one or more substituents Q; and $R^1$, $R^2$, $R^3$, $R^4$, $R^6$, $R^{1a}$, $R^{1b}$, $R^{1c}$, $R^{1d}$, $R^{5a}$, $R^{5b}$, $R^{5d}$, $R^{5e}$, X, Y, and Z are each as defined herein.

In one embodiment, the compound of Formula IX has the structure of Formula IXa:

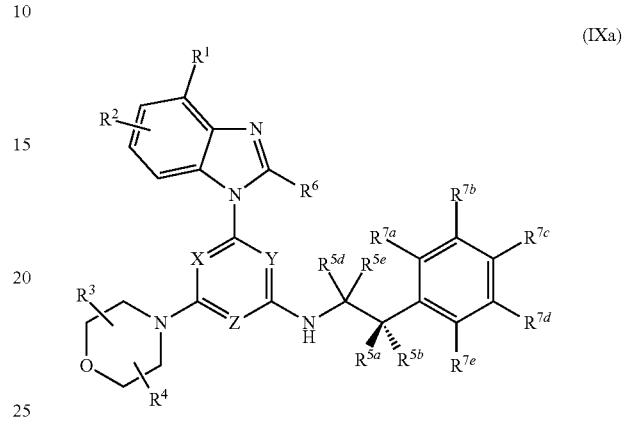

(IXa)

or an isotopic variant thereof; or a pharmaceutically acceptable salt, solvate, hydrate, or prodrug thereof wherein $R^1$, $R^2$, $R^3$, $R^4$, $R^6$, $R^{5a}$, $R^{5b}$, $R^{5d}$, $R^{5e}$, $R^{7a}$, $R^{7b}$, $R^{7c}$, $R^{7d}$, $R^{7e}$, X, Y, and Z are each as defined herein.

In another embodiment, the compound of Formula IX has the structure of Formula IXb:

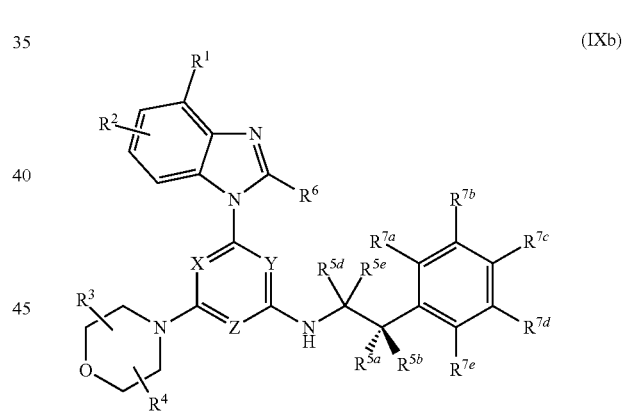

(IXb)

or an isotopic variant thereof; or a pharmaceutically acceptable salt, solvate, hydrate, or prodrug thereof wherein $R^1$, $R^2$, $R^3$, $R^4$, $R^6$, $R^{5a}$, $R^{5b}$, $R^{5d}$, $R^{5e}$, $R^{7a}$, $R^{7b}$, $R^{7c}$, $R^{7d}$, $R^{7e}$, X, Y, and Z are each as defined herein.

In Formula IX, IXa, or IXb, in certain embodiments, one of $R^{7a}$, $R^{7b}$, $R^{7c}$, $R^{7d}$, and $R^{7e}$ is $C_{6-14}$ aryl, heteroaryl, or heterocyclyl, each of which is optionally substituted with one or more substituents Q; in certain embodiments, one of $R^{7a}$, $R^{7b}$, $R^{7c}$, $R^{7d}$, and $R^{7e}$ is $C_{6-14}$ aryl, e.g., phenyl, optionally substituted with one or more substituents Q; in certain embodiments, one of $R^{7a}$, $R^{7b}$, $R^{7c}$, $R^{7d}$, and $R^{7e}$ is heteroaryl, e.g., 5-membered or 6-membered heteroaryl, optionally substituted with one or more substituents Q; in certain embodiments, one of $R^{7a}$, $R^{7b}$, $R^{7c}$, $R^{7d}$, and $R^{7e}$ is heterocyclyl, e.g., 5-membered or 6-membered heterocyclyl, optionally substituted with one or more substituents Q; in certain embodiments, one of $R^{7a}$, $R^{7b}$, $R^{7c}$, $R^{7d}$, and $R^{7e}$ is phenyl, imidazolyl, pyrozolyl, pyridinyl, piperidinyl, or piperazinyl, each optionally substituted with one or more substituents Q; in certain embodiments, one of $R^{7a}$, $R^{7b}$, $R^{7c}$, $R^{7d}$, and $R^{7e}$ is phenyl, imidazolyl, pyrozolyl, pyridinyl, pyrimidinyl, pyrrolidinyl, piperidinyl, or piperazinyl, each optionally substituted with one or more substituents Q; in certain embodiments, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In Formula IX, IXa, or IXb, in certain embodiments, $R^{7a}$ is $C_{6-14}$ aryl, heteroaryl, or heterocyclyl, each of which is optionally substituted with one or more substituents Q; in certain embodiments, $R^{7a}$ is $C_{6-14}$ aryl, e.g., phenyl, optionally substituted with one or more substituents Q; in certain embodiments, $R^{7a}$ is heteroaryl, e.g., 5-membered or 6-membered heteroaryl, optionally substituted with one or more substituents Q; in certain embodiments, $R^{7a}$ is heterocyclyl, e.g., 5-membered or 6-membered heterocyclyl, optionally substituted with one or more substituents Q; in certain embodiments, $R^{7a}$ is phenyl, imidazolyl, pyrozolyl, pyridinyl, piperidinyl, or piperazinyl, each optionally substituted with one or more substituents Q; in certain embodiments, $R^{7a}$ is phenyl, imidazolyl, pyrozolyl, pyridinyl, pyrimidinyl, pyrrolidinyl, piperidinyl, or piperazinyl, each optionally substituted with one or more substituents Q; in certain embodiments, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In one embodiment, in Formula IX, IXa, or IXb,
$R^1$ is hydrogen or —$OR^{1a}$, where $R^{1a}$ is $C_{1-6}$ alkyl, optionally substituted with one or more substituents Q;
$R^2$ is hydrogen;
$R^3$ and $R^4$ are hydrogen;
$R^6$ is $C_{6-14}$ alkyl, optionally substituted with one or more substituents Q;
$R^{5a}$ and $R^{5b}$ are each independently hydrogen, halo, $C_{1-6}$ alkyl, optionally substituted with one or more substituents Q;
$R^{5d}$ and $R^{5e}$ are each independently $C_{6-14}$ alkyl, optionally substituted with one or more substituents Q;
$R^{7a}$ is $C_{6-14}$ aryl, heteroaryl, or heterocyclyl, each of which is optionally substituted with one or more substituents Q;
$R^{7b}$, $R^{7c}$, $R^{7d}$, and $R^{7e}$ are hydrogen; and
X, Y, and Z are each independently N or $CR^X$, with the proviso that at least two of X, Y, and Z are N; where $R^X$ is a hydrogen or $C_{1-6}$ alkyl, optionally substituted with one or more substituents Q.

In another embodiment, in Formula IX, IXa, or IXb,
$R^1$ is hydrogen or methoxy;
$R^2$ is hydrogen;
$R^3$ and $R^4$ are hydrogen;
$R^6$ is $C_{6-14}$ alkyl, optionally substituted with one or more halo;
$R^{5a}$ and $R^{5b}$ are hydrogen;
$R^{5d}$ and $R^{5e}$ are each independently $C_{6-14}$ alkyl;
$R^{7a}$ is $C_{6-14}$ aryl, heteroaryl, or heterocyclyl, each of which is optionally substituted with one or more substituents Q;
$R^{7b}$, $R^{7c}$, $R^{7d}$, and $R^{7e}$ are hydrogen; and
X, Y, and Z are each independently N or CH.

In yet another embodiment, in Formula IX, IXa, or IXb,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are hydrogen;
$R^{5d}$ and $R^{5e}$ are methyl;
$R^{7a}$ is $C_{6-14}$ aryl, monocyclic heteroaryl, or monocyclic heterocyclyl, each of which is optionally substituted with one or more substituents Q;
$R^{7b}$, $R^{7c}$, $R^{7d}$, and $R^{7e}$ are hydrogen; and
X, Y, and Z are each independently N or CH.

In yet another embodiment, in Formula IX, IXa, or IXb,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are hydrogen;
$R^{5d}$ and $R^{5e}$ are methyl;
$R^{7a}$ is phenyl, 5- or 6-membered heteroaryl, or 5- or 6-membered heterocyclyl, each of which is optionally substituted with one or more substituents Q;
$R^{7b}$, $R^{7c}$, $R^{7d}$, and $R^{7e}$ are hydrogen; and
X, Y, and Z are each independently N or CH.

In yet another embodiment, in Formula IX, IXa, or IXb,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are hydrogen;
$R^{5d}$ and $R^{5e}$ are methyl;
$R^{7a}$ is phenyl, imidazolyl, pyrozolyl, pyridinyl, pyrimidinyl, pyrrolidinyl, piperidinyl, or piperazinyl, each of which is optionally substituted with one or more substituents Q;

$R^{7b}$, $R^{7c}$, $R^{7d}$, and $R^{7e}$ are hydrogen; and

X, Y, and Z are each independently N or CH.

In still another embodiment, in Formula IX, IXa, or IXb, $R^1$ is hydrogen or methoxy;

$R^2$ is hydrogen;

$R^3$ and $R^4$ are hydrogen;

$R^6$ is difluoromethyl;

$R^{5a}$ and $R^{5b}$ are hydrogen;

$R^{5d}$ and $R^{5e}$ are methyl;

$R^{7a}$ is phenyl, imidazolyl, pyrozolyl, pyridinyl, piperidinyl, or piperazinyl, each of which is optionally substituted with one or more substituents Q;

$R^{7b}$, $R^{7c}$, $R^{7d}$, and $R^{7e}$ are hydrogen; and

X, Y, and Z are each independently N or CH.

In yet another embodiment, provided herein is a compound of Formula X:

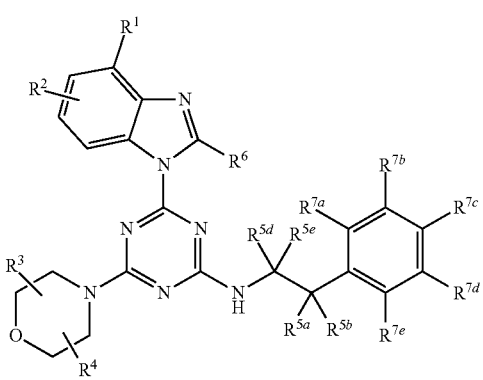

(X)

or an enantiomer, a mixture of enantiomers, a mixture of two or more diastereomers, or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{5d}$, $R^{5e}$, $R^{7a}$, $R^{7b}$, $R^{7c}$, $R^{7d}$, and, $R^{7e}$ are each as defined herein.

In one embodiment, the compound of Formula X has the structure of Formula Xa:

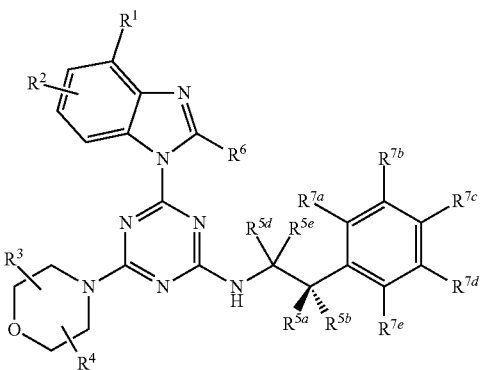

(Xa)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{5d}$, $R^{5e}$, $R^{7a}$, $R^{7b}$, $R^{7c}$, $R^{7d}$, and $R^{7e}$ are each as defined herein.

In another embodiment, the compound of Formula X has the structure of Formula Xb:

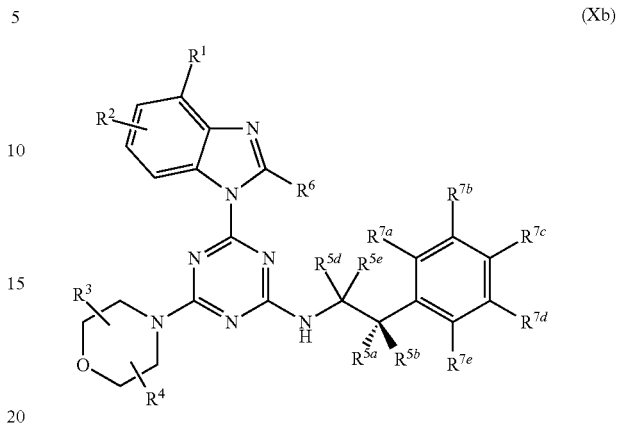

(Xb)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{5d}$, $R^{5e}$, $R^{7a}$, $R^{7b}$, $R^{7c}$, $R^{7d}$, and $R^{7e}$ are each as defined herein.

In Formula X, Xa, or Xb, in certain embodiments, one of $R^{7a}$, $R^{7b}$, $R^{7c}$, $R^{7d}$, and $R^{7e}$ is $C_{6-14}$ aryl, heteroaryl, or heterocyclyl, each of which is optionally substituted with one or more substituents Q; in certain embodiments, one of $R^{7a}$, $R^{7b}$, $R^{7c}$, $R^{7d}$, and $R^{7e}$ is $C_{6-14}$ aryl, e.g., phenyl, optionally substituted with one or more substituents Q; in certain embodiments, one of $R^{7a}$, $R^{7b}$, $R^{7c}$, $R^{7d}$, and $R^{7e}$ is heteroaryl, e.g., 5-membered or 6-membered heteroaryl, optionally substituted with one or more substituents Q; in certain embodiments, one of $R^{7a}$, $R^{7b}$, $R^{7c}$, $R^{7d}$, and $R^{7e}$ is heterocyclyl, e.g., 5-membered or 6-membered heterocyclyl, optionally substituted with one or more substituents Q; in certain embodiments, one of $R^{7a}$, $R^{7b}$, $R^{7c}$, $R^{7d}$, and $R^{7e}$ is phenyl, imidazolyl, pyrozolyl, pyridinyl, piperidinyl, or piperazinyl, each optionally substituted with one or more substituents Q; in certain embodiments, one of $R^{7a}$, $R^{7b}$, $R^{7c}$, $R^{7d}$, and $R^{7e}$ is phenyl, imidazolyl, pyrozolyl, pyridinyl, pyrimidinyl, pyrrolidinyl, piperidinyl, or piperazinyl, each optionally substituted with one or more substituents Q; in certain embodiments, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In Formula X, Xa, or Xb, in certain embodiments, $R^{7a}$ is $C_{6-14}$ aryl, heteroaryl, or heterocyclyl, each of which is optionally substituted with one or more substituents Q; in certain embodiments, $R^{7a}$ is $C_{6-14}$ aryl, e.g., phenyl, optionally substituted with one or more substituents Q; in certain embodiments, $R^{7a}$ is heteroaryl, e.g., 5-membered or 6-membered heteroaryl, optionally substituted with one or more substituents Q; in certain embodiments, $R^{7a}$ is heterocyclyl, e.g., 5-membered or 6-membered heterocyclyl, optionally substituted with one or more substituents Q; in certain embodiments, $R^{7a}$ is phenyl, imidazolyl, pyrozolyl, pyridinyl, piperidinyl, or piperazinyl, each optionally substituted with one or more substituents Q; in certain embodiments, $R^{7a}$ is phenyl, imidazolyl, pyrozolyl, pyridinyl, pyrimidinyl, pyrrolidinyl, piperidinyl, or piperazinyl, each optionally substituted with one or more substituents Q; in certain embodiments, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In one embodiment, in Formula X, Xa, or Xb,
$R^1$ is hydrogen or —$OR^{1a}$, where $R^{1a}$ is $C_{1-6}$ alkyl, optionally substituted with one or more substituents Q;
$R^2$ is hydrogen;
$R^3$ and $R^4$ are hydrogen;
$R^6$ is $C_{6-14}$ alkyl, optionally substituted with one or more substituents Q;
$R^{5a}$ and $R^{5b}$ are each independently hydrogen, halo, $C_{1-6}$ alkyl, optionally substituted with one or more substituents Q;
$R^{5d}$ and $R^{5e}$ are each independently $C_{6-14}$ alkyl, optionally substituted with one or more substituents Q;
$R^{7a}$ is $C_{6-14}$ aryl, heteroaryl, or heterocyclyl, each of which is optionally substituted with one or more substituents Q; and
$R^{7b}$, $R^{7c}$, $R^{7d}$, and $R^{7e}$ are hydrogen.

In another embodiment, in Formula X, Xa, or Xb,
$R^1$ is hydrogen or methoxy;
$R^2$ is hydrogen;
$R^3$ and $R^4$ are hydrogen;
$R^6$ is $C_{6-14}$ alkyl, optionally substituted with one or more halo;
$R^{5a}$ and $R^{5b}$ are hydrogen;
$R^{5d}$ and $R^{5e}$ are each independently $C_{6-14}$ alkyl;
$R^{7a}$ is $C_{6-14}$ aryl, heteroaryl, or heterocyclyl, each of which is optionally substituted with one or more substituents Q; and
$R^{7b}$, $R^{7c}$, $R^{7d}$, and $R^{7e}$ are hydrogen.

In yet another embodiment, in Formula X, Xa, or Xb,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are hydrogen;
$R^{5d}$ and $R^{5e}$ are methyl;
$R^{7a}$ is $C_{6-14}$ aryl, monocyclic heteroaryl, or monocyclic heterocyclyl, each of which is optionally substituted with one or more substituents Q; and
$R^{7b}$, $R^{7c}$, $R^{7d}$, and $R^{7e}$ are hydrogen.

In yet another embodiment, in Formula X, Xa, or Xb,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are hydrogen;
$R^{5d}$ and $R^{5e}$ are methyl;
$R^{7a}$ is phenyl, 5- or 6-membered heteroaryl, or 5- or 6-membered heterocyclyl, each of which is optionally substituted with one or more substituents Q; and
$R^{7b}$, $R^{7c}$, $R^{7d}$, and $R^{7e}$ are hydrogen.

In yet another embodiment, in Formula X, Xa, or Xb,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are hydrogen;
$R^{5d}$ and $R^{5e}$ are methyl;
$R^{7a}$ is phenyl, imidazolyl, pyrozolyl, pyridinyl, pyrimidinyl, pyrrolidinyl, piperidinyl, or piperazinyl, each of which is optionally substituted with one or more substituents Q; and
$R^{7b}$, $R^{7c}$, $R^{7d}$, and $R^{7e}$ are hydrogen.

In still another embodiment, in Formula X, Xa, or Xb,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are hydrogen;
$R^{5d}$ and $R^{5e}$ are methyl;
$R^{7a}$ is phenyl, imidazolyl, pyrozolyl, pyridinyl, piperidinyl, or piperazinyl, each of which is optionally substituted with one or more substituents Q; and
$R^{7b}$, $R^{7c}$, $R^{7d}$, and $R^{7e}$ are hydrogen.

In yet another embodiment, provided herein is a compound of Formula XI:

(XI)

or an enantiomer, a mixture of enantiomers, a mixture of two or more diastereomers, or an isotopic variant thereof; or a pharmaceutically acceptable salt, solvate, hydrate, or prodrug thereof; wherein:

$R^{7a}$, $R^{7b}$, $R^{7c}$, $R^{7d}$, and $R^{7e}$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

two of R$^{7a}$, R$^{7b}$, R$^{7c}$, R$^{7d}$, and R$^{7e}$ that are adjacent to each other form C$_{3-10}$ cycloalkenyl, C$_{6-14}$ aryl, heteroaryl, or heterocyclyl, each optionally substituted with one or more substituents Q; and R$^1$, R$^2$, R$^3$, R$^4$, R$^6$, R$^{1a}$, R$^{1b}$, R$^{1c}$, R$^{1d}$, R$^{5a}$, R$^{5b}$, R$^{5f}$, R$^{5g}$, X, Y, and Z are each as defined herein.

In one embodiment, the compound of Formula XI has the structure of Formula XIa:

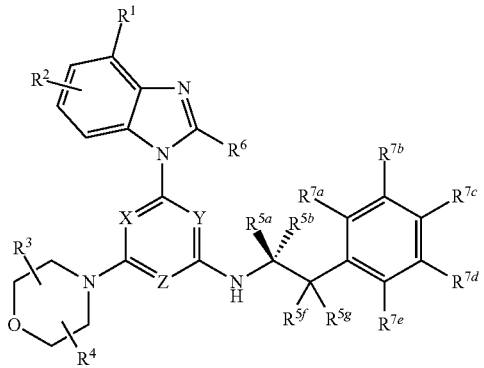

(XIa)

or an isotopic variant thereof; or a pharmaceutically acceptable salt, solvate, hydrate, or prodrug thereof wherein R$^1$, R$^2$, R$^3$, R$^4$, R$^6$, R$^{5a}$, R$^{5b}$, R$^{5f}$, R$^{5g}$, R$^{7a}$, R$^{7b}$, R$^{7c}$, R$^{7d}$, R$^{7e}$, X, Y, and Z are each as defined herein.

In another embodiment, the compound of Formula XI has the structure of Formula XIb:

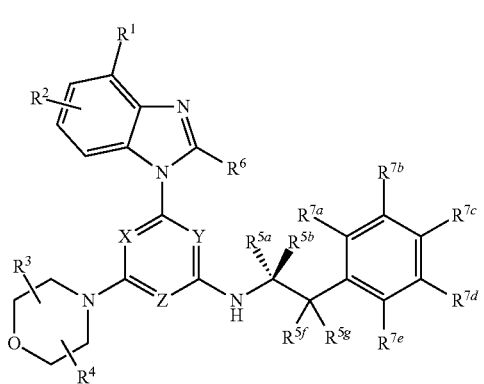

(XIb)

or an isotopic variant thereof; or a pharmaceutically acceptable salt, solvate, hydrate, or prodrug thereof; wherein R$^1$, R$^2$, R$^3$, R$^4$, R$^6$, R$^{5a}$, R$^{5b}$, R$^{5f}$, R$^{5g}$, R$^{7a}$, R$^{7b}$, R$^{7c}$, R$^{7d}$, R$^{7e}$, X, Y, and Z are each as defined herein.

In one embodiment, provided herein is a compound of Formula XI, XIa, or XIb as described herein, or an enantiomer, a mixture of enantiomers, a mixture of two or more diastereomers, or an isotopic variant thereof; or a pharmaceutically acceptable salt, solvate, hydrate, or prodrug thereof; wherein R$^{5a}$ and R$^{5b}$ are each independently (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, OC(NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; and R$^1$, R$^2$, R$^3$, R$^4$, R$^{5f}$, R$^{5g}$, R$^6$, R$^{7a}$, R$^{7b}$, R$^{7c}$, R$^{7d}$, R$^{7e}$, X, Y, Z, R$^{1a}$, R$^{1b}$, R$^{1c}$, and R$^{1d}$ are defined herein elsewhere.

In Formula XI, XIa, or XIb, in certain embodiments, one of R$^{7a}$, R$^{7b}$, R$^{7c}$, R$^{7d}$, and R$^{7e}$ is C$_{6-14}$ aryl, heteroaryl, or heterocyclyl, each of which is optionally substituted with one or more substituents Q; in certain embodiments, one of R$^{7a}$, R$^{7b}$, R$^{7c}$, R$^{7d}$, and R$^{7e}$ is C$_{6-14}$ aryl, e.g., phenyl, optionally substituted with one or more substituents Q; in certain embodiments, one of R$^{7a}$, R$^{7b}$, R$^{7c}$, R$^{7d}$, and R$^{7e}$ is heteroaryl, e.g., 5-membered or 6-membered heteroaryl, optionally substituted with one or more substituents Q; in certain embodiments, one of R$^{7a}$, R$^{7b}$, R$^{7c}$, R$^{7d}$, and R$^{7e}$ is heterocyclyl, e.g., 5-membered or 6-membered heterocyclyl, optionally substituted with one or more substituents Q; in certain embodiments, one of R$^{7a}$, R$^{7b}$, R$^{7c}$, R$^{7d}$, and R$^{7e}$ is phenyl, imidazolyl, pyrozolyl, pyridinyl, piperidinyl, or piperazinyl, each optionally substituted with one or more substituents Q; in certain embodiments, one of R$^{7a}$, R$^{7b}$, R$^{7c}$, R$^{7d}$, and R$^{7e}$ is phenyl, imidazolyl, pyrozolyl, pyridinyl, pyrimidinyl, pyrrolidinyl, piperidinyl, or piperazinyl, each optionally substituted with one or more substituents Q; in certain embodiments, one of R$^{7a}$, R$^{7b}$, R$^{7c}$, R$^{7d}$, and R$^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, one of R$^{7a}$, R$^{7b}$, R$^{7c}$, R$^{7d}$, and R$^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In Formula XI, XIa, or XIb, in certain embodiments, R$^{7a}$ is C$_{6-14}$ aryl, heteroaryl, or heterocyclyl, each of which is optionally substituted with one or more substituents Q; in certain embodiments, R$^{7a}$ is C$_{6-14}$ aryl, e.g., phenyl, optionally substituted with one or more substituents Q; in certain embodiments, $R^{7a}$ is heteroaryl, e.g., 5-membered or 6-membered heteroaryl, optionally substituted with one or more substituents Q; in certain embodiments, $R^{7a}$ is heterocyclyl, e.g., 5-membered or 6-membered heterocyclyl, optionally substituted with one or more substituents Q; in certain embodiments, $R^{7a}$ is phenyl, imidazolyl, pyrozolyl, pyridinyl, piperidinyl, or piperazinyl, each optionally substituted with one or more substituents Q; in certain embodiments, $R^{7a}$ is phenyl, imidazolyl, pyrozolyl, pyridinyl, pyrimidinyl, pyrrolidinyl, piperidinyl, or piperazinyl, each optionally substituted with one or more substituents Q; in certain embodiments, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In one embodiment, in Formula XI, XIa, or XIb, $R^1$ is hydrogen or —$OR^{1a}$, where $R^{1a}$ is $C_{1-6}$ alkyl, optionally substituted with one or more substituents Q;

$R^2$ is hydrogen;

$R^3$ and $R^4$ are hydrogen;

$R^6$ is $C_{6-14}$ alkyl, optionally substituted with one or more substituents Q;

$R^{5a}$ and $R^{5b}$ are each independently $C_{6-14}$ alkyl, optionally substituted with one or more substituents Q;

$R^{5f}$ and $R^{5g}$ are each independently hydrogen, halo, $C_{1-6}$ alkyl, optionally substituted with one or more substituents Q; or $R^{5f}$ and $R^{5g}$ together with the carbon atom to which they are attached form $C_{1-10}$ cycloalkyl or heterocyclyl, each of which is optionally substituted with one or more substituents Q;

$R^{7a}$ is $C_{6-14}$ aryl, heteroaryl, or heterocyclyl, each of which is optionally substituted with one or more substituents Q;

$R^{7b}$, $R^{7c}$, $R^{7d}$, and $R^{7e}$ are hydrogen; and

X, Y, and Z are each independently N or $CR^X$, with the proviso that at least two of X, Y, and Z are N; where $R^X$ is a hydrogen or $C_{1-6}$ alkyl, optionally substituted with one or more substituents Q.

In another embodiment, in Formula XI, XIa, or Xib, $R^1$ is hydrogen or methoxy;

$R^2$ is hydrogen;

$R^3$ and $R^4$ are hydrogen;

$R^6$ is $C_{6-14}$ alkyl, optionally substituted with one or more halo;

$R^{5a}$ and $R^{5b}$ are each independently $C_{6-14}$ alkyl;

$R^{5f}$ and $R^{5g}$ are each independently hydrogen or $C_{1-6}$ alkyl; or $R^{5f}$ and $R^{5g}$ together with the carbon atom to which they are attached form $C_{1-10}$ cycloalkyl;

$R^{7a}$ is $C_{6-14}$ aryl, heteroaryl, or heterocyclyl, each of which is optionally substituted with one or more substituents Q;

$R^{7b}$, $R^{7c}$, $R^{7d}$, and $R^{7e}$ are hydrogen; and

X, Y, and Z are each independently N or CH.

In yet another embodiment, in Formula XI, XIa, or XIb, $R^1$ is hydrogen or methoxy;

$R^2$ is hydrogen;

$R^3$ and $R^4$ are hydrogen;

$R^6$ is difluoromethyl;

$R^{5a}$ and $R^{5b}$ are methyl;

$R^{5f}$ and $R^{5g}$ are hydrogen; or $R^{5f}$ and $R^{5g}$ together with the carbon atom to which they are attached form cyclopropyl, cyclobutyl, cyclpentyl, or cyclohexyl;

$R^{7a}$ is $C_{6-14}$ aryl, monocyclic heteroaryl, or monocyclic heterocyclyl, each of which is optionally substituted with one or more substituents Q;

$R^{7b}$, $R^{7c}$, $R^{7d}$, and $R^{7e}$ are hydrogen; and

X, Y, and Z are each independently N or CH.

In yet another embodiment, in Formula XI, XIa, or XIb, $R^1$ is hydrogen or methoxy;

$R^2$ is hydrogen;

$R^3$ and $R^4$ are hydrogen;

$R^6$ is difluoromethyl;

$R^{5a}$ and $R^{5b}$ are methyl;

$R^{5f}$ and $R^{5g}$ are hydrogen; or $R^{5f}$ and $R^{5g}$ together with the carbon atom to which they are attached form cyclopropyl, cyclobutyl, cyclpentyl, or cyclohexyl;

$R^{7a}$ is phenyl, 5- or 6-membered heteroaryl, or 5- or 6-membered heterocyclyl, each of which is optionally substituted with one or more substituents Q;

$R^{7b}$, $R^{7c}$, $R^{7d}$, and $R^{7e}$ are hydrogen; and

X, Y, and Z are each independently N or CH.

In yet another embodiment, in Formula XI, XIa, or XIb, $R^1$ is hydrogen or methoxy;

$R^2$ is hydrogen;

$R^3$ and $R^4$ are hydrogen;

$R^6$ is difluoromethyl;

$R^{5a}$ and $R^{5b}$ are methyl;

$R^{5f}$ and $R^{5g}$ are hydrogen; or $R^{5f}$ and $R^{5g}$ together with the carbon atom to which they are attached form cyclopropyl, cyclobutyl, cyclpentyl, or cyclohexyl;

$R^{7a}$ is phenyl, imidazolyl, pyrozolyl, pyridinyl, pyrimidinyl, pyrrolidinyl, piperidinyl, or piperazinyl, each of which is optionally substituted with one or more substituents Q;

$R^{7b}$, $R^{7c}$, $R^{7d}$, and $R^{7e}$ are hydrogen; and

X, Y, and Z are each independently N or CH.

In still another embodiment, in Formula XI, XIa, or XIb, $R^1$ is hydrogen or methoxy;

$R^2$ is hydrogen;

$R^3$ and $R^4$ are hydrogen;

$R^6$ is difluoromethyl;

$R^{5a}$ and $R^{5b}$ are methyl;

$R^{5f}$ and $R^{5g}$ are hydrogen; or $R^{5f}$ and $R^{5g}$ together with the carbon atom to which they are attached form cyclopropyl, cyclobutyl, cyclpentyl, or cyclohexyl;

$R^{7a}$ is phenyl, imidazolyl, pyrozolyl, pyridinyl, piperidinyl, or piperazinyl, each of which is optionally substituted with one or more substituents Q;

$R^{7b}$, $R^{7c}$, $R^{7d}$, and $R^{7e}$ are hydrogen; and

X, Y, and Z are each independently N or CH.

In yet another embodiment, provided herein is a compound of Formula XII:

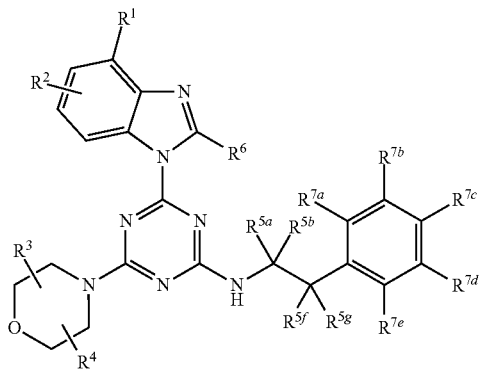

(XII)

or an enantiomer, a mixture of enantiomers, a mixture of two or more diastereomers, or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{5f}$, $R^{5g}$, $R^{7a}$, $R^{7b}$, $R^{7c}$, $R^{7d}$, and $R^{7e}$ are each as defined herein.

In one embodiment, the compound of Formula XII has the structure of Formula XIIa:

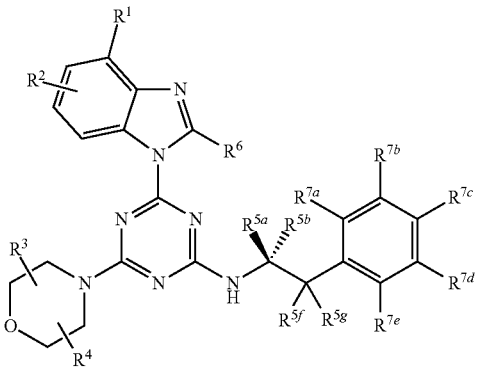

(XIIa)

or an isotopic variant thereof; or a pharmaceutically acceptable salt, solvate, hydrate, or prodrug thereof wherein $R^1$, $R^2$, $R^3$, $R^4$, $R^6$, $R^{5a}$, $R^{5b}$, $R^{5f}$, $R^{5g}$, $R^{7a}$, $R^{7b}$, $R^{7c}$, $R^{7d}$, and $R^{7e}$ are each as defined herein.

In another embodiment, the compound of Formula XII has the structure of Formula XIIb:

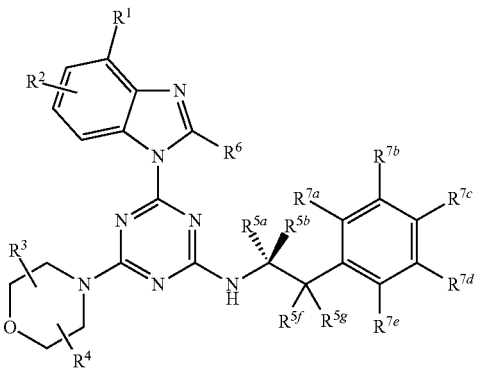

(XIIb)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{5f}$, $R^{5g}$, $R^{7a}$, $R^{7b}$, $R^{7c}$, $R^{7d}$, and $R^{7e}$ are each as defined herein.

In one embodiment, provided herein is a compound of Formula XII, XIIa, or XIIb as described herein, or an enantiomer, a mixture of enantiomers, a mixture of two or more diastereomers, or an isotopic variant thereof; or a pharmaceutically acceptable salt, solvate, hydrate, or prodrug thereof; wherein $R^{5a}$ and $R^{5b}$ are each independently (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, or —S(O)$_2$N$R^{1b}R^{1c}$; and $R^1$, $R^2$, $R^3$, $R^4$, $R^{5f}$, $R^{5g}$, $R^6$, $R^{7a}$, $R^{7b}$, $R^{7c}$, $R^{7d}$, $R^{7e}$, $R^{1a}$, $R^{1b}$, $R^{1c}$, and $R^{1d}$ are defined herein elsewhere.

In Formula XII, XIIa, or XIIb, in certain embodiments, one of $R^{7a}$, $R^{7b}$, $R^{7c}$, $R^{7d}$, and $R^{7e}$ is $C_{6-14}$ aryl, heteroaryl, or heterocyclyl, each of which is optionally substituted with one or more substituents Q; in certain embodiments, one of $R^{7a}$, $R^{7b}$, $R^{7c}$, $R^{7d}$, and $R^{7e}$ is $C_{6-14}$ aryl, e.g., phenyl, optionally substituted with one or more substituents Q; in certain embodiments, one of $R^{7a}$, $R^{7b}$, $R^{7c}$, $R^{7d}$, and $R^{7e}$ is heteroaryl, e.g., 5-membered or 6-membered heteroaryl, optionally substituted with one or more substituents Q; in certain embodiments, one of $R^{7a}$, $R^{7b}$, $R^{7c}$, $R^{7d}$, and $R^{7e}$ is heterocyclyl, e.g., 5-membered or 6-membered heterocyclyl, optionally substituted with one or more substituents Q; in certain embodiments, one of $R^{7a}$, $R^{7b}$, $R^{7c}$, $R^{7d}$, and $R^{7e}$ is phenyl, imidazolyl, pyrozolyl, pyridinyl, piperidinyl, or piperazinyl, each optionally substituted with one or more substituents Q; in certain embodiments, one of $R^{7a}$, $R^{7b}$, $R^{7c}$, $R^{7d}$, and $R^{7e}$ is phenyl, imidazolyl, pyrozolyl, pyridinyl, pyrimidinyl, pyrrolidinyl, piperidinyl, or piperazinyl, each optionally substituted with one or more substituents Q; in certain embodiments, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In Formula XII, XIIa, or XIIb, in certain embodiments, $R^{7a}$ is $C_{6-14}$ aryl, heteroaryl, or heterocyclyl, each of which is optionally substituted with one or more substituents Q; in certain embodiments, $R^{7a}$ is $C_{6-14}$ aryl, e.g., phenyl, optionally substituted with one or more substituents Q; in certain embodiments, $R^{7a}$ is heteroaryl, e.g., 5-membered or 6-membered heteroaryl, optionally substituted with one or more substituents Q; in certain embodiments, $R^{7a}$ is heterocyclyl, e.g., 5-membered or 6-membered heterocyclyl, optionally substituted with one or more substituents Q; in certain embodiments, $R^{7a}$ is phenyl, imidazolyl, pyrozolyl, pyridinyl, piperidinyl, or piperazinyl, each optionally substituted with one or more substituents Q; in certain embodiments, $R^{7a}$ is phenyl, imidazolyl, pyrozolyl, pyridinyl, pyrimidinyl, pyrrolidinyl, piperidinyl, or piperazinyl, each optionally substituted with one or more substituents Q; in certain embodiments, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In one embodiment, in Formula XII, XIIa, or XIIb,
$R^1$ is hydrogen or —$OR^{1a}$, where $R^{1a}$ is $C_{1-6}$ alkyl, optionally substituted with one or more substituents Q;
$R^2$ is hydrogen;
$R^3$ and $R^4$ are hydrogen;
$R^6$ is $C_{6-14}$ alkyl, optionally substituted with one or more substituents Q;
$R^{5a}$ and $R^{5b}$ are each independently $C_{6-14}$ alkyl, optionally substituted with one or more substituents Q;
$R^{5f}$ and $R^{5g}$ are each independently hydrogen, halo, $C_{1-6}$ alkyl, optionally substituted with one or more substituents Q; or $R^{5f}$ and $R^{5g}$ together with the carbon atom to which they are attached form $C_{1-10}$ cycloalkyl or heterocyclyl, each of which is optionally substituted with one or more substituents Q;
$R^{7a}$ is $C_{6-14}$ aryl, heteroaryl, or heterocyclyl, each of which is optionally substituted with one or more substituents Q; and
$R^{7b}$, $R^{7c}$, $R^{7d}$, and $R^{7e}$ are hydrogen.

In another embodiment, in Formula XII, XIIa, or XIIb,
$R^1$ is hydrogen or methoxy;
$R^2$ is hydrogen;
$R^3$ and $R^4$ are hydrogen;
$R^6$ is $C_{6-14}$ alkyl, optionally substituted with one or more halo;
$R^{5a}$ and $R^{5b}$ are each independently $C_{6-14}$ alkyl;
$R^{5f}$ and $R^{5g}$ are each independently hydrogen or $C_{1-6}$ alkyl; or $R^{5f}$ and $R^{5g}$ together with the carbon atom to which they are attached form $C_{1-10}$ cycloalkyl;

$R^{7a}$ is $C_{6-14}$ aryl, heteroaryl, or heterocyclyl, each of which is optionally substituted with one or more substituents Q; and
$R^{7b}$, $R^{7c}$, $R^{7d}$, and $R^{7e}$ are hydrogen.

In yet another embodiment, in Formula XII, XIIa, or XIIb,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are methyl;
$R^{5f}$ and $R^{5g}$ are hydrogen; or $R^{5f}$ and $R^{5g}$ together with the carbon atom to which they are attached form cyclopropyl, cyclobutyl, cyclpentyl, or cyclohexyl;
$R^{7a}$ is $C_{6-14}$ aryl, monocyclic heteroaryl, or monocyclic heterocyclyl, each of which is optionally substituted with one or more substituents Q; and
$R^{7b}$, $R^{7c}$, $R^{7d}$, and $R^{7e}$ are hydrogen.

In yet another embodiment, in Formula XII, XIIa, or XIIb,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are methyl;
$R^{5f}$ and $R^{5g}$ are hydrogen; or $R^{5f}$ and $R^{5g}$ together with the carbon atom to which they are attached form cyclopropyl, cyclobutyl, cyclpentyl, or cyclohexyl;
$R^{7a}$ is phenyl, 5- or 6-membered heteroaryl, or 5- or 6-membered heterocyclyl, each of which is optionally substituted with one or more substituents Q; and
$R^{7b}$, $R^{7c}$, $R^{7d}$, and $R^{7e}$ are hydrogen.

In yet another embodiment, in Formula XII, XIIa, or XIIb,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are methyl;
$R^{5f}$ and $R^{5g}$ are hydrogen; or $R^{5f}$ and $R^{5g}$ together with the carbon atom to which they are attached form cyclopropyl, cyclobutyl, cyclpentyl, or cyclohexyl;
$R^{7a}$ is phenyl, imidazolyl, pyrozolyl, pyridinyl, pyrimidinyl, pyrrolidinyl, piperidinyl, or piperazinyl, each of which is optionally substituted with one or more substituents Q; and
$R^{7b}$, $R^{7c}$, $R^{7d}$, and $R^{7e}$ are hydrogen.

In still another embodiment, in Formula XII, XIIa, or XIIb,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are methyl;
$R^{5f}$ and $R^{5g}$ are hydrogen; or $R^{5f}$ and $R^{5g}$ together with the carbon atom to which they are attached form cyclopropyl, cyclobutyl, cyclpentyl, or cyclohexyl;
$R^{7a}$ is phenyl, imidazolyl, pyrozolyl, pyridinyl, piperidinyl, or piperazinyl, each of which is optionally substituted with one or more substituents Q; and
$R^{7b}$, $R^{7c}$, $R^{7d}$, and $R^{7e}$ are hydrogen.

In yet another embodiment, provided herein is a compound of Formula XIII:

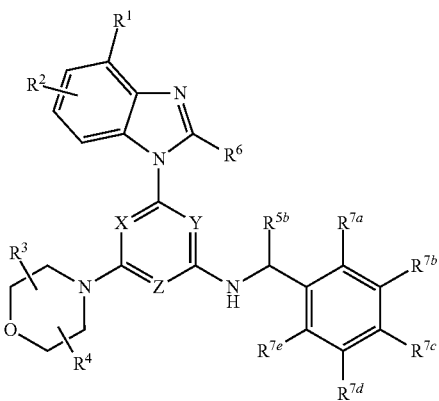

(XIII)

or an enantiomer, a mixture of enantiomers, a mixture of two or more diastereomers, or an isotopic variant thereof; or a pharmaceutically acceptable salt, solvate, hydrate, or prodrug thereof; wherein $R^1$, $R^2$, $R^3$, $R^4$, $R^6$, $R^{5b}$, $R^{7a}$, $R^{7b}$, $R^{7c}$, $R^{7d}$, $R^{7e}$, X, Y and Z are each as defined herein.

In one embodiment, the compound of Formula XIII has the structure of Formula XIIIa:

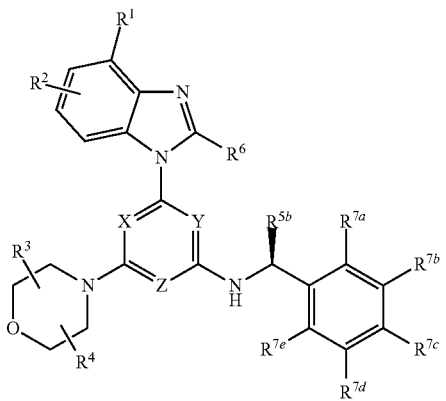

(XIIIa)

or an isotopic variant thereof; or a pharmaceutically acceptable salt, solvate, hydrate, or prodrug thereof; wherein $R^1$, $R^2$, $R^3$, $R^4$, $R^6$, $R^{5b}$, $R^{7a}$, $R^{7b}$, $R^{7c}$, $R^{7d}$, $R^{7e}$, X, Y, and Z are each as defined herein.

In another embodiment, the compound of Formula XIII has the structure of Formula XIIIb:

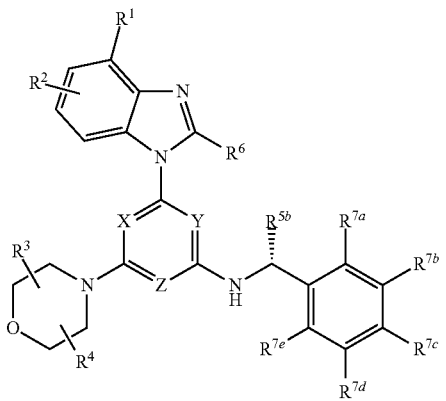

(XIIIb)

or an isotopic variant thereof; or a pharmaceutically acceptable salt, solvate, hydrate, or prodrug thereof; wherein $R^1$, $R^2$, $R^3$, $R^4$, $R^6$, $R^{5b}$, $R^{7a}$, $R^{7b}$, $R^{7c}$, $R^{7d}$, $R^{7e}$, X, Y, and Z are each as defined herein.

In yet another embodiment, provided herein is a compound of Formula XIV:

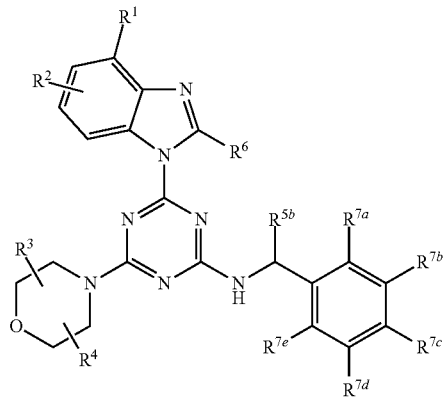

(XIV)

or an enantiomer, a mixture of enantiomers, a mixture of two or more diastereomers, or an isotopic variant thereof; or a pharmaceutically acceptable salt, solvate, hydrate, or prodrug thereof; wherein $R^1$, $R^2$, $R^3$, $R^4$, $R^6$, $R^{5b}$, $R^{7a}$, $R^{7b}$, $R^{7c}$, $R^{7d}$, and $R^{7e}$ are each as defined herein.

In one embodiment, the compound of Formula XIV has the structure of Formula XIVa:

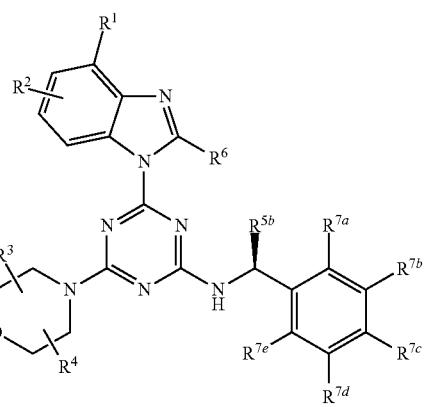

(XIVa)

or an isotopic variant thereof; or a pharmaceutically acceptable salt, solvate, hydrate, or prodrug thereof; wherein $R^1$, $R^2$, $R^3$, $R^4$, $R^6$, $R^{5b}$, $R^{7a}$, $R^{7b}$, $R^{7c}$, $R^{7d}$, and $R^{7e}$ are each as defined herein.

In another embodiment, the compound of Formula XIV has the structure of Formula XIVb:

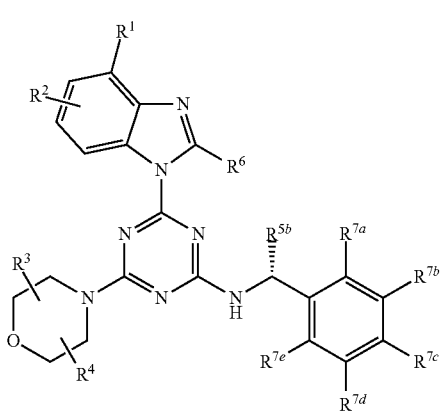

(XIVb)

or an isotopic variant thereof; or a pharmaceutically acceptable salt, solvate, hydrate, or prodrug thereof; wherein $R^1$, $R^2$, $R^3$, $R^4$, $R^6$, $R^{5b}$, $R^{7a}$, $R^{7b}$, $R^{7c}$, $R^{7d}$, and $R^{7e}$ are each as defined herein.

In yet another embodiment, provided herein is a compound of Formula XV:

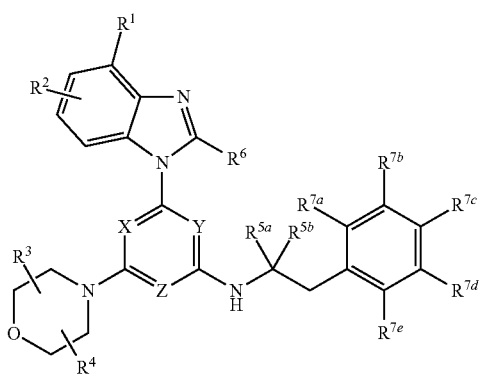

(XV)

or an enantiomer, a mixture of enantiomers, a mixture of two or more diastereomers, or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{7a}$, $R^{7b}$, $R^{7c}$, $R^{7d}$, $R^{7e}$, R, X, Y and Z are each as defined herein.

In one embodiment, in Formula XV, one of $R^{7a}$, $R^{7b}$, $R^{7c}$, $R^{7d}$, and $R^{7e}$ is $C_{6-14}$ aryl, heteroaryl, or heterocyclyl, each of which is optionally substituted with one or more substituents Q; and $R^1$, $R^2$, $R^3$, $R^4$, $R^6$, $R^{5a}$, $R^{5b}$ the remaining of $R^{7a}$, $R^{7b}$, $R^{7c}$, $R^{7d}$, and $R^{7e}$, X, Y, and Z are each as defined herein.

In another embodiment, in Formula XV, one of $R^{7a}$, $R^{7b}$, $R^{7c}$, $R^{7d}$, and $R^{7e}$ is $C_{6-14}$ aryl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XV, one of $R^{7a}$, $R^{7b}$, $R^{7c}$, $R^{7d}$, and $R^{7e}$ is heteroaryl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XV, one of $R^{7a}$, $R^{7b}$, $R^{7c}$, $R^{7d}$, and $R^{7e}$ is 5-membered or 6-membered heteroaryl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XV, one of $R^{7a}$, $R^{7b}$, $R^{7c}$, $R^{7d}$, and $R^{7e}$ is heterocyclyl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XV, one of $R^{7a}$, $R^{7b}$, $R^{7c}$, $R^{7d}$, and $R^{7e}$ is 5-membered or 6-membered heterocyclyl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XV, one of $R^{7a}$, $R^{7b}$, $R^{7c}$, $R^{7d}$, and $R^{7e}$ is phenyl, imidazolyl, pyrozolyl, pyridinyl, piperidinyl, or piperazinyl, each optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XV, one of $R^{7a}$, $R^{7b}$, $R^{7c}$, $R^{7d}$, and $R^{7e}$ is phenyl, imidazolyl, pyrozolyl, pyridinyl, pyrimidinyl, pyrrolidinyl, piperidinyl, or piperazinyl, each optionally substituted with one or more substituents Q; and $R^1$, $R^2$, $R^3$, $R^4$, $R^6$, $R^{5a}$, $R^{b5}$, the remaining of $R^{7a}$, $R^{7b}$, $R^{7c}$, $R^{7d}$, and $R^{7e}$, X, Y, and Z are each as defined herein.

In yet another embodiment, in Formula XV, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In still another embodiment, in Formula XV, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment, in Formula XV, $R^{7a}$ is $C_{6-14}$ aryl, heteroaryl, or heterocyclyl, each of which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In another embodiment, in Formula XV, $R^{7a}$ is $C_{6-14}$ aryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XV, $R^{7a}$ is heteroaryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XV, $R^{7a}$ is 5-membered or 6-membered heteroaryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XV, $R^{7a}$ is heterocyclyl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XV, $R^{7a}$ is 5-membered or 6-membered heterocyclyl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XV, $R^{7a}$ is phenyl, imidazolyl, pyrozolyl, pyridinyl, pyrozolyl, piperidinyl, or piperazinyl, each optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XV, $R^{7a}$ is phenyl, imidazolyl, pyrozolyl, pyridinyl, pyrimidinyl, pyrrolidinyl, piperidinyl, or piperazinyl, each optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XV, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In still another embodiment, in Formula XV, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment, in Formula XV,
$R^1$ is hydrogen or —$OR^{1a}$, where $R^{1a}$ is $C_{1-6}$ alkyl, optionally substituted with one or more substituents Q;
$R^2$ is hydrogen;
$R^3$ and $R^4$ are hydrogen;
$R^6$ is $C_{6-14}$ alkyl, optionally substituted with one or more substituents Q;
$R^{5a}$ and $R^{5b}$ are each independently $C_{6-14}$ alkyl, optionally substituted with one or more substituents Q;
$R^{7a}$ is $C_{6-14}$ aryl, heteroaryl, or heterocyclyl, each of which is optionally substituted with one or more substituents Q;
$R^{7b}$, $R^{7c}$, $R^{7d}$, and $R^{7e}$ are hydrogen; and
X, Y, and Z are each independently N or $CR^X$, with the proviso that at least two of X, Y, and Z are N; where $R^X$ is a hydrogen or $C_{1-6}$ alkyl, optionally substituted with one or more substituents Q.

In another embodiment, in Formula XV,
$R^1$ is hydrogen or methoxy;
$R^2$ is hydrogen;
$R^3$ and $R^4$ are hydrogen;
$R^6$ is $C_{6-14}$ alkyl, optionally substituted with one or more halo;
$R^{5a}$ and $R^{5b}$ are each independently $C_{6-14}$ alkyl;
$R^{7a}$ is $C_{6-14}$ aryl, heteroaryl, or heterocyclyl, each of which is optionally substituted with one or more substituents Q;
$R^{7b}$, $R^{7c}$, $R^{7d}$, and $R^{7e}$ are hydrogen; and
X, Y, and Z are each independently N or CH.

In yet another embodiment, in Formula XV,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are methyl;
$R^{7a}$ is $C_{6-14}$ aryl, monocyclic heteroaryl, or monocyclic heterocyclyl, each of which is optionally substituted with one or more substituents Q;
$R^{7b}$, $R^{7c}$, $R^{7d}$, and $R^{7e}$ are hydrogen; and
X, Y, and Z are each independently N or CH.

In yet another embodiment, in Formula XV,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are methyl;
$R^{7a}$ is phenyl, 5- or 6-membered heteroaryl, or 5- or 6-membered heterocyclyl, each of which is optionally substituted with one or more substituents Q;
$R^{7b}$, $R^{7c}$, $R^{7d}$, and $R^{7e}$ are hydrogen; and
X, Y, and Z are each independently N or CH.

In yet another embodiment, in Formula XV,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are methyl;
$R^{7a}$ is phenyl, imidazolyl, pyrozolyl, pyridinyl, pyrimidinyl, pyrrolidinyl, piperidinyl, or piperazinyl, each of which is optionally substituted with one or more substituents Q;
$R^{7b}$, $R^{7c}$, $R^{7d}$, and $R^{7e}$ are hydrogen; and
X, Y, and Z are each independently N or CH.

In still another embodiment, in Formula XV,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are methyl;
$R^{7a}$ is phenyl, imidazolyl, pyrozolyl, pyridinyl, piperidinyl, or piperazinyl, each of which is optionally substituted with one or more substituents Q;
$R^{7b}$, $R^{7c}$, $R^{7d}$, and $R^{7e}$ are hydrogen; and
X, Y, and Z are each independently N or CH.

In one embodiment, the compound of Formula XV has the structure of Formula XVa:

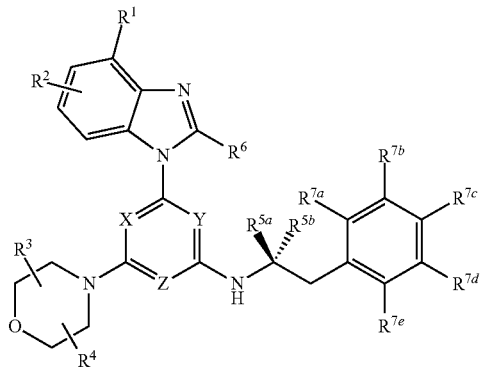

(XVa)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{7a}$, $R^{7b}$, $R^{7c}$, $R^{7d}$, $R^{7e}$, X, Y, and Z are each as defined herein.

In one embodiment, in Formula XVa, one of $R^{7a}$, $R^{7b}$, $R^{7c}$, $R^{7d}$, and $R^{7e}$ is $C_{6-14}$ aryl, heteroaryl, or heterocyclyl, each of which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In another embodiment, in Formula XVa, one of $R^{7a}$, $R^{7b}$, $R^{7c}$, $R^{7d}$, and $R^{7e}$ is $C_{6-14}$ aryl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVa, one of $R^{7a}$, $R^{7b}$, $R^{7c}$, $R^{7d}$, and $R^{7e}$ is heteroaryl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVa, one of $R^{7a}$, $R^{7b}$, $R^{7c}$, $R^{7d}$, and $R^{7e}$ is 5-membered or 6-membered heteroaryl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVa, one of $R^{7a}$, $R^{7b}$, $R^{7c}$, $R^{7d}$, and $R^{7e}$ is heterocyclyl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVa, one of $R^{7a}$, $R^{7b}$, $R^{7c}$, $R^{7d}$, and $R^{7e}$ is 5-membered or 6-membered heterocyclyl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVa, one of $R^{7a}$, $R^{7b}$, $R^{7c}$, $R^{7d}$, and $R^{7e}$ is phenyl, imidazolyl, pyrozolyl, pyridinyl, piperidinyl, or piperazinyl, each optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVa, one of $R^{7a}$, $R^{7b}$, $R^{7c}$, $R^{7d}$, and $R^{7e}$ is phenyl, imidazolyl, pyrozolyl, pyridinyl, pyrimidinyl, pyrrolidinyl, piperidinyl, or piperazinyl, each optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVa, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In still another embodiment, in Formula XVa, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment, in Formula XVa, $R^{7a}$ is $C_{6-14}$ aryl, heteroaryl, or heterocyclyl, each of which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In another embodiment, in Formula XVa, $R^{7a}$ is $C_{6-14}$ aryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVa, $R^{7a}$ is heteroaryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVa, $R^{7a}$ is 5-membered or 6-membered heteroaryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVa, $R^{7a}$ is heterocyclyl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVa, $R^{7a}$ is 5-membered or 6-membered heterocyclyl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVa, $R^{7a}$ is phenyl, imidazolyl, pyrozolyl, pyridinyl, piperidinyl, or piperazinyl, each optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVa, $R^{7a}$ is phenyl, imidazolyl, pyrozolyl, pyridinyl, pyrimidinyl, pyrrolidinyl, piperidinyl, or piperazinyl, each optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVa, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In still another embodiment, in Formula XVa, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment, in Formula XVa,
$R^1$ is hydrogen or —$OR^{1a}$, where $R^{1a}$ is $C_{1-6}$ alkyl, optionally substituted with one or more substituents Q;
$R^2$ is hydrogen;
$R^3$ and $R^4$ are hydrogen;
$R^6$ is $C_{6-14}$ alkyl, optionally substituted with one or more substituents Q;
$R^{5a}$ and $R^{5b}$ are each independently hydrogen or $C_{6-14}$ alkyl, optionally substituted with one or more substituents Q;
$R^{7a}$ is $C_{6-14}$ aryl, heteroaryl, or heterocyclyl, each of which is optionally substituted with one or more substituents Q;
$R^{7b}$, $R^{7c}$, $R^{7d}$, and $R^{7e}$ are hydrogen; and
X, Y, and Z are each independently N or $CR^X$, with the proviso that at least two of X, Y, and Z are N; where $R^X$ is a hydrogen or $C_{1-6}$ alkyl, optionally substituted with one or more substituents Q.

In another embodiment, in Formula XVa,
$R^1$ is hydrogen or methoxy;
$R^2$ is hydrogen;
$R^3$ and $R^4$ are hydrogen;
$R^6$ is $C_{6-14}$ alkyl, optionally substituted with one or more halo;
$R^{5a}$ and $R^{5b}$ are each independently hydrogen or $C_{6-14}$ alkyl;
$R^{7a}$ is $C_{6-14}$ aryl, heteroaryl, or heterocyclyl, each of which is optionally substituted with one or more substituents Q;
$R^{7b}$, $R^{7c}$, $R^{7d}$, and $R^{7e}$ are hydrogen; and
X, Y, and Z are each independently N or CH.

In yet another embodiment, in Formula XVa,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{6-14}$ alkyl;
$R^{7a}$ is $C_{6-14}$ aryl, monocyclic heteroaryl, or monocyclic heterocyclyl, each of which is optionally substituted with one or more substituents Q;
$R^{7b}$, $R^{7c}$, $R^{7d}$, and $R^{7e}$ are hydrogen; and
X, Y, and Z are each independently N or CH.

In yet another embodiment, in Formula XVa,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{6-14}$ alkyl;
$R^{7a}$ is phenyl, 5- or 6-membered heteroaryl, or 5- or 6-membered heterocyclyl, each of which is optionally substituted with one or more substituents Q;
$R^{7b}$, $R^{7c}$, $R^{7d}$, and $R^{7e}$ are hydrogen; and
X, Y, and Z are each independently N or CH.

In yet another embodiment, in Formula XVa,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{6-14}$ alkyl;
$R^{7a}$ is phenyl, imidazolyl, pyrozolyl, pyridinyl, pyrimidinyl, pyrrolidinyl, piperidinyl, or piperazinyl, each of which is optionally substituted with one or more substituents Q;
$R^{7b}$, $R^{7c}$, $R^{7d}$, and $R^{7e}$ are hydrogen; and
X, Y, and Z are each independently N or CH.

In still another embodiment, in Formula XVa,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{6-14}$ alkyl;
$R^{7a}$ is phenyl, imidazolyl, pyrozolyl, pyridinyl, piperidinyl, or piperazinyl, each of which is optionally substituted with one or more substituents Q;
$R^{7b}$, $R^{7c}$, $R^{7d}$, and $R^{7e}$ are hydrogen; and
X, Y, and Z are each independently N or CH.

In another embodiment, the compound of Formula XV has the structure of Formula XVb:

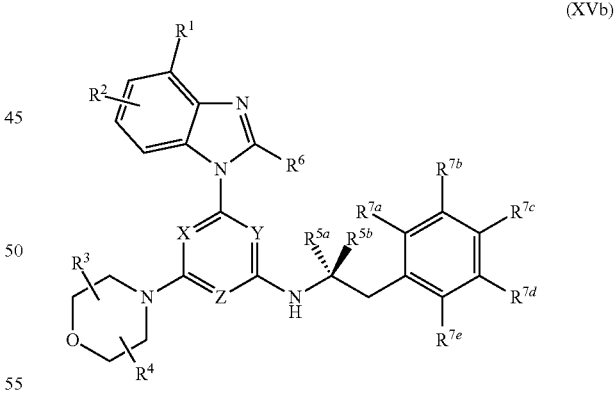

(XVb)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{7a}$, $R^{7b}$, $R^{7c}$, $R^{7d}$, $R^{7e}$, X, Y, and Z are each as defined herein.

In one embodiment, in Formula XVb, one of $R^{7a}$, $R^{7b}$, $R^{7c}$, $R^{7d}$, and $R^{7e}$ is $C_{6-14}$ aryl, heteroaryl, or heterocyclyl, each of which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In another embodiment, in Formula XVb, one of $R^{7a}$, $R^{7b}$, $R^{7c}$, $R^{7d}$, and $R^{7e}$ is $C_{6-14}$ aryl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVb, one of $R^{7a}$, $R^{7b}$, $R^{7c}$, $R^{7d}$, and $R^{7e}$ is heteroaryl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVb, one of $R^{7a}$, $R^{7b}$, $R^{7c}$, $R^{7d}$, and $R^{7e}$ is 5-membered or 6-membered heteroaryl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVb, one of $R^{7a}$, $R^{7b}$, $R^{7c}$, $R^{7d}$, and $R^{7e}$ is heterocyclyl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVb, one of $R^{7a}$, $R^{7b}$, $R^{7c}$, $R^{7d}$, and $R^{7e}$ is 5-membered or 6-membered heterocyclyl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVb, one of $R^{7a}$, $R^{7b}$, $R^{7c}$, $R^{7d}$, and $R^{7e}$ is phenyl, imidazolyl, pyrozolyl, pyridinyl, piperidinyl, or piperazinyl, each optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVb, one of $R^{7a}$, $R^{7b}$, $R^{7c}$, $R^{7d}$, and $R^{7e}$ is phenyl, imidazolyl, pyrozolyl, pyridinyl, pyrimidinyl, pyrrolidinyl, piperidinyl, or piperazinyl, each optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVb, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In still another embodiment, in Formula XVb, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment, in Formula XVb, $R^{7a}$ is $C_{6-14}$ aryl, heteroaryl, or heterocyclyl, each of which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In another embodiment, in Formula XVb, $R^{7a}$ is $C_{6-14}$ aryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVb, $R^{7a}$ is heteroaryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVb, $R^{7a}$ is 5-membered or 6-membered heteroaryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y and Z are each as defined herein.

In yet another embodiment, in Formula XVb, $R^{7a}$ is heterocyclyl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVb, $R^{7a}$ is 5-membered or 6-membered heterocyclyl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVb, $R^{7a}$ is phenyl, imidazolyl, pyrozolyl, pyridinyl, piperidinyl, or piperazinyl, each optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVb, $R^{7a}$ is phenyl, imidazolyl, pyrozolyl, pyridinyl, pyrimidinyl, pyrrolidinyl, piperidinyl, or piperazinyl, each optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVb, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In still another embodiment, in Formula XVb, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment, in Formula XVb, $R^1$ is hydrogen or —$OR^{1a}$, where $R^{1a}$ is $C_{1-6}$ alkyl, optionally substituted with one or more substituents Q;

$R^2$ is hydrogen;

$R^3$ and $R^4$ are hydrogen;

R[6] is C$_{6-14}$ alkyl, optionally substituted with one or more substituents Q;

R[5a] and R[5b] are each independently hydrogen or C$_{6-14}$ alkyl, optionally substituted with one or more substituents Q;

R[7a] is C$_{6-14}$ aryl, heteroaryl, or heterocyclyl, each of which is optionally substituted with one or more substituents Q;

R[7b], R[7c], R[7d], and R[7e] are hydrogen; and

X, Y, and Z are each independently N or CR$^X$, with the proviso that at least two of X, Y, and Z are N; where R$^X$ is a hydrogen or C$_{1-6}$ alkyl, optionally substituted with one or more substituents Q.

In another embodiment, in Formula XVb,

R[1] is hydrogen or methoxy;
R[2] is hydrogen;
R[3] and R[4] are hydrogen;
R[6] is C$_{6-14}$ alkyl, optionally substituted with one or more halo;
R[5a] and R[5b] are each independently hydrogen or C$_{6-14}$ alkyl;
R[7a] is C$_{6-14}$ aryl, heteroaryl, or heterocyclyl, each of which is optionally substituted with one or more substituents Q;
R[7b], R[7c], R[7d], and R[7e] are hydrogen; and
X, Y, and Z are each independently N or CH.

In yet another embodiment, in Formula XVb,
R[1] is hydrogen or methoxy;
R[2] is hydrogen;
R[3] and R[4] are hydrogen;
R[6] is difluoromethyl;
R[5a] and R[5b] are each independently hydrogen or C$_{6-14}$ alkyl;
R[7a] is C$_{6-14}$ aryl, monocyclic heteroaryl, or monocyclic heterocyclyl, each of which is optionally substituted with one or more substituents Q;
R[7b], R[7c], R[7d], and R[7e] are hydrogen; and
X, Y, and Z are each independently N or CH.

In yet another embodiment, in Formula XVb,
R[1] is hydrogen or methoxy;
R[2] is hydrogen;
R[3] and R[4] are hydrogen;
R[6] is difluoromethyl;
R[5a] and R[5b] are each independently hydrogen or C$_{6-14}$ alkyl;
R[7a] is phenyl, 5- or 6-membered heteroaryl, or 5- or 6-membered heterocyclyl, each of which is optionally substituted with one or more substituents Q;
R[7b], R[7c], R[7d], and R[7e] are hydrogen; and
X, Y, and Z are each independently N or CH.

In yet another embodiment, in Formula XVb,
R[1] is hydrogen or methoxy;
R[2] is hydrogen;
R[3] and R[4] are hydrogen;
R[6] is difluoromethyl;
R[5a] and R[5b] are each independently hydrogen or C$_{6-14}$ alkyl;
R[7a] is phenyl, imidazolyl, pyrozolyl, pyridinyl, pyrimidinyl, pyrrolidinyl, piperidinyl, or piperazinyl, each of which is optionally substituted with one or more substituents Q;
R[7b], R[7c], R[7d], and R[7e] are hydrogen; and
X, Y, and Z are each independently N or CH.

In still another embodiment, in Formula XVb,
R[1] is hydrogen or methoxy;
R[2] is hydrogen;
R[3] and R[4] are hydrogen;
R[6] is difluoromethyl;
R[5a] and R[5b] are each independently hydrogen or C$_{6-14}$ alkyl;
R[7a] is phenyl, imidazolyl, pyrozolyl, pyridinyl, piperidinyl, or piperazinyl, each of which is optionally substituted with one or more substituents Q;
R[7b], R[7c], R[7d], and R[7e] are hydrogen; and
X, Y, and Z are each independently N or CH.

In one embodiment, provided herein is a compound of Formula XV, XVa, or XVb as described herein, or an enantiomer, a mixture of enantiomers, a mixture of two or more diastereomers, or an isotopic variant thereof; or a pharmaceutically acceptable salt, solvate, hydrate, or prodrug thereof; wherein R[5a] and R[5b] are each independently (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R[1a], —C(O)OR[1a], —C(O)NR[1b]R[1c], —C(NR[1a])NR[1b]R[1c], —OR[1a], —OC(O)R[1a], —OC(O)OR[1a], —OC(O)NR[1b]R[1c], —OC(=NR[1a])NR[1b]R[1c], —OS(O)R[1a], —OS(O)$_2$R[1a], —OS(O)NR[1b]R[1c], —OS(O)$_2$NR[1b]R[1c], —NR[1b]R[1c], —NR[1a]C(O)R[1d], —NR[1a]C(O)OR[1d], —NR[1a]C(O)NR[1b]R[1c], —NR[1a]C(NR[1d])NR[1b]R[1c], —NR[1a]S(O)R[1d], —NR[1a]S(O)$_2$R[1d], —NR[1a]S(O)NR[1b]R[1c], —NR[1a]S(O)$_2$NR[1b]R[1c], —SR[1a], —S(O)R[1a], —S(O)$_2$R[1a], —S(O)NR[1b]R[1c], or —S(O)$_2$NR[1b]R[1c]; and R[1], R[2], R[3], R[4], R[6], R[7a], R[7b], R[7c], R[7d], R[7e], X, Y, Z, R[1a], R[1b], R[1c], and R[1d] are defined herein elsewhere.

In yet another embodiment, provided herein is a compound of Formula XVI:

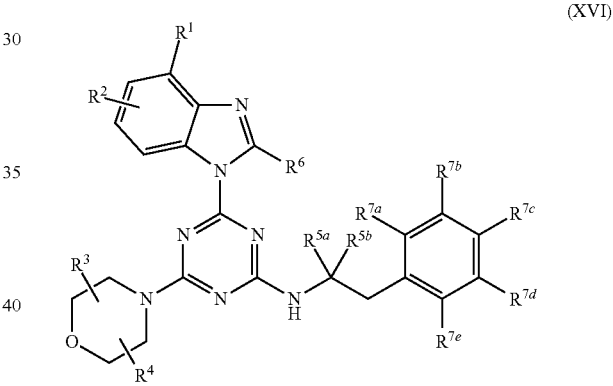

(XVI)

or an enantiomer, a mixture of enantiomers, a mixture of two or more diastereomers, or an isotopic variant thereof; or a pharmaceutically acceptable salt, solvate, hydrate, or prodrug thereof; wherein R[1], R[2], R[3], R[4], R[6], R[5a], R[5b], R[7a], R[7b], R[7c], R[7d], and R[7e] are each as defined herein.

In one embodiment, in Formula XVI, one of R[7a], R[7b], R[7c], R[7d], and R[7e] is C$_{6-14}$ aryl, heteroaryl, or heterocyclyl, each of which is optionally substituted with one or more substituents Q; and R[1], R[2], R[3], R[4], R[6], R[5a], the remaining of R[7a], R[7b], R[7c], R[7d], and R[7e], X, Y, and Z are each as defined herein.

In another embodiment, in Formula XVI, one of R[7a], R[7b], R[7c], R[7d], and R[7e] is C$_{6-14}$ aryl, which is optionally substituted with one or more substituents Q; and R[1], R[2], R[3], R[4], R[6], R[5a], R[5b], the remaining of R[7a], R[7b], R[7c], R[7d], and R[7e], X, Y, and Z are each as defined herein.

In yet another embodiment, in Formula XVI, one of R[7a], R[7b], R[7c], R[7d], and R[7e] is heteroaryl, which is optionally substituted with one or more substituents Q; and R[1], R[2], R[3], R[4], R[6], R[5a], R[5b], the remaining of R[7a], R[7b], R[7c], R[7d], and R[7e], X, Y, and Z are each as defined herein.

In yet another embodiment, in Formula XVI, one of R[7a], R[7b], R[7c], R[7d], and R[7e] is 5-membered or 6-membered heteroaryl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVI, one of $R^{7a}$, $R^{7b}$, $R^{7c}$, $R^{7d}$, and $R^{7e}$ is heterocyclyl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVI, one of $R^{7a}$, $R^{7b}$, $R^{7c}$, $R^{7d}$, and $R^{7e}$ is 5-membered or 6-membered heterocyclyl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVI, one of $R^{7a}$, $R^{7b}$, $R^{7c}$, $R^{7d}$, and $R^{7e}$ is phenyl, imidazolyl, pyrozolyl, pyridinyl, piperidinyl, or piperazinyl, each optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVI, one of $R^{7a}$, $R^{7b}$, $R^{7c}$, $R^{7d}$, and $R^{7e}$ is phenyl, imidazolyl, pyrozolyl, pyridinyl, pyrimidinyl, pyrrolidinyl, piperidinyl, or piperazinyl, each optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVI, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In still another embodiment, in Formula XVI, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment, in Formula XVI, $R^{7a}$ is $C_{6-14}$ aryl, heteroaryl, or heterocyclyl, each of which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In another embodiment, in Formula XVI, $R^{7a}$ is $C_{6-14}$ aryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVI, $R^{7a}$ is heteroaryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVI, $R^{7a}$ is 5-membered or 6-membered heteroaryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVI, $R^{7a}$ is heterocyclyl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVI, $R^{7a}$ is 5-membered or 6-membered heterocyclyl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVI, $R^{7a}$ is phenyl, imidazolyl, pyrozolyl, pyridinyl, piperidinyl, or piperazinyl, each optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVI, $R^{7a}$ is phenyl, imidazolyl, pyrozolyl, pyridinyl, pyrimidinyl, pyrrolidinyl, piperidinyl, or piperazinyl, each optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVI, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In still another embodiment, in Formula XVI, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment, in Formula XVI, $R^1$ is hydrogen or —$OR^{1a}$, where $R^{1a}$ is $C_{1-6}$ alkyl, optionally substituted with one or more substituents Q;

$R^2$ is hydrogen;

$R^3$ and $R^4$ are hydrogen;

$R^6$ is $C_{6-14}$ alkyl, optionally substituted with one or more substituents Q;

$R^{5a}$ and $R^{5b}$ are each independently $C_{6-14}$ alkyl, optionally substituted with one or more substituents Q;

$R^{7a}$ is $C_{6-14}$ aryl, heteroaryl, or heterocyclyl, each of which is optionally substituted with one or more substituents Q; and $R^{7b}$, $R^{7c}$, $R^{7d}$, and $R^{7e}$ are hydrogen.

In another embodiment, in Formula XVI, $R^1$ is hydrogen or methoxy;

$R^2$ is hydrogen;

$R^3$ and $R^4$ are hydrogen;

$R^6$ is $C_{6-14}$ alkyl, optionally substituted with one or more halo;

$R^{5a}$ and $R^{5b}$ are each independently $C_{6-14}$ alkyl;

$R^{7a}$ is $C_{6-14}$ aryl, heteroaryl, or heterocyclyl, each of which is optionally substituted with one or more substituents Q; and $R^{7b}$, $R^{7c}$, $R^{7d}$, and $R^{7e}$ are hydrogen.

In yet another embodiment, in Formula XVI,
R¹ is hydrogen or methoxy;
R² is hydrogen;
R³ and R⁴ are hydrogen;
R⁶ is difluoromethyl;
R⁵ᵃ and R⁵ᵇ are methyl;
R⁷ᵃ is C₆₋₁₄ aryl, monocyclic heteroaryl, or monocyclic heterocyclyl, each of which is optionally substituted with one or more substituents Q; and
R⁷ᵇ, R⁷ᶜ, R⁷ᵈ, and R⁷ᵉ are hydrogen.

In yet another embodiment, in Formula XVI,
R¹ is hydrogen or methoxy;
R² is hydrogen;
R³ and R⁴ are hydrogen;
R⁶ is difluoromethyl;
R⁵ᵃ and R⁵ᵇ are methyl;
R⁷ᵃ is phenyl, 5- or 6-membered heteroaryl, or 5- or 6-membered heterocyclyl, each of which is optionally substituted with one or more substituents Q; and
R⁷ᵇ, R⁷ᶜ, R⁷ᵈ, and R⁷ᵉ are hydrogen.

In yet another embodiment, in Formula XVI,
R¹ is hydrogen or methoxy;
R² is hydrogen;
R³ and R⁴ are hydrogen;
R⁶ is difluoromethyl;
R⁵ᵃ and R⁵ᵇ are methyl;
R⁷ᵃ is phenyl, imidazolyl, pyrozolyl, pyridinyl, pyrimidinyl, pyrrolidinyl, piperidinyl, or piperazinyl, each of which is optionally substituted with one or more substituents Q; and
R⁷ᵇ, R⁷ᶜ, R⁷ᵈ, and R⁷ᵉ are hydrogen.

In still another embodiment, in Formula XVI,
R¹ is hydrogen or methoxy;
R² is hydrogen;
R³ and R⁴ are hydrogen;
R⁶ is difluoromethyl;
R⁵ᵃ and R⁵ᵇ are methyl;
R⁷ᵃ is phenyl, imidazolyl, pyrozolyl, pyridinyl, piperidinyl, or piperazinyl, each of which is optionally substituted with one or more substituents Q; and
R⁷ᵇ, R⁷ᶜ, R⁷ᵈ, and R⁷ᵉ are hydrogen.

In one embodiment, the compound of Formula XVI has the structure of Formula XVIa:

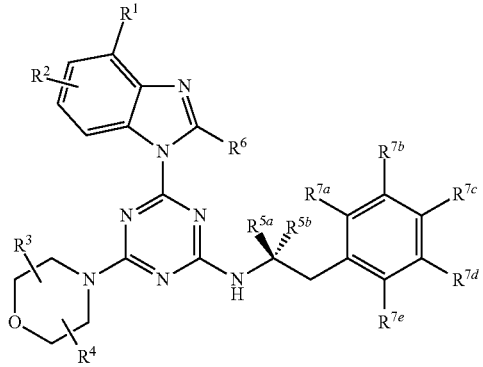

(XVIa)

or an isotopic variant thereof; or a pharmaceutically acceptable salt, solvate, hydrate, or prodrug thereof; wherein R¹, R², R³, R⁴, R⁶, R⁵ᵃ, R⁵ᵇ, R⁷ᵃ, R⁷ᵇ, R⁷ᶜ, R⁷ᵈ, and R⁷ᵉ are each as defined herein.

In one embodiment, in Formula XVIa, one of R⁷ᵃ, R⁷ᵇ, R⁷ᶜ, R⁷ᵈ, and R⁷ᵉ is C₆₋₁₄ aryl, heteroaryl, or heterocyclyl, each of which is optionally substituted with one or more substituents Q; and R¹, R², R³, R⁴, R⁶, R⁵ᵃ, R⁵ᵇ, the remaining of R⁷ᵃ, R⁷ᵇ, R⁷ᶜ, R⁷ᵈ, and R⁷ᵉ, X, Y, and Z are each as defined herein.

In another embodiment, in Formula XVIa, one of R⁷ᵃ, R⁷ᵇ, R⁷ᶜ, R⁷ᵈ, and R⁷ᵉ is C₆₋₁₄ aryl, which is optionally substituted with one or more substituents Q; and R¹, R², R³, R⁴, R⁶, R⁵ᵃ, R⁵ᵇ, the remaining of R⁷ᵃ, R⁷ᵇ, R⁷ᶜ, R⁷ᵈ, and R⁷ᵉ, X, Y, and Z are each as defined herein.

In yet another embodiment, in Formula XVIa, one of R⁷ᵃ, R⁷ᵇ, R⁷ᶜ, R⁷ᵈ, and R⁷ᵉ is heteroaryl, which is optionally substituted with one or more substituents Q; and R¹, R², R³, R⁴, R⁶, R⁵ᵃ, R⁵ᵇ, the remaining of R⁷ᵃ, R⁷ᵇ, R⁷ᶜ, R⁷ᵈ, and R⁷ᵉ, X, Y, and Z are each as defined herein.

In yet another embodiment, in Formula XVIa, one of R⁷ᵃ, R⁷ᵇ, R⁷ᶜ, R⁷ᵈ, and R⁷ᵉ is 5-membered or 6-membered heteroaryl, which is optionally substituted with one or more substituents Q; and R¹, R², R³, R⁴, R⁶, R⁵ᵃ, R⁵ᵇ, the remaining of R⁷ᵃ, R⁷ᵇ, R⁷ᶜ, R⁷ᵈ, and R⁷ᵉ, X, Y, and Z are each as defined herein.

In yet another embodiment, in Formula XVIa, one of R⁷ᵃ, R⁷ᵇ, R⁷ᶜ, R⁷ᵈ, and R⁷ᵉ is heterocyclyl, which is optionally substituted with one or more substituents Q; and R¹, R², R³, R⁴, R⁶, R⁵ᵃ, R⁵ᵇ, the remaining of R⁷ᵃ, R⁷ᵇ, R⁷ᶜ, R⁷ᵈ, and R⁷ᵉ, X, Y, and Z are each as defined herein.

In yet another embodiment, in Formula XVIa, one of R⁷ᵃ, R⁷ᵇ, R⁷ᶜ, R⁷ᵈ, and R⁷ᵉ is 5-membered or 6-membered heterocyclyl, which is optionally substituted with one or more substituents Q; and R¹, R², R³, R⁴, R⁶, R⁵ᵃ, R⁵ᵇ, the remaining of R⁷ᵃ, R⁷ᵇ, R⁷ᶜ, R⁷ᵈ, and R⁷ᵉ, X, Y, and Z are each as defined herein.

In yet another embodiment, in Formula XVIa, one of R⁷ᵃ, R⁷ᵇ, R⁷ᶜ, R⁷ᵈ, and R⁷ᵉ is phenyl, imidazolyl, pyrozolyl, pyridinyl, piperidinyl, or piperazinyl, each optionally substituted with one or more substituents Q; and R¹, R², R³, R⁴, R⁶, R⁵ᵃ, R⁵ᵇ, the remaining of R⁷ᵃ, R⁷ᵇ, R⁷ᶜ, R⁷ᵈ, and R⁷ᵉ, X, Y, and Z are each as defined herein.

In yet another embodiment, in Formula XVIa, one of R⁷ᵃ, R⁷ᵇ, R⁷ᶜ, R⁷ᵈ, and R⁷ᵉ is phenyl, imidazolyl, pyrozolyl, pyridinyl, pyrimidinyl, pyrrolidinyl, piperidinyl, or piperazinyl, each optionally substituted with one or more substituents Q; and R¹, R², R³, R⁴, R⁶, R⁵ᵃ, R⁵ᵇ, the remaining of R⁷ᵃ, R⁷ᵇ, R⁷ᶜ, R⁷ᵈ, and R⁷ᵉ, X, Y, and Z are each as defined herein.

In yet another embodiment, in Formula XVIa, one of R⁷ᵃ, R⁷ᵇ, R⁷ᶜ, R⁷ᵈ, and R⁷ᵉ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In still another embodiment, in Formula XVIa, one of R⁷ᵃ, R⁷ᵇ, R⁷ᶜ, R⁷ᵈ, and R⁷ᵉ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment, in Formula XVIa, $R^{7a}$ is $C_{6-14}$ aryl, heteroaryl, or heterocyclyl, each of which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In another embodiment, in Formula XVIa, $R^{7a}$ is $C_{6-14}$ aryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVIa, $R^{7a}$ is heteroaryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVIa, $R^{7a}$ is 5-membered or 6-membered heteroaryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVIa, $R^{7a}$ is heterocyclyl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVIa, $R^{7a}$ is 5-membered or 6-membered heterocyclyl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVIa, $R^{7a}$ is phenyl, imidazolyl, pyrozolyl, pyridinyl, piperidinyl, or piperazinyl, each optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVIa, $R^{7a}$ is phenyl, imidazolyl, pyrozolyl, pyridinyl, pyrimidinyl, pyrrolidinyl, piperidinyl, or piperazinyl, each optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVIa, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In still another embodiment, in Formula XVIa, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment, in Formula XVIa,
$R^1$ is hydrogen or —$OR^{1a}$, where $R^{1a}$ is $C_{1-6}$ alkyl, optionally substituted with one or more substituents Q;
$R^2$ is hydrogen;
$R^3$ and $R^4$ are hydrogen;
$R^6$ is $C_{6-14}$ alkyl, optionally substituted with one or more substituents Q;
$R^{5a}$ and $R^{5b}$ are each independently hydrogen or $C_{6-14}$ alkyl, optionally substituted with one or more substituents Q;
$R^{7a}$ is $C_{6-14}$ aryl, heteroaryl, or heterocyclyl, each of which is optionally substituted with one or more substituents Q; and
$R^{7b}$, $R^{7c}$, $R^{7d}$, and $R^{7e}$ are hydrogen.

In another embodiment, in Formula XVIa,
$R^1$ is hydrogen or methoxy;
$R^2$ is hydrogen;
$R^3$ and $R^4$ are hydrogen;
$R^6$ is $C_{6-14}$ alkyl, optionally substituted with one or more halo;
$R^{5a}$ and $R^{5b}$ are each independently hydrogen or $C_{6-14}$ alkyl;
$R^{7a}$ is $C_{6-14}$ aryl, heteroaryl, or heterocyclyl, each of which is optionally substituted with one or more substituents Q; and
$R^{7b}$, $R^{7c}$, $R^{7d}$, and $R^{7e}$ are hydrogen.

In yet another embodiment, in Formula XVIa,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{6-14}$ alkyl;
$R^{7a}$ is $C_{6-14}$ aryl, monocyclic heteroaryl, or monocyclic heterocyclyl, each of which is optionally substituted with one or more substituents Q; and
$R^{7b}$, $R^{7c}$, $R^{7d}$, and $R^{7e}$ are hydrogen.

In yet another embodiment, in Formula XVIa,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{6-14}$ alkyl;
$R^{7a}$ is phenyl, 5- or 6-membered heteroaryl, or 5- or 6-membered heterocyclyl, each of which is optionally substituted with one or more substituents Q; and
$R^{7b}$, $R^{7c}$, $R^{7d}$, and $R^{7e}$ are hydrogen.

In yet another embodiment, in Formula XVIa,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{6-14}$ alkyl;
$R^{7a}$ is phenyl, imidazolyl, pyrozolyl, pyridinyl, pyrrolidinyl, piperidinyl, piperidinyl, or piperazinyl, each of which is optionally substituted with one or more substituents Q; and
$R^{7b}$, $R^{7c}$, $R^{7d}$, and $R^{7e}$ are hydrogen.

In still another embodiment, in Formula XVIa,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{6-14}$ alkyl;
$R^{7a}$ is phenyl, imidazolyl, pyrozolyl, pyridinyl, piperidinyl, or piperazinyl, each of which is optionally substituted with one or more substituents Q; and
$R^{7b}$, $R^{7c}$, $R^{7d}$, and $R^{7e}$ are hydrogen.

In another embodiment, the compound of Formula XVI has the structure of Formula XVIb:

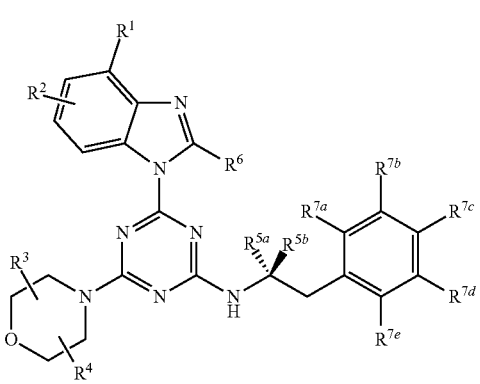

(XVIb)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{7a}$, $R^{7b}$, $R^{7c}$, $R^{7d}$, and $R^{7e}$ are each as defined herein.

In one embodiment, in Formula XVIb, one of $R^{7a}$, $R^{7b}$, $R^{7c}$, $R^{7d}$, and $R^{7e}$ is $C_{6-14}$ aryl, heteroaryl, or heterocyclyl, each of which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In another embodiment, in Formula XVIb, one of $R^{7a}$, $R^{7b}$, $R^{7c}$, $R^{7d}$, and $R^{7e}$ is $C_{6-14}$ aryl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVIb, one of $R^{7a}$, $R^{7b}$, $R^{7c}$, $R^{7d}$, and $R^{7e}$ is heteroaryl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVIb, one of $R^{7a}$, $R^{7b}$, $R^{7c}$, $R^{7d}$, and $R^{7e}$ is 5-membered or 6-membered heteroaryl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVIb, one of $R^{7a}$, $R^{7b}$, $R^{7c}$, $R^{7d}$, and $R^{7e}$ is heterocyclyl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVIb, one of $R^{7a}$, $R^{7b}$, $R^{7c}$, $R^{7d}$, and $R^{7e}$ is 5-membered or 6-membered heterocyclyl, which is optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVIb, one of $R^{7a}$, $R^{7b}$, $R^{7c}$, $R^{7d}$, and $R^{7e}$ is phenyl, imidazolyl, pyrozolyl, pyridinyl, piperidinyl, or piperazinyl, each optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVIb, one of $R^{7a}$, $R^{7b}$, $R^{7c}$, $R^{7d}$, and $R^{7e}$ is phenyl, imidazolyl, pyrozolyl, pyridinyl, pyrimidinyl, pyrrolidinyl, piperidinyl, or piperazinyl, each optionally substituted with one or more substituents Q; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment, in Formula XVIb, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In still another embodiment, in Formula XVIb, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment, in Formula XVIb, $R^{7a}$ is $C_{6-14}$ aryl, heteroaryl, or heterocyclyl, each of which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In another embodiment, in Formula XVIb, $R^{7a}$ is $C_{6-14}$ aryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVIb, $R^{7a}$ is heteroaryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVIb, $R^{7a}$ is 5-membered or 6-membered heteroaryl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVIb, $R^{7a}$ is heterocyclyl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVIb, $R^{7a}$ is 5-membered or 6-membered heterocyclyl, which is optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVIb, $R^{7a}$ is phenyl, imidazolyl, pyrozolyl, pyridinyl, piperidinyl, or piperazinyl, each optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVIb, $R^{7a}$ is phenyl, imidazolyl, pyrozolyl, pyridinyl, pyrimidinyl, pyrrolidinyl, piperidinyl, or piperazinyl, each optionally substituted with one or more substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment, in Formula XVIb, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In still another embodiment, in Formula XVIb, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment, in Formula XVIb,
$R^1$ is hydrogen or —$OR^{1a}$, where $R^{1a}$ is $C_{1-6}$ alkyl, optionally substituted with one or more substituents Q;
$R^2$ is hydrogen;
$R^3$ and $R^4$ are hydrogen;
$R^6$ is $C_{6-14}$ alkyl, optionally substituted with one or more substituents Q;
$R^{5a}$ and $R^{5b}$ are each independently hydrogen or $C_{6-14}$ alkyl, optionally substituted with one or more substituents Q;
$R^{7a}$ is $C_{6-14}$ aryl, heteroaryl, or heterocyclyl, each of which is optionally substituted with one or more substituents Q; and
$R^{7b}$, $R^{7c}$, $R^{7d}$, and $R^{7e}$ are hydrogen.

In another embodiment, in Formula XVIb,
$R^1$ is hydrogen or methoxy;
$R^2$ is hydrogen;
$R^3$ and $R^4$ are hydrogen;
$R^6$ is $C_{6-14}$ alkyl, optionally substituted with one or more halo;
$R^{5a}$ and $R^{5b}$ are each independently hydrogen or $C_{6-14}$ alkyl;
$R^{7a}$ is $C_{6-14}$ aryl, heteroaryl, or heterocyclyl, each of which is optionally substituted with one or more substituents Q; and
$R^{7b}$, $R^{7c}$, $R^{7d}$, and $R^{7e}$ are hydrogen.

In yet another embodiment, in Formula XVIb,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{6-14}$ alkyl;
$R^{7a}$ is $C_{6-14}$ aryl, monocyclic heteroaryl, or monocyclic heterocyclyl, each of which is optionally substituted with one or more substituents Q; and
$R^{7b}$, $R^{7c}$, $R^{7d}$, and $R^{7e}$ are hydrogen.

In yet another embodiment, in Formula XVIb,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{6-14}$ alkyl;
$R^{7a}$ is phenyl, 5- or 6-membered heteroaryl, or 5- or 6-membered heterocyclyl, each of which is optionally substituted with one or more substituents Q; and
$R^{7b}$, $R^{7c}$, $R^{7d}$, and $R^{7e}$ are hydrogen.

In yet another embodiment, in Formula XVIb, $R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{6-14}$ alkyl;
$R^{7a}$ is phenyl, imidazolyl, pyrozolyl, pyridinyl, pyrimidinyl, pyrrolidinyl, piperidinyl, or piperazinyl, each of which is optionally substituted with one or more substituents Q; and
$R^{7b}$, $R^{7c}$, $R^{7d}$, and $R^{7e}$ are hydrogen.

In still another embodiment, in Formula XVIb,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{6-14}$ alkyl;
$R^{7a}$ is phenyl, imidazolyl, pyrozolyl, pyridinyl, piperidinyl, or piperazinyl, each of which is optionally substituted with one or more substituents Q; and
$R^{7b}$, $R^{7c}$, $R^{7d}$, and $R^{7e}$ are hydrogen.

In one embodiment, provided herein is a compound of Formula XVI, XVIa, or XVIb as described herein, or an enantiomer, a mixture of enantiomers, a mixture of two or more diastereomers, or an isotopic variant thereof; or a pharmaceutically acceptable salt, solvate, hydrate, or prodrug thereof; wherein $R^{5a}$ and $R^{5b}$ are each independently (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}S(O)OR^{1d}$, —$NR^{1a}C(O)NR^{1b}R^{1c}$, —$NR^{1a}C(=NR^1)NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2NR^1$, —$S(O)NR^{1b}R^{1c}$, or —$S(O)_2NR^{1b}R^{1c}$; and $R^1$, $R^2$, $R^3$, $R^4$, $R^6$, $R^{7a}$, $R^{7b}$, $R^{7c}$, $R^{7d}$, $R^{7e}$, $R^{1a}$, $R^{1b}$, $R^{1c}$, and $R^{1d}$ are defined herein elsewhere.

In one embodiment, in any of the formulae provided herein,
$R^1$ is hydrogen or —$OR^{1a}$, where $R^{1a}$ is $C_{1-6}$ alkyl, optionally substituted with one or more substituents Q;
$R^2$ is hydrogen;
$R^3$ and $R^4$ are hydrogen;
$R^6$ is $C_{6-14}$ alkyl, optionally substituted with one or more substituents Q;
$R^{5a}$ and $R^{5b}$ are each independently hydrogen or $C_{6-14}$ alkyl optionally substituted with one or more substituents Q;
$R^{7a}$ is $C_{6-14}$ aryl, heteroaryl, or heterocyclyl, each of which is optionally substituted with one or more substituents Q;
$R^{7b}$, $R^{7c}$, $R^{7d}$, and $R^{7e}$ are hydrogen; and
X, Y, and Z are each independently N or $CR^X$, with the proviso that at least two of X, Y, and Z are N; where $R^X$ is a hydrogen or $C_{1-6}$ alkyl, optionally substituted with one or more substituents Q.

In another embodiment, in any of the formulae provided herein,
$R^1$ is hydrogen or methoxy;
$R^2$ is hydrogen;

$R^3$ and $R^4$ are hydrogen;
$R^6$ is $C_{6-14}$ alkyl, optionally substituted with one or more halo;
$R^{5a}$ and $R^{5b}$ are each independently hydrogen or $C_{6-14}$ alkyl;
$R^{7a}$ is $C_{6-14}$ aryl, heteroaryl, or heterocyclyl, each of which is optionally substituted with one or more substituents Q;
$R^{7b}$, $R^{7c}$, $R^{7d}$, and $R^{7e}$ are hydrogen; and
X, Y, and Z are each independently N or CH.

In yet another embodiment, in any of the formulae provided herein,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{6-14}$ alkyl;
$R^{7a}$ is $C_{6-14}$ aryl, monocyclic heteroaryl, or monocyclic heterocyclyl, each of which is optionally substituted with one or more substituents Q;
$R^{7b}$, $R^{7c}$, $R^{7d}$, and $R^{7e}$ are hydrogen; and
X, Y, and Z are each independently N or CH.

In yet another embodiment, in any of the formulae provided herein,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{6-14}$ alkyl;
$R^{7a}$ is phenyl, 5- or 6-membered heteroaryl, or 5- or 6-membered heterocyclyl, each of which is optionally substituted with one or more substituents Q;
$R^{7b}$, $R^{7c}$, $R^{7d}$, and $R^{7e}$ are hydrogen; and
X, Y, and Z are each independently N or CH.

In yet another embodiment, in any of the formulae provided herein,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{6-14}$ alkyl;
$R^{7a}$ is phenyl, imidazolyl, pyrozolyl, pyridinyl, pyrimidinyl, pyrrolidinyl, piperidinyl, or piperazinyl, each of which is optionally substituted with one or more substituents Q;
$R^{7b}$, $R^{7c}$, $R^{7d}$, and $R^{7e}$ are hydrogen; and
X, Y, and Z are each independently N or CH.

In still another embodiment, in any of the formulae provided herein,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{6-14}$ alkyl;
$R^{7a}$ is phenyl, imidazolyl, pyrozolyl, pyridinyl, piperidinyl, or piperazinyl, each of which is optionally substituted with one or more substituents Q;
$R^{7b}$, $R^{7c}$, $R^{7d}$, and $R^{7e}$ are hydrogen; and
X, Y, and Z are each independently N or CH.

The groups or variables, $R^1$, $R^2$, $R^3$, $R^4$, $R^6$, $R^{5a}$, $R^{5b}$, $R^{5c}$, $R^{5d}$, $R^{5e}$, $R^{5f}$, $R^{5g}$, $R^{7a}$, $R^{7b}$, $R^{7c}$, $R^{7d}$, $R^{7e}$, m, n, X, Y, and Z in Formulae provided herein, e.g., Formulae I to XVI, Ia to XVIa, and Ib to XVIb are further defined in the embodiments described herein. All combinations of the embodiments provided herein for such groups and/or variables are within the scope of this disclosure.

In certain embodiments, $R^1$ is hydrogen. In certain embodiments, $R^1$ is cyano. In certain embodiments, $R^1$ is halo. In certain embodiments, $R^1$ is fluoro, chloro, bromo, or iodo. In certain embodiments, $R^1$ is nitro. In certain embodiments, $R^1$ is $C_{1-6}$ alkyl, optionally substituted with one or more substituents Q as described herein. In certain embodiments, $R^1$ is $C_{2-6}$ alkenyl, optionally substituted with one or more substituents Q as described herein. In certain embodiments, $R^1$ is $C_{2-6}$ alkynyl, optionally substituted with one or more substituents Q as described herein. In certain embodiments, $R^1$ is $C_{3-10}$ cycloalkyl, optionally substituted with one or more substituents Q as described herein. In certain embodiments, $R^1$ is $C_{6-14}$ aryl, optionally substituted with one or more substituents Q as described herein. In certain embodiments, $R^1$ is $C_{7-15}$ aralkyl, optionally substituted with one or more substituents Q as described herein. In certain embodiments, $R^1$ is heteroaryl, optionally substituted with one or more substituents Q as described herein. In certain embodiments, $R^1$ is heterocyclyl, optionally substituted with one or more substituents Q as described herein.

In certain embodiments, $R^1$ is —C(O)$R^{1a}$, wherein $R^{1a}$ is as defined herein. In certain embodiments, $R^1$ is —C(O)OR$^{1a}$, wherein $R^{1a}$ is as defined herein. In certain embodiments, $R^1$ is —C(O)NR$^{1b}$R$^{1c}$, wherein $R^{1b}$ and $R^{1c}$ are each as defined herein. In certain embodiments, $R^1$ is —C(NR$^{1a}$)NR$^{1b}$R$^{1c}$, wherein $R^{1a}$, $R^{1b}$ and $R^{1c}$ are each as defined herein. In certain embodiments, $R^1$ is —OR$^{1a}$, wherein $R^{1a}$ is as defined herein. In certain embodiments, $R^1$ is —O—$C_{1-6}$ alkyl, wherein the alkyl is optionally substituted with one or more substituents Q as described herein. In certain embodiments, $R^1$ is methoxy, ethoxy, propoxy, isopropoxy, or 3-dimethylaminopropoxy. In certain embodiments, $R^1$ is —OC(O)R$^{1a}$, wherein $R^{1a}$ is as defined herein. In certain embodiments, $R^1$ is —OC(O)OR$^{1a}$, wherein $R^{1a}$ is as defined herein. In certain embodiments, $R^1$ is —OC(O)NR$^{1b}$R$^{1c}$, wherein $R^{1b}$ and $R^{1c}$ are each as defined herein. In certain embodiments, $R^1$ is —OC(=NR$^{1a}$)NR$^{1b}$R$^{1c}$ wherein $R^{1a}$, $R^{1b}$, and $R^{1c}$ are each as defined herein. In certain embodiments, $R^1$ is —OS(O)R$^{1a}$, wherein $R^{1a}$ is as defined herein. In certain embodiments, $R^1$ is —OS(O)$_2$R$^{1a}$, wherein $R^{1a}$ is as defined herein. In certain embodiments, $R^1$ is —OS(O)NR$^{1b}$R$^{1c}$, wherein $R^{1b}$ and $R^{1c}$ are each as defined herein. In certain embodiments, $R^1$ is —OS(O)$_2$NR$^{1b}$R$^{1c}$, wherein $R^{1b}$ and $R^{1c}$ are each as defined herein. In certain embodiments, $R^1$ is —NR$^{1b}$R$^{1c}$, wherein $R^{1b}$ and $R^{1c}$ are each as defined herein. In certain embodiments, $R^1$ is —NR$^{1a}$C(O)R$^{1d}$, wherein $R^{1a}$ and $R^{1d}$ are each as defined herein. In certain embodiments, $R^1$ is —NR$^{1a}$C(O)OR$^{1d}$, wherein $R^{1a}$ and $R^{1d}$ are each as defined herein. In certain embodiments, $R^1$ is —NR$^{1a}$C(O)NR$^{1b}$R$^{1c}$, wherein $R^{1a}$, $R^{1b}$, and $R^{1c}$ are each as defined herein. In certain embodiments, $R^1$ is —NR$^{1a}$C(NR$^{1d}$)NR$^{1b}$R$^{1c}$, wherein $R^{1a}$, $R^{1b}$, $R^{1c}$, and $R^{1d}$ are each as defined herein. In certain embodiments, $R^1$ is —NR$^{1a}$S(O)R$^{1d}$, wherein $R^{1a}$ and $R^{1d}$ are each as defined herein. In certain embodiments, $R^1$ is —NR$^{1a}$S(O)$_2$R$^{1d}$, wherein $R^{1a}$ and $R^{1d}$ are each as defined herein. In certain embodiments, $R^1$ is —NR$^{1a}$S(O)NR$^{1b}$R$^{1c}$, wherein $R^{1a}$, $R^{1b}$, and $R^{1c}$ are each as defined herein. In certain embodiments, $R^1$ is —NR$^{1a}$S(O)$_2$NR$^{1b}$R$^{1c}$, wherein $R^{1a}$, $R^{1b}$, and $R^{1c}$ are each as defined herein. In certain embodiments, $R^1$ is —SR$^{1a}$, wherein $R^{1a}$ is as defined herein. In certain embodiments, $R^1$ is —S(O)R$^{1a}$, wherein $R^{1a}$ is as defined herein. In certain embodiments, $R^1$ is —S(O)$_2$R$^{1a}$, wherein $R^{1a}$ is as defined herein. In certain embodiments, $R^1$ is —S(O)NR$^{1b}$R$^{1c}$, wherein $R^{1b}$ and $R^{1c}$ are each as defined herein. In certain embodiments, $R^1$ is —$S(O)_2NR^{1b}R^{1c}$; wherein $R^{1b}$ and $R^{1c}$ are each as defined herein.

In certain embodiments, $R^2$ is hydrogen. In certain embodiments, $R^2$ is cyano. In certain embodiments, $R^2$ is halo. In certain embodiments, $R^2$ is fluoro, chloro, bromo, or iodo. In certain embodiments, $R^2$ is nitro. In certain embodiments, $R^2$ is $C_{1-6}$ alkyl, optionally substituted with one or more substituents Q as described herein. In certain embodiments, $R^2$ is $C_{2-6}$ alkenyl, optionally substituted with one or more substituents Q as described herein. In certain embodiments, $R^2$ is $C_{2-6}$ alkynyl, optionally substituted with one or more substituents Q as described herein. In certain embodiments, $R^2$ is $C_{3-10}$ cycloalkyl, optionally substituted with one or more substituents Q as described herein. In certain embodiments, $R^2$ is $C_{3-7}$ cycloalkyl, optionally substituted with one or more substituents Q as described herein. In certain embodiments, $R^2$ is $C_{6-14}$ aryl, optionally substituted with one or more substituents Q as described herein. In certain embodiments, $R^2$ is $C_{7-15}$ aralkyl, optionally substituted with one or more substituents Q as described herein. In certain embodiments, $R^2$ is heteroaryl, optionally substituted with one or more substituents Q as described herein. In certain embodiments, $R^2$ is heterocyclyl, optionally substituted with one or more substituents Q as described herein.

In certain embodiments, $R^2$ is —$C(O)R^{1a}$, wherein $R^{1a}$ is as defined herein. In certain embodiments, $R^2$ is —$C(O)OR^{1a}$, wherein $R^{1a}$ is as defined herein. In certain embodiments, $R^2$ is —$C(O)NR^{1b}R^{1c}$, wherein $R^{1b}$ and $R^{1c}$ are each as defined herein. In certain embodiments, $R^2$ is —$C(NR^{1a})NR^{1b}R^{1c}$, wherein $R^{1a}$, $R^{1b}$, and $R^{1c}$ are each as defined herein. In certain embodiments, $R^2$ is —$OR^{1a}$, wherein $R^{1a}$ is as defined herein. In certain embodiments, $R^1$ is —O—$C_{1-6}$ alkyl, wherein the alkyl is optionally substituted with one or more substituents Q as described herein. In certain embodiments, $R^1$ is methoxy, ethoxy, propoxy, isopropoxy, or 3-dimethylaminopropoxy. In certain embodiments, $R^2$ is —$OC(O)R^{1a}$, wherein $R^{1a}$ is as defined herein. In certain embodiments, $R^2$ is —$OC(O)OR^{1a}$, wherein $R^{1a}$ is as defined herein. In certain embodiments, $R^2$ is —$OC(O)NR^{1b}R^{1c}$ wherein $R^{1b}$ and $R^{1c}$ are each as defined herein. In certain embodiments, $R^2$ is —$OC(=NR^{1a})NR^{1b}R^{1c}$, wherein $R^{1a}$, $R^{1b}$, and $R^{1c}$ are each as defined herein. In certain embodiments, $R^2$ is —$OS(O)R^{1a}$, wherein $R^{1a}$ is as defined herein. In certain embodiments, $R^2$ is —$OS(O)_2R^{1a}$, wherein $R^{1a}$ is as defined herein. In certain embodiments, $R^2$ is —$OS(O)NR^{1b}R^{1c}$, wherein $R^{1b}$ and $R^{1c}$ are each as defined herein. In certain embodiments, $R^2$ is —$OS(O)_2NR^{1b}R^{1c}$, wherein $R^{1b}$ and $R^{1c}$ are each as defined herein. In certain embodiments, $R^2$ is —$NR^{1b}R^{1c}$ wherein $R^{1b}$ and $R^{1c}$ are each as defined herein. In certain embodiments, $R^2$ is amino (—$NH_2$). In certain embodiments, $R^2$ is —$NR^{1a}C(O)R^{1d}$, wherein $R^{1a}$ and $R^{1d}$ are each as defined herein. In certain embodiments, $R^2$ is —$NR^{1a}C(O)OR^{1d}$, wherein $R^{1a}$ and $R^{1d}$ are each as defined herein. In certain embodiments, $R^2$ is —$NR^{1a}C(O)NR^{1b}R^{1c}$, wherein $R^{1a}$, $R^{1b}$, and $R^{1c}$ are each as defined herein. In certain embodiments, $R^2$ is —$NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^2$ is —$NR^{1a}S(O)R^{1d}$, wherein $R^{1a}$ and $R^{1d}$ are each as defined herein. In certain embodiments, $R^2$ is —$NR^{1a}S(O)_2R^{1d}$, wherein $R^{1a}$ and $R^{1d}$ are each as defined herein. In certain embodiments, $R^2$ is —$NR^{1a}S(O)NR^{1b}R^{1c}$, wherein $R^{1a}$, $R^{1b}$, and $R^{1c}$ are each as defined herein. In certain embodiments, $R^2$ is —$NR^{1a}S(O)_2NR^{1b}R^{1c}$, wherein $R^{1a}$, $R^{1b}$, and $R^{1c}$ are each as defined herein. In certain embodiments, $R^2$ is —$SR^{1a}$, wherein $R^{1a}$ is as defined herein. In certain embodiments, $R^2$ is —$S(O)R^{1a}$, wherein $R^{1a}$ is as defined herein. In certain embodiments, $R^2$ is —$S(O)_2R^{1a}$, wherein $R^{1a}$ is as defined herein. In certain embodiments, $R^2$ is —$S(O)NR^{1b}R^{1c}$, wherein $R^{1b}$ and $R^{1c}$ are each as defined herein. In certain embodiments, $R^2$ is —$S(O)_2NR^{1b}R^{1c}$; wherein $R^{1b}$ and $R^{1c}$ are each as defined herein.

In certain embodiments, $R^3$ is hydrogen. In certain embodiments, $R^3$ is $C_{1-6}$ alkyl, optionally substituted with one or more substituents Q as described herein. In certain embodiments, $R^3$ is hydrogen, methyl, ethyl, or propyl (e.g., n-propyl, isopropyl, or 2-isopropyl).

In certain embodiments, $R^4$ is hydrogen. In certain embodiments, $R^4$ is $C_{1-6}$ alkyl, optionally substituted with one or more substituents Q as described herein. In certain embodiments, $R^4$ is hydrogen, methyl, ethyl, or propyl (e.g., n-propyl, isopropyl, or 2-isopropyl).

In certain embodiments, $R^3$ and $R^4$ are linked together to form a bond. In certain embodiments, $R^3$ and $R^4$ are linked together to form $C_{1-6}$ alkylene, optionally substituted with one or more substituents Q as described herein. In certain embodiments, $R^3$ and $R^4$ are linked together to form methylene, ethylene, or propylene, each optionally substituted with one or more substituents Q as described herein. In certain embodiments, $R^3$ and $R^4$ are linked together to form $C_{1-6}$ heteroalkylene, optionally substituted with one or more substituents Q as described herein. In certain embodiments, $R^3$ and $R^4$ are linked together to form $C_{2-6}$ alkenylene, optionally substituted with one or more substituents Q as described herein. In certain embodiments, $R^3$ and $R^4$ are linked together to form $C_{2-6}$ heteroalkenylene, optionally substituted with one or more substituents Q as described herein.

In certain embodiments, $R^6$ is hydrogen. In certain embodiments, $R^6$ is $C_{1-6}$ alkyl, optionally substituted with one or more substituents Q as described herein. In certain embodiments, $R^6$ is $C_{1-6}$ alkyl, optionally substituted with one or more, in one embodiment, one, two, or three, halo. In certain embodiments, $R^6$ is $C_{1-6}$ alkyl, optionally substituted with one or more, in one embodiment, one, two, or three, fluoro. In certain embodiments, $R^6$ is methyl, fluoromethyl, difluoromethyl, or trifluoromethyl. In certain embodiments, $R^6$ is difluoromethyl. In certain embodiments, $R^6$ is —S—$C_{1-6}$ alkyl, wherein the alkyl is optionally substituted with one or more substituents Q as described herein. In certain embodiments, $R^6$ is —$S(O)$—$C_{1-6}$ alkyl, wherein the alkyl is optionally substituted with one or more substituents Q as described herein. In certain embodiments, $R^6$ is —$SO_2$—$C_{1-6}$ alkyl, wherein the alkyl is optionally substituted with one or more substituents Q as described herein.

In certain embodiments, $R^{5a}$ is hydrogen. In certain embodiments, $R^{5a}$ is not hydrogen. In certain embodiments, $R^{5a}$ is halo. In certain embodiments, $R^{5a}$ is fluoro, chloro, bromo, or iodo. In certain embodiments, $R^{5a}$ is $C_{1-6}$ alkyl, optionally substituted with one or more substituents Q as described herein. In certain embodiments, $R^{5a}$ is methyl, ethyl, propyl, or butyl, each optionally substituted with one or more substituents Q as described herein. In certain embodiments, $R^{5a}$ is methyl, ethyl, n-propyl, isopropyl, n-butyl, isobutyl, or t-butyl. In certain embodiments, $R^{5a}$ is methyl. In certain embodiments, $R^{5a}$ is $C_{2-6}$ alkenyl, optionally substituted with one or more substituents Q as described herein. In certain embodiments, $R^{5a}$ is $C_{2-6}$ alkynyl, optionally substituted with one or more substituents Q as described herein. In certain embodiments, $R^{5a}$ is $C_{3-10}$ cycloalkyl, optionally substituted with one or more substituents Q as described herein. In certain embodiments, $R^{5a}$ is $C_{3-7}$ cycloalkyl, optionally substituted with one or more substituents Q as described herein. In certain embodiments, $R^{5a}$ is $C_{6-14}$ aryl, optionally substituted with one or more substituents Q as described herein. In certain embodiments, $R^{5a}$ is $C_{7-15}$ aralkyl, optionally substituted with one or more substituents Q as described herein. In certain embodiments, $R^{5a}$ is heteroaryl, optionally substituted with one or more substituents Q as described herein. In certain embodiments, $R^{5a}$ is heterocyclyl, optionally substituted with one or more substituents Q as described herein.

In certain embodiments, $R^{5a}$ is —C(O)$R^{1a}$, wherein $R^{1a}$ is as defined herein. In certain embodiments, $R^{5a}$ is —C(O)O$R^{1a}$, wherein $R^{1a}$ is as defined herein. In certain embodiments, $R^{5a}$ is —C(O)O$R^{1a}$, wherein $R^{1a}$ is $C_{1-6}$ alkyl, optionally substituted with one or more substituents Q as described herein. In certain embodiments, $R^{5a}$ is —C(O)OCH$_3$. In certain embodiments, $R^{5a}$ is —C(O)N$R^{1b}R^{1c}$, wherein $R^{1b}$ and $R^{1c}$ are each as defined herein. In certain embodiments, $R^{5a}$ is —C(N$R^{1a}$)N$R^{1b}R^{1c}$, wherein $R^{1a}$, $R^{1b}$, and $R^{1c}$ are each as defined herein. In certain embodiments, $R^{5a}$ is —O$R^{1a}$, wherein $R^{1a}$ is as defined herein. In certain embodiments, $R^{5a}$ is —OC(O)$R^{1a}$, wherein $R^{1a}$ is as defined herein. In certain embodiments, $R^{5a}$ is —OC(O)O$R^{1a}$, wherein $R^{1a}$ is as defined herein. In certain embodiments, $R^{5a}$ is —OC(O)N$R^{1b}R^{1c}$, wherein $R^{1b}$ and $R^{1c}$ are each as defined herein. In certain embodiments, $R^{5a}$ is —OC(=N$R^{1a}$)N$R^{1b}R^{1c}$, wherein $R^{1a}$, $R^{1b}$, and $R^{1c}$ are each as defined herein. In certain embodiments, $R^{5a}$ is —OS(O)$R^{1a}$, wherein $R^{1a}$ is as defined herein. In certain embodiments, $R^{5a}$ is —OS(O)$_2R^{1a}$, wherein $R^{1a}$ is as defined herein. In certain embodiments, $R^{5a}$ is —OS(O)N$R^{1b}R^{1c}$, wherein $R^{1b}$ and $R^{1c}$ are each as defined herein. In certain embodiments, $R^{5a}$ is —OS(O)$_2$N$R^{1b}R^{1c}$, wherein $R^{1b}$ and $R^{1c}$ are each as defined herein. In certain embodiments, $R^{5a}$ is —N$R^{1b}R^{1c}$, wherein $R^{1b}$ and $R^{1c}$ are each as defined herein. In certain embodiments, $R^{5a}$ is amino (—NH$_2$). In certain embodiments, $R^{5a}$ is —N$R^{1a}$C(O)$R^{1d}$, wherein $R^{1a}$ and $R^{1d}$ are each as defined herein. In certain embodiments, $R^{5a}$ is —N$R^{1a}$C(O)O$R^{1d}$, wherein $R^{1a}$ and $R^{1d}$ are each as defined herein. In certain embodiments, $R^{5a}$ is —N$R^{1a}$C(O)N$R^{1b}R^{1c}$, wherein $R^{1a}$, $R^{1b}$, and $R^{1c}$ are each as defined herein. In certain embodiments, $R^{5a}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{5a}$ is —N$R^{1a}$S(O)$R^{1d}$, wherein $R^{1a}$ and $R^{1d}$ are each as defined herein. In certain embodiments, $R^{5a}$ is —N$R^{1a}$S(O)$_2R^{1d}$, wherein $R^{1a}$ and $R^{1d}$ are each as defined herein. In certain embodiments, $R^{5a}$ is —N$R^{1a}$S(O)N$R^{1b}R^{1c}$, wherein $R^{1a}$, $R^{1b}$, and $R^{1c}$ are each as defined herein. In certain embodiments, $R^{5a}$ is —N$R^{1a}$S(O)$_2$N$R^{1b}R^{1c}$, wherein $R^{1a}$, $R^{1b}$, and $R^{1c}$ are each as defined herein. In certain embodiments, $R^{5a}$ is —S$R^{1a}$, wherein $R^{1a}$ is as defined herein. In certain embodiments, $R^{5a}$ is —S(O)$R^{1a}$, wherein $R^{1a}$ is as defined herein. In certain embodiments, $R^{5a}$ is —S(O)$_2R^{1a}$, wherein $R^{1a}$ is as defined herein. In certain embodiments, $R^{5a}$ is —S(O)N$R^{1b}R^{1c}$, wherein $R^{1b}$ and $R^{1c}$ are each as defined herein. In certain embodiments, $R^{5a}$ is —S(O)$_2$N$R^{1b}R^{1c}$; wherein $R^{1b}$ and $R^{1c}$ are each as defined herein.

In certain embodiments, $R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, or heteroaryl, each of which is optionally substituted with one or more substituents Q; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$. In certain embodiments, $R^{5a}$ is (a) hydrogen or halo; or (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, or heteroaryl, each of which is optionally substituted with one or more substituents Q.

In certain embodiments, $R^{5b}$ is halo. In certain embodiments, $R^{5b}$ is fluoro, chloro, bromo, or iodo. In certain embodiments, $R^{5b}$ is $C_{1-6}$ alkyl, optionally substituted with one or more substituents Q as described herein. In certain embodiments, $R^{5b}$ is methyl, ethyl, propyl, or butyl, each optionally substituted with one or more substituents Q as described herein. In certain embodiments, $R^{5b}$ is methyl, ethyl, n-propyl, isopropyl, n-butyl, isobutyl, or t-butyl. In certain embodiments, $R^{5b}$ is methyl. In certain embodiments, $R^{5b}$ is $C_{2-6}$ alkenyl, optionally substituted with one or more substituents Q as described herein. In certain embodiments, $R^{5b}$ is $C_{2-6}$ alkynyl, optionally substituted with one or more substituents Q as described herein. In certain embodiments, $R^{5b}$ is $C_{3-10}$ cycloalkyl, optionally substituted with one or more substituents Q as described herein. In certain embodiments, $R^{5b}$ is $C_{3-7}$ cycloalkyl, optionally substituted with one or more substituents Q as described herein. In certain embodiments, $R^{5b}$ is $C_{6-14}$ aryl, optionally substituted with one or more substituents Q as described herein. In certain embodiments, $R^{5b}$ is $C_{7-15}$ aralkyl, optionally substituted with one or more substituents Q as described herein. In certain embodiments, $R^{5b}$ is heteroaryl, optionally substituted with one or more substituents Q as described herein. In certain embodiments, $R^{5b}$ is heterocyclyl, optionally substituted with one or more substituents Q as described herein. In certain embodiments, $R^{5b}$ is not heterocyclyl.

In certain embodiments, $R^{5b}$ is —C(O)$R^{1a}$, wherein $R^{1a}$ is as defined herein. In certain embodiments, $R^{5b}$ is —C(O)O$R^{1a}$, wherein $R^{1a}$ is as defined herein. In certain embodiments, $R^{5b}$ is —C(O)O$R^{1a}$, wherein $R^{1a}$ is $C_{1-6}$ alkyl, optionally substituted with one or more substituents Q as described herein. In certain embodiments, $R^{5b}$ is —C(O)OCH$_3$. In certain embodiments, $R^{5b}$ is —C(O)N$R^{1b}R^{1c}$, wherein $R^{1b}$ and $R^{1c}$ are each as defined herein. In certain embodiments, $R^{5b}$ is —C(N$R^{1a}$)N$R^{1b}R^{1c}$, wherein $R^{1a}$, $R^{1b}$, and $R^{1c}$ are each as defined herein. In certain embodiments, $R^{5b}$ is —O$R^{1a}$, wherein $R^{1a}$ is as defined herein. In certain embodiments, $R^{5b}$ is —OC(O)$R^{1a}$, wherein $R^{1a}$ is as defined herein. In certain embodiments, $R^{5b}$ is —OC(O)O$R^{1a}$, wherein $R^{1a}$ is as defined herein. In certain embodiments, $R^{5b}$ is —OC(O)N$R^{1b}R^{1c}$, wherein $R^{1b}$ and $R^{1c}$ are each as defined herein. In certain embodiments, $R^{5b}$ is —OC(=N$R^{1a}$)N$R^{1b}R^{1c}$, wherein $R^{1a}$, $R^{1b}$, and $R^{1c}$ are each as defined herein. In certain embodiments, $R^{5b}$ is —OS(O)$R^{1a}$, wherein $R^{1a}$ is as defined herein. In certain embodiments, $R^{5b}$ is —OS(O)$_2R^{1a}$, wherein $R^{1a}$ is as defined herein. In certain embodiments, $R^{5b}$ is —OS(O)N$R^{1b}R^{1c}$, wherein $R^{1b}$ and $R^{1c}$ are each as defined herein. In certain embodiments, $R^{5b}$ is —OS(O)$_2$N$R^{1b}R^{1c}$, wherein $R^{1b}$ and $R^{1c}$ are each as defined herein. In certain embodiments, $R^{5b}$ is —N$R^{1b}R^{1c}$, wherein $R^{1b}$ and $R^{1c}$ are each as defined herein. In certain embodiments, $R^{5b}$ is amino (—NH$_2$). In certain embodiments, $R^{5b}$ is —N$R^{1a}$C(O)$R^{1d}$, wherein $R^{1a}$ and $R^{1d}$ are each as defined herein. In certain embodiments, $R^{5b}$ is —N$R^{1a}$C(O)O$R^{1d}$, wherein $R^{1a}$ and $R^{1d}$ are each as defined herein. In certain embodiments, $R^{5b}$ is —N$R^{1a}$C(O)N$R^{1b}R^{1c}$, wherein $R^{1a}$, $R^{1b}$, and $R^{1c}$ are each as defined herein. In certain embodiments, $R^{5b}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{5b}$ is —N$R^{1a}$S(O)$R^{1d}$, wherein $R^{1a}$ and $R^{1d}$ are each as defined herein. In certain embodiments, $R^{5b}$ is —N$R^{1a}$S(O)$_2R^{1d}$, wherein $R^{1a}$ and $R^{1d}$ are each as defined herein. In certain embodiments, $R^{5b}$ is —N$R^{1a}$S(O)N$R^{1b}R^{1c}$, wherein $R^{1a}$, $R^{1b}$, and $R^{1c}$ are each as defined herein. In certain embodiments, $R^{5b}$ is —NR$^{1a}$S(O)$_2$NR$^{1b}$R$^{1c}$, wherein R$^{1a}$, R$^{1b}$, and R$^{1c}$ are each as defined herein. In certain embodiments, R$^{5b}$ is —SR$^{1a}$, wherein R$^{1a}$ is as defined herein. In certain embodiments, R$^{5b}$ is —S(O)R$^{1a}$, wherein R$^{1a}$ is as defined herein. In certain embodiments, R$^{5b}$ is —S(O)$_2$R$^{1a}$, wherein R$^{1a}$ is as defined herein. In certain embodiments, R$^{5b}$ is —S(O)NR$^{1b}$R$^{1c}$, wherein R$^{1b}$ and R$^{1c}$ are each as defined herein. In certain embodiments, R$^{5b}$ is —S(O)$_2$NR$^{1b}$R$^{1c}$; wherein R$^{1b}$ and R$^{1c}$ are each as defined herein.

In certain embodiments, R$^{5a}$ and R$^{5b}$ are each independently methyl, ethyl, n-propyl, isopropyl, n-butyl, isobutyl, or t-butyl, each optionally substituted with one or more substituents Q as described herein. In certain embodiments, R$^{5a}$ and R$^{5b}$ are each independently methyl, ethyl, n-propyl, isopropyl, n-butyl, isobutyl, or t-butyl, each optionally substituted with one or more halo. In certain embodiments, R$^{5a}$ and R$^{5b}$ are each independently methyl, ethyl, n-propyl, isopropyl, n-butyl, isobutyl, or t-butyl. In certain embodiments, R$^{5a}$ and R$^{5b}$ are each methyl.

In certain embodiments, R$^{5c}$ is C$_{6-14}$ aryl, optionally substituted with one or more substituents Q as described herein. In certain embodiments, R$^{5b}$ is C$_{6-14}$ aryl substituted at the 2-position with one substituent Q as described herein. In certain embodiments, R$^{5c}$ is phenyl or naphthyl, each optionally substituted with one or more substituents Q as described herein. In certain embodiments, R$^{5c}$ is phenyl, naphtha-1-yl, or naphtha-2-yl, each optionally substituted with one or more substituents Q as described herein. In certain embodiments, R$^{5c}$ is phenyl, 4-chlorophenyl, 4-methoxyphenyl, or naphtha-2-yl. In certain embodiments, R$^{5c}$ is heteroaryl, optionally substituted with one or more substituents as described herein. In certain embodiments, R$^{5c}$ is monocyclic heteroaryl, optionally substituted with one or more substituents as described herein. In certain embodiments, R$^{5c}$ is 5- or 6-membered heteroaryl, optionally substituted with one or more substituents as described herein. In certain embodiments, R$^{5c}$ is bicyclic heteroaryl, optionally substituted with one or more substituents as described herein.

In certain embodiments, R$^{5c}$ is —(CR$^{5f}$R$^{5g}$)$_n$—(C$_{6-14}$ aryl), wherein the C$_{6-14}$ aryl is optionally substituted with one or more substituents Q as described herein. In certain embodiments, R$^{5c}$ is benzyl, 2-phenethyl, 3-phenylpropyl, or 4-phenylbutyl, wherein each of the phenyl moiety is optionally substituted with one or more substituents Q as described herein. In certain embodiments, R$^{5c}$ is benzyl, 2-phenethyl, 3-phenylpropyl, or 4-phenylbutyl. In certain embodiments, R$^{5c}$ is benzyl, fluorobenzyl, chlorobenzyl, bromobenzyl, cyanobenzyl, methylbenzyl, or methoxylbenzyl. In certain embodiments, R$^{5c}$ is (naphthalen-1-yl)methyl, (naphthalen-2-yl)methyl 2-(naphthalen-1-yl)ethyl, 2-(naphthalen-2-yl)ethyl, 3-(naphthalen-1-yl)propyl, 3-(naphthalen-2-yl)propyl, 4-(naphthalen-1-yl)butyl, or 4-(naphthalen-2-yl)butyl, wherein each of the naphthyl moiety is optionally substituted with one or more substituents Q as described herein. In certain embodiments, n is 0 or 1. In one embodiment, n is 1. In one embodiment, n is 1, 2, 3, or 4. In certain embodiments, R$^{5c}$ is —CH$_2$—(C$_{6-14}$ aryl), wherein the C$_{6-14}$ aryl is optionally substituted with one or more substituents Q as described herein. In certain embodiments, R$^{5c}$ is —C(CH$_3$)$_2$—(C$_{6-14}$ aryl), wherein the C$_{6-14}$ aryl is optionally substituted with one or more substituents Q as described herein. In certain embodiments, R$^{5c}$ is —CH$_2$-phenyl or —CH$_2$-naphthyl, wherein the phenyl or naphthyl is each optionally substituted with one or more substituents Q as described herein, such as, e.g., optionally substituted with one or more F, Cl, Br, I, —CN, —CH$_3$, —CF$_3$, —OCH$_3$, or —OCF$_3$. In certain embodiments, R$^{5c}$ is —CH$_2$-phenyl, —CH$_2$-naphtha-1-yl, or —CH$_2$-naphtha-2-yl, wherein the phenyl or naphthyl is each optionally substituted with one or more substituents Q as described herein, such as, e.g., optionally substituted with one or more F, Cl, Br, I, —CN, —CH$_3$, —CF$_3$, —OCH$_3$, or —OCF$_3$. In certain embodiments, R$^{5c}$ is —CH$_2$-phenyl, —CH$_2$-naphtha-1-yl, or —CH$_2$-naphtha-2-yl, wherein the phenyl or naphthyl is each optionally substituted with one or more F, Cl, Br, I, —CN, —CH$_3$, —CF$_3$, —OCH$_3$, or —OCF$_3$. In other embodiments, R$^{5c}$ is —CH$_2$-phenyl, —CH$_2$-naphtha-1-yl, or —CH$_2$-naphtha-2-yl, wherein the phenyl or naphthyl is each optionally substituted with one or more F, Cl, Br, I, —CN, —CH$_3$, —CF$_3$, —OCH$_3$, —OCF$_3$, —O—(C$_{1-4}$ alkylene)-N—(C$_{1-4}$ alkyl)$_2$ (e.g., —O—CH$_2$CH$_2$—N(CH$_3$)$_2$), —O-heterocyclyl (e.g., —O—(N-methylpiperidinyl) or —O-piperidinyl), —O-heteroaryl (e.g., —O-pyridyl), —NH-heterocyclyl (e.g., —NH—(N-methylpiperidinyl), —NH—(N-methylpyrrolidinyl), —NH-piperidinyl, or —NH-pyrrolidinyl), —NH-heteroaryl (e.g., —NH-pyridyl), —NCH$_3$-heterocyclyl (e.g., —NCH$_3$—(N-methylpiperidinyl), —NCH$_3$—(N-methylpyrrolidinyl), —NCH$_3$-piperidinyl, or —NCH$_3$-pyrrolidinyl), —NCH$_3$-heteroaryl (e.g., —NCH$_3$-pyridyl), heterocyclyl (e.g., piperidinyl, piperazinyl, N-methylpiperidinyl, or N-methylpiperazinyl), or heteroaryl (e.g., pyridyl or imidazolyl). In certain embodiments, R$^{5c}$ is —CH$_2$-phenyl, —C(CH$_3$)$_2$-phenyl, —CH$_2$-(2-methylphenyl), —CH$_2$-(2-methoxylphenyl), —CH$_2$-(2-fluorophenyl), —CH$_2$-(2-chlorophenyl), —CH$_2$-(2-bromophenyl), —CH$_2$-(3-methylphenyl), —CH$_2$-(3-methoxylphenyl), —CH$_2$-(3-fluorophenyl), —CH$_2$-(3-chlorophenyl), —CH$_2$-(3-bromophenyl), —CH$_2$-(4-methylphenyl), —CH$_2$-(4-methoxylphenyl), —CH$_2$-(4-fluorophenyl), —CH$_2$-(4-chlorophenyl), —CH$_2$-(4-bromophenyl), —CH$_2$-naphtha-1-yl, or —CH$_2$-naphtha-2-yl.

In certain embodiments, R$^{5c}$ is —(CR$^{5f}$R$^{5g}$)—(C$_{6-14}$ aryl), wherein the C$_{6-14}$ aryl is optionally substituted with one or more substituents Q as described herein, and wherein R$^{5f}$ and R$^{5g}$ together with the carbon atom to which they are attached form a 3- to 6-membered cycloalkyl or heterocyclyl. In one embodiment, R$^{5c}$ is -cyclopropyl-phenyl. In one embodiment, R$^{5c}$ is -cyclobutyl-phenyl. In one embodiment, R$^{5c}$ is -cyclopentyl-phenyl. In one embodiment, R$^{5c}$ is -cyclohexyl-phenyl.

In certain embodiments, R$^{5c}$ is —(CR$^{5f}$R$^{5g}$)$_n$-heteroaryl, wherein the heteroaryl is optionally substituted with one or more substituents Q as described herein, wherein n is defined herein elsewhere. In certain embodiments, R$^{5c}$ is —CH$_2$-(monocyclic heteroaryl), wherein the heteroaryl is optionally substituted with one or more substituents as described herein. In certain embodiments, R$^{5c}$ is —CH$_2$-(5- or 6-membered heteroaryl), wherein the heteroaryl is optionally substituted with one or more substituents as described herein. In certain embodiments, R$^{5c}$ is —CH$_2$-(bicyclic heteroaryl), wherein the heteroaryl is optionally substituted with one or more substituents as described herein.

In certain embodiments, R$^{5d}$ is hydrogen. In certain embodiments, R$^{5d}$ is halo. In certain embodiments, R$^{5d}$ is fluoro, chloro, bromo, or iodo. In certain embodiments, R$^{5d}$ is C$_{1-6}$ alkyl, optionally substituted with one or more substituents Q as described herein. In certain embodiments, R$^{5d}$ is methyl, optionally substituted with one or more substituents Q as described herein. In certain embodiments, R$^{5d}$ is methyl. In certain embodiments, R$^{5d}$ is methyl, ethyl, propyl, or butyl, each optionally substituted with one or more substituents Q as described herein. In certain embodiments, R$^{5d}$ is methyl, ethyl, n-propyl, isopropyl, n-butyl, isobutyl, or t-butyl. In certain embodiments, R$^{5d}$ is C$_{2-6}$ alkenyl, optionally substituted with one or more substituents Q as described herein. In certain embodiments, R$^{5d}$ is C$_{2-6}$ alkynyl, optionally substituted with one or more substituents Q as described herein. In certain embodiments, $R^{5d}$ is $C_{3-10}$ cycloalkyl, optionally substituted with one or more substituents Q as described herein. In certain embodiments, $R^{5d}$ is $C_{6-14}$ aryl, optionally substituted with one or more substituents Q as described herein. In certain embodiments, $R^{5d}$ is $C_{7-15}$ aralkyl, optionally substituted with one or more substituents Q as described herein. In certain embodiments, $R^{5d}$ is heteroaryl, optionally substituted with one or more substituents Q as described herein. In certain embodiments, $R^{5d}$ is heterocyclyl, optionally substituted with one or more substituents Q as described herein.

In certain embodiments, $R^{5d}$ is —C(O)$R^{1a}$, wherein $R^{1a}$ is as defined herein. In certain embodiments, $R^{5d}$ is —C(O)O$R^{1a}$, wherein $R^{1a}$ is as defined herein. In certain embodiments, $R^{5d}$ is —C(O)O$R^{1a}$, wherein $R^{1a}$ is $C_{1-6}$ alkyl, optionally substituted with one or more substituents Q as described herein. In certain embodiments, $R^{5d}$ is —C(O)OCH$_3$. In certain embodiments, $R^{5d}$ is —C(O)N$R^{1b}R^{1c}$, wherein $R^{1b}$ and $R^{1c}$ are each as defined herein. In certain embodiments, $R^{5d}$ is —C(N$R^{1a}$)N$R^{1b}R^{1c}$, wherein $R^{1a}$, $R^{1b}$, and $R^{1c}$ are each as defined herein. In certain embodiments, $R^{5d}$ is —O$R^{1a}$, wherein $R^{1a}$ is as defined herein. In certain embodiments, $R^{5d}$ is —OC(O)$R^{1a}$, wherein $R^{1a}$ is as defined herein. In certain embodiments, $R^{5d}$ is —OC(O)O$R^{1a}$, wherein $R^{1a}$ is as defined herein. In certain embodiments, $R^{5d}$ is —OC(O)N$R^{1b}R^{1c}$, wherein $R^{1b}$ and $R^{1c}$ are each as defined herein. In certain embodiments, $R^{5d}$ is —OC(=N$R^{1a}$)N$R^{1b}R^{1c}$, wherein $R^{1a}$, $R^{1b}$, and $R^{1c}$ are each as defined herein. In certain embodiments, $R^{5d}$ is —OS(O)$R^{1a}$, wherein $R^{1a}$ is as defined herein. In certain embodiments, $R^{5d}$ is —OS(O)$_2R^{1a}$, wherein $R^{1a}$ is as defined herein. In certain embodiments, $R^{5d}$ is —OS(O)N$R^{1b}R^{1c}$, wherein $R^{1b}$ and $R^{1c}$ are each as defined herein. In certain embodiments, $R^{5d}$ is —OS(O)$_2$N$R^{1b}R^{1c}$, wherein $R^{1b}$ and $R^{1c}$ are each as defined herein. In certain embodiments, $R^{5d}$ is —N$R^{1b}R^{1c}$, wherein $R^{1b}$ and $R^{1c}$ are each as defined herein. In certain embodiments, $R^{5d}$ is amino (—NH$_2$). In certain embodiments, $R^{5d}$ is —N$R^{1a}$C(O)$R^{1d}$, wherein $R^{1a}$ and $R^{1d}$ are each as defined herein. In certain embodiments, $R^{5d}$ is —N$R^{1a}$C(O)O$R^{1d}$, wherein $R^{1a}$ and $R^{1d}$ are each as defined herein. In certain embodiments, $R^{5d}$ is —N$R^{1a}$C(O)N$R^{1b}R^{1c}$, wherein $R^{1a}$, $R^{1b}$, and $R^{1c}$ are each as defined herein. In certain embodiments, $R^{5d}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{5d}$ is —N$R^{1a}$S(O)$R^{1d}$, wherein $R^{1a}$ and $R^{1d}$ are each as defined herein. In certain embodiments, $R^{5d}$ is —N$R^{1a}$S(O)$_2R^{1d}$, wherein $R^{1a}$ and $R^{1d}$ are each as defined herein. In certain embodiments, $R^{5d}$ is —N$R^{1a}$S(O)N$R^{1b}R^{1c}$, wherein $R^{1a}$, $R^{1b}$, and $R^{1c}$ are each as defined herein. In certain embodiments, $R^{5d}$ is —N$R^{1a}$S(O)$_2$N$R^{1b}R^{1c}$, wherein $R^{1a}$, $R^{1b}$, and $R^{1c}$ are each as defined herein. In certain embodiments, $R^{5d}$ is —S$R^{1a}$, wherein $R^{1a}$ is as defined herein. In certain embodiments, $R^{5d}$ is —S(O)$R^{1a}$, wherein $R^{1a}$ is as defined herein. In certain embodiments, $R^{5d}$ is —S(O)$_2R^{1a}$, wherein $R^{1a}$ is as defined herein. In certain embodiments, $R^{5d}$ is —S(O)N$R^{1b}R^{1c}$, wherein $R^{1b}$ and $R^{1c}$ are each as defined herein. In certain embodiments, $R^{5d}$ is —S(O)$_2$N$R^{1b}R^{1c}$; wherein $R^{1b}$ and $R^{1c}$ are each as defined herein.

In certain embodiments, $R^{5e}$ is hydrogen. In certain embodiments, $R^{5e}$ is halo. In certain embodiments, $R^{5e}$ is fluoro, chloro, bromo, or iodo. In certain embodiments, $R^{5e}$ is $C_{1-6}$ alkyl, optionally substituted with one or more substituents Q as described herein. In certain embodiments, $R^{5e}$ is methyl, optionally substituted with one or more substituents Q as described herein. In certain embodiments, $R^{5e}$ is methyl. In certain embodiments, $R^{5e}$ is methyl, ethyl, propyl, or butyl, each optionally substituted with one or more substituents Q as described herein. In certain embodiments, $R^{5e}$ is methyl, ethyl, n-propyl, isopropyl, n-butyl, isobutyl, or t-butyl. In certain embodiments, $R^{5e}$ is $C_{2-6}$ alkenyl, optionally substituted with one or more substituents Q as described herein. In certain embodiments, $R^{5e}$ is $C_{2-6}$ alkynyl, optionally substituted with one or more substituents Q as described herein. In certain embodiments, $R^{5e}$ is $C_{3-10}$ cycloalkyl, optionally substituted with one or more substituents Q as described herein. In certain embodiments, $R^{5e}$ is $C_{6-14}$ aryl, optionally substituted with one or more substituents Q as described herein. In certain embodiments, $R^{5e}$ is $C_{7-15}$ aralkyl, optionally substituted with one or more substituents Q as described herein. In certain embodiments, $R^{5e}$ is heteroaryl, optionally substituted with one or more substituents Q as described herein. In certain embodiments, $R^{5e}$ is heterocyclyl, optionally substituted with one or more substituents Q as described herein.

In certain embodiments, $R^{5e}$ is —C(O)$R^{1a}$, wherein $R^{1a}$ is as defined herein. In certain embodiments, $R^{5e}$ is —C(O)O$R^{1a}$, wherein $R^{1a}$ is as defined herein. In certain embodiments, $R^{5e}$ is —C(O)O$R^{1a}$, wherein $R^{1a}$ is $C_{1-6}$ alkyl, optionally substituted with one or more substituents Q as described herein. In certain embodiments, $R^{5e}$ is —C(O)OCH$_3$. In certain embodiments, $R^{5e}$ is —C(O)N$R^{1b}R^{1c}$, wherein $R^{1b}$ and $R^{1c}$ are each as defined herein. In certain embodiments, $R^{5e}$ is —C(N$R^{1a}$)N$R^{1b}R^{1c}$, wherein $R^{1a}$, $R^{1b}$, and $R^{1c}$ are each as defined herein. In certain embodiments, $R^{5e}$ is —O$R^{1a}$, wherein $R^{1a}$ is as defined herein. In certain embodiments, $R^{5e}$ is —OC(O)$R^{1a}$, wherein $R^{1a}$ is as defined herein. In certain embodiments, $R^{5e}$ is —OC(O)O$R^{1a}$, wherein $R^{1a}$ is as defined herein. In certain embodiments, $R^{5e}$ is —OC(O)N$R^{1b}R^{1c}$, wherein $R^{1b}$ and $R^{1c}$ are each as defined herein. In certain embodiments, $R^{5e}$ is —OC(=N$R^{1a}$)N$R^{1b}R^{1c}$, wherein $R^{1a}$, $R^{1b}$, and $R^{1c}$ are each as defined herein. In certain embodiments, $R^{5e}$ is —OS(O)$R^{1a}$, wherein $R^{1a}$ is as defined herein. In certain embodiments, $R^{5e}$ is —OS(O)$_2R^{1a}$, wherein $R^{1a}$ is as defined herein. In certain embodiments, $R^{5e}$ is —OS(O)N$R^{1b}R^{1c}$, wherein $R^{1b}$ and $R^{1c}$ are each as defined herein. In certain embodiments, $R^{5e}$ is —OS(O)$_2$N$R^{1b}R^{1c}$, wherein $R^{1b}$ and $R^{1c}$ are each as defined herein. In certain embodiments, $R^{5e}$ is —N$R^{1b}R^{1c}$, wherein $R^{1b}$ and $R^{1c}$ are each as defined herein. In certain embodiments, $R^{5e}$ is amino (—NH$_2$). In certain embodiments, $R^{5e}$ is —N$R^{1a}$C(O)$R^{1d}$, wherein $R^{1a}$ and $R^{1d}$ are each as defined herein. In certain embodiments, $R^{5e}$ is —N$R^{1a}$C(O)O$R^{1d}$, wherein $R^{1a}$ and $R^{1d}$ are each as defined herein. In certain embodiments, $R^{5e}$ is —N$R^{1a}$C(O)N$R^{1b}R^{1c}$, wherein $R^{1a}$, $R^{1b}$, and $R^{1c}$ are each as defined herein. In certain embodiments, $R^{5e}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{5e}$ is —N$R^{1a}$S(O)$R^{1d}$, wherein $R^{1a}$ and $R^{1d}$ are each as defined herein. In certain embodiments, $R^{5e}$ is —N$R^{1a}$S(O)$_2R^{1d}$, wherein $R^{1a}$ and $R^{1d}$ are each as defined herein. In certain embodiments, $R^{5e}$ is —N$R^{1a}$S(O)N$R^{1b}R^{1c}$, wherein $R^{1a}$, $R^{1b}$, and $R^{1c}$ are each as defined herein. In certain embodiments, $R^{5e}$ is —N$R^{1a}$S(O)$_2$N$R^{1b}R^{1c}$, wherein $R^{1a}$, $R^{1b}$, and $R^{1c}$ are each as defined herein. In certain embodiments, $R^{5e}$ is —S$R^{1a}$, wherein $R^{1a}$ is as defined herein. In certain embodiments, $R^{5e}$ is —S(O)$R^{1a}$, wherein $R^{1a}$ is as defined herein. In certain embodiments, $R^{5e}$ is —S(O)$_2R^{1a}$, wherein $R^{1a}$ is as defined herein. In certain embodiments, $R^{5e}$ is —S(O)N$R^{1b}R^{1c}$, wherein $R^{1b}$ and $R^{1c}$ are each as defined herein. In certain embodiments, $R^{5e}$ is —S(O)$_2$N$R^{1b}R^{1c}$; wherein $R^{1b}$ and $R^{1c}$ are each as defined herein.

In certain embodiments, $R^{5f}$ is hydrogen. In certain embodiments, $R^{5f}$ is halo. In certain embodiments, $R^{5f}$ is fluoro, chloro, bromo, or iodo. In certain embodiments, $R^{5f}$ is $C_{1-6}$ alkyl, optionally substituted with one or more substituents Q as described herein. In certain embodiments, $R^{5f}$ is methyl, optionally substituted with one or more substituents Q as described herein. In certain embodiments, $R^{5f}$ is methyl. In certain embodiments, $R^{5f}$ is methyl, ethyl, propyl, or butyl, each optionally substituted with one or more substituents Q as described herein. In certain embodiments, $R^{5f}$ is methyl, ethyl, n-propyl, isopropyl, n-butyl, isobutyl, or t-butyl. In certain embodiments, $R^{5f}$ is $C_{2-6}$ alkenyl, optionally substituted with one or more substituents Q as described herein. In certain embodiments, $R^{5f}$ is $C_{2-6}$ alkynyl, optionally substituted with one or more substituents Q as described herein. In certain embodiments, $R^{5f}$ is $C_{3-10}$ cycloalkyl, optionally substituted with one or more substituents Q as described herein. In certain embodiments, $R^{5f}$ is $C_{6-14}$ aryl, optionally substituted with one or more substituents Q as described herein. In certain embodiments, $R^{5f}$ is $C_{7-15}$ aralkyl, optionally substituted with one or more substituents Q as described herein. In certain embodiments, $R^{5f}$ is heteroaryl, optionally substituted with one or more substituents Q as described herein. In certain embodiments, $R^{5f}$ is heterocyclyl, optionally substituted with one or more substituents Q as described herein.

In certain embodiments, $R^{5f}$ is —C(O)$R^{1a}$, wherein $R^{1a}$ is as defined herein. In certain embodiments, $R^{5f}$ is —C(O)O$R^{1a}$, wherein $R^{1a}$ is as defined herein. In certain embodiments, $R^{5f}$ is —C(O)O$R^{1a}$, wherein $R^{1a}$ is $C_{1-6}$ alkyl, optionally substituted with one or more substituents Q as described herein. In certain embodiments, $R^{5f}$ is —C(O)OCH$_3$. In certain embodiments, $R^{5f}$ is —C(O)N$R^{1b}R^{1c}$, wherein $R^{1b}$ and $R^{1c}$ are each as defined herein. In certain embodiments, $R^{5f}$ is —C(N$R^{1a}$)N$R^{1b}R^{1c}$, wherein $R^{1a}$, $R^{1b}$, and $R^{1c}$ are each as defined herein. In certain embodiments, $R^{5f}$ is —O$R^{1a}$, wherein $R^{1a}$ is as defined herein. In certain embodiments, $R^{5f}$ is —OC(O)$R^{1a}$, wherein $R^{1a}$ is as defined herein. In certain embodiments, $R^{5f}$ is —OC(O)O$R^{1a}$, wherein $R^{1a}$ is as defined herein. In certain embodiments, $R^{5f}$ is —OC(O)N$R^{1b}R^{1c}$, wherein $R^{1b}$ and $R^{1c}$ are each as defined herein. In certain embodiments, $R^{5f}$ is —OC(=N$R^{1a}$)N$R^{1b}R^{1c}$, wherein $R^{1a}$, $R^{1b}$, and $R^{1c}$ are each as defined herein. In certain embodiments, $R^{5f}$ is —OS(O)$R^{1a}$, wherein $R^{1a}$ is as defined herein. In certain embodiments, $R^{5f}$ is —OS(O)$_2R^{1a}$, wherein $R^{1a}$ is as defined herein. In certain embodiments, $R^{5f}$ is —OS(O)N$R^{1b}R^{1c}$, wherein $R^{1b}$ and $R^{1c}$ are each as defined herein. In certain embodiments, $R^{5f}$ is —OS(O)$_2$N$R^{1b}R^{1c}$, wherein $R^{1b}$ and $R^{1c}$ are each as defined herein. In certain embodiments, $R^{5f}$ is —N$R^{1b}R^{1c}$, wherein $R^{1b}$ and $R^{1c}$ are each as defined herein. In certain embodiments, $R^{5f}$ is amino (—NH$_2$). In certain embodiments, $R^{5f}$ is —N$R^{1a}$C(O)$R^{1d}$, wherein $R^{1a}$ and $R^{1d}$ are each as defined herein. In certain embodiments, $R^{5f}$ is —N$R^{1a}$C(O)O$R^{1d}$, wherein $R^{1a}$ and $R^{1d}$ are each as defined herein. In certain embodiments, $R^{5f}$ is —N$R^{1a}$C(O)N$R^{1b}R^{1c}$, wherein $R^{1a}$, $R^{1b}$, and $R^{1c}$ are each as defined herein. In certain embodiments, $R^{5f}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{5f}$ is —N$R^{1a}$S(O)$R^{1d}$, wherein $R^{1a}$ and $R^{1d}$ are each as defined herein. In certain embodiments, $R^{5f}$ is —N$R^{1a}$S(O)$_2R^{1d}$, wherein $R^{1a}$ and $R^{1d}$ are each as defined herein. In certain embodiments, $R^{5f}$ is —N$R^{1a}$S(O)N$R^{1b}R^{1c}$, wherein $R^{1a}$, $R^{1b}$, and $R^{1c}$ are each as defined herein. In certain embodiments, $R^{5f}$ is —N$R^{1a}$S(O)$_2$N$R^{1b}R^{1c}$, wherein $R^{1a}$, $R^{1b}$, and $R^{1c}$ are each as defined herein. In certain embodiments, $R^{5f}$ is —S$R^{1a}$, wherein $R^{1a}$ is as defined herein. In certain embodiments, $R^{5f}$ is —S(O)$R^{1a}$, wherein $R^{1a}$ is as defined herein. In certain embodiments, $R^{5f}$ is —S(O)$_2R^{1a}$, wherein $R^{1a}$ is as defined herein. In certain embodiments, $R^{5f}$ is —S(O)N$R^{1b}R^{1c}$, wherein $R^{1b}$ and $R^{1c}$ are each as defined herein. In certain embodiments, $R^{5f}$ is —S(O)$_2$N$R^{1b}R^{1c}$, wherein $R^{1b}$ and $R^{1c}$ are each as defined herein.

In certain embodiments, $R^{5g}$ is hydrogen. In certain embodiments, $R^{5g}$ is halo. In certain embodiments, $R^{5g}$ is fluoro, chloro, bromo, or iodo. In certain embodiments, $R^{5g}$ is $C_{1-6}$ alkyl, optionally substituted with one or more substituents Q as described herein. In certain embodiments, $R^{5g}$ is methyl, optionally substituted with one or more substituents Q as described herein. In certain embodiments, $R^{5g}$ is methyl. In certain embodiments, $R^{5g}$ is methyl, ethyl, propyl, or butyl, each optionally substituted with one or more substituents Q as described herein. In certain embodiments, $R^{5g}$ is methyl, ethyl, n-propyl, isopropyl, n-butyl, isobutyl, or t-butyl. In certain embodiments, $R^{5g}$ is $C_{2-6}$ alkenyl, optionally substituted with one or more substituents Q as described herein. In certain embodiments, $R^{5g}$ is $C_{2-6}$ alkynyl, optionally substituted with one or more substituents Q as described herein. In certain embodiments, $R^{5g}$ is $C_{3-10}$ cycloalkyl, optionally substituted with one or more substituents Q as described herein. In certain embodiments, $R^{5g}$ is $C_{6-14}$ aryl, optionally substituted with one or more substituents Q as described herein. In certain embodiments, $R^{5g}$ is $C_{7-15}$ aralkyl, optionally substituted with one or more substituents Q as described herein. In certain embodiments, $R^{5g}$ is heteroaryl, optionally substituted with one or more substituents Q as described herein. In certain embodiments, $R^{5g}$ is heterocyclyl, optionally substituted with one or more substituents Q as described herein.

In certain embodiments, $R^{5g}$ is —C(O)$R^{1a}$, wherein $R^{1a}$ is as defined herein. In certain embodiments, $R^{5g}$ is —C(O)O$R^{1a}$, wherein $R^{1a}$ is as defined herein. In certain embodiments, $R^{5g}$ is —C(O)O$R^{1a}$, wherein $R^{1a}$ is $C_{1-6}$ alkyl, optionally substituted with one or more substituents Q as described herein. In certain embodiments, $R^{5g}$ is —C(O)OCH$_3$. In certain embodiments, $R^{5g}$ is —C(O)N$R^{1b}R^{1c}$, wherein $R^{1b}$ and $R^{1c}$ are each as defined herein. In certain embodiments, $R^{5g}$ is —C(N$R^{1a}$)N$R^{1b}R^{1c}$, wherein $R^{1a}$, $R^{1b}$, and $R^{1c}$ are each as defined herein. In certain embodiments, $R^{5g}$ is —O$R^{1a}$, wherein $R^{1a}$ is as defined herein. In certain embodiments, $R^{5g}$ is —OC(O)$R^{1a}$, wherein $R^{1a}$ is as defined herein. In certain embodiments, $R^{5g}$ is —OC(O)O$R^{1a}$, wherein $R^{1a}$ is as defined herein. In certain embodiments, $R^{5g}$ is —OC(O)N$R^{1b}R^{1c}$, wherein $R^{1b}$ and $R^{1c}$ are each as defined herein. In certain embodiments, $R^{5g}$ is —OC(=N$R^{1a}$)N$R^{1b}R^{1c}$, wherein $R^{1a}$, $R^{1b}$, and $R^{1c}$ are each as defined herein. In certain embodiments, $R^{5g}$ is —OS(O)$R^{1a}$, wherein $R^{1a}$ is as defined herein. In certain embodiments, $R^{5g}$ is —OS(O)$_2R^{1a}$, wherein $R^{1a}$ is as defined herein. In certain embodiments, $R^{5g}$ is —OS(O)N$R^{1b}R^{1c}$, wherein $R^{1b}$ and $R^{1c}$ are each as defined herein. In certain embodiments, $R^{5g}$ is —OS(O)$_2$N$R^{1b}R^{1c}$, wherein $R^{1b}$ and $R^{1c}$ are each as defined herein. In certain embodiments, $R^{5g}$ is —N$R^{1b}R^{1c}$, wherein $R^{1b}$ and $R^{1c}$ are each as defined herein. In certain embodiments, $R^{5g}$ is amino (—NH$_2$). In certain embodiments, $R^{5g}$ is —N$R^{1a}$C(O)$R^{1d}$, wherein $R^{1a}$ and $R^{1d}$ are each as defined herein. In certain embodiments, $R^{5g}$ is —N$R^{1a}$C(O)O$R^{1d}$, wherein $R^{1a}$ and $R^{1d}$ are each as defined herein. In certain embodiments, $R^{5g}$ is —N$R^{1a}$C(O)N$R^{1b}R^{1c}$, wherein $R^{1a}$, $R^{1b}$, and $R^{1c}$ are each as defined herein. In certain embodiments, $R^{5g}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{5g}$ is —N$R^{1a}$S(O)$R^{1d}$, wherein $R^{1a}$ and $R^{1d}$ are each as defined herein. In certain embodiments, $R^{5g}$ is —N$R^{1a}$S(O)$_2R^{1d}$, wherein $R^{1a}$ and $R^{1d}$ are each as defined herein. In certain embodiments, $R^{5g}$ is —N$R^{1a}$S(O)N$R^{1b}R^{1c}$, wherein $R^{1a}$, $R^{1b}$, and $R^{1c}$ are each as defined herein. In certain embodiments, $R^{5g}$ is —N$R^{1a}$S(O)$_2$N$R^{1b}R^{1c}$, wherein $R^{1a}$, $R^{1b}$, and $R^{1c}$ are each as defined herein. In certain embodiments, $R^{5g}$ is —$SR^{1a}$, wherein $R^{1a}$ is as defined herein. In certain embodiments, $R^{5g}$ is —$S(O)R^{1a}$, wherein $R^{1a}$ is as defined herein. In certain embodiments, $R^{5g}$ is —$S(O)_2R^{1a}$, wherein $R^{1a}$ is as defined herein. In certain embodiments, $R^{5g}$ is —$S(O)NR^{1b}R^{1c}$, wherein $R^{1b}$ and $R^{1c}$ are each as defined herein. In certain embodiments, $R^{5g}$ is —$S(O)_2NR^{1b}R^{1c}$; wherein $R^{1b}$ and $R^{1c}$ are each as defined herein.

In certain embodiments, when one occurrence of $R^{5f}$ and one occurrence of $R^{5g}$ are attached to the same carbon atom, the $R^{5f}$ and $R^{5g}$ together with the carbon atom to which they are attached form a $C_{3-10}$ cycloalkyl, optionally substituted with one or more substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a $C_{3-7}$ cycloalkyl, optionally substituted with one or more substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cyclopropyl, optionally substituted with one or more substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cyclobutyl, optionally substituted with one or more substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cyclopentyl, optionally substituted with one or more substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cyclohexyl, optionally substituted with one or more substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cycloheptyl, optionally substituted with one or more substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cyclopropyl.

In certain embodiments, when one occurrence of $R^{5f}$ and one occurrence of $R^{5g}$ are attached to the same carbon atom, the $R^{5f}$ and $R^{5g}$ together with the carbon atom to which they are attached form a heterocyclyl, optionally substituted with one or more substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a 3-membered heterocyclyl, optionally substituted with one or more substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a 4-membered heterocyclyl, optionally substituted with one or more substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a 5-membered heterocyclyl, optionally substituted with one or more substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a 6-membered heterocyclyl, optionally substituted with one or more substituents Q as described herein.

In certain embodiments, $R^{7a}$ is hydrogen. In certain embodiments, $R^{7a}$ is cyano. In certain embodiments, $R^{7a}$ is halo. In certain embodiments, $R^{7a}$ is fluoro, chloro, bromo, or iodo. In certain embodiments, $R^{7a}$ is nitro. In certain embodiments, $R^{7a}$ is $C_{1-6}$ alkyl, optionally substituted with one or more substituents Q as described herein. In certain embodiments, $R^{7a}$ is $C_{2-6}$ alkenyl, optionally substituted with one or more substituents Q as described herein. In certain embodiments, $R^{7a}$ is $C_{2-6}$ alkynyl, optionally substituted with one or more substituents Q as described herein. In certain embodiments, $R^{7a}$ is $C_{3-7}$ cycloalkyl, optionally substituted with one or more substituents Q as described herein. In certain embodiments, $R^{7a}$ is $C_{3-10}$ cycloalkyl, optionally substituted with one or more substituents Q as described herein. In certain embodiments, $R^{7a}$ is $C_{6-14}$ aryl, optionally substituted with one or more substituents Q as described herein. In certain embodiments, $R^{7a}$ is phenyl, optionally substituted with one or more substituents Q as described herein. In certain embodiments, $R^{7a}$ is phenyl, optionally substituted with one or more substituents, each of which is selected independently from the group consisting of fluoro, chloro, bromo, methyl, and methoxy. In certain embodiments, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl. In certain embodiments, $R^{7a}$ is $C_{7-15}$ aralkyl, optionally substituted with one or more substituents Q as described herein. In certain embodiments, $R^{7a}$ is heteroaryl, optionally substituted with one or more substituents Q as described herein. In certain embodiments, $R^{7a}$ is monocyclic heteroaryl, optionally substituted with one or more substituents Q as described herein. In certain embodiments, $R^{7a}$ is 5-membered heteroaryl, optionally substituted with one or more substituents Q as described herein. In certain embodiments, $R^{7a}$ is imidazolyl or pyrozolyl, optionally substituted with one or more substituents Q as described herein. In certain embodiments, $R^{7a}$ is imidazol-1-yl, pyrozol-4-yl, 1-methylpyrozol-4-yl, or 2-methylpyrozol-3-yl. In certain embodiments, $R^{7a}$ is 6-membered heteroaryl, optionally substituted with one or more substituents Q as described herein. In certain embodiments, $R^{7a}$ is pyridinyl, optionally substituted with one or more substituents Q as described herein. In certain embodiments, $R^{7a}$ is pyridin-2-yl, pyridin-3-yl, pyridin-4-yl, 2-methylpyridin-4-yl, or 2-methoxypyridin-4-yl. In certain embodiments, $R^{7a}$ is heterocyclyl, optionally substituted with one or more substituents Q as described herein. In certain embodiments, $R^{7a}$ is monocyclic heterocyclyl, optionally substituted with one or more substituents Q as described herein. In certain embodiments, $R^{7a}$ is 5-membered heterocyclyl, optionally substituted with one or more substituents Q as described herein. In certain embodiments, $R^{7a}$ is 6-membered heterocyclyl, optionally substituted with one or more substituents Q as described herein. In certain embodiments, $R^{7a}$ is piperidinyl or piperazinyl, optionally substituted with one or more substituents Q as described herein. In certain embodiments, $R^{7a}$ is 1-methylpiperidin-4-yl, or 4-methylpiperazin-1-yl. In certain embodiments, $R^{7a}$ is —$C(O)R^{1a}$, wherein $R^{1a}$ is as defined herein. In certain embodiments, $R^{7a}$ is —$C(O)OR^{1a}$, wherein $R^{1a}$ is as defined herein. In certain embodiments, $R^{7a}$ is —$C(O)NR^{1b}R^{1c}$, wherein $R^{1b}$ and $R^{1c}$ are each as defined herein. In certain embodiments, $R^{7a}$ is —$C(NR^{1a})NR^{1b}R^{1c}$, wherein $R^{1a}$, $R^{1b}$, and $R^{1c}$ are each as defined herein. In certain embodiments, $R^{7a}$ is —$OR^{1a}$, wherein $R^{1a}$ is as defined herein. In certain embodiments, $R^1$ is —O—$C_{1-6}$ alkyl, wherein the alkyl is optionally substituted with one or more substituents Q as described herein. In certain embodiments, $R^1$ is methoxy, ethoxy, propoxy, isopropoxy, or 3-dimethylaminopropoxy. In certain embodiments, $R^{7a}$ is —OC(O)$R^{1a}$, wherein $R^{1a}$ is as defined herein. In certain embodiments, $R^{7a}$ is —OC(O)O$R^{1a}$, wherein $R^{1a}$ is h, as defined herein. In certain embodiments, $R^{7a}$ is —OC(O)N$R^{1a}R^{1c}$ wherein $R^{1b}$ and $R^{1c}$ are each as defined herein. In certain embodiments, $R^{7a}$ is —OC(=N$R^{1a}$)N$R^{1b}R^{1c}$, wherein $R^{1a}$, $R^{1b}$, and $R^{1c}$ are each as defined herein. In certain embodiments, $R^{7a}$ is —OS(O)$R^{1a}$, wherein $R^{1a}$ is as defined herein. In certain embodiments, $R^{7a}$ is —OS(O)$_2R^{1a}$, wherein $R^{1a}$ is as defined herein. In certain embodiments, $R^{7a}$ is —OS(O)N$R^{1a}R^{1c}$ wherein $R^{1b}$ and $R^{1c}$ are each as defined herein. In certain embodiments, $R^{7a}$ is —OS(O)$_2$N$R^{1b}R^{1c}$, wherein $R^{1b}$ and $R^{1c}$ are each as defined herein. In certain embodiments, $R^{7a}$ is —N$R^{1b}R^{1c}$, wherein $R^{1b}$ and $R^{1c}$ are each as defined herein. In certain embodiments, $R^{7a}$ is amino (—NH$_2$). In certain embodiments, $R^{7a}$ is —N$R^{1a}$C(O)$R^{1d}$, wherein $R^{1a}$ and $R^{1d}$ are each as defined herein. In certain embodiments, $R^{7a}$ is —N$R^{1a}$C(O)O$R^{1d}$, wherein $R^{1a}$ and $R^{1d}$ are each as defined herein. In certain embodiments, $R^{7a}$ is —N$R^{1a}$C(O)N$R^{1b}R^{1c}$, wherein $R^{1a}$, $R^{1b}$, and $R^{1c}$ are each as defined herein. In certain embodiments, $R^{7a}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{7a}$ is —N$R^{1a}$S(O)$R^{1d}$, wherein $R^{1a}$ and $R^{1d}$ are each as defined herein. In certain embodiments, $R^{7a}$ is —N$R^{1a}$S(O)$_2R^{1d}$, wherein $R^{1a}$ and $R^{1d}$ are each as defined herein. In certain embodiments, $R^{7a}$ is —N$R^{1a}$S(O)N$R^{1b}R^{1c}$, wherein $R^{1a}$, $R^{1b}$, and $R^{1c}$ are each as defined herein. In certain embodiments, $R^{7a}$ is —N$R^{1a}$S(O)$_2$N$R^{1b}R^{1c}$, wherein $R^{1a}$, $R^{1b}$, and $R^{1c}$ are each as defined herein. In certain embodiments, $R^{7a}$ is —S$R^{1a}$, wherein $R^{1a}$ is as defined herein. In certain embodiments, $R^{7a}$ is —S(O)$R^{1a}$, wherein $R^{1a}$ is as defined herein. In certain embodiments, $R^{7a}$ is —S(O)$_2R^{1a}$, wherein $R^{1a}$ is as defined herein. In certain embodiments, $R^{7a}$ is —S(O)N$R^{1b}R^{1c}$, wherein $R^{1b}$ and $R^{1c}$ are each as defined herein. In certain embodiments, $R^{7a}$ is —S(O)$_2$N$R^{1b}R^{1c}$; wherein $R^{1b}$ and $R^{1c}$ are each as defined herein.

In certain embodiments, $R^{7a}$ is phenyl, imidazolyl, pyrozolyl, pyridinyl, pyrimidinyl, pyrrolidinyl, piperidinyl, or piperazinyl, each optionally substituted with one or more substituents Q. In certain embodiments, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments, $R^{7b}$ is hydrogen. In certain embodiments, $R^{7b}$ is cyano. In certain embodiments, $R^{7b}$ is halo. In certain embodiments, $R^{7b}$ is fluoro, chloro, bromo, or iodo. In certain embodiments, $R^{7b}$ is nitro. In certain embodiments, $R^{7b}$ is $C_{1-6}$ alkyl, optionally substituted with one or more substituents Q as described herein. In certain embodiments, $R^{7b}$ is $C_{2-6}$ alkenyl, optionally substituted with one or more substituents Q as described herein. In certain embodiments, $R^{7b}$ is $C_{2-6}$ alkynyl, optionally substituted with one or more substituents Q as described herein. In certain embodiments, $R^{7b}$ is $C_{3-10}$ cycloalkyl, optionally substituted with one or more substituents Q as described herein. In certain embodiments, $R^{7b}$ is $C_{3-7}$ cycloalkyl, optionally substituted with one or more substituents Q as described herein. In certain embodiments, $R^{7b}$ is $C_{6-14}$ aryl, optionally substituted with one or more substituents Q as described herein. In certain embodiments, $R^{7b}$ is $C_{7-15}$ aralkyl, optionally substituted with one or more substituents Q as described herein. In certain embodiments, $R^{7b}$ is heteroaryl, optionally substituted with one or more substituents Q as described herein. In certain embodiments, $R^{7b}$ is heterocyclyl, optionally substituted with one or more substituents Q as described herein.

In certain embodiments, $R^{7b}$ is —C(O)$R^{1a}$, wherein $R^{1a}$ is as defined herein. In certain embodiments, $R^{7b}$ is —C(O)O$R^{1a}$, wherein $R^{1a}$ is as defined herein. In certain embodiments, $R^{7b}$ is —C(O)N$R^{1b}R^{1c}$, wherein $R^{1b}$ and $R^{1c}$ are each as defined herein. In certain embodiments, $R^{7b}$ is —C(N$R^{1a}$)N$R^{1b}R^{1c}$, wherein $R^{1a}$, $R^{1b}$, and $R^{1c}$ are each as defined herein. In certain embodiments, $R^{7b}$ is —O$R^{1a}$, wherein $R^{1a}$ is as defined herein. In certain embodiments, $R^1$ is —O—$C_{1-6}$ alkyl, wherein the alkyl is optionally substituted with one or more substituents Q as described herein. In certain embodiments, $R^1$ is methoxy, ethoxy, propoxy, isopropoxy, or 3-dimethylaminopropoxy. In certain embodiments, $R^{7b}$ is —OC(O)$R^{1a}$, wherein $R^{1a}$ is as defined herein. In certain embodiments, $R^{7b}$ is —OC(O)O$R^{1a}$, wherein $R^{1a}$ is as defined herein. In certain embodiments, $R^{7b}$ is —OC(O)N$R^{1b}R^{1c}$, wherein $R^{1b}$ and $R^{1c}$ are each as defined herein. In certain embodiments, $R^{7b}$ is —OC(=N$R^{1a}$)N$R^{1b}R^{1c}$, wherein $R^{1a}$, $R^{1b}$, and $R^{1c}$ are each as defined herein. In certain embodiments, $R^{7b}$ is —OS(O)$R^{1a}$, wherein $R^{1a}$ is as defined herein. In certain embodiments, $R^{7b}$ is —OS(O)$_2R^{1a}$, wherein $R^{1a}$ is as defined herein. In certain embodiments, $R^{7b}$ is —OS(O)N$R^{1b}R^{1c}$, wherein $R^{1b}$ and $R^{1c}$ are each as defined herein. In certain embodiments, $R^{7b}$ is —OS(O)$_2$N$R^{1b}R^{1c}$, wherein $R^{1b}$ and $R^{1c}$ are each as defined herein. In certain embodiments, $R^{7b}$ is —N$R^{1b}R^{1c}$, wherein $R^{1b}$ and $R^{1c}$ are each as defined herein. In certain embodiments, $R^{7b}$ is amino (—NH$_2$). In certain embodiments, $R^{7b}$ is —N$R^{1a}$C(O)$R^{1d}$, wherein $R^{1a}$ and $R^{1d}$ are each as defined herein. In certain embodiments, $R^{7b}$ is —N$R^{1a}$C(O)O$R^{1d}$, wherein $R^{1a}$ and $R^{1d}$ are each as defined herein. In certain embodiments, $R^{7b}$ is —N$R^{1a}$C(O)N$R^{1b}R^{1c}$, wherein $R^{1a}$, $R^{1b}$, and $R^{1c}$ are each as defined herein. In certain embodiments, $R^{7b}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{7b}$ is —N$R^{1a}$S(O)$R^{1d}$, wherein $R^{1a}$ and $R^{1d}$ are each as defined herein. In certain embodiments, $R^{7b}$ is —N$R^{1a}$S(O)$_2R^{1d}$, wherein $R^{1a}$ and $R^{1d}$ are each as defined herein. In certain embodiments, $R^{7b}$ is —N$R^{1a}$S(O)N$R^{1b}R^{1c}$, wherein $R^{1a}$, $R^{1b}$, and $R^{1c}$ are each as defined herein. In certain embodiments, $R^{7b}$ is —N$R^{1a}$S(O)$_2$N$R^{1b}R^{1c}$, wherein $R^{1a}$, $R^{1b}$, and $R^{1c}$ are each as defined herein. In certain embodiments, $R^{7b}$ is —S$R^{1a}$, wherein $R^{1a}$ is as defined herein. In certain embodiments, $R^{7b}$ is —S(O)$R^{1a}$, wherein $R^{1a}$ is as defined herein. In certain embodiments, $R^{7b}$ is —S(O)$_2R^{1a}$, wherein $R^{1a}$ is as defined herein. In certain embodiments, $R^{7b}$ is —S(O)N$R^{1b}R^{1c}$, wherein $R^{1b}$ and $R^{1c}$ are each as defined herein. In certain embodiments, $R^{7b}$ is —S(O)$_2$N$R^{1b}R^{1c}$; wherein $R^{1b}$ and $R^{1c}$ are each as defined herein.

In certain embodiments, $R^{7b}$ is phenyl, imidazolyl, pyrozolyl, pyridinyl, pyrimidinyl, pyrrolidinyl, piperidinyl, or piperazinyl, each optionally substituted with one or more substituents Q. In certain embodiments, $R^{7b}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments, $R^{7c}$ is hydrogen. In certain embodiments, $R^{7c}$ is cyano. In certain embodiments, $R^{7c}$ is halo. In certain embodiments, $R^{7c}$ is fluoro, chloro, bromo, or iodo. In certain embodiments, $R^{7c}$ is nitro. In certain embodiments, $R^{7c}$ is $C_{1-6}$ alkyl, optionally substituted with one or more substituents Q as described herein. In certain embodiments, $R^{7c}$ is $C_{2-6}$ alkenyl, optionally substituted with one or more substituents Q as described herein. In certain embodiments, $R^{7c}$ is $C_{2-6}$ alkynyl, optionally substituted with one or more substituents Q as described herein. In certain embodiments, $R^{7c}$ is $C_{3-10}$ cycloalkyl, optionally substituted with one or more substituents Q as described herein. In certain embodiments, $R^{7c}$ is $C_{3-7}$ cycloalkyl, optionally substituted with one or more substituents Q as described herein. In certain embodiments, $R^{7c}$ is $C_{6-14}$ aryl, optionally substituted with one or more substituents Q as described herein. In certain embodiments, $R^{7c}$ is $C_{7-15}$ aralkyl, optionally substituted with one or more substituents Q as described herein. In certain embodiments, $R^{7c}$ is heteroaryl, optionally substituted with one or more substituents Q as described herein. In certain embodiments, $R^{7c}$ is heterocyclyl, optionally substituted with one or more substituents Q as described herein.

In certain embodiments, $R^{7c}$ is —C(O)$R^{1a}$, wherein $R^{1a}$ is as defined herein. In certain embodiments, $R^{7c}$ is —C(O)O$R^{1a}$, wherein $R^{1a}$ is as defined herein. In certain embodiments, $R^{7c}$ is —C(O)N$R^{1b}R^{1c}$, wherein $R^{1b}$ and $R^{1c}$ are each as defined herein. In certain embodiments, $R^{7c}$ is —C(N$R^{1a}$)N$R^{1b}R^{1c}$, wherein $R^{1a}$, $R^{1b}$, and $R^{1c}$ are each as defined herein. In certain embodiments, $R^{7c}$ is —O$R^{1a}$, wherein $R^{1a}$ is as defined herein. In certain embodiments, $R^1$ is —O—$C_{1-6}$ alkyl, wherein the alkyl is optionally substituted with one or more substituents Q as described herein. In certain embodiments, $R^1$ is methoxy, ethoxy, propoxy, isopropoxy, or 3-dimethylaminopropoxy. In certain embodiments, $R^{7c}$ is —OC(O)$R^{1a}$, wherein $R^{1a}$ is as defined herein. In certain embodiments, $R^{7c}$ is —OC(O)O$R^{1a}$, wherein $R^{1a}$ is as defined herein. In certain embodiments, $R^{7c}$ is —OC(O)N$R^{1b}R^{1c}$, wherein $R^{1b}$ and $R^{1c}$ are each as defined herein. In certain embodiments, $R^{7c}$ is —OC(=N$R^{1a}$)N$R^{1b}R^{1c}$, wherein $R^{1a}$, $R^{1b}$, and $R^{1c}$ are each as defined herein. In certain embodiments, $R^{7c}$ is —OS(O)$R^{1a}$, wherein $R^{1a}$ is as defined herein. In certain embodiments, $R^{7c}$ is —OS(O)$_2R^{1a}$, wherein $R^{1a}$ is as defined herein. In certain embodiments, $R^{7c}$ is —OS(O)N$R^{1b}R^{1c}$, wherein $R^{1b}$ and $R^{1c}$ are each as defined herein. In certain embodiments, $R^{7c}$ is —OS(O)$_2$N$R^{1b}R^{1c}$, wherein $R^{1b}$ and $R^{1c}$ are each as defined herein. In certain embodiments, $R^{7c}$ is —N$R^{1b}R^{1c}$, wherein $R^{1b}$ and $R^{1c}$ are each as defined herein. In certain embodiments, $R^{7c}$ is amino (—NH$_2$). In certain embodiments, $R^{7c}$ is —N$R^{1a}$C(O)$R^{1d}$, wherein $R^{1a}$ and $R^{1d}$ are each as defined herein. In certain embodiments, $R^{7c}$ is —N$R^{1a}$C(O)O$R^{1d}$, wherein $R^{1a}$ and $R^{1d}$ are each as defined herein. In certain embodiments, $R^{7c}$ is —N$R^{1a}$C(O)N$R^{1b}R^{1c}$, wherein $R^{1a}$, $R^{1b}$, and $R^{1c}$ are each as defined herein. In certain embodiments, $R^{7c}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{7c}$ is —N$R^{1a}$S(O)$R^{1d}$, wherein $R^{1a}$ and $R^{1d}$ are each as defined herein. In certain embodiments, $R^{7c}$ is —N$R^{1a}$S(O)$_2R^{1d}$, wherein $R^{1a}$ and $R^{1d}$ are each as defined herein. In certain embodiments, $R^{7c}$ is —N$R^{1a}$S(O)N$R^{1b}R^{1c}$, wherein $R^{1a}$, $R^{1b}$, and $R^{1c}$ are each as defined herein. In certain embodiments, $R^{7c}$ is —N$R^{1a}$S(O)$_2$N$R^{1b}R^{1c}$, wherein $R^{1a}$, $R^{1b}$, and $R^{1c}$ are each as defined herein. In certain embodiments, $R^{7c}$ is —S$R^{1a}$, wherein $R^{1a}$ is as defined herein. In certain embodiments, $R^{7c}$ is —S(O)$R^{1a}$, wherein $R^{1a}$ is as defined herein. In certain embodiments, $R^{7c}$ is —S(O)$_2R^{1a}$, wherein $R^{1a}$ is as defined herein. In certain embodiments, $R^{7c}$ is —S(O)N$R^{1b}R^{1c}$, wherein $R^{1b}$ and $R^{1c}$ are each as defined herein. In certain embodiments, $R^{7c}$ is —S(O)$_2$N$R^{1b}R^{1c}$; wherein $R^{1b}$ and $R^{1c}$ are each as defined herein.

In certain embodiments, $R^{7c}$ is phenyl, imidazolyl, pyrozolyl, pyridinyl, pyrimidinyl, pyrrolidinyl, piperidinyl, or piperazinyl, each optionally substituted with one or more substituents Q. In certain embodiments, $R^{7c}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments, $R^{7d}$ is hydrogen. In certain embodiments, $R^{7d}$ is cyano. In certain embodiments, $R^{7d}$ is halo. In certain embodiments, $R^{7d}$ is fluoro, chloro, bromo, or iodo. In certain embodiments, $R^{7d}$ is nitro. In certain embodiments, $R^{7d}$ is $C_{1-6}$ alkyl, optionally substituted with one or more substituents Q as described herein. In certain embodiments, $R^{7d}$ is $C_{2-6}$ alkenyl, optionally substituted with one or more substituents Q as described herein. In certain embodiments, $R^{7d}$ is $C_{2-6}$ alkynyl, optionally substituted with one or more substituents Q as described herein. In certain embodiments, $R^{7d}$ is $C_{3-10}$ cycloalkyl, optionally substituted with one or more substituents Q as described herein. In certain embodiments, $R^{7d}$ is $C_{3-7}$ cycloalkyl, optionally substituted with one or more substituents Q as described herein. In certain embodiments, $R^{7d}$ is $C_{6-14}$ aryl, optionally substituted with one or more substituents Q as described herein. In certain embodiments, $R^{7d}$ is $C_{7-15}$ aralkyl, optionally substituted with one or more substituents Q as described herein. In certain embodiments, $R^{7d}$ is heteroaryl, optionally substituted with one or more substituents Q as described herein. In certain embodiments, $R^{7d}$ is heterocyclyl, optionally substituted with one or more substituents Q as described herein.

In certain embodiments, $R^{7d}$ is —C(O)$R^{1a}$, wherein $R^{1a}$ is as defined herein. In certain embodiments, $R^{7d}$ is —C(O)O$R^{1a}$, wherein $R^{1a}$ is as defined herein. In certain embodiments, $R^{7d}$ is —C(O)N$R^{1b}R^{1c}$, wherein $R^{1b}$ and $R^{1c}$ are each as defined herein. In certain embodiments, $R^{7d}$ is —C(N$R^{1a}$)N$R^{1b}R^{1c}$, wherein $R^{1a}$, $R^{1b}$, and $R^{1c}$ are each as defined herein. In certain embodiments, $R^{7d}$ is —O$R^{1a}$, wherein $R^{1a}$ is as defined herein. In certain embodiments, $R^1$ is —O—$C_{1-6}$ alkyl, wherein the alkyl is optionally substituted with one or more substituents Q as described herein. In certain embodiments, $R^1$ is methoxy, ethoxy, propoxy, isopropoxy, or 3-dimethylaminopropoxy. In certain embodiments, $R^{7d}$ is —OC(O)$R^{1a}$, wherein $R^{1a}$ is as defined herein. In certain embodiments, $R^{7d}$ is —OC(O)O$R^{1a}$, wherein $R^{1a}$ is as defined herein. In certain embodiments, $R^{7d}$ is —OC(O)N$R^{1b}R^{1c}$, wherein $R^{1b}$ and $R^{1c}$ are each as defined herein. In certain embodiments, $R^{7d}$ is —OC(=N$R^{1a}$)N$R^{1b}R^{1c}$, wherein $R^{1a}$, $R^{1b}$, and $R^{1c}$ are each as defined herein. In certain embodiments, $R^{7d}$ is —OS(O)$R^{1a}$, wherein $R^{1a}$ is as defined herein. In certain embodiments, $R^{7d}$ is —OS(O)$_2R^{1a}$, wherein $R^{1a}$ is as defined herein. In certain embodiments, $R^{7d}$ is —OS(O)N$R^{1b}R^{1c}$, wherein $R^{1b}$ and $R^{1c}$ are each as defined herein. In certain embodiments, $R^{7d}$ is —OS(O)$_2$N$R^{1b}R^{1c}$, wherein $R^{1b}$ and $R^{1c}$ are each as defined herein. In certain embodiments, $R^{7d}$ is —N$R^{1b}R^{1c}$, wherein $R^{1b}$ and $R^{1c}$ are each as defined herein. In certain embodiments, $R^{7d}$ is amino (—NH$_2$). In certain embodiments, $R^{7d}$ is —N$R^{1a}$C(O)$R^{1d}$, wherein $R^{1a}$ and $R^{1d}$ are each as defined herein. In certain embodiments, $R^{7d}$ is —N$R^{1a}$C(O)O$R^{1d}$, wherein $R^{1a}$ and $R^{1d}$ are each as defined herein. In certain embodiments, $R^{7d}$ is —N$R^{1a}$C(O)N$R^{1b}R^{1c}$, wherein $R^{1a}$, $R^{1b}$, and $R^{1c}$ are each as defined herein. In certain embodiments, $R^{7d}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{7d}$ is —N$R^{1a}$S(O)$R^{1d}$, wherein $R^{1a}$ and $R^{1d}$ are each as defined herein. In certain embodiments, $R^{7d}$ is —N$R^{1a}$S(O)$_2R^{1d}$, wherein $R^{1a}$ and $R^{1d}$ are each as defined herein. In certain embodiments, $R^{7d}$ is —N$R^{1a}$S(O)N$R^{1b}R^{1c}$, wherein $R^{1a}$, $R^{1b}$, and $R^{1c}$ are each as defined herein. In certain embodiments, $R^{7d}$ is —N$R^{1a}$S(O)$_2$N$R^{1b}R^{1c}$, wherein $R^{1a}$, $R^{1b}$, and $R^{1c}$ are each as defined herein. In certain embodiments, $R^{7d}$ is —S$R^{1a}$, wherein $R^{1a}$ is as defined herein. In certain embodiments, $R^{7d}$ is —S(O)$R^{1a}$, wherein $R^{1a}$ is as defined herein. In certain embodiments, $R^{7d}$ is —S(O)$_2R^{1a}$, wherein $R^{1a}$ is as defined herein. In certain embodiments, $R^{7d}$ is —S(O)N$R^{1b}R^{1c}$, wherein $R^{1b}$ and $R^{1c}$ are each as defined herein. In certain embodiments, $R^{7d}$ is —S(O)$_2$N$R^{1b}R^{1c}$; wherein $R^{1b}$ and $R^{1c}$ are each as defined herein.

In certain embodiments, $R^{7d}$ is phenyl, imidazolyl, pyrozolyl, pyridinyl, pyrimidinyl, pyrrolidinyl, piperidinyl, or piperazinyl, each optionally substituted with one or more substituents Q. In certain embodiments, $R^{7d}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments, $R^{7e}$ is hydrogen. In certain embodiments, $R^{7e}$ is cyano. In certain embodiments, $R^{7e}$ is halo. In certain embodiments, $R^{7e}$ is fluoro, chloro, bromo, or iodo. In certain embodiments, $R^{7e}$ is nitro. In certain embodiments, $R^{7e}$ is $C_{1-6}$ alkyl, optionally substituted with one or more substituents Q as described herein. In certain embodiments, $R^{7e}$ is $C_{2-6}$ alkenyl, optionally substituted with one or more substituents Q as described herein. In certain embodiments, $R^{7e}$ is $C_{2-6}$ alkynyl, optionally substituted with one or more substituents Q as described herein. In certain embodiments, $R^{7e}$ is $C_{3-10}$ cycloalkyl, optionally substituted with one or more substituents Q as described herein. In certain embodiments, $R^{7e}$ is $C_{3-7}$ cycloalkyl, optionally substituted with one or more substituents Q as described herein. In certain embodiments, $R^{7e}$ is $C_{6-14}$ aryl, optionally substituted with one or more substituents Q as described herein. In certain embodiments, $R^{7e}$ is $C_{7-15}$ aralkyl, optionally substituted with one or more substituents Q as described herein. In certain embodiments, $R^{7e}$ is heteroaryl, optionally substituted with one or more substituents Q as described herein. In certain embodiments, $R^{7e}$ is heterocyclyl, optionally substituted with one or more substituents Q as described herein.

In certain embodiments, $R^{7e}$ is —C(O)$R^{1a}$, wherein $R^{1a}$ is as defined herein. In certain embodiments, $R^{7e}$ is —C(O)O$R^{1a}$, wherein $R^{1a}$ is as defined herein. In certain embodiments, $R^{7e}$ is —C(O)N$R^{1b}R^{1c}$, wherein $R^{1b}$ and $R^{1c}$ are each as defined herein. In certain embodiments, $R^{7e}$ is —C(N$R^{1a}$)N$R^{1b}R^{1c}$, wherein $R^{1a}$, $R^{1b}$, and $R^{1c}$ are each as defined herein. In certain embodiments, $R^{7e}$ is —O$R^{1a}$, wherein $R^{1a}$ is as defined herein. In certain embodiments, $R^1$ is —O—$C_{1-6}$ alkyl, wherein the alkyl is optionally substituted with one or more substituents Q as described herein. In certain embodiments, $R^1$ is methoxy, ethoxy, propoxy, isopropoxy, or 3-dimethylaminopropoxy. In certain embodiments, $R^{7e}$ is —OC(O)$R^{1a}$, wherein $R^{1a}$ is as defined herein. In certain embodiments, $R^{7e}$ is —OC(O)O$R^{1a}$, wherein $R^{1a}$ is as defined herein. In certain embodiments, $R^{7e}$ is —OC(O)N$R^{1a}R^{1c}$, wherein $R^{1b}$ and $R^{1c}$ are each as defined herein. In certain embodiments, $R^{7e}$ is —OC(=N$R^{1a}$)N$R^{1b}R^{1c}$, wherein $R^{1a}$, $R^{1b}$, and $R^{1c}$ are each as defined herein. In certain embodiments, $R^{7e}$ is —OS(O)$R^{1a}$, wherein $R^{1a}$ is as defined herein. In certain embodiments, $R^{7e}$ is —OS(O)$_2R^{1a}$, wherein $R^{1a}$ is as defined herein. In certain embodiments, $R^{7e}$ is —OS(O)N$R^{1a}R^{1c}$, wherein $R^{1b}$ and $R^{1c}$ are each as defined herein. In certain embodiments, $R^{7e}$ is —OS(O)$_2$N$R^{1b}R^{1c}$, wherein $R^{1b}$ and $R^{1c}$ are each as defined herein. In certain embodiments, $R^{7e}$ is —N$R^{1b}R^{1c}$, wherein $R^{1b}$ and $R^{1c}$ are each as defined herein. In certain embodiments, $R^{7e}$ is amino (—NH$_2$). In certain embodiments, $R^{7e}$ is —N$R^{1a}$C(O)$R^{1d}$, wherein $R^{1a}$ and $R^{1d}$ are each as defined herein. In certain embodiments, $R^{7e}$ is —N$R^{1a}$C(O)O$R^{1d}$, wherein $R^{1a}$ and $R^{1d}$ are each as defined herein. In certain embodiments, $R^{7e}$ is —N$R^{1a}$C(O)N$R^{1b}R^{1c}$, wherein $R^{1a}$, $R^{1b}$, and $R^{1c}$ are each as defined herein. In certain embodiments, $R^{7e}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{7e}$ is —N$R^{1a}$S(O)$R^{1d}$, wherein $R^{1a}$ and $R^{1d}$ are each as defined herein. In certain embodiments, $R^{7e}$ is —N$R^{1a}$S(O)$_2R^{1d}$, wherein $R^{1a}$ and $R^{1d}$ are each as defined herein. In certain embodiments, $R^{7e}$ is —N$R^{1a}$S(O)N$R^{1b}R^{1c}$, wherein $R^{1a}$, $R^{1b}$, and $R^{1c}$ are each as defined herein. In certain embodiments, $R^{7e}$ is —N$R^{1a}$S(O)$_2$N$R^{1b}R^{1c}$, wherein $R^{1a}$, $R^{1b}$, and $R^{1c}$ are each as defined herein. In certain embodiments, $R^{7e}$ is —S$R^{1a}$, wherein $R^{1a}$ is as defined herein. In certain embodiments, $R^{7e}$ is —S(O)$R^{1a}$, wherein $R^{1a}$ is as defined herein. In certain embodiments, $R^{7e}$ is —S(O)$_2R^{1a}$, wherein $R^{1a}$ is as defined herein. In certain embodiments, $R^{7e}$ is —S(O)N$R^{1b}R^{1c}$, wherein $R^{1b}$ and $R^{1c}$ are each as defined herein. In certain embodiments, $R^{7e}$ is —S(O)$_2$N$R^{1b}R^{1c}$; wherein $R^{1b}$ and $R^{1c}$ are each as defined herein.

In certain embodiments, $R^{7e}$ is phenyl, imidazolyl, pyrozolyl, pyridinyl, pyrimidinyl, pyrrolidinyl, piperidinyl, or piperazinyl, each optionally substituted with one or more substituents Q. In certain embodiments, $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments, $R^{7a}$ and $R^{7b}$ together with the carbon atoms to which they are attached form $C_{3-10}$ cycloalkenyl, $C_{6-14}$ aryl, heteroaryl, or heterocyclyl, each optionally substituted with one or more substituents Q. In certain embodiments, $R^{7a}$ and $R^{7b}$ together with the carbon atoms to which they are attached form $C_{3-10}$ cycloalkenyl, optionally substituted with one or more substituents Q. In certain embodiments, $R^{7a}$ and $R^{7b}$ together with the carbon atoms to which they are attached form cyclohexenyl, optionally substituted with one or more substituents Q. In certain embodiments, $R^{7a}$ and $R^{7b}$ together with the carbon atoms to which they are attached form $C_{6-14}$ aryl, optionally substituted with one or more substituents Q. In certain embodiments, $R^{7a}$ and $R^{7b}$ together with the carbon atoms to which they are attached form phenyl, optionally substituted with one or more substituents Q. In certain embodiments, $R^{7a}$ and $R^{7b}$ together with the carbon atoms to which they are attached form heteroaryl, optionally substituted with one or more substituents Q. In certain embodiments, $R^{7a}$ and $R^{7b}$ together with the carbon atoms to which they are attached form monocyclic heteroaryl, optionally substituted with one or more substituents Q. In certain embodiments, $R^{7a}$ and $R^{7b}$ together with the carbon atoms to which they are attached form 5- or 6-membered heteroaryl, optionally substituted with one or more substituents Q. In certain embodiments, $R^{7a}$ and $R^{7b}$ together with the carbon atoms to which they are attached form bicyclic heteroaryl, optionally substituted with one or more substituents Q. In certain embodiments, $R^{7a}$ and $R^{7b}$ together with the carbon atoms to which they are attached form heterocyclyl, optionally substituted with one or more substituents Q. In certain embodiments, $R^{7a}$ and $R^{7b}$ together with the carbon atoms to which they are attached form monocyclic heterocyclyl, optionally substituted with one or more substituents Q. In certain embodiments, $R^{7a}$ and $R^{7b}$ together with the carbon atoms to which they are attached form 5- or 6-membered heterocyclyl, optionally substituted with one or more substituents Q. In certain embodiments, $R^{7a}$ and $R^{7b}$ together with the carbon atoms to which they are attached form bicyclic heterocyclyl, optionally substituted with one or more substituents Q.

In certain embodiments, $R^{7b}$ and $R^{7a}$ together with the carbon atoms to which they are attached form $C_{3-10}$ cycloalkenyl, $C_{6-14}$ aryl, heteroaryl, or heterocyclyl, each optionally substituted with one or more substituents Q. In certain embodiments, $R^{7b}$ and $R^{7a}$ together with the carbon atoms to which they are attached form $C_{3-10}$ cycloalkenyl, optionally substituted with one or more substituents Q. In certain embodiments, $R^{7b}$ and $R^{7a}$ together with the carbon atoms to which they are attached form cyclohexenyl, optionally substituted with one or more substituents Q. In certain embodiments, $R^{7b}$ and $R^{7a}$ together with the carbon atoms to which they are attached form $C_{6-14}$ aryl, optionally substituted with one or more substituents Q. In certain embodiments, $R^{7b}$ and $R^{7a}$ together with the carbon atoms to which they are attached form phenyl, optionally substituted with one or more substituents Q. In certain embodiments, $R^{7b}$ and $R^{7a}$ together with the carbon atoms to which they are attached form heteroaryl, optionally substituted with one or more substituents Q. In certain embodiments, $R^{7b}$ and $R^{7a}$ together with the carbon atoms to which they are attached form monocyclic heteroaryl, optionally substituted with one or more substituents Q. In certain embodiments, $R^{7b}$ and $R^{7a}$ together with the carbon atoms to which they are attached form 5- or 6-membered heteroaryl, optionally substituted with one or more substituents Q. In certain embodiments, $R^{7b}$ and $R^{7a}$ together with the carbon atoms to which they are attached form bicyclic heteroaryl, optionally substituted with one or more substituents Q. In certain embodiments, $R^{7b}$ and $R^{7a}$ together with the carbon atoms to which they are attached form heterocyclyl, optionally substituted with one or more substituents Q. In certain embodiments, $R^{7b}$ and $R^{7a}$ together with the carbon atoms to which they are attached form monocyclic heterocyclyl, optionally substituted with one or more substituents Q. In certain embodiments, $R^{7b}$ and $R^{7a}$ together with the carbon atoms to which they are attached form 5- or 6-membered heterocyclyl, optionally substituted with one or more substituents Q. In certain embodiments, $R^{7b}$ and $R^{7a}$ together with the carbon atoms to which they are attached form bicyclic heterocyclyl, optionally substituted with one or more substituents Q.

In certain embodiments, $R^{7c}$ and $R^{7d}$ together with the carbon atoms to which they are attached form $C_{3-10}$ cycloalkenyl, $C_{6-14}$ aryl, heteroaryl, or heterocyclyl, each optionally substituted with one or more substituents Q. In certain embodiments, $R^{7c}$ and $R^{7d}$ together with the carbon atoms to which they are attached form $C_{3-10}$ cycloalkenyl, optionally substituted with one or more substituents Q. In certain embodiments, $R^{7c}$ and $R^{7d}$ together with the carbon atoms to which they are attached form cyclohexenyl, optionally substituted with one or more substituents Q. In certain embodiments, $R^{7c}$ and $R^{7d}$ together with the carbon atoms to which they are attached form $C_{6-14}$ aryl, optionally substituted with one or more substituents Q. In certain embodiments, $R^{7c}$ and $R^{7d}$ together with the carbon atoms to which they are attached form phenyl, optionally substituted with one or more substituents Q. In certain embodiments, $R^{7c}$ and $R^{7d}$ together with the carbon atoms to which they are attached form heteroaryl, optionally substituted with one or more substituents Q. In certain embodiments, $R^{7c}$ and $R^{7d}$ together with the carbon atoms to which they are attached form monocyclic heteroaryl, optionally substituted with one or more substituents Q. In certain embodiments, $R^{7c}$ and $R^{7d}$ together with the carbon atoms to which they are attached form 5- or 6-membered heteroaryl, optionally substituted with one or more substituents Q. In certain embodiments, $R^{7c}$ and $R^{7d}$ together with the carbon atoms to which they are attached form bicyclic heteroaryl, optionally substituted with one or more substituents Q. In certain embodiments, $R^{7c}$ and $R^{7d}$ together with the carbon atoms to which they are attached form heterocyclyl, optionally substituted with one or more substituents Q. In certain embodiments, $R^{7c}$ and $R^{7d}$ together with the carbon atoms to which they are attached form monocyclic heterocyclyl, optionally substituted with one or more substituents Q. In certain embodiments, $R^{7c}$ and $R^{7d}$ together with the carbon atoms to which they are attached form 5- or 6-membered heterocyclyl, optionally substituted with one or more substituents Q. In certain embodiments, $R^{7c}$ and $R^{7d}$ together with the carbon atoms to which they are attached form bicyclic heterocyclyl, optionally substituted with one or more substituents Q.

In certain embodiments, $R^{7d}$ and $R^{7e}$ together with the carbon atoms to which they are attached form $C_{3-10}$ cycloalkenyl, $C_{6-14}$ aryl, heteroaryl, or heterocyclyl, each optionally substituted with one or more substituents Q. In certain embodiments, $R^{7d}$ and $R^{7e}$ together with the carbon atoms to which they are attached form $C_{3-10}$ cycloalkenyl, optionally substituted with one or more substituents Q. In certain embodiments, $R^{7d}$ and $R^{7e}$ together with the carbon atoms to which they are attached form cyclohexenyl, optionally substituted with one or more substituents Q. In certain embodiments, $R^{7d}$ and $R^{7e}$ together with the carbon atoms to which they are attached form $C_{6-14}$ aryl, optionally substituted with one or more substituents Q. In certain embodiments, $R^{7d}$ and $R^{7e}$ together with the carbon atoms to which they are attached form phenyl, optionally substituted with one or more substituents Q. In certain embodiments, $R^{7d}$ and $R^{7e}$ together with the carbon atoms to which they are attached form heteroaryl, optionally substituted with one or more substituents Q. In certain embodiments, $R^{7d}$ and $R^{7e}$ together with the carbon atoms to which they are attached form monocyclic heteroaryl, optionally substituted with one or more substituents Q. In certain embodiments, $R^{7d}$ and $R^{7e}$ together with the carbon atoms to which they are attached form 5- or 6-membered heteroaryl, optionally substituted with one or more substituents Q. In certain embodiments, $R^{7d}$ and $R^{7e}$ together with the carbon atoms to which they are attached form bicyclic heteroaryl, optionally substituted with one or more substituents Q. In certain embodiments, $R^{7d}$ and $R^{7e}$ together with the carbon atoms to which they are attached form heterocyclyl, optionally substituted with one or more substituents Q. In certain embodiments, $R^{7d}$ and $R^{7e}$ together with the carbon atoms to which they are attached form monocyclic heterocyclyl, optionally substituted with one or more substituents Q. In certain embodiments, $R^{7d}$ and $R^{7e}$ together with the carbon atoms to which they are attached form 5- or 6-membered heterocyclyl, optionally substituted with one or more substituents Q. In certain embodiments, $R^{7d}$ and $R^{7e}$ together with the carbon atoms to which they are attached form bicyclic heterocyclyl, optionally substituted with one or more substituents Q.

In certain embodiments, m is 0. In certain embodiments, m is 1.

In certain embodiments, n is 0. In certain embodiments, n is 1. In certain embodiments, n is 2. In certain embodiments, n is 3. In certain embodiments, n is 4. In certain embodiments, n is 0, 1, or 2. In certain embodiments, n is 0, 1, 2, or 3. In certain embodiments, n is 1, 2, or 3. In certain embodiments, n is 1 or 2.

In certain embodiments, m is 0, and n is 0, 1, 2, or 3. In certain embodiments, m is 0, n is 0, 1, or 2. In certain embodiments, m is 0, n is 0 or 1. In certain embodiments, m is 0, n is 0. In certain embodiments, m is 0, n is 1. In certain embodiments, m is 1, n is 0, 1, 2, or 3. In certain embodiments, m is 1, n is 0, 1, or 2. In certain embodiments, m is 1, n is 0 or 1. In certain embodiments, m is 1, n is 0. In certain embodiments, m is 1, n is 1.

In specific embodiments, m is 0, n is 1, and $R^{5a}$ and $R^{5b}$ are each methyl.

In certain embodiments, X is N In certain embodiments, X is $CR^X$, wherein $R^X$ is as defined herein. In certain embodiments, X is CH.

In certain embodiments, Y is N In certain embodiments, Y is $CR^X$, wherein $R^X$ is as defined herein. In certain embodiments, Y is CH.

In certain embodiments, Z is N In certain embodiments, Z is $CR^X$, wherein $R^X$ is as defined herein. In certain embodiments, Z is CH.

In certain embodiments, X, Y, and Z are N. In certain embodiments, X and Y are N, and Z is CH. In certain embodiments, X and Z are N, and Y is CH. In certain embodiments, Y and Z are N, and X is CH.

In certain embodiments, the compound provided herein is not 4-(2-(difluoromethyl)-1H-benzo[d]imidazol-1-yl)-6-morpholino-N-(2-phenyl-2-(pyrrolidin-1-yl)ethyl)-1,3,5-triazin-2-amine. In certain embodiments, the compound provided herein is not 6-(2-(difluoromethyl)-1H-benzo[d]imidazol-1-yl)-N-(1-(4-4R)-3-(methoxymethyl)morpholino)phenyl)ethyl)-2-morpholinopyrimidin-4-amine.

In certain embodiments, when X, Y, and Z are N, and $R^{5a}$ is hydrogen, $R^{5b}$ is not heterocyclyl. In certain embodiments, when X, Y, and Z are N, and $R^{5a}$ is hydrogen, $R^{5b}$ is not 5-membered heterocyclyl. In certain embodiments, when X, Y, and Z are N, and $R^{5a}$ is hydrogen, $R^{5b}$ is not pyrrolidinyl. In certain embodiments, when X, Y, and Z are N, and $R^{5a}$ is hydrogen, $R^{5b}$ is not pyrrolidin-1-yl.

In certain embodiments, when X and Z are N, Y is CH, and $R^{5a}$ is hydrogen, $R^{5b}$ is morpholino-substituted pheny. In certain embodiments, when X and Z are N, Y is CH, and $R^{5a}$ is hydrogen, $R^{5b}$ is not 4-((R)-3-(methoxymethyl)morpholino)phenyl.

In one embodiment, provided herein is a compound selected from:

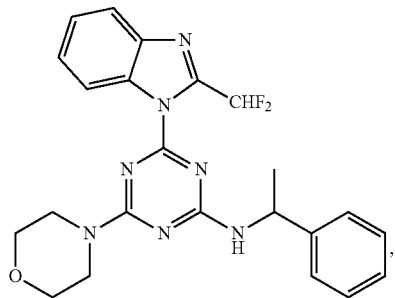

A1

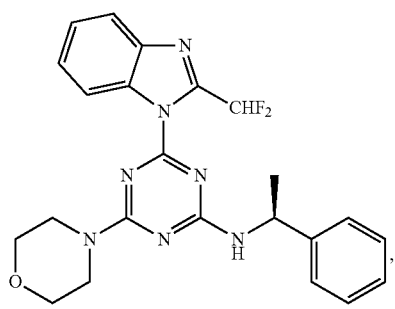

A2

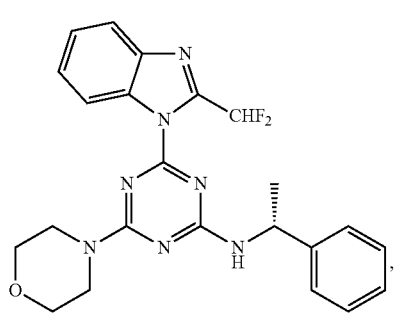

A3

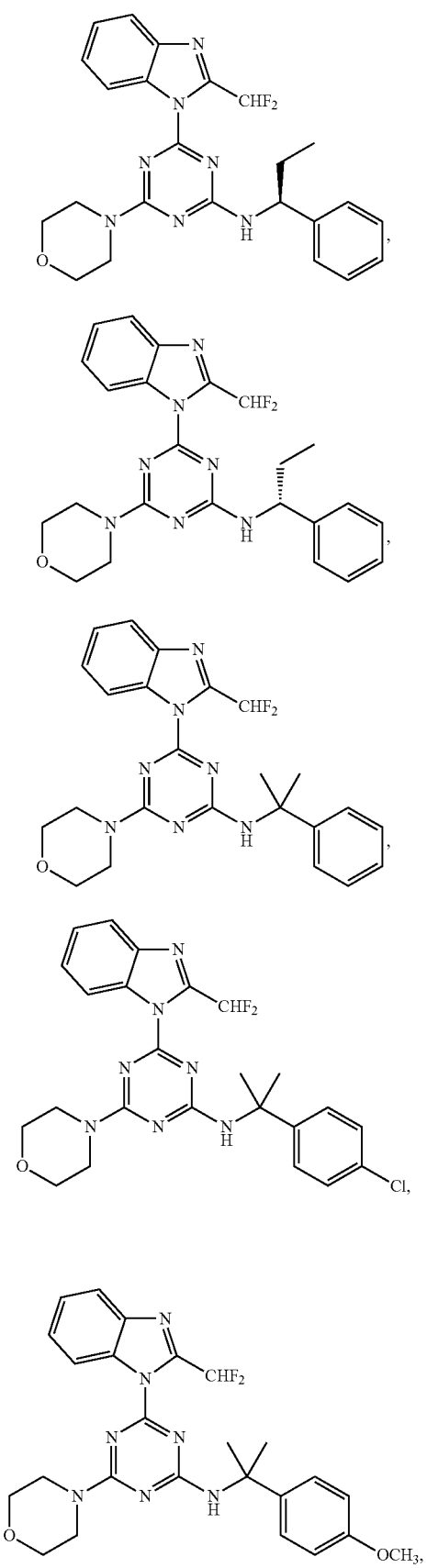
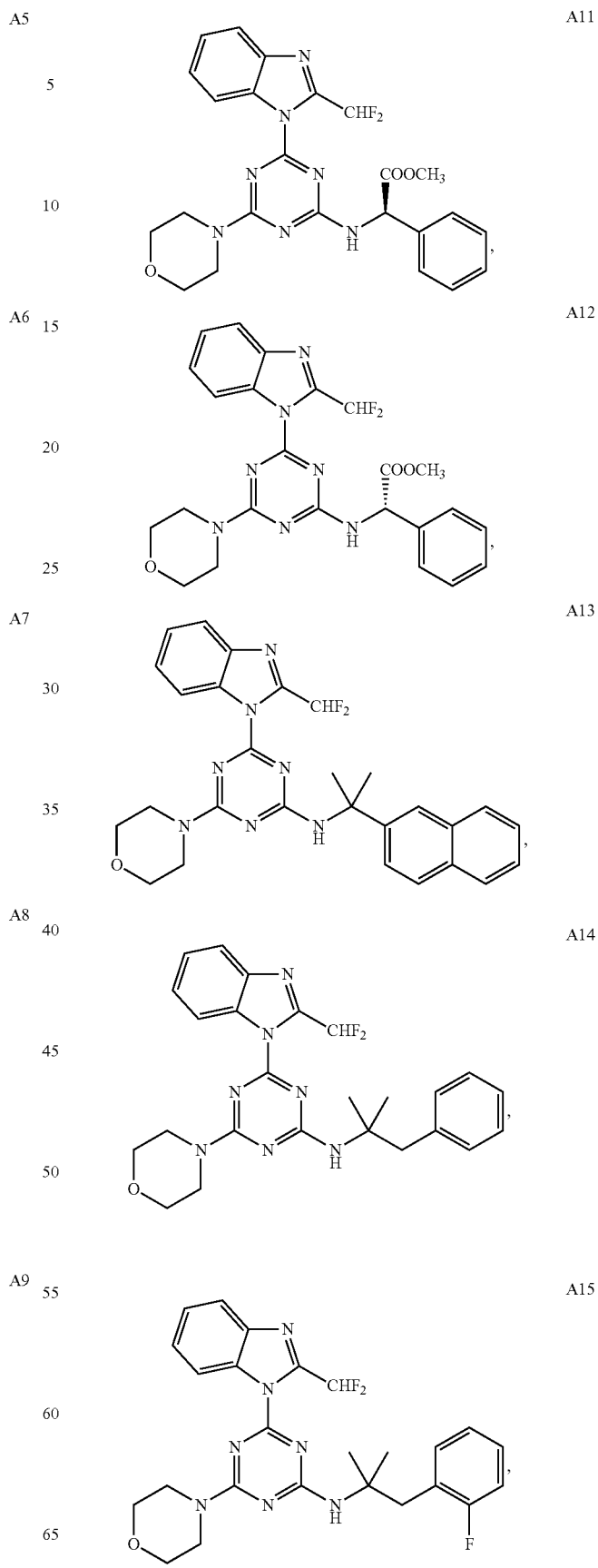

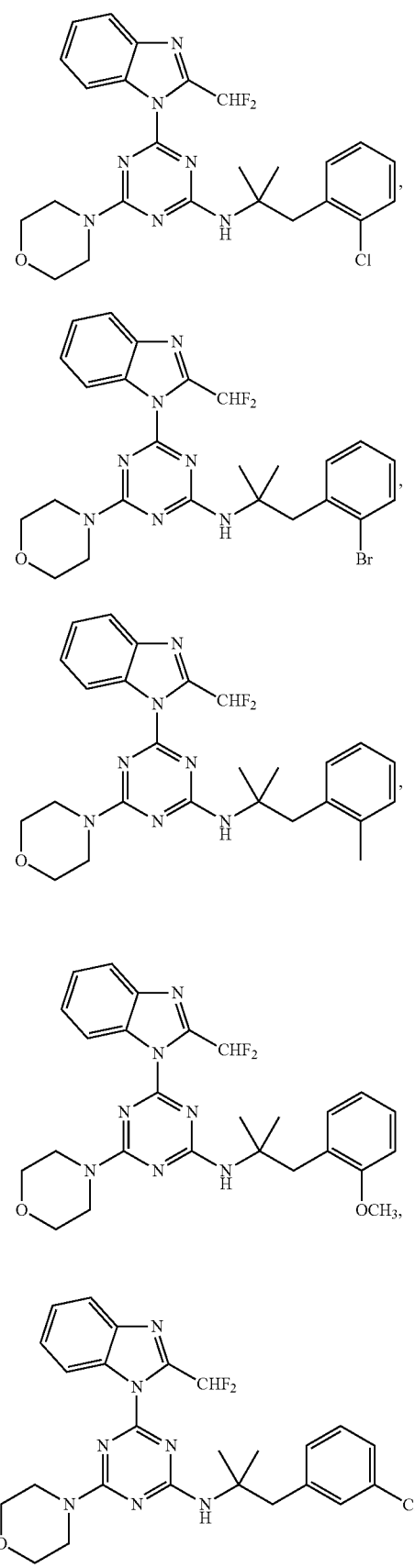
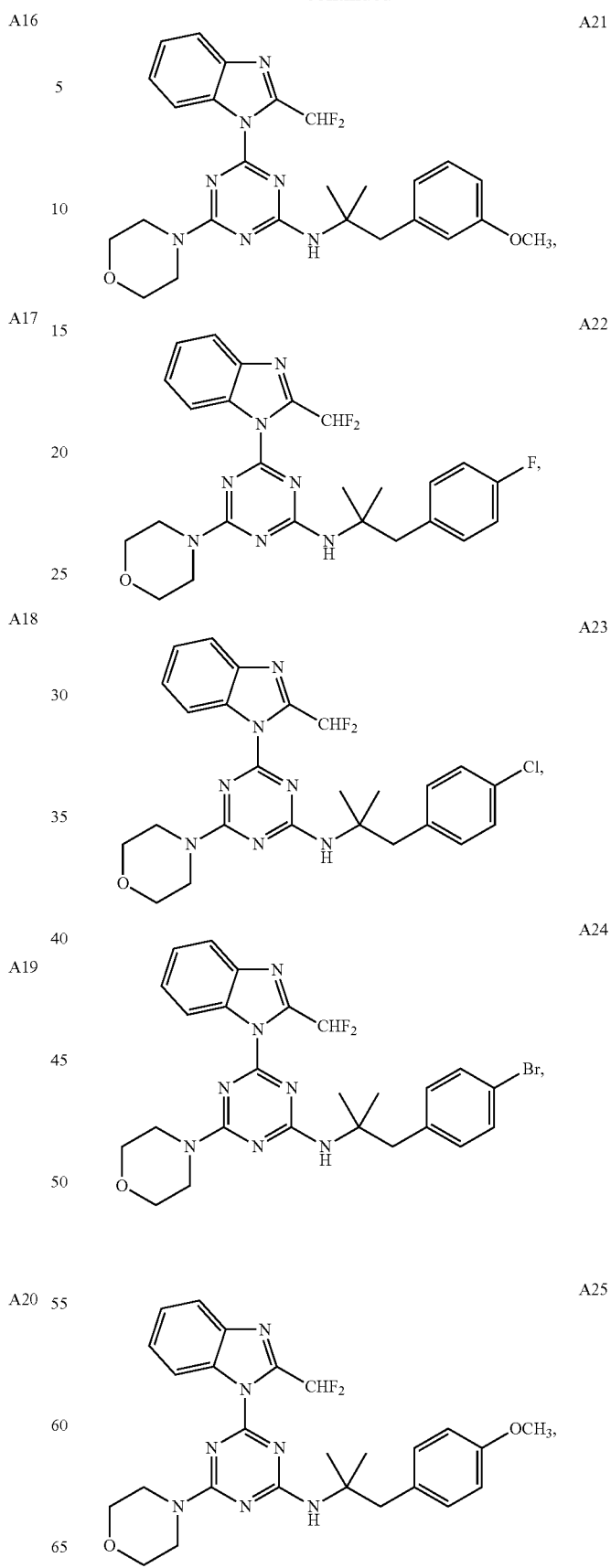

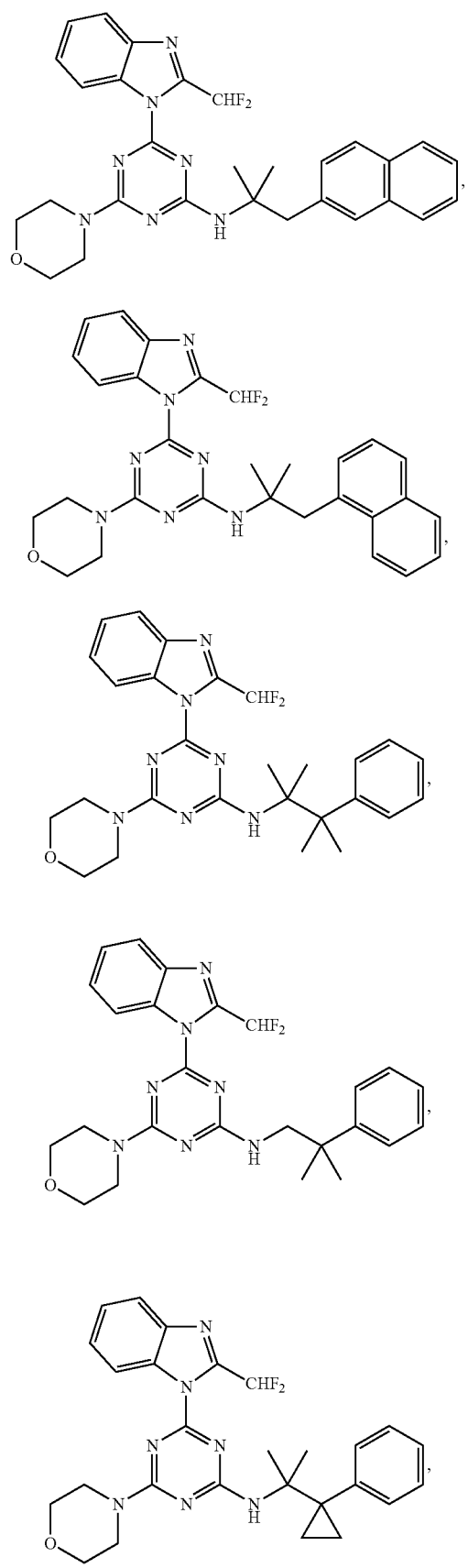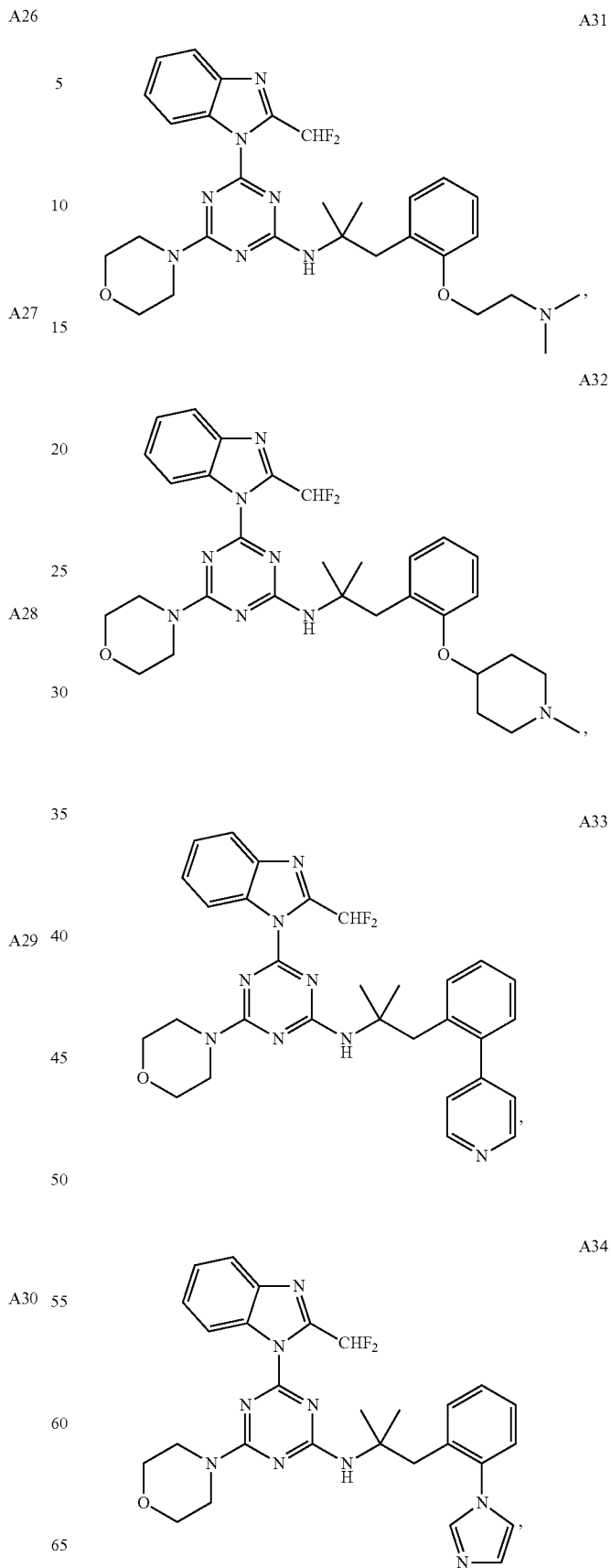

-continued
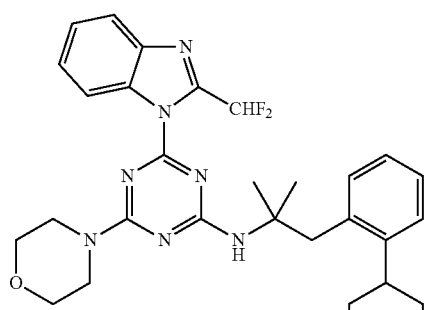
A35
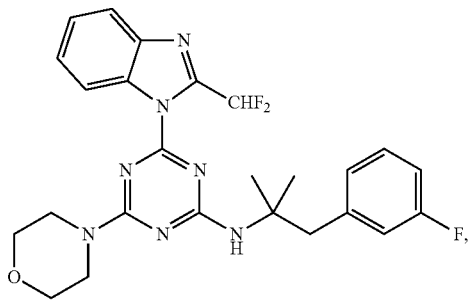
A39
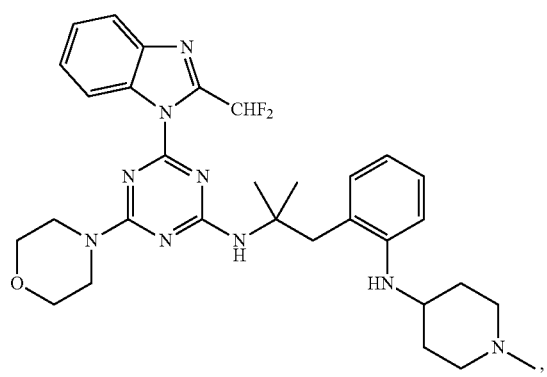
A36
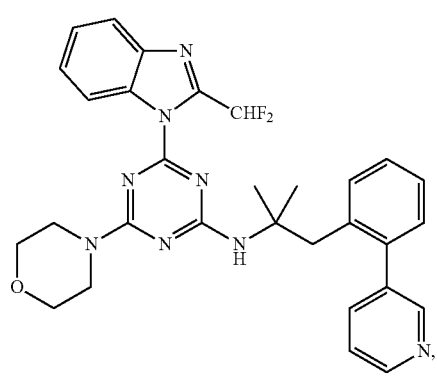
A40
A37
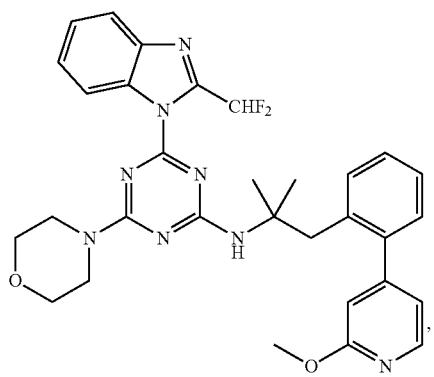
A41
A38
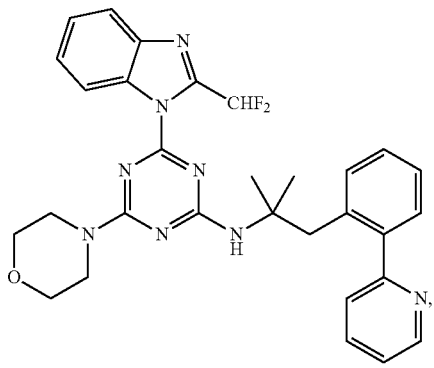
A42

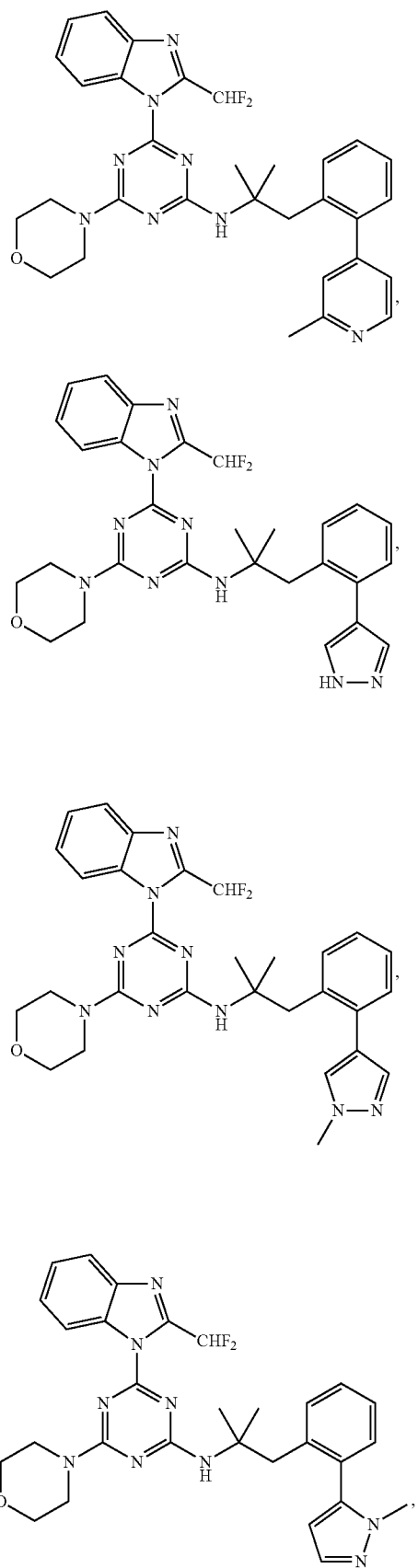
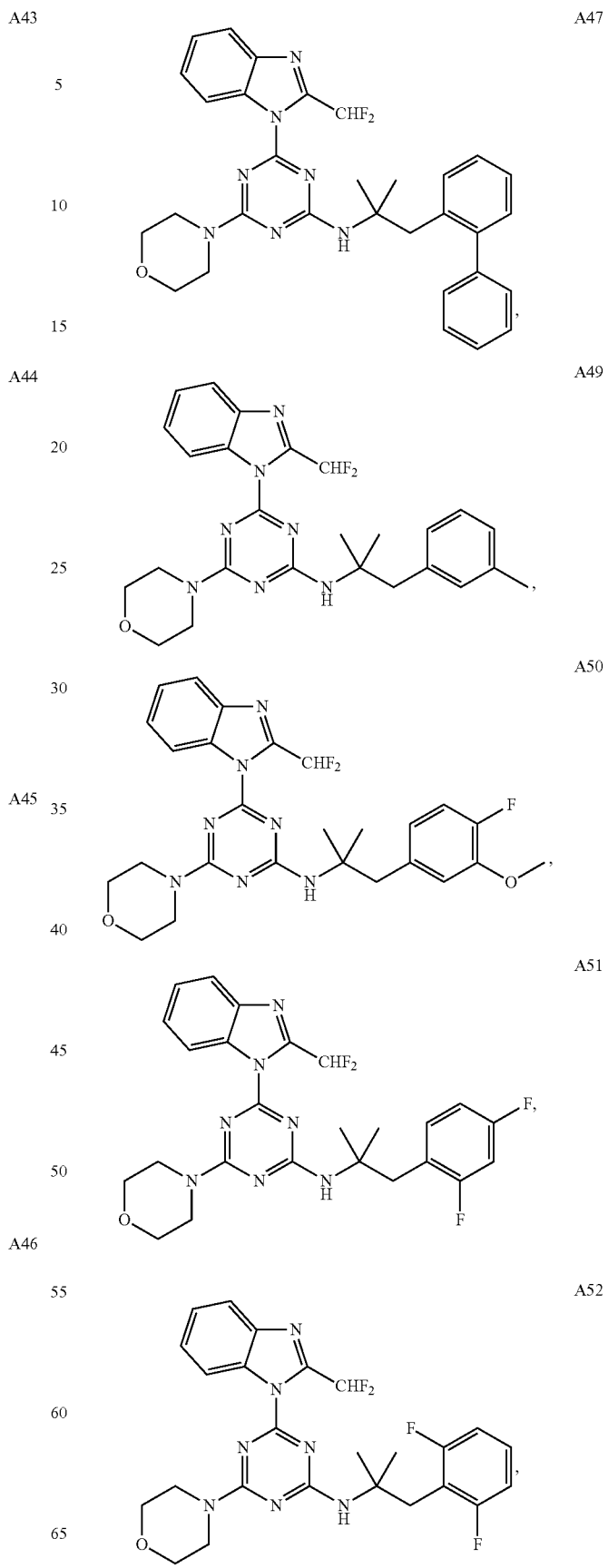

107
-continued
A59
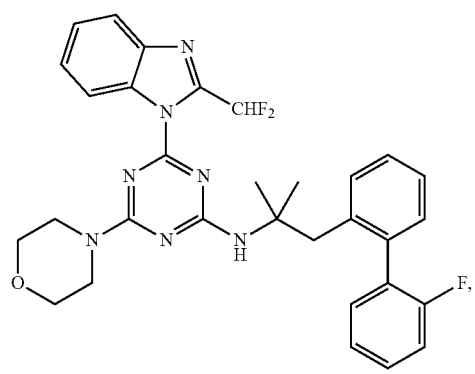
A60
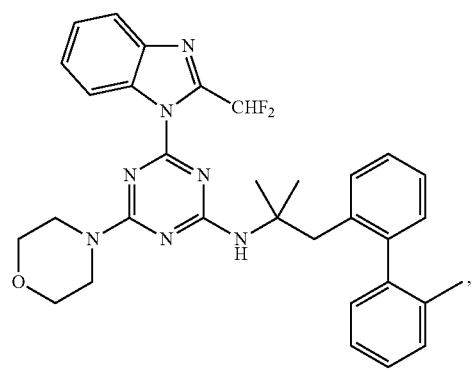
A61
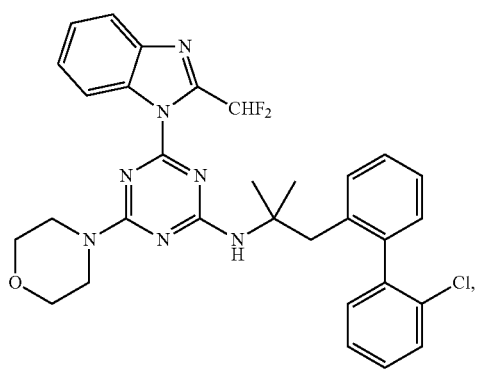
A62
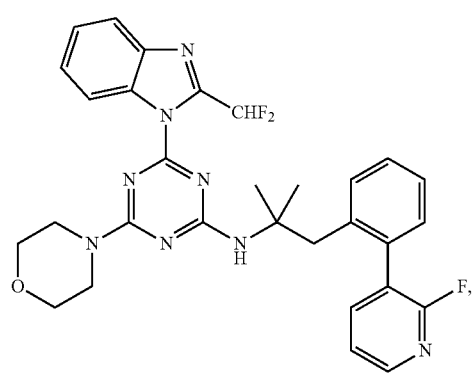
108
-continued
A63
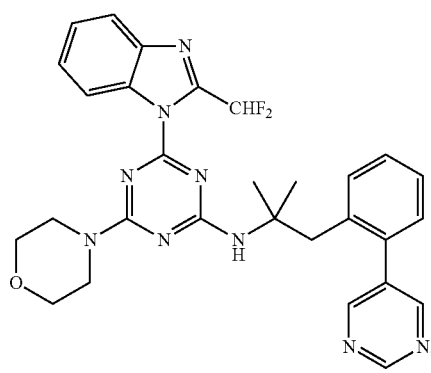
A64
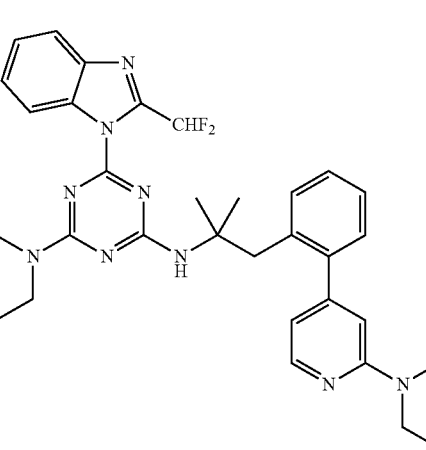
A65
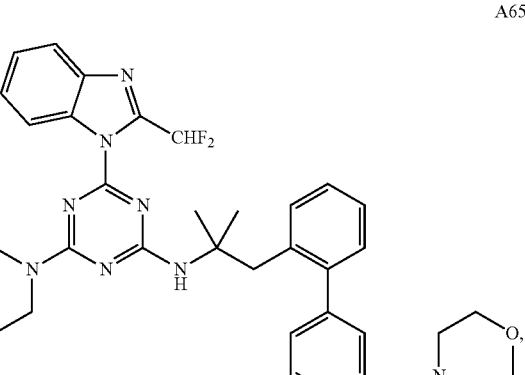
A66
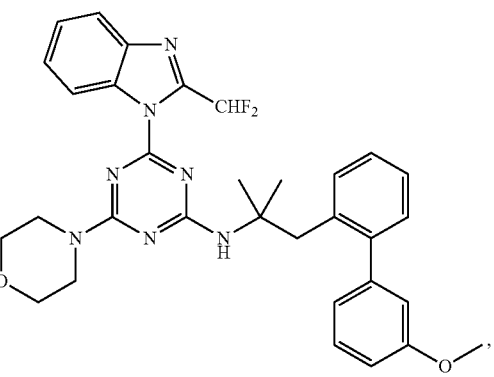

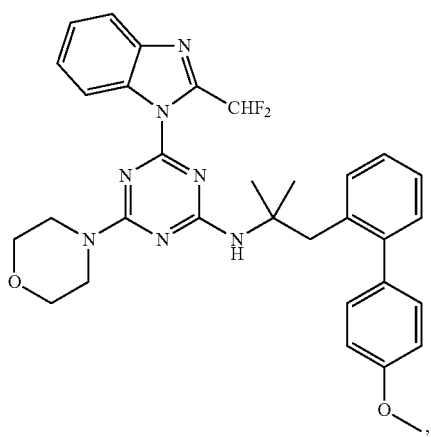
A67
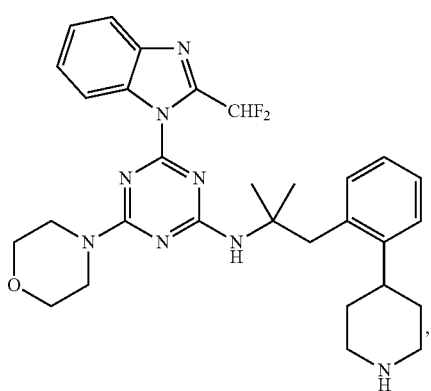
A68
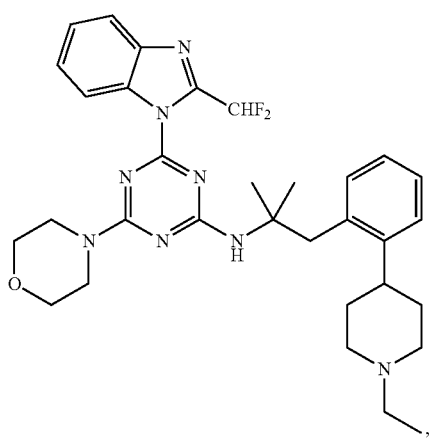
A70
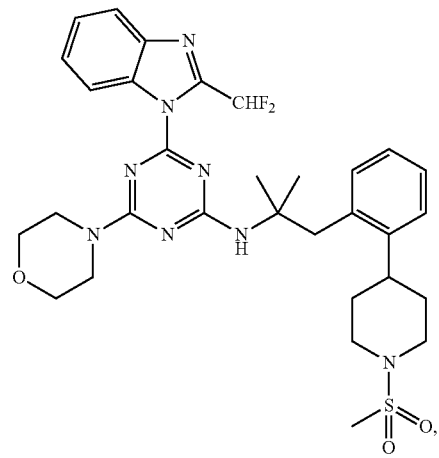
A73
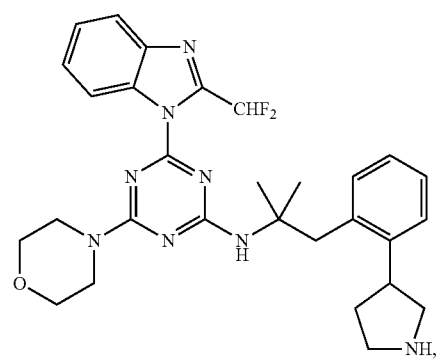
A74
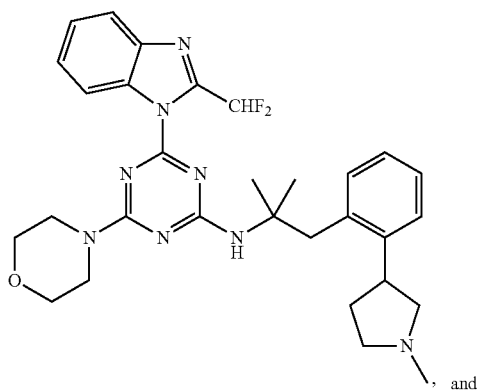
A75
, and
A76 and enantiomers, mixtures of enantiomers, mixtures of two or more diastereomers, and isotopic variants thereof; and pharmaceutically acceptable salts, solvates, hydrates, and prodrugs thereof.

The compounds provided herein are intended to encompass all possible stereoisomers, unless a particular stereochemistry is specified. Where the compound provided herein contains an alkenyl or alkenylene group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I, and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs*, 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

Methods of Synthesis

The compound provided herein can be prepared, isolated, or obtained by any method known to one of skill in the art, and the following examples are only representative and do not exclude other related procedures.

Scheme I

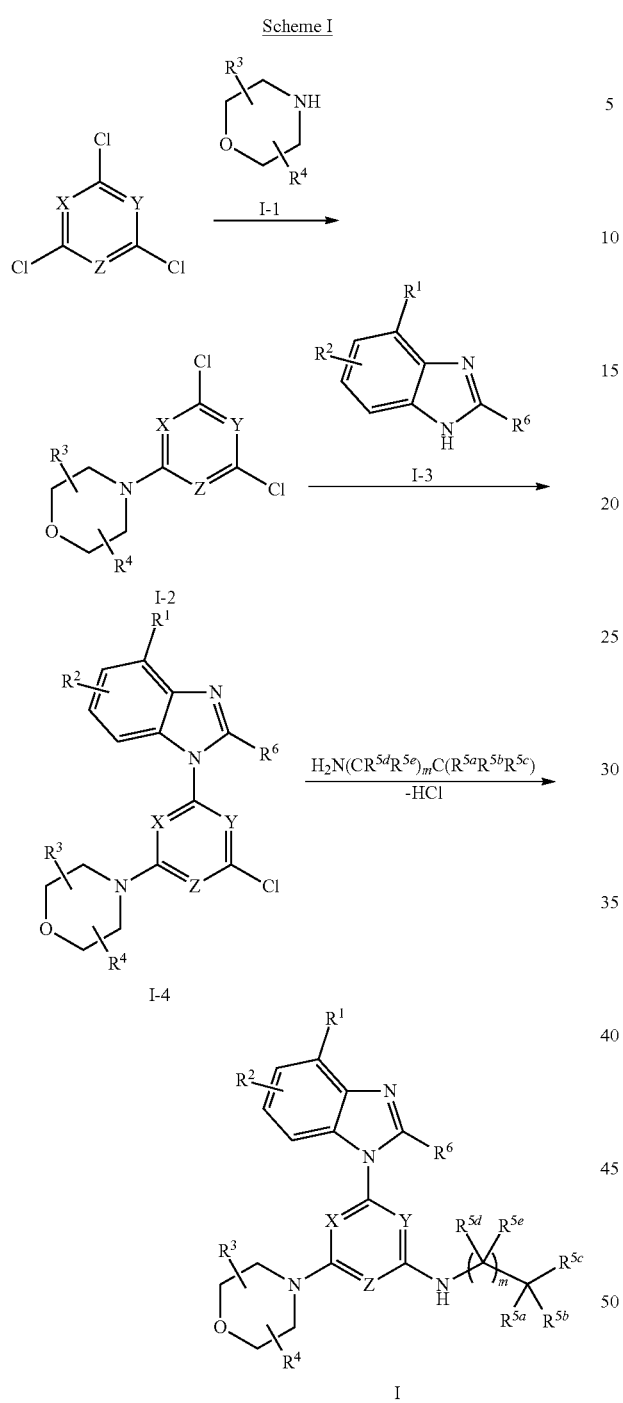

midine with compound I-1 to form compound I-2, which can subsequently be converted to compound I-4 via a second aromatic substitution reaction with compound I-3. Compound I-4 can then be converted to a compound of Formula II via a third aromatic substitution reaction with $NH_2C(R^{5a}R^{5b}R^{5c})$.

Scheme II

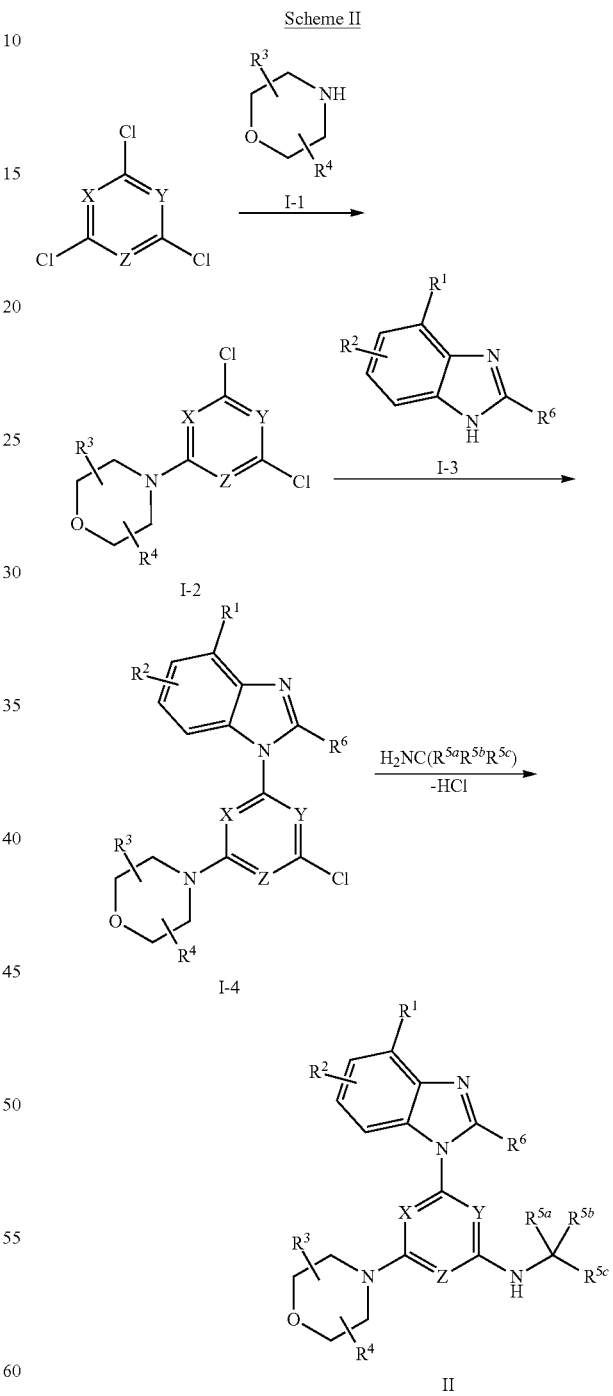

In one embodiment, for example, a compound of Formula I can be prepared, as shown in Scheme I, via a first aromatic substitution reaction of a trihalo-substituted triazine or pyrimidine with compound I-1 to form compound I-2, which can subsequently be converted to compound I-4 via a second aromatic substitution reaction with compound I-3. Compound I-4 can then be converted to a compound of Formula I via a third aromatic substitution reaction with $NH_2(CR^{5d}R^{5e})_mC(R^{5a}R^{5b}R^{5c})$.

In one embodiment, for example, a compound of Formula II can be prepared, as shown in Scheme II, via a first aromatic substitution reaction of a trihalo-substituted triazine or pyri-

Pharmaceutical Compositions

In one embodiment, provided herein is a pharmaceutical composition comprising a compound of Formula I, or an enantiomer, a mixture of enantiomers, a mixture of two or more diastereomers, or an isotopic variant thereof; or a pharmaceutically acceptable salt, solvate, hydrate, or prodrug thereof; and a pharmaceutically acceptable excipient, adjuvant, carrier, buffer, or stabiliser.

In one embodiment, the pharmaceutical compositions are provided in a dosage form for oral administration, which comprise a compound provided herein, and one or more pharmaceutically acceptable excipients or carriers. The pharmaceutical compositions provided herein that are formulated for oral administration may be in tablet, capsule, powder, or liquid form. A tablet may comprise a solid carrier or an adjuvant. Liquid pharmaceutical compositions generally comprise a liquid carrier such as water, petroleum, animal or vegetable oils, mineral oil, or synthetic oil. Physiological saline solution, dextrose or other saccharide solution, or glycols such as ethylene glycol, propylene glycol, or polyethylene glycol may be included. A capsule may comprise a solid carrier such as gelatin.

In another embodiment, the pharmaceutical compositions are provided in a dosage form for parenteral administration, which comprise a compound provided herein, and one or more pharmaceutically acceptable excipients or carriers. Where pharmaceutical compositions may be formulated for intravenous, cutaneous or subcutaneous injection, the active ingredient will be in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. Preservatives, stabilisers, buffers, antioxidants, and/or other additives may be included as required.

In yet another embodiment, the pharmaceutical compositions are provided in a dosage form for topical administration, which comprise a compound provided herein, and one or more pharmaceutically acceptable excipients or carriers.

The pharmaceutical compositions can also be formulated as modified release dosage forms, including delayed-, extended-, prolonged-, sustained-, pulsatile-, controlled-, accelerated-, fast-, targeted-, and programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd Edition, Rathbone et al., Eds., Marcel Dekker, Inc.: New York, N.Y., 2008).

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In certain embodiments, the pharmaceutical compositions provided herein further comprise one or more chemotherapeutic agents as defined herein.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, Remington: The Science and Practice of Pharmacy, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: The Science and Practice of Pharmacy, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid;. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Develop-* ment and Industrial Pharmacy 2000, 26, 695-708; Verma et al., J. Controlled Release 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 µm to about 3 mm, about 50 µm to about 2.5 mm, or from about 100 µm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided herein is a method for treating, preventing, or ameliorating one or more symptoms of a PI3K-mediated disorder, disease, or condition in a subject, comprising administering to the subject a therapeutically effective amount of a compound disclosed herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof.

In certain embodiments, the PI3K is a wild type PI3K. In certain embodiments, the PI3K is a PI3K variant.

In certain embodiments, the PI3K is a Class I kinase. In certain embodiments, the PI3K is PI3Kα, PI3Kβ, PI31Kδ, or PI3Kγ. In certain embodiments, the PI3K is p110α, p110β, p110δ, or p110γ. In certain embodiments, the PI3K is a wild type of a Class I kinase. In certain embodiments, the PI3K is a variant of a Class I kinase.

In certain embodiments, the PI3K is p110α. In certain embodiments, the PI3K is a wild type of p110α. In certain embodiments, the PI3K is a p110α mutant. In certain embodiments, the p110α mutant is R38H, G106V, K111N, K227E, N345K, C420R, P539R, E542K, E545A, E545G, E545K, Q546K, Q546P, E453Q, H710P, 1800L, T1025S, M1043I, M1043V, H1047L, H1047R, or H1047Y. In certain embodiments, the p110α mutant is R38H, K111N, N345K, C420R, P539R, E542K, E545A, E545G, E545K, Q546K, Q546P, 1800L, T1025S, M1043I, H1047L, H1047R, or H1047Y. In certain embodiments, the p110α mutant is C420R, E542K, E545A, E545K, Q546K, 1800L, M1043I, H1047L, or H1047Y.

In certain embodiments, the PI3K is PI3Kγ. In certain embodiments, the PI3K is a wild type of PI3Kγ. In certain embodiments, the PI3K is a variant of PI3Kγ.

In certain embodiments, the compound provided herein selectively targets PI3Kδ. In certain embodiments, the compound provided herein selectively targets a wild type of PI31Kδ. In certain embodiments, the compound provided herein selectively targets a variant of PI31Kδ.

In certain embodiments, the compound provided herein is a selective inhibitor of PI31Kδ. In certain embodiments, the compound provided herein has a selectivity against PI3Kδ over PI3Kα ranging from about 2 fold, about 4 fold, about 8 fold, about 20 fold, about 50 fold, about 100 fold, about 200 fold, about 500 fold, or about 1000 fold. In certain embodiments, the compound provided herein has a selectivity against PI3Kδ over PI3Kβ ranging from about 2 fold, about 4 fold, about 8 fold, about 20 fold, about 50 fold, about 100 fold, about 200 fold, about 500 fold, or about 1000 fold. In certain embodiments, the compound provided herein has a selectivity against PI3Kδ over PI3Kγ ranging from about 2 fold, about 4 fold, about 8 fold, about 20 fold, about 50 fold, about 100 fold, about 200 fold, about 500 fold, or about 1000 fold. In certain embodiments, the compound provided herein has a selectivity against PI3Kδ over mTOR ranging from about 2 fold, about 4 fold, about 8 fold, about 20 fold, about 50 fold, about 100 fold, about 200 fold, about 500 fold, or about 1000 fold.

In certain embodiments, the compound provided herein is a selective inhibitor of PI3Kβ. In certain embodiments, the compound provided herein has a selectivity against PI3Kβ over PI3Kα ranging from about 2 fold, about 4 fold, about 8 fold, about 20 fold, about 50 fold, about 100 fold, about 200 fold, about 500 fold, or about 1000 fold. In certain embodiments, the compound provided herein has a selectivity against PI3Kβ over PI3Kδ ranging from about 2 fold, about 4 fold, about 8 fold, about 20 fold, about 50 fold, about 100 fold, about 200 fold, about 500 fold, or about 1000 fold. In certain embodiments, the compound provided herein has a selectivity against PI3Kβ over PI3Kγ ranging from about 2 fold, about 4 fold, about 8 fold, about 20 fold, about 50 fold, about 100 fold, about 200 fold, about 500 fold, or about 1000 fold. In certain embodiments, the compound provided herein has a selectivity against PI3Kβ over mTOR ranging from about 2 fold, about 4 fold, about 8 fold, about 20 fold, about 50 fold, about 100 fold, about 200 fold, about 500 fold, or about 1000 fold.

In certain embodiments, the compound provided herein is a selective inhibitor of PI3Kδ and PI3Kβ. In certain embodiments, the compound provided herein has a selectivity against PI3Kδ and PI3Kβ over PI3Kα ranging from about 2 fold, about 4 fold, about 8 fold, about 20 fold, about 50 fold, about 100 fold, about 200 fold, about 500 fold, or about 1000 fold. In certain embodiments, the compound provided herein has a selectivity against PI3Kδ and PI3Kβ over PI3Kγ ranging from about 2 fold, about 4 fold, about 8 fold, about 20 fold, about 50 fold, about 100 fold, about 200 fold, about 500 fold, or about 1000 fold. In certain embodiments, the compound provided herein has a selectivity against PI3Kδ and PI3Kβ over mTOR ranging from about 2 fold, about 4 fold, about 8 fold, about 20 fold, about 50 fold, about 100 fold, about 200 fold, about 500 fold, or about 1000 fold.

In certain embodiments, the PI3K is a Class IV kinase. In certain embodiments, the PI3K is a wild type of a Class IV kinase. In certain embodiments, the PI3K is a variant of a Class IV kinase. In certain embodiments, the PI3K is mTOR, ATM, ATR, or DNA-PK. In certain embodiments, the PI3K is mTOR.

In another embodiments, provided herein is a method for treating, preventing, or ameliorating one or more symptoms of a proliferative disease in a subject, comprising administering to the subject a therapeutically effective amount of a compound disclosed herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof.

In certain embodiments, the subject is a mammal. In certain embodiments, the subject is a human. In certain embodiments, the subject is a primate other than a human, a farm animal such as cattle, a sport animal, or a pet such as a horse, dog, or cat.

In certain embodiments, the proliferative disease is cancer. In certain embodiments, the proliferative disease is hematological cancer. In certain embodiments, the proliferative disease is an inflammatory disease. In certain embodiments, the proliferative disease is an immune disorder.

The disorders, diseases, or conditions treatable with a compound provided herein, include, but are not limited to, (1) inflammatory or allergic diseases, including systemic anaphylaxis and hypersensitivity disorders, atopic dermatitis, urticaria, drug allergies, insect sting allergies, food allergies (including celiac disease and the like), and mastocytosis; (2) inflammatory bowel diseases, including Crohn's disease, ulcerative colitis, ileitis, and enteritis; (3) vasculitis, and Behcet's syndrome; (4) psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; (5) asthma and respiratory allergic diseases, including allergic asthma, exercise induced asthma, allergic rhinitis, otitis media, allergic conjunctivitis, hypersensitivity lung diseases, and chronic obstructive pulmonary disease; (6) autoimmune diseases, including arthritis (including rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma,; and (20) infectious diseases, including HIV.

In certain embodiments, the cancer treatable with the methods provided herein includes, but is not limited to, (1) leukemias, including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML), (2) chronic leukemias, including, but not limited to, chronic myelocytic (granulocytic) leukemia, chronic lymphocytic leukemia, and hairy cell leukemia; (3) polycythemia vera; (4) lymphomas, including, but not limited to, Hodgkin's disease and non-Hodgkin's disease; (5) multiple myelomas, including, but not limited to, smoldering multiple myeloma, nonsecretory myeloma, osteosclerotic myeloma, plasma cell leukemia, solitary plasmacytoma, and extramedullary plasmacytoma; (6) Waldenstrom's macroglobulinemia; (7) monoclonal gammopathy of undetermined significance; (8) benign monoclonal gammopathy; (9) heavy chain disease; (10) bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma; (11) brain tumors, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; (12) breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; (13) adrenal cancer, including, but not limited to, pheochromocytom and adrenocortical carcinoma; (14) thyroid cancer, including, but not limited to, papillary or follicular thyroid cancer, medullary thyroid cancer, and anaplastic thyroid cancer; (15) pancreatic cancer, including, but not limited to, insulinoma, gastrinoma, glucagonoma, vipoma, somatostatin-secreting tumor, and carcinoid or islet cell tumor; (16) pituitary cancer, including, but limited to, Cushing's disease, prolactin-secreting tumor, acromegaly, and diabetes insipius; (17) eye cancer, including, but not limited, to ocular melanoma such as iris melanoma, choroidal melanoma, and cilliary body melanoma, and retinoblastoma; (18) vaginal cancer, including, but not limited to, squamous cell carcinoma, adenocarcinoma, and melanoma; (19) vulvar cancer, including, but not limited to, squamous cell carcinoma, melanoma, adenocarcinoma, basal cell carcinoma, sarcoma, and Paget's disease; (20) cervical cancers, including, but not limited to, squamous cell carcinoma, and adenocarcinoma; (21) uterine cancer, including, but not limited to, endometrial carcinoma and uterine sarcoma; (22) ovarian cancer, including, but not limited to, ovarian epithelial carcinoma, borderline tumor, germ cell tumor, and stromal tumor; (23) esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; (24) stomach cancer, including, but not limited to, adenocarcinoma, fungating (polypoid), ulcerating, superficial spreading, diffusely spreading, malignant lymphoma, liposarcoma, fibrosarcoma, and carcinosarcoma; (25) colon cancer; (26) rectal cancer; (27) liver cancer, including, but not limited to, hepatocellular carcinoma and hepatoblastoma; (28) gallbladder cancer, including, but not limited to, adenocarcinoma; (29) cholangiocarcinomas, including, but not limited to, pappillary, nodular, and diffuse; (30) lung cancer, including, but not limited to, non-small cell lung cancer, squamous cell carcinoma (epidermoid carcinoma), adenocarcinoma, large-cell carcinoma, and small-cell lung cancer; (31) testicular cancer, including, but not limited to, germinal tumor, seminoma, anaplastic, classic (typical), spermatocytic, nonseminoma, embryonal carcinoma, teratoma carcinoma, and choriocarcinoma (yolk-sac tumor); (32) prostate cancer, including, but not limited to, adenocarcinoma, leiomyosarcoma, and rhabdomyosarcoma; (33) penal cancer; (34) oral cancer, including, but not limited to, squamous cell carcinoma; (35) basal cancer; (36) salivary gland cancer, including, but not limited to, adenocarcinoma, mucoepidermoid carcinoma, and adenoidcystic carcinoma; (37) pharynx cancer, including, but not limited to, squamous cell cancer and verrucous; (38) skin cancer, including, but not limited to, basal cell carcinoma, squamous cell carcinoma and melanoma, superficial spreading melanoma, nodular melanoma, lentigo malignant melanoma, and acral lentiginous melanoma; (39) kidney cancer, including, but not limited to, renal cell cancer, adenocarcinoma, hypernephroma, fibrosarcoma, and transitional cell cancer (renal pelvis and/or uterer); (40) Wilms' tumor; (41) bladder cancer, including, but not limited to, transitional cell carcinoma, squamous cell cancer, adenocarcinoma, and carcinosarcoma; and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas (See Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

Depending on the disorder, disease, or condition to be treated, and the subject's condition, the compounds or pharmaceutical compositions provided herein can be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable excipients, carriers, adjuvants, and vehicles appropriate for each route of administration. Also provided is administration of the compounds or pharmaceutical compositions provided herein in a depot formulation, in which the active ingredient is released over a predefined time period.

In the treatment, prevention, or amelioration of one or more symptoms of the disorders, diseases, or conditions described herein, an appropriate dosage level generally is ranging from about 0.001 to 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day.

For oral administration, the pharmaceutical compositions provided herein can be formulated in the form of tablets containing from about 1.0 to about 1,000 mg of the active ingredient, in one embodiment, about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The pharmaceutical compositions can be administered on a regimen of 1 to 4 times per day, including once, twice, three times, and four times per day.

It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also provided herein are methods of modulating PI3K activity, comprising contacting a PIK3 enzyme with a compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof. In one embodiment, the PIK3 enzyme is inside a cell.

In certain embodiments, the PI3K is a wild type PI3K. In certain embodiments, the PI3K is a PI3K variant.

In certain embodiments, the PI3K is a Class I kinase. In certain embodiments, the PI3K is PI3Kα, PI3Kβ, PI31Kδ, or PI3Kγ. In certain embodiments, the PI3K is p110α, p110α, p110δ, or p110γ. In certain embodiments, the PI3K is a wild type of a Class I kinase. In certain embodiments, the PI3K is a variant of a Class I kinase.

In certain embodiments, the PI3K is p110α. In certain embodiments, the PI3K is a wild type of p110α. In certain embodiments, the PI3K is a p110α mutant. In certain embodiments, the p110α mutant is R38H, G106V, K111N, K227E, N345K, C420R, P539R, E542K, E545A, E545G, E545K, Q546K, Q546P, E453Q, H710P, I800L, T1025S, M1043I, M1043V, H1047L, H1047R, or H1047Y. In certain embodiments, the p110α mutant is R38H, K111N, N345K, C420R, P539R, E542K, E545A, E545G, E545K, Q546K, Q546P, I800L, T1025S, M1043I, H1047L, H1047R, or H1047Y. In certain embodiments, the p110αmutant is C420R, E542K, E545A, E545K, Q546K, I800L, M1043I, H1047L, or H1047Y.

In certain embodiments, the PI3K is PI3Kγ. In certain embodiments, the PI3K is a wild type of PI3Kγ. In certain embodiments, the PI3K is a variant of PI3Kγ.

In certain embodiments, the compound provided herein selectively targets PI3Kγ. In certain embodiments, the compound provided herein selectively targets a wild type of PI3Kγ. In certain embodiments, the compound provided herein selectively targets a variant of PI3Kγ.

In certain embodiments, the PI3K is a Class IV kinase. In certain embodiments, the PI3K is a wild type of a Class IV kinase. In certain embodiments, the PI3K is a variant of a Class IV kinase. In certain embodiments, the PI3K is mTOR, ATM, ATR, or DNA-PK. In certain embodiments, the PI3K is mTOR.

In certain embodiments, the compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof shows inhibitory activity against a PI3K and a variant thereof.

In certain embodiments, the compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof; shows inhibitory activity against a wild type of a PI3K. In certain embodiments, the PI3K is PI3Kγ.

In certain embodiments, the compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof; shows inhibitory activity against a PI3K variant. In certain embodiments, the PI3K variant is a p110α mutant. In certain embodiments, the p110αmutant is C420R, E542K, E545A, E545K, Q546K, 1800L, M1043I, H1047L, or H1047Y.

The compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof; can also be combined or used in combination with other agents or therapies useful in the treatment, prevention, or amelioration of one or more symptoms of the disorders, diseases, or conditions for which the compounds provided herein are useful, including asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, infectious diseases, and those pathologies noted herein.

Suitable other therapeutic agents can also include, but are not limited to, (1) alpha-adrenergic agents; (2) antiarrhythmic agents; (3) anti-atherosclerotic agents, such as ACAT inhibitors; (4) antibiotics, such as anthracyclines, bleomycins, mitomycin, dactinomycin, and plicamycin; (5) anticancer agents and cytotoxic agents, e.g., alkylating agents, such as nitrogen mustards, alkyl sulfonates, nitrosoureas, ethylenimines, and triazenes; (6) anticoagulants, such as acenocoumarol, argatroban, bivalirudin, lepirudin, fondaparinux, heparin, phenindione, warfarin, and ximelagatran; (7) antidiabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; (8) antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; (9) antiinflammatories, e.g., non-steroidal antiinflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; (10) antimetabolites, such as folate antagonists, purine analogues, and pyrimidine analogues; (11) anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; (12) antiproliferatives, such as methotrexate, FK506 (tacrolimus), and mycophenolate mofetil; (13) anti-TNF antibodies or soluble TNF receptor, such as etanercept, rapamycin, and leflunimide; (14) aP2 inhibitors; (15) beta-adrenergic agents, such as carvedilol and metoprolol; (16) bile acid sequestrants, such as questran; (17) calcium channel blockers, such as amlodipine besylate; (18) chemotherapeutic agents; (19) cyclooxygenase-2 (COX-2) inhibitors, such as celecoxib and rofecoxib; (20) cyclosporine; (21) cytotoxic drugs, such as azathioprine and cyclophosphamide; (22) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (23) endothelin converting enzyme (ECE) inhibitors, such as phosphoramidon; (24) enzymes, such as L-asparaginase; (25) Factor VIIa Inhibitors and Factor Xa Inhibitors; (26) farnesyl-protein transferase inhibitors; (27) fibrates; (28) growth factor inhibitors, such as modulators of PDGF activity; (29) growth hormone secretagogues; (30) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (31) hormonal agents, such as glucocorticoids (e.g., cortisone), estrogens/antiestrogens, androgens/antiandrogens, progestins, and luteinizing hormone-releasing hormone antagonists, and octreotide acetate; (32) immunosuppressants; (33) mineralocorticoid receptor antagonists, such as spironolactone and eplerenone; (34) microtubule-disruptor agents, such as ecteinascidins; (35) microtubule-stabilizing agents, such as pacitaxel, docetaxel, and epothilones A-F; (36) MTP Inhibitors; (37) niacin; (38) phosphodiesterase inhibitors, such as PDE III inhibitors (e.g., cilostazol) and PDE V inhibitors (e.g., sildenafil, tadalafil, and vardenafil); (39) plant-derived products, such as vinca alkaloids, epipodophyllotoxins, and taxanes; (40) platelet activating factor (PAF) antagonists; (41) platinum coordination complexes, such as cisplatin, satraplatin, and carboplatin; (42) potassium channel openers; (43) prenyl-protein transferase inhibitors; (44) protein tyrosine kinase inhibitors; (45) renin inhibitors; (46) squalene synthetase inhibitors; (47) steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; (48) TNF-alpha inhibitors, such as tenidap; (49) thrombin inhibitors, such as hirudin; (50) thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); (51) thromboxane receptor antagonists, such as ifetroban; (52) topoisomerase inhibitors; (53) vasopeptidase inhibitors (dual NEP-ACE inhibitors), such as omapatrilat and gemopatrilat; and (54) other miscellaneous agents, such as, hydroxyurea, procarbazine, mitotane, hexamethylmelamine, and gold compounds.

In certain embodiments, the other therapies that may be used in combination with the compounds provided herein include, but are not limited to, surgery, endocrine therapy, biologic response modifiers (e.g., interferons, interleukins, and tumor necrosis factor (TNF)), hyperthermia and cryotherapy, and agents to attenuate any adverse effects (e.g., antiemetics).

In certain embodiments, the other therapeutic agents that may be used in combination with the compounds provided herein include, but are not limited to, alkylating drugs (mechlorethamine, chlorambucil, cyclophosphamide, melphalan, and ifosfamide), antimetabolites (cytarabine (also known as cytosine arabinoside or Ara-C), HDAC (high dose cytarabine), and methotrexate), purine antagonists and pyrimidine antagonists (6-mercaptopurine, 5-fluorouracil, cytarbine, and gemcitabine), spindle poisons (vinblastine, vincristine, and vinorelbine), podophyllotoxins (etoposide, irinotecan, and topotecan), antibiotics (daunorubicin, doxorubicin, bleomycin, and mitomycin), nitrosoureas (carmustine and lomustine), enzymes (asparaginase), and hormones (tamoxifen, leuprolide, flutamide, and megestrol), imatinib, adriamycin, dexamethasone, and cyclophosphamide. For a more comprehensive discussion of updated cancer therapies; See, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

In another embodiment, the method provided herein comprises administration of a compound provided herein, e.g., a compound of Formula I, or an enantiomer, a mixture of enantiomers, a mixture of two or more diastereomers, or an isotopic variant thereof, or a pharmaceutically acceptable salt, solvate, hydrate, or prodrug thereof, together with administering one or more chemotherapeutic agents and/or therapies selected from: alkylation agents (e.g., cisplatin, carboplatin); antimetabolites (e.g., methotrexate and 5-FU); antitumour antibiotics (e.g., adriamymycin and bleomycin); antitumour vegetable alkaloids (e.g., taxol and etoposide); antitumor hormones (e.g., dexamethasone and tamoxifen); antitumour immunological agents (e.g., interferon α, β, and γ); radiation therapy; and surgery. In certain embodiments, the one or more chemotherapeutic agents and/or therapies are administered to the subject before, during, or after the administration of the compound provided herein.

Such other agents, or drugs, can be administered, by a route and in an amount commonly used therefor, simultaneously or sequentially with the compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof. When a compound provided herein is used contemporaneously with one or more other drugs, a pharmaceutical composition containing such other drugs in addition to the compound provided herein can be utilized, but is not required. Accordingly, the pharmaceutical compositions provided herein include those that also contain one or more other active ingredients or therapeutic agents, in addition to a compound provided herein.

The weight ratio of a compound provided herein to the second active ingredient can be varied, and will depend upon the effective dose of each ingredient. Generally, an effective dose of each will be used. Thus, for example, when a compound provided herein is combined with a NSAID, the weight ratio of the compound to the NSAID can range from about 1,000:1 to about 1:1,000, or about 200:1 to about 1:200. Combinations of a compound provided herein and other active ingredients will generally also be within the aforementioned range, but in each case, an effective dose of each active ingredient should be used.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof.

In certain embodiments, the kit includes a container comprising a dosage form of the compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof; in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); M (molar); mM (millimolar); µM (micromolar); eq. (equivalent); mmol (millimoles); Hz (Hertz); MHz (megahertz); hr or hrs (hour or hours); min (minutes); and MS (mass spectrometry).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies illustrated herein are intended to exemplify the applicable chemistry through the use of specific examples and are not indicative of the scope of the disclosure.

Example 1

Synthesis of 4-(2-(difluoromethyl)-1H-benzo[d]imidazol-1-yl)-6-morpholino-N-(1-phenylethyl)-1,3,5-triazin-2-amine A1

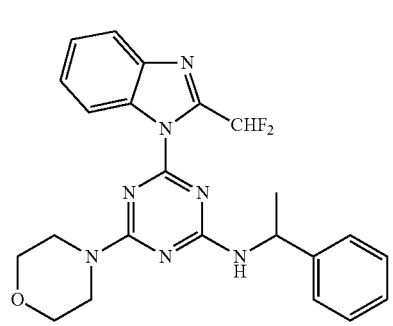

A1

Compound A1 was prepared according to Scheme 1, where compound 1 (1-[4-chloro-6-(4-morpholinyl)-1,3,5-tianzin-2-yl]-2-(difluoromethyl)-1H-benzimidazole) was synthesized according to the procedure as described in U.S. Pat. Appl. Publ. No. 2007/244110, the disclosure of which is incorporated herein by reference in its entirety.

Scheme 1

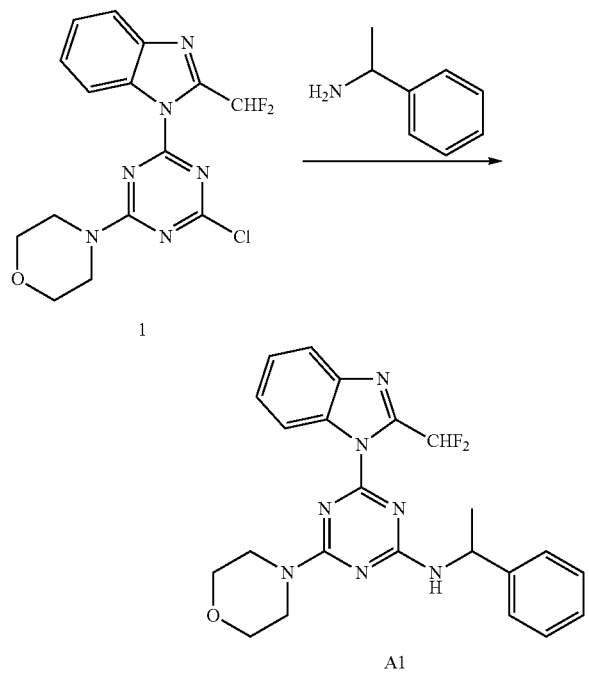

A mixture of compound 1 (184 mg, 0.502 mmol) and α-methylbenzylamine (121 mg, 1.00 mmol) in dioxane (25 mL) was refluxed overnight. The mixture was poured into water to precipitate a white solid, which was recrystallized from ethanol to give 185 mg (81% yield) of compound A1 as a white solid: 97.1% purity (HPLC); MS m/z: 452 (M+1); $^1$H NMR (CDCl$_3$, 500 MHz) (rotamers) δ 8.42 (d, J=8.0 Hz, 0.5H), 8.09 (d, J=8.0 Hz, 0.5H), 7.90-7.86 (m, 1H), 7.65 (t, J$_{HF}$=53.5 Hz, 0.5H), 7.44-7.28 (m, 8H), 5.59 (d, J=6.5 Hz, 0.5H), 5.19-5.06 (m, 1H), 3.76-3.91 (m, 8H), 1.63 (d, J=7.0 Hz, 3H) ppm.

Example 2

Synthesis of (S)-4-(2-(difluoromethyl)-1H-benzo[d] imidazol-1-yl)-6-morpholino-N-(1-phenylethyl)-1,3, 5-triazin-2-amine A2

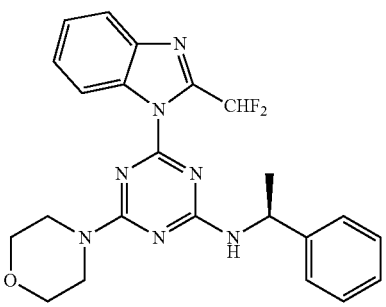

A2

Compound A2 was synthesized according to the procedure for compound A1, substituting (S)-α-methylbenzylamine in place of α-methylbenzylamine to give the product in 82% yield: 90.6% purity (HPLC); MS m/z: 452.2 (M+1); $^1$H NMR (CDCl$_3$, 500 MHz) (rotamers) δ 8.42 (d, J=8.0 Hz, 0.5H), 8.09 (d, J=7.5 Hz, 0.5H), 7.91-7.85 (m, 1H), 7.65 (t, J$_{HF}$=54.0 Hz, 0.5H), 7.41-7.22 (m, 8H), 5.61-5.57 (m, 0.5H), 5.25-5.17 (m, 1H), 3.87-3.66 (m, 8H), 1.68-1.61 (m, 3H) ppm.

Example 3

Synthesis of (R)-4-(2-(difluoromethyl)-1H-benzo[d] imidazol-1-yl)-6-morpholino-N-(1-phenylethyl)-1,3, 5-triazin-2-amine A3

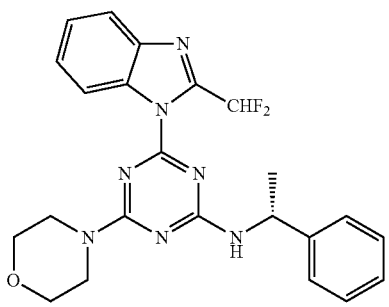

A3

Compound A3 was synthesized according to the procedure for compound A1, substituting (R)-α-methylbenzylamine in place of α-methylbenzylamine to give a 68% yield of the product: 98.7% purity (HPLC); MS m/z: 452 (M+1); $^1$H NMR (CDCl$_3$, 500 MHz) δ 8.41 (d, J=8.0 Hz, 0.5H), 8.08 (d, J=8.0 Hz, 0.5H), 7.86 (m, 1H), 7.64 (t, J$_{HF}$=54.0 Hz, 0.5H), 7.44-7.19 (m, 7.5H), 5.58 (d, J=7.5 Hz, 0.5H), 5.20 (m, 1H), 3.88-3.65 (m, 8H), 1.62 (d, J=7.0 Hz, 3H) ppm.

Example 4

Synthesis of (S)-4-(2-(difluoromethyl)-1H-benzo[d]imidazol-1-yl)-6-morpholino-N-(1-phenylpropyl)-1,3,5-triazin-2-amine A5

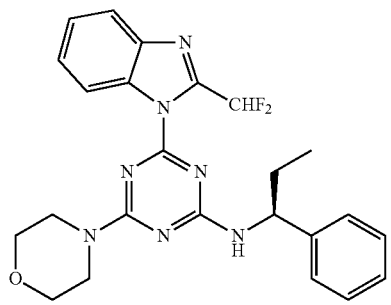

A5

Compound A5 was synthesized according to the procedure for compound A1, substituting (S)-α-ethylbenzylamine in place of α-methylbenzylamine to give the product in 73% yield: 96.7% purity (LCMS); MS m/z: 466.2 (M+1); $^1$H NMR (DMSO$_{d6}$, 500 MHz) (rotamers) δ 8.58 (d, J=8.5 Hz, 0.6H), 8.49 (d, J=8.0 Hz, 0.6H), 8.46 (d, J=8.5 Hz, 0.4H), 8.11 (m, 0.4H), 7.91 (t, J$_{HF}$=53.0 Hz, 0.6H), 7.85-7.78 (m, 1H), 7.61 (t, J$_{HF}$=53.0 Hz, 0.4H), 7.49 (t, J=7.5 Hz, 0.5H), 7.45-7.38 (m, 3H), 7.38-7.31 (m, 2H), 7.27-7.20 (m, 1H), 4.90 (m, 1H), 3.88-3.55 (m, 8H), 1.95-1.65 (m, 1H), 0.93 (m, 3H) ppm.

Example 5

Synthesis of (R)-4-(2-(difluoromethyl)-1H-benzo[d]imidazol-1-yl)-6-morpholino-N-(1-phenylpropyl)-1,3,5-triazin-2-amine A6

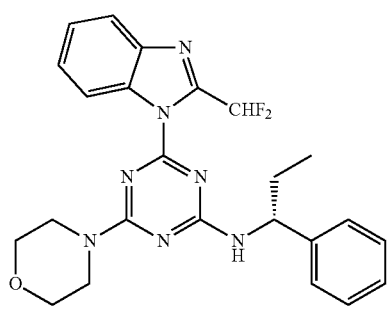

A6

Compound A6 was synthesized according to the procedure for compound A1, substituting (R)-α-ethylbenzylamine in place of α-methylbenzylamine to give a 62% yield of product: 96.2% purity (HPLC); MS m/z: 466.2 (M+1); $^1$H NMR (CDCl$_3$, 500 MHz) (rotamers) δ 8.41 (d, J=8.0 Hz, 0.4H), 8.11 (d, J=8.0 Hz, 0.6H), 7.89 (d, J=8.0 Hz, 0.4H), 7.86 (d, J=7.5 Hz, 0.6H), 7.65 (t, J$_{HF}$=53.5 Hz, 0.6H), 7.46-7.25 (m, 7.4H), 5.62 (m, 0.5H), 4.99 (m, 0.5H), 4.92 (m, 0.5H), 3.87-3.65 (m, 8H), 2.02-1.89 (m, 2H), 1.04-0.98 (m, 3H) ppm.

Example 6

Synthesis of (R)-methyl 2-((4-(2-(difluoromethyl)-1H-benzo[d]imidazol-1-yl)-6-morpholino-1,3,5-triazin-2-yl)amino)-2-phenylacetate A11

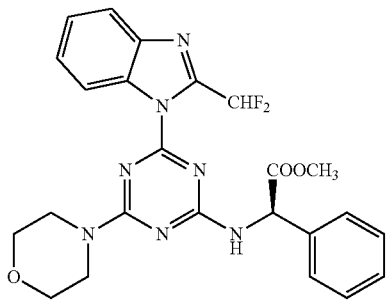

A11

Saturated aqueous sodium bicarbonate was added dropwise to a solution of (R)-2-phenylglycine methyl ester hydrochloride (83 mg, 0.41 mmol) in water (4 mL) at 0° C. until pH=8. Then the mixture was extracted with ethyl acetate, dried over anhydrous sodium sulfate, and concentrated in vacuo. The residue was added to a mixture of compound 1 (50 mg, 0.14 mmol) in dioxane (5 mL) and the resulting mixture was refluxed for 4 hrs. After the volatiles were removed in vacuo, the residue was taken up in water and ethyl acetate. The organic extracts were dried over anhydrous sodium sulfate and concentrated in vacuo. The crude product was purified by silica gel column chromatography (ethyl acetate/petroleum ether=1/5) to give 44 mg (65% yield) of compound A11 as a yellow solid: 98.71% purity (LCMS); MS m/z: 496.1 (M+1); $^1$H NMR (CDCl$_3$, 500 MHz) (rotamers) δ 8.43 (d, J=8.0 Hz, 0.5H), 8.11 (d, J=8.0 Hz, 0.5H), 7.88 (m, 1H), 7.64 (t, J$_{HF}$=53.5 Hz, 0.5H), 7.52-7.35 (m, 7.5H), 6.33 and 6.25 (2d, J=6.5 and 6.0 Hz, 1H), 5.69 and 5.60 (2d, J=6.5 and 6.0 Hz, 1H), 3.89-3.70 (m, 11H) ppm.

Example 7

Synthesis of (S)-methyl 2-((4-(2-(difluoromethyl)-1H-benzo[d]imidazol-1-yl)-6-morpholino-1,3,5-triazin-2-yl)amino)-2-phenylacetate A12

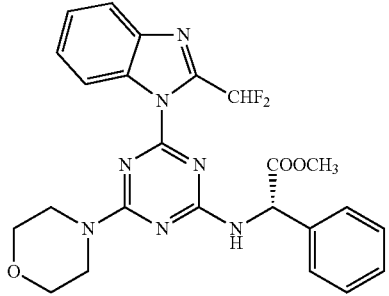

A12

Compound A12 was synthesized according to the procedure for compound A11, substituting (S)-2-phenylglycine methyl ester hydrochloride in place of (R)-2-phenylglycine methyl ester hydrochloride to give the product in 67% yield: 95.5% purity (HPLC); MS m/z: 496.1 (M+1); $^1$H NMR (CDCl$_3$, 500 MHz) δ 8.45 (d, J=8.5 Hz, 0.5H), 8.13 (d, J=8.0 Hz, 0.5H), 7.89 (m, 1H), 7.64 (t, J$_{HF}$=53.5 Hz, 0.5H), 7.52-7.36 (m, 7.5H), 6.32 and 6.25 (2d, J=6.0 and 5.5 Hz, 1H), 5.69 and 5.60 (2d, J=6.5 and 6.0 Hz, 1H), 3.89-3.62 (m, 11H) ppm.

Example 8

Synthesis of 4-(2-(difluoromethyl)-1H-benzo[d]imidazol-1-yl)-6-morpholino-N-(2-phenylpropan-2-yl)-1,3,5-triazin-2-amine A7

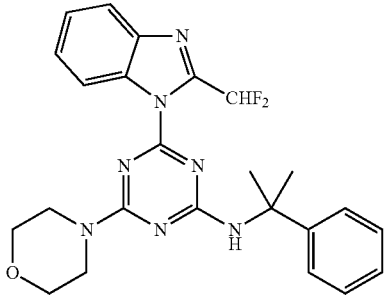

A7

A mixture of compound 1 (184 mg, 0.502 mmol) and 2-phenylpropan-2-amine (170 mg, 1.26 mmol) in dioxane (5 mL) was refluxed overnight. The volatiles were removed in vacuo and the residue was separated by ethyl acetate and water. The organic extracts were washed sequentially with aq. sodium hydroxide (1 N), water and brine, dried over anhydrous sodium sulfate, and concentrated in vacuo. The crude product was purified by flash chromatography (10-21% ethyl acetate in petroleum ether) to give 148 mg (63% yield) as a white solid: 99.6% purity (HPLC); MS m/z: 466.2 (M+1); $^1$H NMR (CDCl$_3$, 500 MHz) (rotamers) δ 8.45 (d, J=8.0 Hz, 0.5H), 7.90 (d, J=7.5 Hz, 0.5H), 7.79 (d, J=8.0 Hz, 0.5H), 7.66 (t, J$_{HF}$=53.5 Hz, 0.5H), 7.50 (d, J=8.0 Hz, 1H), 7.47-7.38 (m, 3.5H), 7.35-7.26 (m, 2H), 7.22 (t, J=7.5 Hz, 0.5H), 7.13 (t, J=7.5 Hz, 0.5H), 6.82 (t, J$_{HF}$=53.5 Hz, 0.5H), 5.82 (s, 1H), 3.87 (m, 2H), 3.81 (m, 2H), 3.74 (m, 1H), 3.67 (m, 1H), 3.41 (m, 1H), 3.31 (m, 1H), 1.80 and 1.78 (2s, 6H) ppm.

Example 9

Synthesis of 4-(2-(difluoromethyl)-1H-benzo[d]imidazol-1-yl)-6-morpholino-N-(2-(naphthalen-2-yl)propan-2-yl)-1,3,5-triazin-2-amine A13

A13

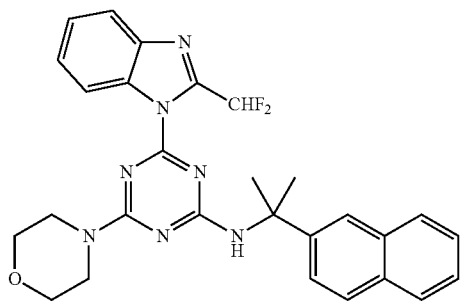

Methylmagnesium bromide (3.6 mL, 3.0 M in tetrahydrofuran, 10.5 mmol) was added to a solution of naphthalene-2-carbonitrile (459 mg, 3.0 mmol) in anhydrous tetrahydrofuran (4 mL) at room temperature under a nitrogen atmosphere. The reaction mixture was heated in a microwave at 100° C. for 10 min. The resulting mixture was added titanium tetraisopropanolate (0.9 mL, 3.0 mmol) and then irradiated with microwave at 50° C. for 1 hr. The mixture was poured into water and extracted with dichloromethane. The combined organic extracts were dried over anhydrous sodium sulfate and concentrated in vacuo to give a crude product, which was triturated by the dropwise addition of hydrochloric acid in ether (1 N) to precipitate 2-(naphthalen-2-yl)propan-2-amine as its hydrochloric acid salt (600 mg, 90%) as a yellow solid: 84.7% purity (LCMS); MS m/z: 171 (M+1).

The crude 2-(naphthalen-2-yl)propan-2-amine hydrochloride (246 mg, 1.09 mmol), compound 1 (200 mg, 0.550 mmol), and potassium carbonate (377 mg, 2.73 mmol) were suspended in dioxane (25 mL) and the mixture was refluxed overnight. The mixture was diluted with water and extracted with ethyl acetate. The organic extracts were dried with anhydrous sodium sulfate and concentrated in vacuo. The crude product was purified by preparative-HPLC to give 150 mg (53% yield) of compound A13 as a white solid: 98.5% purity (HPLC); MS m/z: 516.2 (M+1); $^1$H NMR (CDCl$_3$, 500 MHz) δ 8.43 (d, J=8.0 Hz, 0.6H), 7.98-7.36 (m, 10H), 7.15-6.87 (m, 1H), 6.26 (t, J=8.0 Hz, 0.4H), 5.88 and 5.83 (2s, 1H), 3.87-2.89 (m, 8H), 1.89 and 1.86 (2s, 6H) ppm.

Example 10

Synthesis of N-(2-(4-chlorophenyl)propan-2-yl)-4-(2-(difluoromethyl)-1H-benzo[d]imidazol-1-yl)-6-morpholino-1,3,5-triazin-2-amine A8

A8

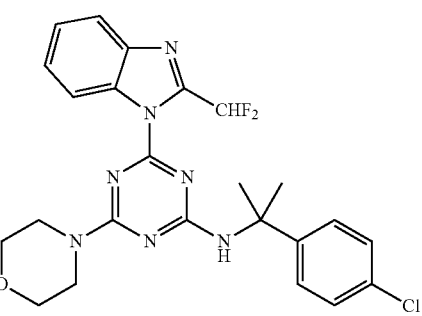

Compound A8 was synthesized in two steps according to the procedure for compound A13, substituting 4-chlorobenzonitrile in place of naphthalene-2-carbonitrile. The crude product was purified by preparative HPLC to give 125 mg (41% yield for 2 steps) of compound A8 as a white solid: 99.5% purity (HPLC); MS m/z: 500.2 (M+1); $^1$H NMR (CDCl$_3$, 500 MHz) δ 8.44 (d, J=8.0 Hz, 0.6H), 7.90 (d, J=7.5 Hz, 0.6H), 7.80 (d, J=8.0 Hz, 0.4H), 7.65 (t, J$_{HF}$=54.0 Hz, 0.6H), 7.49-7.33 (m, 4H), 7.33-7.27 (m, 2H), 7.15-6.87 (m, 0.8H), 5.75 and 5.72 (2s, 1H), 3.86 (m, 2H), 3.81 (m, 2H), 3.76 (m, 1H), 3.69 (m, 1H), 3.46 (m, 1H), 3.30 (m, 1H), 1.79 and 1.76 (2s, 6H) ppm

Example 11

Synthesis of 4-(2-(difluoromethyl)-1H-benzo[d]imidazol-1-yl)-N -(2-(4-methoxyphenyl)propan-2-yl)-6-morpholino-1,3,5-triazin-2-amine A9

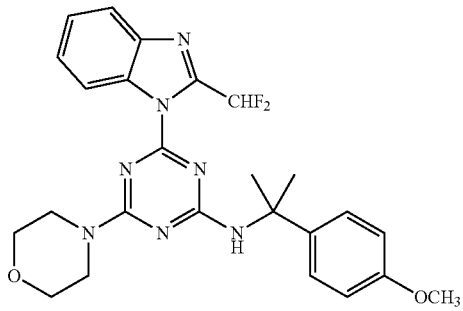

A9

Compound A9 was synthesized in two steps according to the procedure for compound A13, substituting 4-methoxybenzonitrile in place of naphthalene-2-carbonitrile. The crude compound A9 was purified by preparative HPLC to give 150 mg (50% yield for 2 steps) of product as a white solid: 98.0% purity (LCMS), MS m/z: 496.2 (M+1); $^1$H NMR (CDCl$_3$, 500 MHz) δ 8.44 (d, J=8.5 Hz, 0.5H), 7.90 (d, J=8.0 Hz, 0.5H), 7.80 (d, J=8.0 Hz, 0.5H), 7.65 (t, J$_{HF}$=53.5 Hz, 0.5H), 7.53 (d, J=8.5 Hz, 0.5H), 7.47-7.33 (m, 3H), 7.31 (t, J=7.5 Hz, 0.5H), 7.16 (t, J=7.5 Hz, 0.5H), 6.95 (d, J=9.0 Hz, 1H), 6.85 (d, J=9.0 Hz, 1H), 6.85 (t, J$_{HF}$=53.0 Hz, 0.5H), 5.77 (d, J=8.5 Hz, 1H), 3.87 (m, 2H), 3.81 (m, 5H), 3.76 (m, 1H), 3.69 (m, 1H), 3.48 (m, 1H), 3.40 (m, 1H), 1.79 and 1.75 (2s, 6H) ppm.

Example 12

Synthesis of 4-(2-(difluoromethyl)-1H-benzo[d]imidazol-1-yl)-N -(1-(4-fluorophenyl)-2-methylpropan-2-yl)-6-morpholino-1,3,5-triazin-2-amine A22

A22

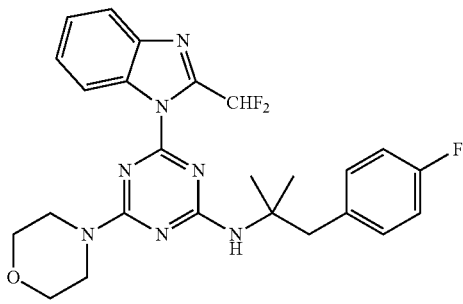

A mixture of 1-(4-fluorophenyl)-2-methylpropan-2-amine (125 mg, 0.748 mmol) and compound 1 (183 mg, 0.499 mmol) in dioxane (15 mL) was refluxed overnight. The volatiles were removed in vacuo and the residue was purified by prep-HPLC to give 4-(2-(difluoromethyl)-1H-benzo[d]imidazol-1-yl)-N-(1-(4-fluorophenyl)-2-methylpropan-2-yl)-6-morpholino-1,3,5-triazin-2-amine (35 mg, 14% yield) as a white solid: 98.1% purity (HPLC); MS m/z: 498.2 (M+1); $^1$H NMR (CDCl$_3$, 500 MHz) δ 8.37 (d, J=7.5 Hz, 1H), 7.88 (d, J=7.5 Hz, 1H), 7.63 (t, J$_{HF}$=54.0 Hz, 1H), 7.41 (m, 2H), 7.04 (t, J=8.0 Hz, 2H), 6.96 (t, J=8.5 Hz, 2H), 5.10 (s, 1H), 4.00-3.72 (m, 8H), 3.18 (s, 2H), 1.45 (s, 6H) ppm.

Example 13

Synthesis of 4-(2-(difluoromethyl)-1H-benzo[d]imidazol-1-yl)-N -(2-methyl-1-phenylpropan-2-yl)-6-morpholino-1,3,5-triazin-2-amine A14

A14

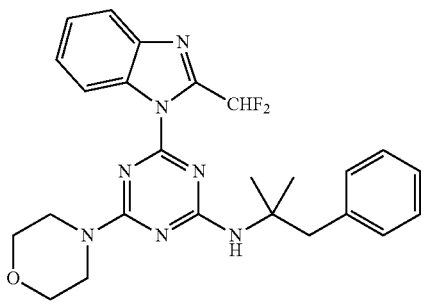

To a mixture of 2-methyl-1-phenyl-2-propanol (1.5 g, 10 mmol) and acetonitrile (3 mL) in acetic acid (15 mL) was added concentrated sulfuric acid (3 mL) dropwise at room temperature. The mixture was stirred at 65° C. for 3 hours and then poured into ice-water (ca. 200 mL). The aqueous solution was basified with saturated aqueous sodium hydroxide until pH>11. The suspension was stirred for further 0.5 hour, and then the precipitated solid was filtered and washed with water. The white solid was air-dried to give N-(2-methyl-1-phenylpropan-2-yl)acetamide (1.5 g, 78% yield), which was used for the next step without further purification.

A mixture of N-(2-methyl-1-phenylpropan-2-yl)acetamide (191 mg, 1.00 mmol) and potassium hydroxide (1 g) in ethylene glycol (10 mL) was refluxed for 8 hours. The mixture was diluted with ice-water and extracted with ethyl acetate. The combined organic fractions were washed with water, dried over anhydrous sodium sulfate and concentrated in vacuo to give crude 2-methyl-1-phenylpropan-amine (200 mg) as a brown oil, which was used for the next step without further purification.

Compound A14 was synthesized according to the procedure for compound A22, substituting the crude 2-methyl-1-phenylpropan-amine in place of 1-(4-fluorophenyl)-2-methylpropan-2-amine. The product was purified by preparative HPLC to give compound A14 (30 mg, 13% yield for 2 steps) as a white solid: 96.4% purity (HPLC); MS m/z: 480.3 (M+1); $^1$H NMR (CDCl$_3$, 500 MHz) δ 8.39 (d, J=7.5 Hz, 1H), 7.90 (d, J=7.5 Hz, 1H), 7.65 (t, J$_{HF}$=54.0 Hz, 1H), 7.42 (m, 2H), 7.28 (m, 3H), 7.16-7.10 (m, 2H), 5.15 (s, 1H), 4.01-3.75 (m, 8H), 3.22 (s, 2H), 1.49 (s, 6H) ppm.

Example 14

Synthesis of 4-(2-(difluoromethyl)-1H-benzo[d]imidazol-1-yl)-N -(1-(2-chlorophenyl)-2-methylpropan-2-yl)-6-morpholino-1,3,5-triazin-2-amine A16

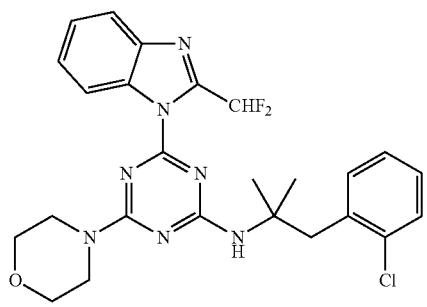

A16

A mixture of 1-(2-chlorophenyl)-2-methylpropan-2-amine hydrochloride (165 mg, 0.750 mmol), compound 1 (184 mg, 0.502 mmol) and potassium carbonate (138 mg, 1.00 mmol) in dioxane (15 mL) was refluxed for 12 hours. The volatiles were removed in vacuo and the residue was purified by reverse phase flash chromatography (0 to 80% acetonitrile in aq. 0.5% ammonium bicarbonate) to give 4-(2-(difluoromethyl)-1H-benzo[d]imidazol-1-yl)-N-(1-(2-chlorophenyl)-2-methylpropan-2-yl)-6-morpholino-1,3,5-triazin-2-amine (65 mg, 25% yield) as a white solid: 99.2% purity (HPLC); MS m/z: 514.2 (M+1); $^1$H NMR (CDCl$_3$, 500 MHz) δ 8.41 (d, J=8.0 Hz, 1H), 7.90 (d, J=7.0 Hz, 1H), 7.66 (t, $J_{HF}$=53.5 Hz, 1H), 7.50-7.36 (m, 3H), 7.24-7.05 (m, 3H), 5.34 (s, 1H), 4.05-3.70 (m, 8H), 3.43 (s, 2H), 1.53 (s, 6H) ppm.

Example 15

Synthesis of 4-(2-(difluoromethyl)-1H-benzo[d]imidazol-1-yl)-N -(1-(4-methoxyphenyl)-2-methylpropan-2-yl)-6-morpholino-1,3,5-triazin-2-amine A25

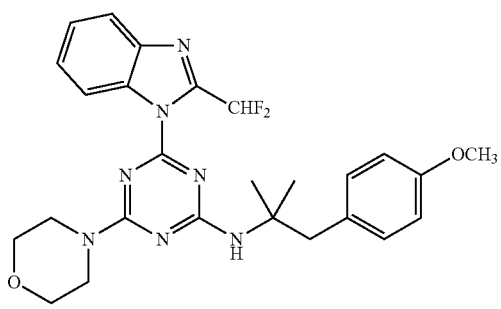

A25

A mixture of 4-(hydroxymethyl)phenol (1.0 g, 8.1 mmol) and 2-nitropropane (4.0 g, 45 mmol) in diglyme (50 mL) was cooled in an ice bath. Potassium tert -butoxide (0.45 g, 4.0 mmol) was added in portions, then the reaction mixture was heated to reflux overnight. After cooling, the mixture was concentrated and the residue was purified by silica gel column chromatography (petroleum ether/ethyl acetate) to give 4-(2-methyl-2-nitropropyl)phenol (1.3 g, 83% yield) as a light yellow solid.

Iodomethane (0.12 mL, 1.3 mmol) was added to a mixture of 4-(2-methyl -2-nitropropyl)phenol (300 mg, 1.5 mmol) and potassium carbonate (425 mg, 3.1 mmol) in tetrahydrofuran (20 mL) and N,N-dimethylformamide (1 mL). After refluxing overnight, the mixture was cooled and concentrated under vacuum. The residue was dissolved in ethyl acetate, washed with water, dried over anhydrous sodium sulfate and concentrated to provide crude 1-methoxy-4-(2-methyl-2-nitropropyl)benzene (200 mg, 62% yield) as yellow oil which was used directly in the next step.

The crude 1-methoxy-4-(2-methyl-2-nitropropyl)benzene (200 mg, 0.96 mmol) was combined with palladium on carbon (40 mg) in methanol (30 mL). The suspension was vigorously stirred at room temperature under a hydrogen atmosphere overnight. The mixture was filtered through Celite and the filtrate was concentrated to give 1-(4-methoxyphenyl)-2-methylpropan-2-amine (150 mg, 88% yield) as a yellow oil which was used without further purification. (MS m/z: 180 (M+1)).

A mixture of the 1-(4-methoxyphenyl)-2-methylpropan-2-amine (73 mg, 0.41 mmol) and compound 1 (100 mg, 0.27 mmol) in dioxane (25 mL) was refluxed overnight. The volatiles were removed under vacuum and the residue was purified by prep-HPLC to give compound A25 (40 mg, 29% yield) as a white solid: >99.5% purity (HPLC); MS m/z: 510.2 (M+1); $^1$H NMR (CDCl$_3$, 500 MHz) δ 8.38 (d, J=8.0 Hz, 1H), 7.89 (d, J=7.5 Hz, 1H), 7.64 (t, $J_{HF}$=54.0 Hz, 1H), 7.41 (m, 2H), 7.01 (d, J=8.5 Hz, 2H), 6.82 (d, J=8.0 Hz, 2H), 5.10 (s, 1H), 3.93 (m, 3H), 3.83 (m, 5H), 3.77 (s, 3H), 3.13 (s, 2H), 1.45 (s, 6H) ppm.

Example 16

Synthesis of 4-(2-(difluoromethyl)-1H-benzo[d]imidazol-1-yl)-N -(1-(2-methoxyphenyl)-2-methylpropan-2-yl)-6-morpholino-1,3,5-triazin-2-amine A19

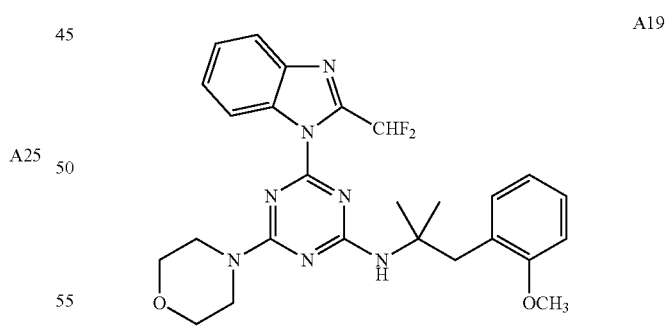

A19

Compound A19 was synthesized according to the procedure for compound A16, substituting 1-(2-methoxyphenyl)-2-methylpropan-2-amine in place of 1-(2-chlorophenyl)-2-methylpropan-2-amine hydrochloride. The product was purified by reverse phase flash chromatography (0 to 80% acetonitrile in water) to give compound A19 (66 mg, 81% yield) as a white solid: >99.5% purity (HPLC); MS m/z: 510.2 (M+1); $^1$H NMR (CDCl$_3$, 500 MHz) δ 8.42 (dd, J=7.5 Hz and 1.5 Hz, 1H), 7.88 (dd, J=6.5 Hz and 2.5 Hz, 1H), 7.67 (t, $J_{HF}$=53.5 Hz, 1H), 7.39 (m, 2H), 7.26 (m, 2H), 7.12 (dd, J=7.5 Hz and 1.5 Hz, 1H), 6.95 (m, 2H), 6.68 (s, 1H), 3.97 (s, 3H), 3.93-3.74 (m, 8H), 3.04 (s, 2H), 1.56 (s, 6H) ppm.

Example 17

Synthesis of N-(1-(4-bromophenyl)-2-methylpropan-2-yl)-4-(2-(difluoromethyl)-1H-benzo[d]imidazol-1-yl)-6-morpholino-1,3,5-triazin-2-amine A24

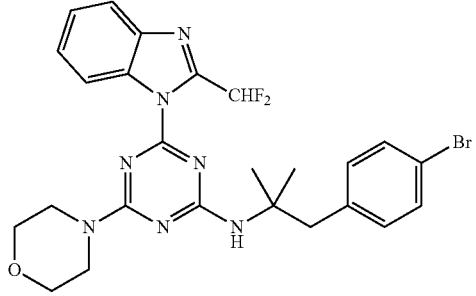

Compound A24 was synthesized according to the procedure for compound A16, substituting 1-(4-bromophenyl)-2-methylpropan-2-amine hydrochloride in place of 1-(2-chlorophenyl)-2-methylpropan-2-amine hydrochloride. The product was purified by reverse phase flash chromatography (0 to 80% acetonitrile in water) which yielded compound A24 (110 mg, 39% yield) as a white solid: 98.6% purity (HPLC); MS m/z: 558.2 (M+1), 560.2 (M+3); $^1$H NMR (CDCl$_3$, 500 MHz) δ 8.38 (d, J=7.5 Hz, 1H), 7.90 (d, J=7.5 Hz, 1H), 7.65 (t, JHF=53.5 Hz, 1H), 7.52-7.38 (m, 4H), 6.97 (d, 2H), 5.07 (s, 1H), 4.00-3.70 (m, 8H), 3.18 (s, 2H), 1.47 (s, 6H) ppm.

Example 18

Synthesis of 4-(2-(difluoromethyl)-1H-benzo[d]imidazol-1-yl)-N-(2-methyl-1-(o-tolyl)propan-2-yl)-6-morpholino-1,3,5-triazin-2-amine A18

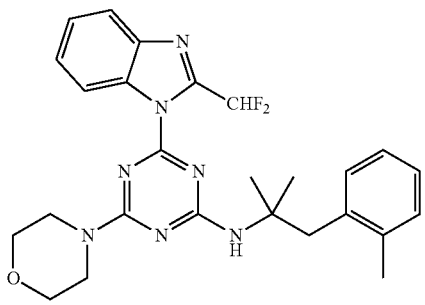

Compound A18 was synthesized according to the procedure for compound A16, substituting 2-methyl-1-(o-tolyl)propan-2-amine hydrochloride in place of 1-(2-chlorophenyl)-2-methylpropan-2-amine hydrochloride. The product was purified by silica gel column chromatography (20% ethyl acetate in petroleum ether) to give compound A18 (120 mg, 89% yield) as a white solid: >99.5% purity (HPLC); MS m/z: 494.2 (M+1); $^1$H NMR (CDCl$_3$, 500 MHz) δ 8.39 (d, J=8.0 Hz, 1H), 7.88 (d, J=7.0 Hz, 1H), 7.64 (t, J$_{HF}$=53.5, 1H), 7.40 (m, 2H), 7.22-6.98 (m, 4H), 5.24 (s, 1H), 4.00-3.75 (m, 8H), 3.25 (s, 2H), 2.36 (s, 3H), 1.49 (s, 6H) ppm.

Example 19

Synthesis of N-(1-(4-chlorophenyl)-2-methylpropan-2-yl)-4-(2-(difluoromethyl)-1H-benzo[d]imidazol-1-yl)-6-morpholino-1,3,5-triazin-2-amine A23

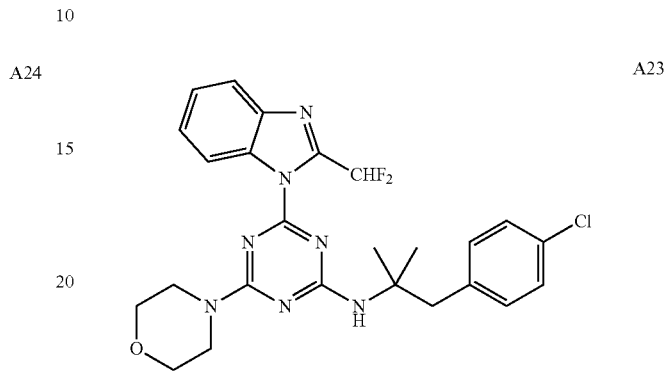

Methylmagnesium bromide (3 M in ether, 5.5 mL, 16.5 mmol) was added dropwise to a solution of methyl 4-chlorophenylacetate (1.0 g, 5.4 mmol) in tetrahydrofuran (20 mL) at 0° C. under a nitrogen atmosphere. The mixture was stirred at room temperature overnight and then quenched by the addition of water (30 mL). The organic phase was washed with brine, dried over sodium sulfate and concentrated to give 1-(4-chlorophenyl)-2-methylpropan-2-ol (1.0 g, 100% yield) as a yellow oil, which was used without further purification.

A solution of the crude alcohol (184 mg, 0.996 mmol) and chloroacetonitrile (150 mg, 1.99 mmol) in acetic acid (3.0 mL) was cooled to 0° C. Concentrated sulfuric acid (1.0 mL) was added to the solution dropwise while keeping the reaction temperature below 10° C. After stirring at room temperature for 1 hour, the resulting solution was poured onto ice and basified by the addition of solid potassium carbonate to pH>8. The mixture was extracted with ethyl acetate and the combined organic fractions were washed with water, dried over sodium sulfate and concentrated under vacuum to give 150 mg of 2-chloro-N -(1-(4-chlorophenyl)-2-methylpropan-2-yl)acetamide as yellow solid. The crude material was used directly in the next step.

To a mixture of 2-chloro-N-(1-(4-chlorophenyl)-2-methylpropan-2-yl)acetamide (259 mg, 1.00 mmol) in dioxane (5.0 mL) was added conc. hydrochloric acid (20 mL). After stirring at 105° C. for 16 hours, the reaction mixture was poured onto ice and basified by the addition of saturated aq. sodium bicarbonate to pH>8. The mixture was extracted with ethyl acetate and the combined organic fractions were washed with water, dried over sodium sulfate and concentrated under vacuum. The crude product was then purified by reverse phase flash chromatography (0 to 25% acetonitrile in aq. 0.01% formic acid) to give 1-(4-chlorophenyl)-2-methylpropan-2-amine (70 mg, 38% yield) as a white solid.

A mixture of 1-(4-chlorophenyl)-2-methylpropan-2-amine (70 mg, 0.38 mmol), compound 1 (93 mg, 0.25 mmol) and potassium carbonate (69 mg, 0.50 mmol) in dioxane (10 mL) was refluxed overnight. The volatiles were removed under vacuum and the residue was purified by reverse phase flash chromatography (0 to 70% acetonitrile in aq. 0.01% ammonium bicarbonate) to give compound A23 (57 mg, 44% yield) as a white solid: 93.1% purity (HPLC); MS m/z: 514.1 (M+1); $^1$H NMR (CDCl$_3$, 500 MHz) δ 8.37 (d, J=8.0 Hz, 1H), 7.89 (d, J=7.5 Hz, 1H), 7.63 (t, J$_{HF}$=54.0 Hz, 1H), 7.41 (m, 2H), 7.25 (m, 2H), 7.18-6.90 (m, 2H), 5.05 (s, 1H), 4.00-3.72 (m, 8H), 3.19 (s, 2H), 1.45 (s, 6H) ppm.

Example 20

Synthesis of N-(1-(3-chlorophenyl)-2-methylpropan-2-yl)-4-(2-(difluoromethyl)-1H-benzo[d]imidazol-1-yl)-6-morpholino-1,3,5-triazin-2-amine A20

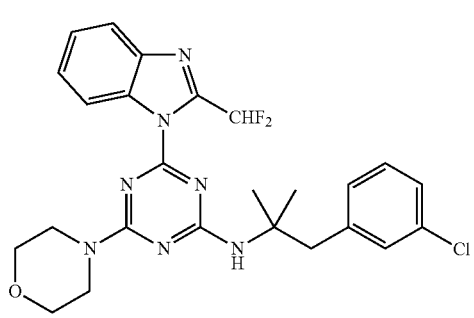

A20

Thionyl chloride (11 g, 100 mmol) was added dropwise to a mixture of 3-chlorophenylacetic acid (1.7 g, 10 mmol) in methanol (20 mL) at 0° C. The resulting mixture was refluxed at 80° C. for 12 hours. The volatiles were removed under vacuum and the residue was diluted with water and extracted with ethyl acetate. The combined organic solution was washed with water, dried over sodium sulfate and the concentrated to give 1.5 g of methyl 2-(3-chlorophenyl)acetate as a yellow oil, which was used without further purification.

Compound A20 was synthesized in 4 steps according to the procedure for compound A23, substituting the crude methyl 2-(3-chlorophenyl)acetate in place of methyl 4-chlorophenylacetate. The final product was purified by reverse phase flash chromatography (0 to 70% acetonitrile in aq. 0.01% ammonium bicarbonate) to give 19 mg of compound A20 as a white solid: >99.5% purity (HPLC); MS m/z: 514.1 (M+1); $^1$H NMR (CDCl$_3$, 500 MHz) δ 8.37 (d, J=8.0 Hz, 1H), 7.89 (d, J=7.5 Hz, 1H), 7.62 (t, $J_{HF}$=54.0 Hz, 1H), 7.41 (m, 2H), 7.21 (m, 2H), 7.10 (s, 1H), 6.96 (m, 1H), 5.10 (s, 1H), 4.00-3.69 (m, 8H), 3.19 (s, 2H), 1.47 (s, 6H) ppm.

Example 21

Synthesis of 4-(2-(difluoromethyl)-1H-benzo[d]imidazol-1-yl)—N—(1-(3-methoxyphenyl)-2-methylpropan-2-yl)-6-morpholino-1,3,5-triazin-2-amine A21

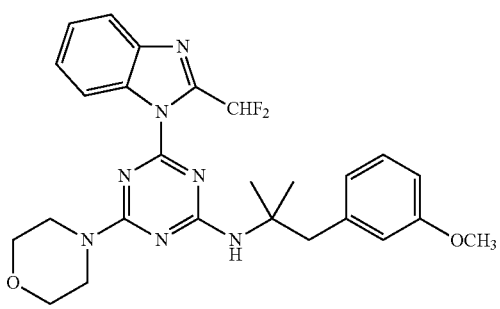

A21

Lithium diisopropylamide (2 M in tetrahydrofuran, 2.71 mL, 5.42 mmol) was added to a mixture of ethyl isobutyrate (600 mg, 5.17 mmol) in tetrahydrofuran (60 mL) at −78° C. and stirred at this temperature for 1 hour. 3-Methoxybenzyl chloride (1.15 g, 7.34 mmol) was added dropwise and the reaction mixture was stirred at −78° C. for another 1 hour and then at room temperature overnight. The mixture was quenched by water and extracted with ethyl acetate. The combined organic fractions were washed with water, dried over sodium sulfate and concentrated under vacuum to give ethyl-3-(3-methoxyphenyl)-2,2-dimethylpropanoate (1.3 g) as a yellow oil, which was used in the next step without further purification.

The crude ethyl-3-(3-methoxyphenyl)-2,2-dimethylpropanoate (1.00 g, 4.23 mmol) was taken up in a solution of ethanol (50 mL) and sodium hydroxide (2 N, 10 mL). The reaction mixture was refluxed overnight and then concentrated under vacuum. The concentrated aqueous solution was acidified with hydrochloric acid (2 N) to pH 3-4 and extracted with ethyl acetate. The combined organic fractions were dried over sodium sulfate and evaporated to yield 3-(3-methoxyphenyl)-2,2-dimethylpropanoic acid (600 mg) as a brown oil, which was used directly in the next step. MS m/z: 207 (M−1).

A mixture of 3-(3-methoxyphenyl)-2,2-dimethylpropanoic acid (200 mg, 0.96 mmol) in acetone (40 mL) and water (4 mL) was cooled to 0° C. Triethyl amine (0.18 mL, 1.3 mmol) was added to the reaction mixture followed by methyl chloroformate (118 mg, 1.25 mmol). The mixture was stirred for 1 hour at 0° C. and then another solution of sodium azide (94 mg, 1.45 mmol) in water (1 mL) was added dropwise. The reaction mixture was stirred at room temperature for another 1 hour. The mixture was diluted with water and extracted with ethyl acetate. The combined organic fractions were washed with water, dried over sodium sulfate and concentrated to give 3-(3-methoxyphenyl)-2,2-dimethylpropanoyl azide (60 mg) as a crude yellow oil, which was used without further purification.

A mixture of the crude 3-(3-methoxyphenyl)-2,2-dimethylpropanoyl azide (160 mg, 0.69 mmol) in toluene (20 mL) was refluxed overnight. The solvent was removed under vacuum to give 1,3-bis(1-(3-methoxyphenyl)-2-methylpropan-2-yl)urea (158 mg) as a brown oil, which was used without purification: MS m/z: 383 (M−1).

A mixture of the crude urea (80 mg, 0.21 mmol) and potassium hydroxide (32 mg, 0.57 mmol) in ethylene glycol (5 mL) was refluxed for 2 hours. The reaction mixture was diluted with water and extracted with ethyl acetate. The combined organic fractions were washed with water, dried over sodium sulfate and concentrated to give 1-(3-methoxyphenyl)-2-methylpropan-2-amine (75 mg) as a brown oil, which was used directly in the next step. MS m/z: 180 (M+1).

A mixture of the crude amine (63 mg, 0.35 mmol) and compound 1 (100 mg, 0.27 mmol) in dioxane (25 mL) was refluxed overnight. The volatiles were removed in vacuo and the residue was purified by prep-HPLC to give compound A21 (30 mg, 22% yield) as a white solid: >99.5% purity (HPLC); MS m/z: 510.2 (M+1); $^1$H NMR (CDCl$_3$, 500 MHz) δ 8.37 (d, J=8.0 Hz, 1H), 7.89 (d, J=7.5 Hz, 1H), 7.62 (t, $J_{HF}$=53.5 Hz, 1H), 7.40 (m, 2H), 7.20 (t, J=7.5 Hz, 1H), 6.79 (dd, J=8.5 Hz & 2.0 Hz, 1H), 6.69 (d, J=7.5 Hz, 1H), 6.65 (s, 1H), 5.14 (s, 1H), 4.00-3.76 (m, 8H), 3.74 (s, 3H), 3.17 (s, 2H), 1.48 (s, 6H) ppm.

Example 22

Synthesis of 4-(2-(difluoromethyl)-1H-benzo[d]imidazol-1-yl)—N—(2-methyl-1-(naphthalen-2-yl)propan-2-yl)-6-morpholino-1,3,5-triazin-2-amine A26

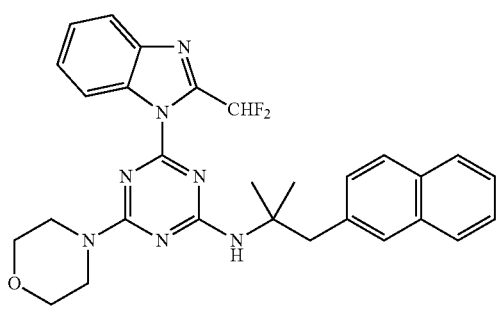

Lithium bis(trimethylsilyl)amide (1 M in tetrahydrofuran, 25.3 mL, 25.3 mmol) was added to a mixture of ethyl isobutyrate (2.67 g, 23.0 mmol) in tetrahydrofuran (25 mL) at −78° C. After stirring for 30 m, a solution of 2-(chloromethyl)naphthalene (400 mg, 2.30 mmol) in tetrahydrofuran (10 mL) was added to the reaction mixture dropwise. The mixture was stirred at −78° C. for another hour and then at room temperature overnight. The mixture was quenched by the addition of water and extracted with ethyl acetate. The combined organic fractions were washed with water, dried over sodium sulfate and concentrated under vacuum to give ethyl 2,2-dimethyl-3-(naphthalene-2-yl)propanoate (1.00 g) as a yellow oil, which was used without further purification.

The crude ester (915 mg) was taken up in dioxane (4 mL) and 20% aqueous sodium hydroxide (8 mL). After stirring at room temperature for 2 hours, the reaction mixture was diluted with ethyl acetate. The aqueous fraction was acidified to pH=2 with concentrated hydrochloric acid and was then extracted with ethyl acetate. The combined organic fractions were dried over sodium sulfate and concentrated to yield 2,2-dimethyl-3-(naphthalene-2-yl)propanoic acid (211 mg, 40% yield for two steps) as a white solid, which was used directly in the next step.

A mixture of the intermediate acid (211 mg, 0.920 mmol) in acetone (3 mL) and water (0.3 mL) was cooled to 0° C. Triethyl amine (0.20 mL, 1.40 mmol) was added to the reaction mixture followed by methyl chloroformate (104 mg, 1.10 mmol). The reaction was stirred at room temperature for 30 minutes and a solution of sodium azide (120 mg, 1.84 mmol) in water (0.5 mL) was added dropwise. After stirring at room temperature for 2 hours, the reaction mixture was diluted with water and extracted with petroleum ether. The combined organic fractions were washed with water, dried over sodium sulfate and evaporated to give crude 2,2-dimethyl-3-(naphthalene-2-yl)propanoyl azide (117 mg, 50% yield) as a colorless oil, which was used without further purification.

The crude acyl azide (117 mg, 0.46 mmol) was refluxed in toluene (3 mL) overnight to generate the intermediate isocyanate. The reaction mixture was allowed to cooled to room temperature and a solution of 10% hydrochloric acid (3 mL) was added. After refluxing for 4 hours, the reaction mixture was concentrated under vacuum to give 2-methyl-1-(naphthalene-2-yl)propan-2-amine (98 mg, 90% yield) as a yellow solid, which was used directly in the next step.

A mixture of the crude amine (98 mg, 0.42 mmol), compound 1 (103 mg, 0.28 mmol) and potassium carbonate (116 mg, 0.84 mmol) in dioxane (3 mL) was refluxed overnight. The reaction mixture was concentrated and the residue was purified by prep-HPLC to give compound A26 (12 mg, 8% yield) as a white solid: >99.5% purity (HPLC); MS m/z: 530.3 (M+1); $^1$H NMR (CDCl$_3$, 500 MHz) δ 8.37 (d, J=8.0 Hz, 1H), 7.85-7.37 (m, 10H), 5.19 (s, 1H), 4.04-3.75 (m, 8H), 3.37 (s, 2H), 1.53 (s, 6H) ppm.

Example 23

Synthesis of 4-(2-(difluoromethyl)-1H-benzo[d]imidazol-1-yl)—N—(2-methyl-1-(naphthalen-1-yl)propan-2-yl)-6-morpholino-1,3,5-triazin-2-amine A27

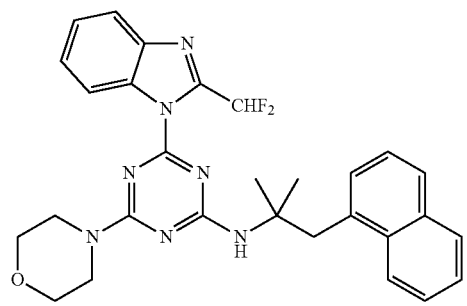

Methylmagnesium bromide (3 M in ether, 10 mL, 30 mmol) was added dropwise to a solution of methyl naphthalene-1-acetate (2.0 g, 10 mmol) in tetrahydrofuran (20 mL) at 0° C. under a nitrogen atmosphere. After stirring at room temperature overnight, the reaction mixtures was quenched by the addition of water. The organic fraction was washed with brine, dried over sodium sulfate and concentrated under vacuum to give crude 2-methyl-1-(naphthalene-1-yl)propan-2-ol (2.0 g) as a yellow oil, which was used directly in the next step.

The crude alcohol (2.0 g, 10 mmol) was dissolved in acetonitrile (10 mL) and concentrated sulfuric acid (4.9 g, 50 mmol) was added dropwise at 0° C. After stirring at room temperature for 2 hours, the reaction mixture was diluted with water and extracted with dichloromethane. The combined organic fractions were dried over sodium sulfate and evaporated. The residue was purified by silical gel column chromatography (petroleum ether/ethyl acetate) to give N—(2-methyl-1-(naphthalene-1-yl)propan-2-yl)acetamide (0.90 g, 37% yield) as a yellow solid.

Concentrated hydrochloric acid (10 mL) was added to a solution of the intermediate acetamide (0.20 g, 0.83 mmol) in dioxane (2 mL) and the resulting mixture was refluxed for 3 days. After cooling to room temperature, the reaction mixture was basified to pH 9 by the addition of solid sodium bicarbonate. The mixture was extracted with ethyl acetate and the combined organic fractions were dried over sodium sulfate and concentrated to give crude 2-methyl-1-(naphthalene-1-yl)propan-2-amine (0.15 g, 23% yield) as a yellow oil, which was used without further purification.

The crude amine (153 mg, 0.25 mmol), compound 1 (48 mg, 0.13 mmol) and potassium carbonate (36 mg, 0.25 mmol) were taken up in dioxane (2 mL) and heated to reflux overnight. The reaction mixture was concentrated under vacuum and the residue was purified by prep-HPLC to give compound A27 (16 mg, 23% yield) as a white solid: >99.5% purity (HPLC); MS m/z: 530.3 (M+1); $^1$H NMR (CDCl$_3$, 500 MHz) δ 8.29 (d, J=8.0 Hz, 1H), 8.15 (d, J=7.0 Hz, 1H), 7.88 (d, J=6.5 Hz, 2H), 7.77 (d, J=8.0 Hz, 1H), 7.56 (t, J$_{HF}$=54.0 Hz, 1H), 7.48 (m, 2H), 7.39 (m, 3H), 7.27 (d, J=7.0 Hz, 1H), 5.29 (s, 1H), 4.02-3.73 (m, 8H), 3.66 (s, 2H), 1.54 (s, 6H) ppm.

Example 24

Synthesis of 4-(2-(difluoromethyl)-1H-benzo[d]imidazol-1-yl)—N—(1-(2-fluorophenyl)-2-methylpropan-2-yl)-6-morpholino-1,3,5-triazin-2-amine A15

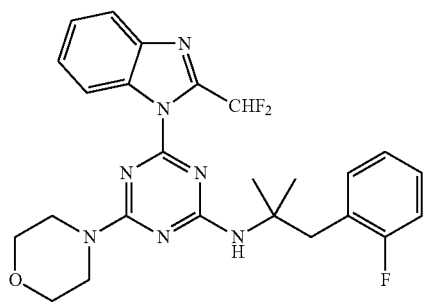

A15

Compound A15 was synthesized in 6 steps according to the procedure for compound A21, substituting 2-fluorobenzyl bromide in place of 3-methoxybenzyl chloride. The final product was purified by prep-HPLC to give compound A15 (30 mg, 22% yield) as a white solid: 99.4% purity (HPLC); MS m/z: 498.2 (M+1); $^1$H NMR (CDCl$_3$, 500 MHz) δ 8.39 (d, J=8.0 Hz, 1H), 7.89 (d, J=7.5 Hz, 1H), 7.65 (t, J$_{HF}$=53.5 Hz, 1H), 7.41 (m, 2H), 7.22 (m, 1H), 7.06 (m, 3H), 5.25 (s, 1H), 4.00-3.73 (m, 8H), 3.28 (s, 2H), 1.49 (s, 6H) ppm.

Example 25

Synthesis of 4-(2-(difluoromethyl)-1H-benzo[d]imidazol-1-yl)—N—(2-methyl-2-phenylpropyl)-6-morpholino-1,3,5-triazin-2-amine A29

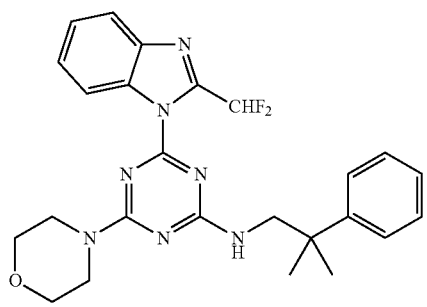

A29

Powdered lithium aluminum hydride (137 mg, 3.61 mmol) was added portionwise to a solution of 2-methyl-2-phenylpropanenitrile (436 mg, 3.00 mmol) in tetrahydrofuran (20 mL). The resulting mixture was stirred at 80° C. overnight. The reaction was then cooled to 0° C. and water (66 μL, 3.7 mmol), 10% sodium hydroxide (1.44 g, 3.6 mmol) and water (195 μL, 10.8 mmol), respectively, were added dropwise into the reaction mixture. The suspension was filtered through anhydrous magnesium sulfate and the solution was concentrated under vacuum to give 2-methyl-2-phenylpropan-1-amine (400 mg) as a yellow oil, which was used for the next step without further purification.

The crude amine (400 mg, 2.7 mmol) and compound 1 (147 mg, 0.401 mmol) were refluxed in dioxane (25 mL) for 4 hours. After cooling, the reaction mixture was concentrated under vacuum. The residue was diluted with saturated sodium bicarbonate and extracted with ethyl acetate. The combined organic fractions were washed with water and brine, dried over sodium sulfate and concentrated. The crude product was purified by prep-HPLC to give compound A29 (75 mg, 35% yield for 2 steps) as a white solid: >99.5% purity (HPLC); MS m/z: 480.2 (M+1); $^1$H NMR (CDCl$_3$, 500 MHz) (rotamers) δ 8.45 (d, J=7.5 Hz, 0.5H), 8.33 (d, J=8.0 Hz, 0.5H), 7.92 (d, J=7.5 Hz, 0.5H), 7.88 (d, J=7.5 Hz, 0.5H), 7.64 and 7.60 (2t, J$_{HF}$=53.5 Hz, 1H), 7.42 (m, 6H), 7.28 (m, 1H), 5.13-5.00 (m, 1H), 4.00-3.70 (m, 10H), 1.45 and 1.44 (2s, 6H) ppm.

Example 26

Synthesis of 4-(2-(difluoromethyl)-1H-benzo[d]imidazol-1-yl)—N—(2-(1-phenylcyclopropyl)propan-2-yl)-6-morpholino-1,3,5-triazin-2-amine A30

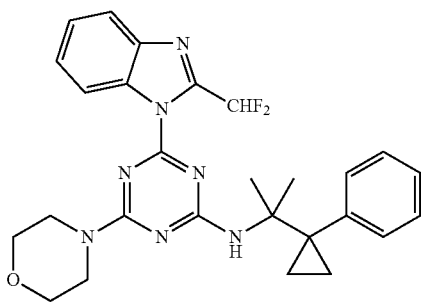

A30

Methylmagnesium bromide (3.0 M in tetrahydrofuran, 3.0 mL, 9.0 mmol) was added to a solution of 1-phenyl-1-cyclopropanecarbonitrile (429 mg, 3.0 mmol) in anhydrous tetrahydrofuran (4 mL) at room temperature under a nitrogen atmosphere. The reaction mixture was heated to 100° C. for 10 minutes in a microwave oven. Then titanium(IV) isopropoxide (0.9 mL, 3.0 mmol) was added and the reaction mixture was heated to 50° C. for 1 hour in the microwave. After cooling, a solution of 25% aqueous ammonia (2 mL) was added dropwise to the reaction mixture. The suspension was filtered through a Celite pad which was washed with tetrahydrofuran. The combined filtrate was diluted with water and extracted with ethyl acetate. The combined organic extracts were dried over anhydrous sodium sulfate and concentrated under vacuum to give 2-(1-phenylcyclopropyl)propan-2-amine (400 mg) as a crude yellow oil: MS m/z: 178 (M+1).

The crude amine (200 mg, 1.1 mmol) was combined with compound 1 (100 mg, 0.27 mmol) and potassium carbonate (150 mg, 1.1 mmol) in dioxane (20 mL) and heated to reflux overnight. The mixture was diluted with water and extracted with ethyl acetate. The organic extracts were dried with anhydrous sodium sulfate and concentrated under vacuum. The crude product was purified by reversed phase flash chromatography (0 to 85% acetonitrile in 0.01% ammonium bicarbonate) to give compound A30 (46 mg 34% yield) as a white solid: 94.4% purity (HPLC); MS m/z: 506.2 (M+1); $^1$H NMR (CDCl$_3$, 500 MHz) δ 8.34 (d, J=7.5 Hz, 1H), 7.90 (d, J=7.5 Hz, 1H), 7.61 (t, J$_{HF}$=54.0 Hz, 1H), 7.42 (m, 2H), 7.35 (m, 2H), 7.29 (m, 2H), 7.24 (m, 1H), 5.26 (s, 1H), 4.00-3.65 (m, 8H), 1.48 (s, 6H), 1.17 (m, 2H), 0.84 (m, 2H) ppm.

Example 27

Synthesis of 4-(2-(difluoromethyl)-1H-benzo[d]imidazol-1-yl)—N—(1-(2-bromophenyl)-2-methylpropan-2-yl)--6-morpholino-1,3,5-triazin-2-amine A17

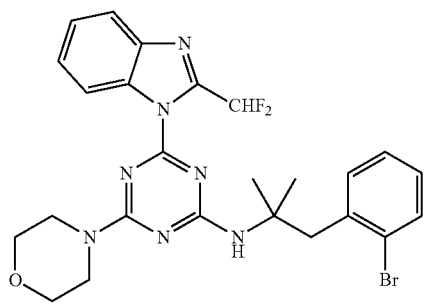

Lithium diisopropylamide (2M in hexane, 1.5 mL, 3.0 mmol) was added to a solution of ethyl isobutyrate (233 mg, 2.01 mmol) in tetrahydrofuran (1 mL) at −78° C. and the reaction mixture was stirred at this temperature for 30 min. Then, a solution of 2-bromobenzyl bromide (250 mg, 1.00 mmol) in tetrahydrofuran (1 mL) was added dropwise. The reaction mixture was stirred at −78° C. for another 1 hr and then at room temperature overnight. The mixture was diluted with water and extracted with ethyl acetate. The combined organic fractions were washed with water, dried over sodium sulfate, and concentrated to give 482 mg of ethyl 3-(2-bromophenyl)-2,2-dimethylpropanoate as a yellow oil. The crude intermediate was used directly in the next step.

A solution of the crude ester (482 mg) in dioxane (2 mL) was combined with aqueous sodium hydroxide (20%, 4 mL) and stirred at room temperature for 2 hrs. The reaction mixture was diluted with ethyl acetate and the aqueous fraction was acidified to pH 2 with conc. hydrochloric acid. After extraction with ethyl acetate, the combined organic fractions were dried over sodium sulfate and concentrated under vacuum to give 121 mg (47% yield for two steps) of 3-(2-bromophenyl)-2,2-dimethylpropanoic acid as a white solid. The crude carboxylic acid was used in the next step without further purification: MS m/z: 255.0 (M−1).

Triethylamine (112 mg, 1.11 mmol) was added to a mixture of the intermediate carboxylic acid (188 mg, 0.731 mmol) in acetone (8 mL) and water (1 mL). The reaction mixture was cooled to 0° C. and methyl chloroformate (84 mg, 0.88 mmol) was added. The mixture was stirred at room temperature for 30 min and then a solution of sodium azide (95 mg, 1.46 mmol) in water (0.5 mL) was added dropwise. After stirring at room temperature overnight, the resulting mixture was diluted with water and extracted with petroleum ether. The combined organic factions were washed with water, dried over sodium sulfate, and concentrated to give 162 mg (79% yield) of 3-(2-bromophenyl)-2,2-dimethylpropanoyl azide as a white solid, which was used directly in the next step: MS m/z: 252.9 (M−28).

A solution of the crude acyl azide (162 mg, 0.574 mmol) in toluene (3 mL) was refluxed overnight to give 1-bromo-2-(2-isocyanato-2-methylpropyl)benzene. Then, the solution was cooled to room temperature and 10% aq. hydrochloric acid (3 mL) was added. The resulting mixture was refluxed for 4 hrs. The volatiles were removed in vacuo to give 129 mg (85% yield) of 1-(2-bromophenyl)-2-methylpropan-2-amine hydrochloride as a white solid. The crude amine hydrochloride salt was used in the next step without further purification: MS m/z: 228.1 (M+1).

A mixture of the amine salt (129 mg, 0.49 mmol), compound 1 (121 mg, 0.33 mmol), and potassium carbonate (183 mg, 1.33 mmol) was refluxed in dioxane (4 mL) overnight. The volatiles were removed under vacuum and the residue was purified by silical gel column chromatography (9% ethyl acetate in petroleum ether) to give 99 mg (54% yield) of compound A17, 4-(2-(difluoromethyl)-1H-benzo[d]imidazol-1-yl)—N—(1-(2-bromophenyl)-2-methylpropan-2-yl)-6-morpholino-1,3,5-triazin-2-amine, as a white solid: >99.5% purity (HPLC); MS m/z: 558.2 (M+1), 560.2 (M+3); $^1$H NMR (CDCl$_3$, 500 MHz) δ 8.42 (d, 1H), 7.91 (d, 1H), 7.67 (t, 1H), 7.60 (d, 1H), 7.48-7.37 (m, 2H), 7.22 (t, 1H), 7.11 (m, 2H), 5.32 (s, 1H), 4.01-3.76 (m, 8H), 3.46 (s, 2H), 1.54 (s, 6H) ppm.

Example 28

Synthesis of 4-(2-(difluoromethyl)-1H-benzo[d]imidazol-1-yl)—N—(2-methyl-1-(2-(pyridin-4-yl)phenyl)propan-2-yl)-6-morpholino-1,3,5-triazin-2-amine A33

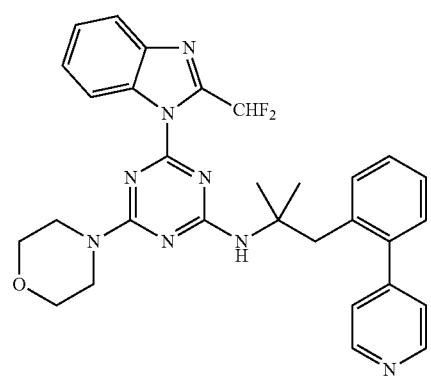

Compound A17 (200 mg, 0.358 mmol), pyridinyl-4-boronic acid (49 mg, 0.40 mmol), sodium carbonate (114 mg, 1.08 mmol), and 1,1'-bis(diphenylphosphino)ferrocene-palladium(II)dichloride dichloromethane complex (29 mg, 0.036 mmol) were taken up in N,N'-dimethylformamide (4 mL) and water (1 mL) and stirred under nitrogen at 100° C. overnight. The reaction mixture was diluted with ethyl acetate and filtered through Celite. The filtrate was washed with water and brine, dried over sodium sulfate, and concentrated. The crude product was purified by prep-HPLC to give 18 mg (9% yield) of compound A33, 4-(2-(difluoromethyl)-1H-benzo[d]imidazol-1-yl)—N—(2-methyl-1-(2-(pyridin-4-yl)phenyl)-propan-2-yl)-6-morpholino-1,3,5-triazin-2-amine, as a white solid: >99.5% purity (HPLC); MS m/z: 557.3 (M+1); $^1$H NMR (CDCl$_3$, 500 MHz) (rotamers) δ 8.53 (br s, 2H), 8.39 (d, 1H), 7.92 (d, 1H), 7.66 (t, 1H), 7.49-7.38 (m, 2H), 7.34 (m, 2H), 7.26 (m, 1H), 7.23-7.15 (m, 3H), 4.88 (s, 1H), 3.95-3.75 (m, 8H), 3.35 (s, 2H), 1.28 (s, 6H) ppm.

Example 29

Synthesis of 4-(2-(difluoromethyl)-1H-benzo[d]imidazol-1-yl)—N—(1-(biphenyl-2-yl)-2-methylpropan-2-yl)-6-morpholino-1,3,5-triazin-2-amine A47

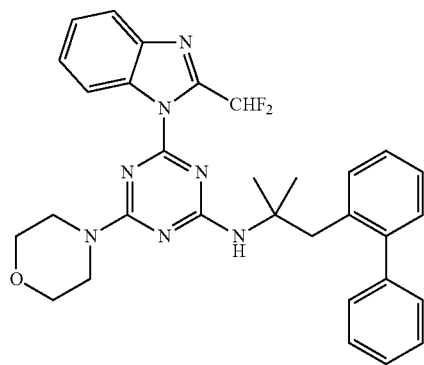

A47

Compound A17 (140 mg, 0.251 mmol), phenylboronic acid (61 mg, 0.500 mmol), sodium carbonate (80 mg, 0.755 mmol), and 1,1'-bis(diphenylphosphino)ferrocene-palladium(II)dichloride dichloromethane complex (21 mg, 0.0257 mmol) were taken up in N,N'-dimethylformamide (8 mL) and water (2 mL) and stirred under nitrogen at 100° C. overnight. The reaction mixture was diluted with ethyl acetate and filtered through Celite. The filtrate was washed with water and brine, dried over sodium sulfate, and concentrated. The crude product was purified by chiral-SFC to give 60 mg (44% yield) of compound A47, 4-(2-(difluoromethyl)-1H-benzo[d]imidazol-1-yl)—N—(1-(biphenyl-2-yl)-2-methylpropan-2-yl)-6-morpholino-1,3,5-triazin-2-amine, as a white solid: >99.5% purity (HPLC); MS m/z: 556.2 (M+1); $^1$H NMR (CDCl$_3$, 500 MHz) (rotamers) δ 8.39 (d, 1H), 7.92 (d, 1H), 7.66 (t, 1H), 7.44 (m, 2H), 7.28 (m, 7H), 7.22 (m, 2H), 4.94 (s, 1H), 3.92-3.55 (m, 8H), 3.37 (s, 2H), 1.28 (s, 6H) ppm.

Example 30

Synthesis of 4-(2-(difluoromethyl)-1H-benzo[d]imidazol-1-yl)—N—(1-(3-fluorophenyl)-2-methylpropan-2-yl)-6-morpholino-1,3,5-triazin-2-amine A39

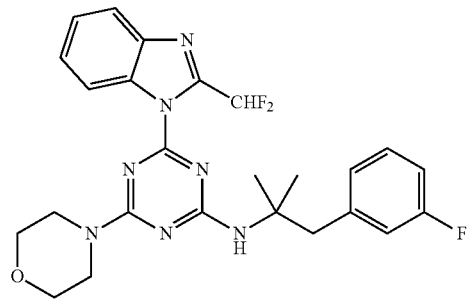

A39

Compound A39 was synthesized in 6 steps according to the procedure for A21, substituting 3-fluorobenzyl bromide in place of 3-methoxybenzyl chloride. The final product was purified by prep-HPLC to give compound A39 (35 mg) as a white solid: 99% purity (HPLC); MS m/z: 498.2 (M+1); $^1$H NMR (DMSO$_{d6}$, 500 MHz) δ 8.60 (d, 1H), 8.01 (t, 1H), 7.84 (d, 1H), 7.54 (s, 1H), 7.45 (m, 2H), 7.30 (m, 1H), 7.03 (m, 1H), 6.94 (m, 2H), 3.85 (m, 4H), 3.75 (m, 4H), 3.25 (s, 2H), 1.40 (s, 6H) ppm.

Example 31

Synthesis of 4-(2-(difluoromethyl)-1H-benzo[d]imidazol-1-yl)—N—(2-methyl-1-m-tolylpropan-2-yl)-6-morpholino-1,3,5-triazin-2-amine A49

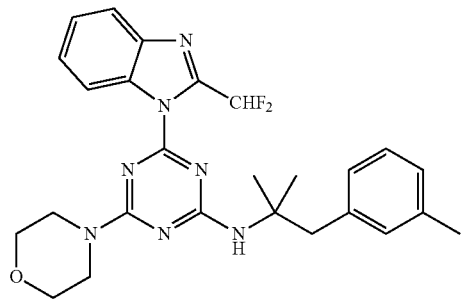

A49

Compound A49 was synthesized in 6 steps according to the procedure for A21, substituting 3-methylbenzyl bromide in place of 3-methoxybenzyl chloride. The final product was purified by prep-HPLC to give compound A49 (15 mg) as a white solid: 98% purity (HPLC); MS m/z: 494.2 (M+1); $^1$H NMR (CDCl$_3$, 500 MHz) δ 8.38 (d, 1H), 7.90 (d, 1H), 7.64 (t, 1H), 7.48 (s, 1H), 7.42 (m, 1H), 7.19 (t, 1H), 7.10-6.88 (m, 3H), 5.17 (s, 1H), 4.10-3.80 (m, 8H), 3.16 (s, 2H), 2.31 (s, 3H), 1.49 (s, 6H) ppm.

Example 32

Synthesis of 4-(2-(difluoromethyl)-1H-benzo[d]imidazol-1-yl)—N—(1-(4-fluoro-3-methoxyphenyl)-2-methylpropan-2-yl)-6-morpholino-1,3,5-triazin-2-amine A50

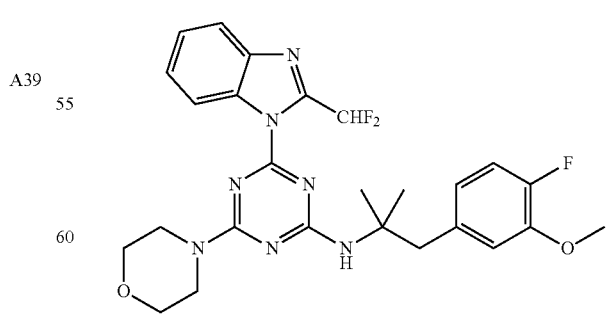

A50

Compound A50 was synthesized in 6 steps according to the procedure for A21, substituting 4-fluoro-3-methoxybenzyl in place of 3-methoxybenzyl chloride. The final product was purified by prep-HPLC to give compound A50 (115 mg) as a white solid: 99% purity (HPLC); MS m/z: 528.2 (M+1); $^1$H NMR (CDCl$_3$, 500 MHz) δ 8.37 (d, 1H), 7.90 (d, 1H), 7.64 (t, 1H), 7.43 (m, 2H), 6.99 (m, 1H), 6.71-6.60 (m, 2H), 5.12 (s, 1H), 4.01-3.78 (m, 8H), 3.77 (s, 3H), 3.17 (s, 2H), 1.49 (s, 6H) ppm.

Example 33

Synthesis of 4-(2-(difluoromethyl)-1H-benzo[d]imidazol-1-yl)—N—(1-(2,4-difluorophenyl)-2-methylpropan-2-yl)-6-morpholino-1,3,5-triazin-2-amine A51

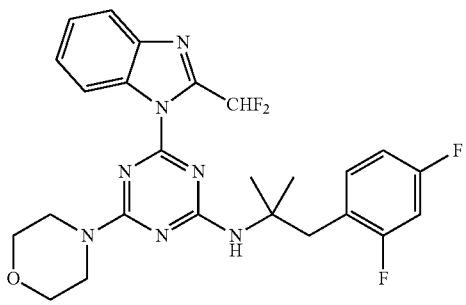

A51

Compound A51 was synthesized in 5 steps according to the procedure for A20, substituting 2,4-difluorophenylacetic acid in place of 3-chlorophenylacetic acid. The final product was purified by prep-HPLC to give compound A51 (60 mg) as a white solid: 99% purity (HPLC); MS m/z: 516.2 (M+1); $^1$H NMR (CDCl$_3$, 500 MHz) δ 8.40 (d, 1H), 7.90 (d, 1H), 7.65 (t, 1H), 7.43 (m, 2H), 7.04 (m, 1H), 6.84 (m, 2H), 5.19 (s, 1H), 4.00-3.75 (m, 8H), 3.26 (s, 2H), 1.49 (s, 6H) ppm.

Example 34

Synthesis of 4-(2-(difluoromethyl)-1H-benzo[d]imidazol-1-yl)—N—(1-(2,6-difluorophenyl)-2-methylpropan-2-yl)-6-morpholino-1,3,5-triazin-2-amine A52

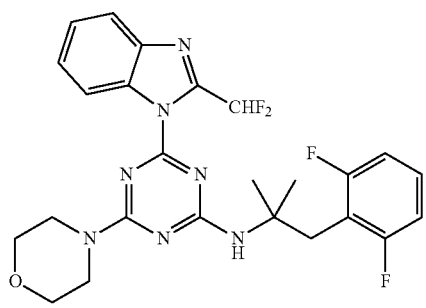

A52

Compound A52 was synthesized in 5 steps according to the procedure for A20, substituting 2,6-difluorophenylacetic acid in place of 3-chlorophenylacetic acid. The final product was purified by prep-HPLC to give compound A52 (38 mg) as a white solid: 98% purity (HPLC); MS m/z: 516.3 (M+1); $^1$H NMR (CDCl$_3$, 500 MHz) δ 8.41 (d, 1H), 7.90 (d, 1H), 7.66 (t, 1H), 7.43 (m, 2H), 7.23 (m, 1H), 6.91 (t, 2H), 5.43 (s, 1H), 4.05-3.70 (m, 8H), 3.33 (s, 2H), 1.53 (s, 6H) ppm.

Example 35

Synthesis of 4-(2-(difluoromethyl)-1H-benzo[d]imidazol-1-yl)—N—(2-methyl-1-(2-(pyridin-3-yl)phenyl)propan-2-yl)-6-morpholino-1,3,5-triazin-2-amine A40

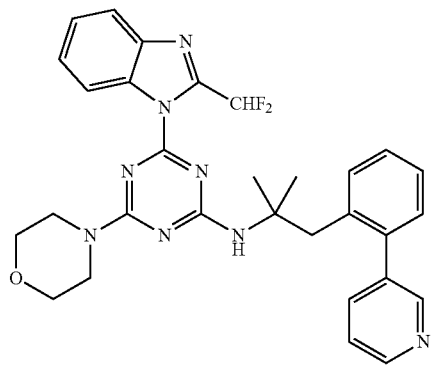

A40

Compound A40 was synthesized according to the procedure for A33, substituting 3-(4,4,5,5-tetramethyl-1,3,2-dioxaborolan-2-yl)pyridine in place of pyridinyl-4-boronic acid. The crude product was purified by prep-HPLC to give compound A40 (41 mg, 41% yield) as a white solid: 98% purity (HPLC); MS m/z: 557.3 (M+1); $^1$H NMR (DMSO$_{d6}$, 500 MHz) δ 8.58 (d, 1H), 8.40 (s, 1H), 8.37 (dd, 1H), 8.01 (t, 1H), 7.84 (d, 1H), 7.58 (dd, 1H), 7.48 (t, 1H), 7.43 (t, 1H), 7.40-7.28 (m, 3H), 7.19 (s, 1H), 7.13 (m, 2H), 3.82-3.60 (m, 8H), 3.34 (s, 2H), 1.23 (s, 6H) ppm.

Example 36

Synthesis of 4-(2-(difluoromethyl)-1H-benzo[d]imidazol-1-yl)—N—(1-(2-(2-methoxypyridin-4-yl)phenyl)-2-methylpropan-2-yl)-6-morpholino-1,3,5-triazin-2-amine A41

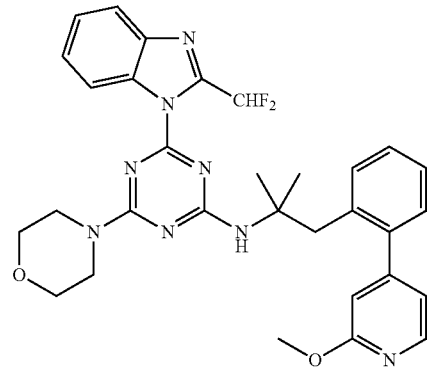

A41

Compound A41 was synthesized according to the procedure for A33, substituting 2-methoxypyridine-4-boronic acid in place of pyridinyl-4-boronic acid. The crude product was purified by prep-HPLC to give compound A41 (250 mg, 24% yield) as a white solid: 95% purity (HPLC); MS m/z: 587.3 (M+1); $^1$H NMR (CDCl$_3$, 500 MHz) δ 8.40 (d, J=8.0 Hz, 1H), 8.06 (d, 1H), 7.91 (d, 1H), 7.65 (t, 1H), 7.43 (m, 2H), 7.33 (m, 2H), 7.25 (t, 1H), 7.16 (d, 1H), 6.78 (d, 1H), 6.62 (s, 1H), 4.85 (s, 1H), 3.95-3.75 (m, 8H), 3.74 (s, 3H), 3.36 (s, 2H), 1.32 (s, 6H) ppm.

Example 37

Synthesis of 4-(2-(difluoromethyl)-1H-benzo[d]imidazol-1-yl)—N—(2-methyl-1-(2-(2-methylpyridin-4-yl)phenyl)propan-2-yl)-6-morpholino-1,3,5-triazin-2-amine A43

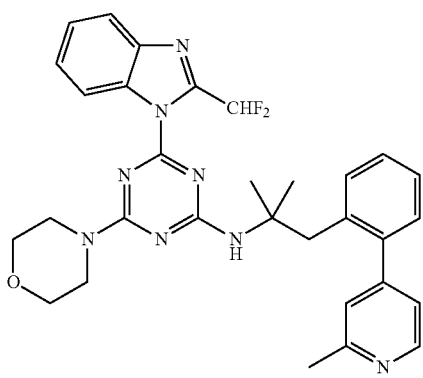

A43

Compound A43 was synthesized according to the procedure for A33, substituting 2-methylpyridine-4-boronic acid in place of pyridinyl-4-boronic acid. The crude product was purified by prep-HPLC to give compound A43 (15 mg, 24% yield) as a white solid: 98% purity (HPLC); MS m/z: 571.2 (M+1); $^1$H NMR (CDCl$_3$, 500 MHz) δ 8.45 (d, 1H), 8.40 (d, 1H), 7.91 (d, 1H), 7.66 (t, 1H), 7.44 (m, 2H), 7.33 (m, 2H), 7.24 (m, 1H), 7.16 (m, 1H), 7.13-6.95 (m, 2H), 4.88 (s, 1H), 4.00-3.75 (m, 8H), 3.36 (s, 2H), 2.49 (s, 3H), 1.28 (s, 6H) ppm.

Example 38

Synthesis of 4-(2-(difluoromethyl)-1H-benzo[d]imidazol-1-yl)—N—(1-(2-(1H-pyrazol-4-yl)phenyl)-2-methylpropan-2-yl)-6-morpholino-1,3,5-triazin-2-amine A44

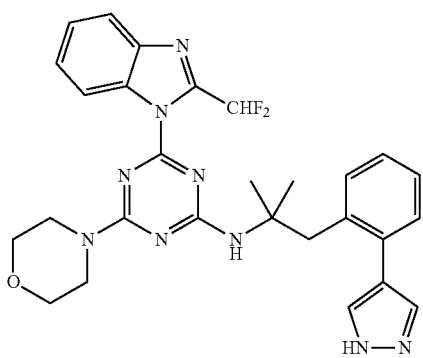

A44

Compound A44 was synthesized according to the procedure for A33, substituting 1-Boc-pyrazole-4-boronic acid pinacol ester in place of pyridinyl-4-boronic acid. The crude product was purified by prep-HPLC to give compound A44 (15 mg, 31% yield) as a white solid: 99% purity (HPLC); MS m/z: 546.3 (M+1); $^1$H NMR (DMSO$_{d6}$, 500 MHz) δ 12.84 (s, 1H), 8.59 (d, 1H), 8.00 (t, 1H), 7.84 (d, 1H), 7.74 (br s, 1H), 7.50 (br s, 1H), 7.48 (t, 1H), 7.42 (t, 1H), 7.37 (s, 1H), 7.20 (m, 4H), 3.85-3.42 (m, 8H), 3.42 (s, 2H), 1.21 (s, 6H) ppm.

Example 39

Synthesis of 4-(2-(difluoromethyl)-1H-benzo[d]imidazol-1-yl)—N—(2-methyl-1-(2-(1-methyl-1H-pyrazol-4-yl)phenyl)propan-2-yl)-6-morpholino-1,3,5-triazin-2-amine A45

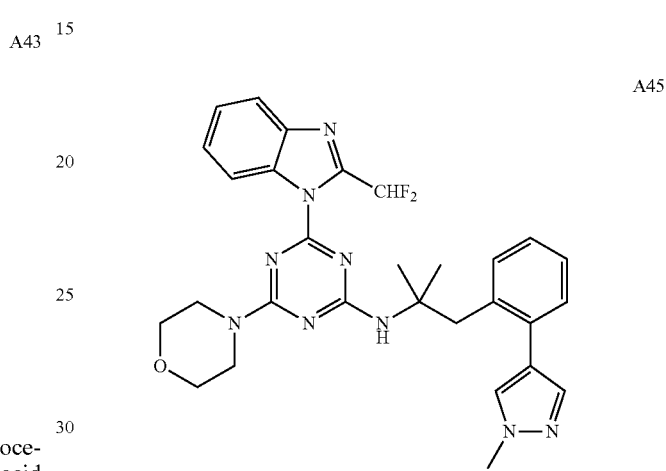

A45

Compound A45 was synthesized according to the procedure for A33, substituting 1-methyl-1H-pyrazole-4-boronic acid pinacol ester in place of pyridinyl-4-boronic acid. The crude product was purified by prep-HPLC to give compound A45 (35 mg, 12% yield) as a white solid: 98% purity (HPLC); MS m/z: 560.3 (M+1); $^1$H NMR (CDCl$_3$, 500 MHz) δ 8.38 (d, 1H), 7.91 (d, 1H), 7.65 (t, 1H), 7.51 (s, 1H), 7.48-7.37 (m, 2H), 7.34 (s, 1H), 7.28-7.17 (m, 4H), 5.04 (s, 1H), 3.95-3.78 (m, 11H), 3.40 (s, 2H), 1.35 (s, 6H) ppm.

Example 40

Synthesis of 4-(2-(difluoromethyl)-1H-benzo[d]imidazol-1-yl)—N—(2-methyl-1-(2-(1-methyl-1H-pyrazol-5-yl)phenyl)propan-2-yl)-6-morpholino-1,3,5-triazin-2-amine A46

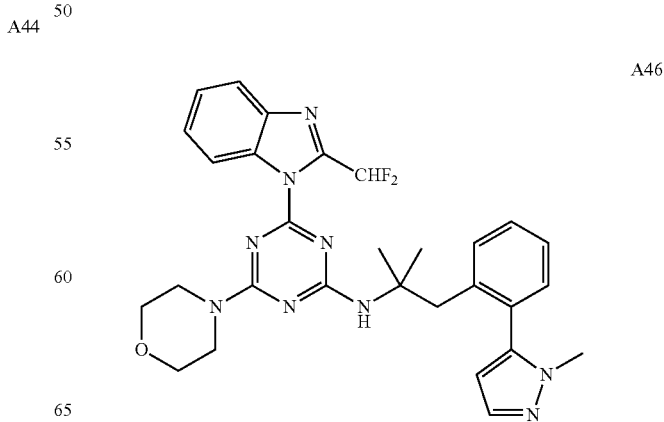

A46

Compound A46 was synthesized according to the procedure for A33, substituting 1-methyl-1H-pyrazole-5-boronic acid pinacol ester in place of pyridinyl-4-boronic acid. The crude product was purified by prep-HPLC to give compound A46 (7 mg, 4% yield) as a white solid: 98% purity (HPLC); MS m/z: 560.3 (M+1); $^1$H NMR (CDCl$_3$, 500 MHz) δ 8.40 (d, 1H), 7.91 (d, 1H), 7.67 (t, 1H), 7.50-7.30 (m, 5H), 7.24 (t, 2H), 6.21 (s, 1H), 5.03 (s, 1H), 3.96-3.75 (m, 8H), 3.65 (s, 3H), 3.21 (s, 2H), 1.32 (s, 6H) ppm.

Example 41

Synthesis of 4-(2-(difluoromethyl)-1H-benzo[d]imidazol-1-yl)—N—(1-(2'-fluorobiphenyl-2-yl)-2-methylpropan-2-yl)-6-morpholino-1,3,5-triazin-2-amine A59

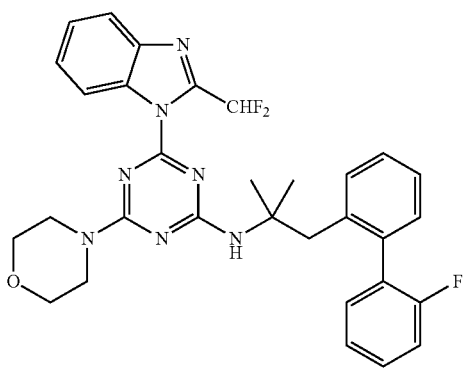

A59

Compound A59 was synthesized according to the procedure for A33, substituting 2-fluorophenylboronic acid in place of pyridinyl-4-boronic acid. The crude product was purified by prep-HPLC to give compound A59 (73 mg, 71% yield) as a white solid: 99% purity (HPLC); MS m/z: 574.2 (M+1); $^1$H NMR (DMSO$_{d6}$, 500 MHz) δ 8.61 (d, 1H), 8.02 (t, 1H), 7.84 (d, 1H), 7.48 (t, 1H), 7.43 (t, 1H), 7.39-7.22 (m, 5H), 7.22 (t, 1H), 7.14 (m, 2H), 6.97 (t, 1H), 3.74 (m, 8H), 3.30 (d, 1H), 3.14 (d, 1H), 1.20 (s, 3H), 1.17 (s, 3H) ppm.

Example 42

Synthesis of 4-(2-(difluoromethyl)-1H-benzo[d]imidazol-1-yl)—N—(2-methyl-1-(2'-methylbiphenyl-2-yl)propan-2-yl)-6-morpholino-1,3,5-triazin-2-amine A60

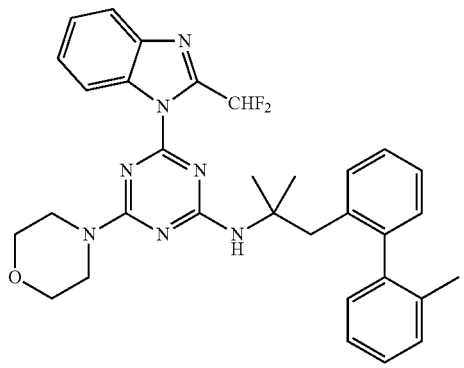

A60

Compound A60 was synthesized according to the procedure for A33, substituting 2-methylphenylboronic acid in place of pyridinyl-4-boronic acid. The crude product was purified by prep-HPLC to give compound A60 (120 mg, 47% yield) as a white solid: 99% purity (HPLC); MS m/z: 570.3 (M+1); $^1$H NMR (CDCl$_3$, 500 MHz) δ 8.42 (d, 1H), 7.92 (d, 1H), 7.68 (t, 1H), 7.44 (m, 2H), 7.35-6.95 (m, 8H), 5.01 (s, 1H), 4.10-3.70 (m, 8H), 3.30 (d, 1H), 2.99 (d, 1H), 2.06 (s, 3H), 1.36 (s, 3H), 1.30 (s, 3H) ppm.

Example 43

Synthesis of 4-(2-(difluoromethyl)-1H-benzo[d]imidazol-1-yl)—N—(1-(6'-chlorobiphenyl-2-yl)-2-methylpropan-2-yl)-6-morpholino-1,3,5-triazin-2-amine A61

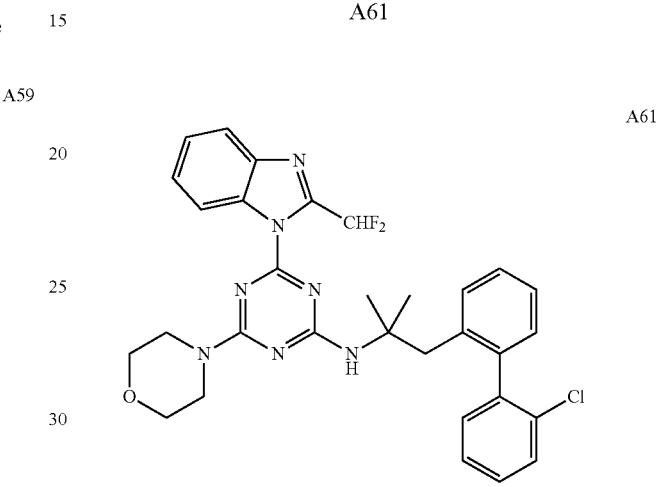

A61

Compound A61 was synthesized according to the procedure for A33, substituting 2-chlorophenylboronic acid in place of pyridinyl-4-boronic acid. The crude product was purified by prep-HPLC to give compound A61 (88 mg, 55% yield) as a white solid: 99% purity (HPLC); MS m/z: 590.2 (M+1); $^1$H NMR (CDCl$_3$, 500 MHz) δ 7.92 (d, 1H), 7.67 (t, 1H), 7.44 (m, 2H), 7.33 (m, 3H), 7.27-7.00 (m, 5H), 4.96 (s, 1H), 4.00-3.75 (m, 8H), 3.24 (d, 2H), 1.33 (s, 6H) ppm.

Example 44

Synthesis of 4-(2-(difluoromethyl)-1H-benzo[d]imidazol-1-yl)—N—(1-(6'-chlorobiphenyl-2-yl)-2-methylpropan-2-yl)-6-morpholino-1,3,5-triazin-2-amine A62

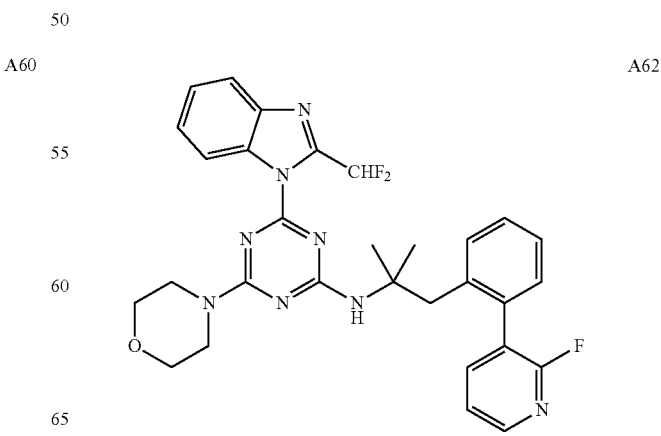

A62

Compound A62 was synthesized according to the procedure for A33, substituting 2-fluoro-3-pyridinylboronic acid in place of pyridinyl-4-boronic acid. The crude product was purified by prep-HPLC to give compound A62 (134 mg, 65% yield) as a white solid: 96% purity (HPLC); MS m/z: 575.3 (M+1); $^1$H NMR (CDCl$_3$, 500 MHz) δ 8.38 (d, 1H), 8.05 (d, 1H), 7.92 (d, 1H), 7.66 (t, 1H), 7.62 (m, 1H), 7.49-7.32 (m, 4H), 7.28 (d, 1H), 7.15 (d, 1H), 6.91 (t, 1H), 4.80 (s, 1H), 4.05-3.70 (m, 8H), 3.60 (d, 1H), 2.99 (d, 1H), 1.42 (s, 3H), 1.27 (s, 3H) ppm.

Example 45

Synthesis of 4-(2-(difluoromethyl)-1H-benzo[d]imidazol-1-yl)—N—(2-methyl-1-(2-(pyrimidin-5-yl)phenyl)propan-2-yl)-6-morpholino-1,3,5-triazin-2-amine A63

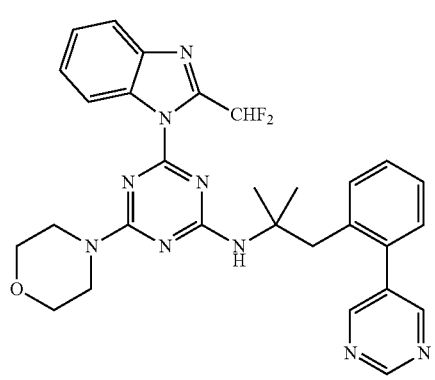

A63

Compound A63 was synthesized according to the procedure for A33, substituting pyrimidine-5-boronic acid pinacol ester in place of pyridinyl-4-boronic acid. The crude product was purified by prep-HPLC to give compound A63 (75 mg, 50% yield) as a white solid: 98% purity (HPLC); MS m/z: 558.3 (M+1); $^1$H NMR (CDCl$_3$, 500 MHz) δ 9.05 (s, 1H), 8.62 (s, 2H), 8.36 (d, 1H), 7.90 (d, 1H), 7.65 (t, 1H), 7.50-7.27 (m, 5H), 7.16 (d, 1H), 4.86 (s, 1H), 3.95-3.80 (m, 8H), 3.34 (s, 2H), 1.32 (s, 6H) ppm.

Example 46

Synthesis of 4-(2-(difluoromethyl)-1H-benzo[d]imidazol-1-yl)—N—(2-methyl-1-(2-(2-(4-methylpiperazin-1-yl)pyridin-4-yl)phenyl)propan-2-yl)-6-morpholino-1,3,5-triazin-2-amine A64

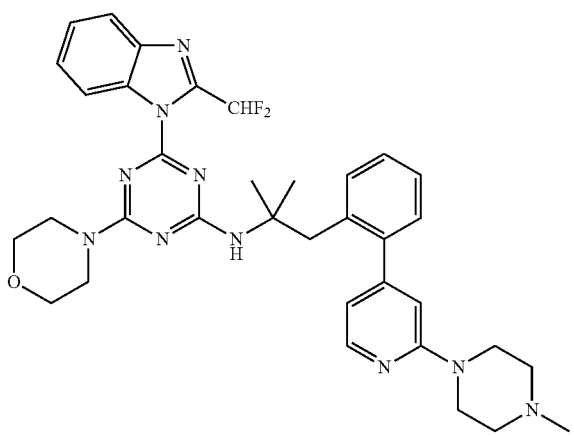

A64

Compound A64 was synthesized according to the procedure for A33, substituting 2-(4-methylpiperazin-1-yl)pyridine-4-boronic acid pinacol ester in place of pyridinyl-4-boronic acid. The crude product was purified by prep-HPLC to give compound A64 (24 mg, 20% yield) as a white solid: 98% purity (HPLC); MS m/z: 655.4 (M+1); $^1$H NMR (DMSO$_{d6}$, 500 MHz) δ 8.58 (d, 1H), 7.99 (t, 1H), 7.96 (d, 1H), 7.84 (d, 1H), 7.48 (t, 1H), 7.43 (t, 1H), 7.37 (d, 1H), 7.35-7.22 (m, 3H), 7.21 (s, 1H), 7.07 (d, 1H), 6.58 (d, 1H), 3.82-3.62 (m, 8H), 3.37 (s, 2H), 3.26 (br s, 4H), 2.25 (br s, 4H), 2.16 (s, 3H), 1.23 (s, 6H) ppm.

Example 47

Synthesis of 4-(2-(difluoromethyl)-1H-benzo[d]imidazol-1-yl)—N—(2-methyl-1-(3'-(morpholinomethyl)biphenyl-2-yl)propan-2-yl)-6-morpholino-1,3,5-triazin-2-amine A65

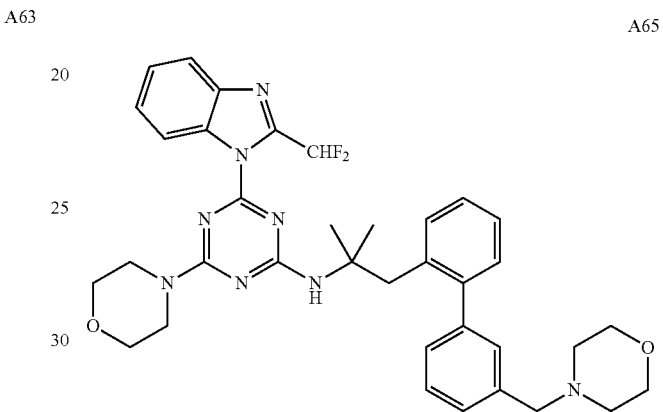

A65

Compound A65 was synthesized according to the procedure for A33, substituting 3-(morpholinomethyl)phenylboronic acid pinacol ester in place of pyridinyl-4-boronic acid. The crude product was purified by prep-HPLC to give compound A65 (40 mg, 17% yield) as a white solid: 99% purity (HPLC); MS m/z: 655.3 (M+1); $^1$H NMR (CDCl$_3$, 500 MHz) δ 8.39 (d, 1H), 7.91 (d, 1H), 7.64 (t, 1H), 7.43 (m, 2H), 7.35-7.10 (m, 8H), 4.97 (s, 1H), 3.93-3.74 (m, 8H), 3.68 (m, 4H), 3.50-3.32 (m, 4H), 2.38 (m, 4H), 1.23 (s, 6H) ppm.

Example 48

Synthesis of 4-(2-(difluoromethyl)-1H-benzo[d]imidazol-1-yl)—N—(1-(3'-methoxybiphenyl-2-yl)-2-methylpropan-2-yl)-6-morpholino-1,3,5-triazin-2-amine A66

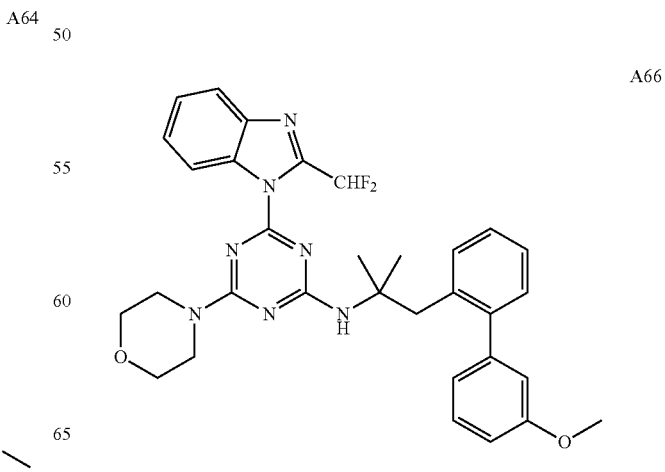

A66

Compound A66 was synthesized according to the procedure for A33, substituting 3-methoxyphenylboronic acid in place of pyridinyl-4-boronic acid. The crude product was purified by prep-HPLC to give compound A66 (18 mg, 11% yield) as a white solid: 99% purity (HPLC); MS m/z: 586.3 (M+1); $^1$H NMR (CDCl$_3$, 500 MHz) δ 8.39 (d, 1H), 7.91 (d, 1H), 7.65 (t, 1H), 7.43 (m, 2H), 7.29 (m, 2H), 7.27-7.17 (m, 3H), 6.88-6.70 (m, 3H), 4.90 (s, 1H), 3.95-3.75 (m, 8H), 3.55 (s, 1H) 3.38 (s, 2H), 1.32 (s, 6H) ppm.

Example 49

Synthesis of 4-(2-(difluoromethyl)-1H-benzo[d]imidazol-1-yl)—N—(1-(4'-methoxybiphenyl-2-yl)-2-methylpropan-2-yl)-6-morpholino-1,3,5-triazin-2-amine A67

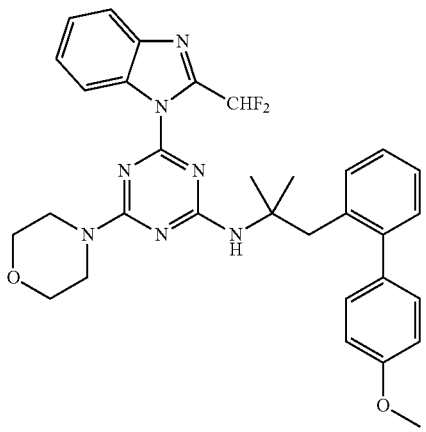

Compound A67 was synthesized according to the procedure for A33, substituting 4-methoxyphenylboronic acid in place of pyridinyl-4-boronic acid. The crude product was purified by prep-HPLC to give compound A67 (83 mg, 39% yield) as a white solid: 99% purity (HPLC); MS m/z: 586.2 (M+1); $^1$H NMR (DMSO$_{d6}$, 500 MHz) δ 8.61 (d, 1H), 7.85 (t, 1H), 7.84 (d, 1H), 7.49 (t, 1H), 7.43 (t, 1H), 7.30-7.19 (m, 4H), 7.08-7.02 (m, 3H), 6.73 (d, 2H), 3.82-3.63 (m, 8H), 3.62 (s, 3H), 3.34 (s, 2H), 1.21 (s, 6H) ppm.

Example 50

Synthesis of 4-(2-(difluoromethyl)-1H-benzo[d]imidazol-1-yl)—N—(2-methyl-1-(2-(piperidin-4-yl)phenyl)propan-2-yl)-6-morpholino-1,3,5-triazin-2-amine A68

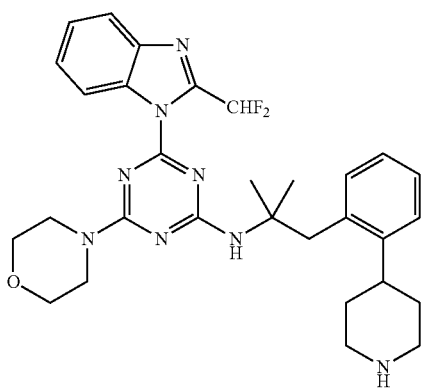

tert-Butyl. 4-(2-(2-((4-(2-(difluoromethyl)-1H-benzo[d]imidazol-1-yl)-6-morpholino-1,3,5-triazin-2-yl)amino)-2-methylpropyl)phenyl)-5,6-dihydropyridine-1(2H)-carboxylate was synthesized according to the procedure for A33, substituting N-Boc-1,2,5,6-tetrahydropyridine-4-boronic acid pinacol ester in place of pyridinyl-4-boronic acid. The crude product was purified by flash chromatography to give tert-butyl 4-(2-(2-((4-(2-(difluoromethyl)-1H-benzo[d]imidazol-1-yl)-6-morpholino-1,3,5-triazin-2-yl)amino)-2-methylpropyl)phenyl)-5,6-dihydropyridine-1(2H)-carboxylate (270 mg, 81% yield) as a white solid: MS m/z: 586.2 (M+1).

A mixture of the Boc-protected dihydropyridine (215 mg, 0.325 mmol) and 10% palladium/carbon (22 mg) in methanol was stirred under a hydrogen atmosphere at 50° C. for 3 hrs. The reaction mixture was filtered through Celite. The filtrate was then concentrated and the residue was purified by flash chromatography to give 70 mg (33% yield) of tert-butyl 4-(2-(2-((4-(2-(difluoromethyl)-1H-benzo[c]imidazol-1-yl)-6-morpholino-1,3,5-triazin-2-yl)amino)-2-methylpropyl)phenyl)piperidine-1-carboxylate as a white solid. MS m/z: 663 (M+1).

A mixture of the Boc-piperidine intermediate (65 mg, 0.098 mmol) and trifluoroacetic acid (2 mL) in dichloromethane (2 mL) was stirred at room temperature for 2 hrs. The volatiles were removed under reduced pressure. The residue was diluted with water and basified at 0° C. with 1M sodium hydroxide to pH~8 and extracted with dichloromethane. The combined extracts were dried over sodium sulfate and concentrated. The crude product was purified by prep-HPLC to give compound A68 (12 mg, 22% yield) as a white solid: 98% purity (HPLC); MS m/z: 563.3 (M+1); $^1$H NMR (CDCl$_3$, 500 MHz) δ 8.37 (d, 1H), 7.89 (d, 1H), 7.66 (t, 1H), 7.41 (m, 2H), 7.33 (d, 1H), 7.28 (t, 1H), 7.16 (t, 1H), 7.07 (d, 1H), 5.16 (s, 1H), 4.00-3.70 (m, 8H), 3.37 (m, 2H), 3.23 (s, 2H), 3.04 (m, 2H), 2.76 (m, 2H), 2.03 (m, 2H), 1.80 (m, 2H), 1.52 (s, 6H) ppm.

Example 51

Synthesis of 4-(2-(difluoromethyl)-1H-benzo[d]imidazol-1-yl)—N—(2-methyl-1-(2-(1-methylpiperidin-4-yl)phenyl)propan-2-yl)-6-morpholino-1,3,5-triazin-2-amine A35

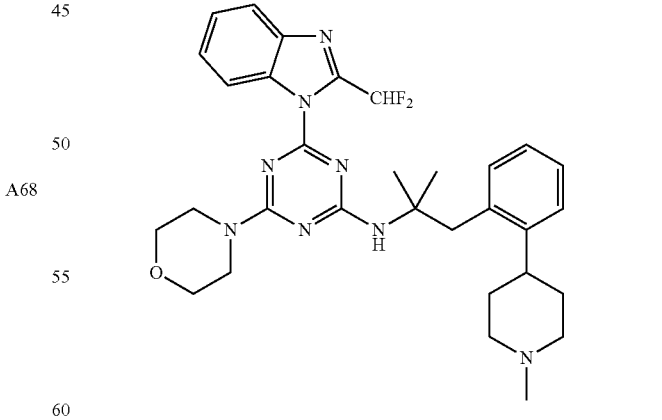

A mixture of compound A68 (80 mg, 0.14 mmol), aq. formaldehyde (37%, 23 mg), and sodium cyanoborohydride (11 mg, 0.17 mmol) in methanol (2 mL) was stirred at room temperature for 1 hr. The crude product was purified by prep-HPLC to give compound A35 (11 mg, 13% yield) as a white solid: 99% purity (HPLC); MS m/z: 577.3 (M+1); $^1$H NMR (CDCl$_3$, 500 MHz) δ 8.37 (d, 1H), 7.90 (d, 1H), 7.64 (t, 1H), 7.42 (m, 2H), 7.32 (d, 1H), 7.24 (t, 1H), 7.13 (t, 1H), 7.07 (d, 1H), 5.15 (s, 1H), 4.00-3.70 (m, 8H), 3.28 (s, 2H), 2.94 (m, 2H), 2.78 (m, 2H), 2.28 (s, 3H), 1.89-1.60 (m, 6H), 1.53 (s, 6H) ppm.

Example 52

Synthesis of 4-(2-(difluoromethyl)-1H-benzo[d]imidazol-1-yl)—N—(1-(2-(1-ethylpiperidin-4-yl)phenyl)-2-methylpropan-2-yl)-6-morpholino-1,3,5-triazin-2-amine A70

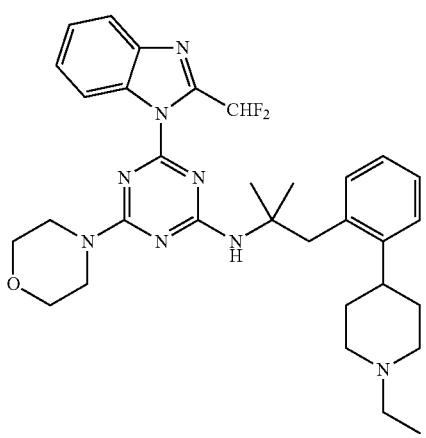

A70

A mixture of compound A68 (0.14 g, 0.25 mmol), sodium cyanoborohydride (19 mg, 0.30 mmol), 40% aq. acetaldehyde (2 mL), and diisopropylethylamine (0.16 g, 1.2 mmol) in acetonitrile (10 mL) was stirred at room temperature for 1 hr. The reaction mixture was concentrated under vacuum and the residue was purified by prep-HPLC to give compound A70 (35 mg, 24% yield) as a white solid: 99% purity (HPLC); MS m/z: 591.3 (M+1); $^1$H NMR (CDCl$_3$, 500 MHz) δ 8.37 (d, 1H), 7.90 (d, 1H), 7.64 (t, 1H), 7.41 (m, 2H), 7.35 (d, 1H), 7.24 (t, 1H), 7.13 (t, 1H), 7.07 (d, 1H), 5.17 (s, 1H), 4.00-3.71 (m, 8H), 3.28 (s, 2H), 3.08 (m, 2H), 2.85 (m, 1H), 2.46 (m, 2H), 1.91 (m, 4H), 1.70 (m, 2H), 1.53 (s, 6H), 1.11 (t, 3H) ppm.

Example 53

Synthesis of 4-(2-(difluoromethyl)-1H-benzo[d]imidazol-1-yl)—N—(1-(2-(1-isopropylpiperidin-4-yl)phenyl)-2-methylpropan-2-yl)-6-morpholino-1,3,5-triazin-2-amine A71

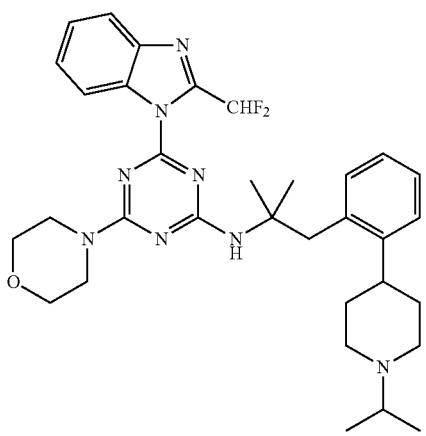

A71

A mixture of compound A68 (70 mg, 0.12 mmol), acetone (2 mL), isopropanol (2 mL), and glacial acetic acid (38 mg, 0.62 mmol) in a sealed vial was stirred at 120° C. for 2 hrs. After the mixture was cooled to room temperature, sodium borohydride (24 mg, 0.62 mmol) was added and the sealed vial was stirred at 80° C. for another 3 hrs. The reaction mixture was basified with saturated aqueous sodium bicarbonate to pH 8. The volatiles were removed under reduced pressure and the residue was purified by prep-HPLC to give compound A70 (40 mg, 53% yield) as a white solid: 97% purity (HPLC); MS m/z: 605.3 (M+1); $^1$H NMR (CDCl$_3$, 500 MHz) δ 8.38 (d, 1H), 7.91 (d, 1H), 7.64 (t, 1H), 7.49-7.35 (m, 3H), 7.24 (t, 1H), 7.13 (t, 1H), 7.07 (d, 1H), 5.15 (s, 1H), 4.01-3.73 (m, 8H), 3.28 (s, 2H), 2.97 (m, 2H), 2.80 (m, 2H), 2.05 (m, 2H), 1.78 (m, 2H), 1.70 (m, 2H), 1.53 (s, 6H), 1.04 (s, 6H) ppm.

Example 54

Synthesis of 4-(2-(difluoromethyl)-1H-benzo[d]imidazol-1-yl)—N—(2-methyl-1-(2-(1-acetylpiperidin-4-yl)phenyl)propan-2-yl)-6-morpholino-1,3,5-triazin-2-amine A72

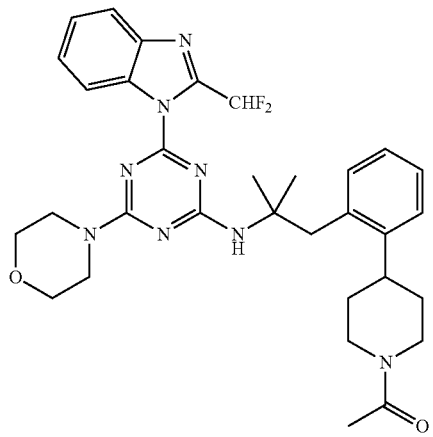

A72

A mixture of compound A68 (50 mg, 0.089 mmol), acetyl bromide (22 mg, 0.18 mmol), and triethylamine (27 mg, 0.27 mmol) in dichloromethane (2 mL) was stirred at room temperature for 2 hrs. The volatiles were removed under vacuum and the residue was purified by prep-HPLC to give compound A72 (26 mg, 48% yield) as a white solid: 99% purity (HPLC); MS m/z: 605.3 (M+1); $^1$H NMR (CDCl$_3$, 500 MHz) δ 8.36 (d, 1H), 7.91 (d, 1H), 7.64 (t, 1H), 7.42 (m, 2H), 7.28-7.20 (m, 2H), 7.15 (t, 1H), 7.08 (d, 1H), 5.15 (s, 1H), 4.78 (m, 1H), 4.00-3.74 (m, 9H), 3.42 (d, 1H), 3.20 (d, 1H), 3.05 (m, 1H), 2.97 (m, 1H), 2.48 (m, 1H), 2.10 (s, 3H), 1.79-1.58 (m, 4H), 1.57 (s, 3H), 1.50 (s, 3H) ppm.

Example 55

Synthesis of 4-(2-(difluoromethyl)-1H-benzo[d]imidazol-1-yl)—N—(2-methyl-1-(2-(1-(methylsulfonyl)piperidin-4-yl)phenyl)propan-2-yl)-6-morpholino-1,3,5-triazin-2-amine A73

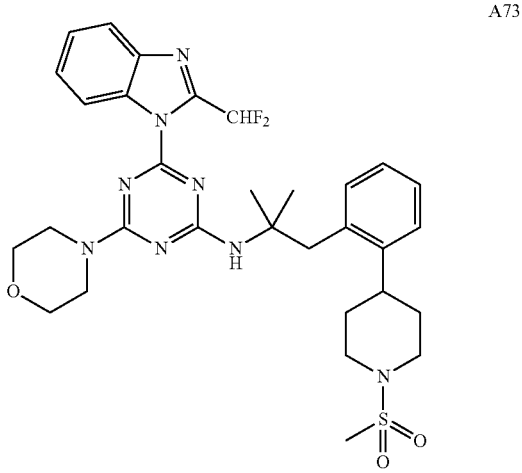

A73

A mixture of compound A68 (50 mg, 0.089 mmol), methanesulfonyl chloride (51 mg, 0.44 mmol), and triethylamine (90 mg, 0.89 mmol) in dichloromethane (4 mL) was stirred at room temperature for 1 hr. The volatiles were removed under vacuum and the residue was purified by prep-HPLC to give compound A73 (22 mg, 38% yield) as a white solid: 99% purity (HPLC); MS m/z: 641.3 (M+1); $^1$H NMR (CDCl$_3$, 500 MHz) δ 8.37 (d, 1H), 7.91 (d, 1H), 7.63 (t, 1H), 7.42 (m, 2H), 7.27 (m, 2H), 7.17 (m, 1H), 7.08 (d, 1H), 5.18 (s, 1H), 3.97-3.71 (m, 10H), 3.29 (s, 2H), 2.92 (m, 1H), 2.76 (s, 3H), 2.59 (m, 2H), 1.90-1.74 (m, 4H), 1.52 (s, 6H) ppm.

Example 56

Synthesis of 4-(2-(difluoromethyl)-1H-benzo[d]imidazol-1-yl)—N—(2-methyl-1-(2-(pyrrolidin-3-yl)phenyl)propan-2-yl)-6-morpholino-1,3,5-triazin-2-amine A74

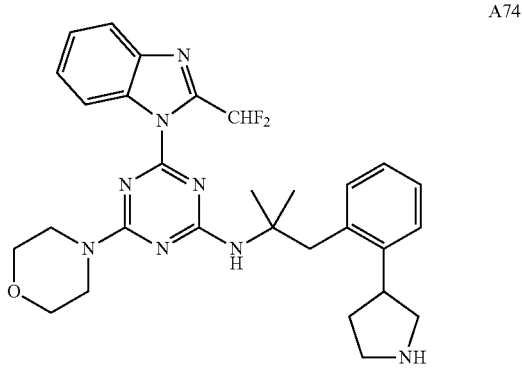

A74

Compound A74 was synthesized according to the procedure for compound A68, substituting N-Boc-2,5-dihydropyrrole-4-boronic acid pinacol ester in place of N-Boc-1,2,5,6-tetrahydropyridine-4-boronic acid pinacol ester. The crude product was purified by prep-HPLC to give compound A74 (13 mg) as a white solid: 92% purity (HPLC); MS m/z: 549 (M+1); $^1$H NMR (CDCl$_3$, 500 MHz) δ 8.39 (d, 1H), 7.90 (d, 1H), 7.67 (t, 1H), 7.42 (m, 2H), 7.35 (d, 1H), 7.27 (t, 1H), 7.14 (t, 1H), 7.05 (d, 1H), 5.23 (s, 1H), 3.97-3.74 (m, 8H), 3.68 (m, 1H), 3.47-3.25 (m, 4H), 3.17 (m, 1H), 2.93 (m, 1H), 2.25 (m, 1H), 1.92 (m, 1H), 1.51 (s, 6H) ppm.

Example 57

Synthesis of 4-(2-(difluoromethyl)-1H-benzo[d]imidazol-1-yl)—N—(2-methyl-1-(2-(1-methylpyrrolidin-3-yl)phenyl)propan-2-yl)-6-morpholino-1,3,5-triazin-2-amine A75

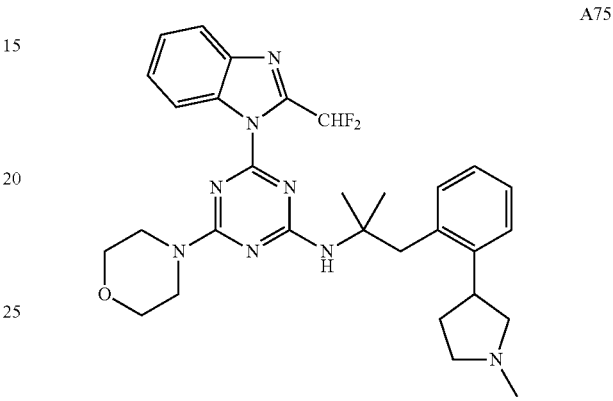

A75

Compound A75 was synthesized according to the procedure for compound A69, substituting A74 in place of compound A68. The crude product was purified by prep-HPLC to give compound A75 (21 mg) as a white solid: 98% purity (HPLC); MS m/z: 563.4 (M+1); $^1$H NMR (CDCl$_3$, 500 MHz) δ 8.40 (d, J=7.5 Hz, 1H), 7.91 (d, J=7.5 Hz, 1H), 7.65 (t, J$_{HF}$=53.5 Hz, 1H), 7.50-7.38 (m, 3H), 7.26 (t, J=7.0 Hz, 1H), 7.11 (t, J=7.5 Hz, 1H), 7.01 (d, J=7.5 Hz, 1H), 5.19 (s, 1H), 3.97-3.70 (m, 9H), 3.32 (s, 2H), 2.98 (m, 1H), 2.85 (m, 1H), 2.72 (m, 1H), 2.48 (m, 1H), 2.43 (s, 3H), 2.34 (m, 1H), 1.88 (m, 1H), 1.51 (s, 3H), 1.48 (s, 3H) ppm.

Example 58

Synthesis of 4-(2-(difluoromethyl)-1H-benzo[d]imidazol-1-yl)—N—(1-(2-(3-(dimethylamino)propyl)phenyl)-2-methylpropan-2-yl)-6-morpholino-1,3,5-triazin-2-amine A76

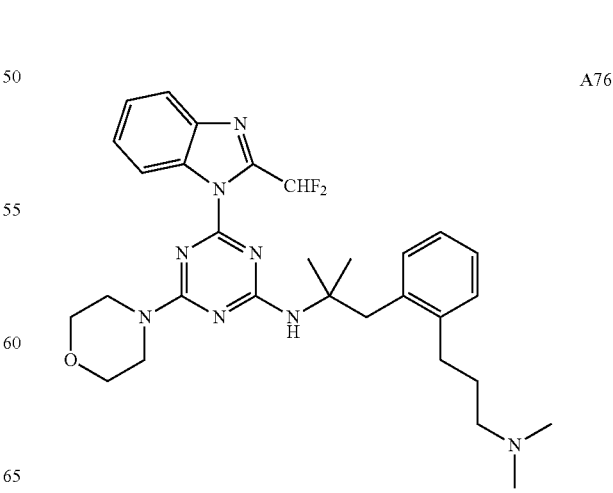

A76

A solution of compound A17 (0.30 g, 0.54 mmol), 1-dimethylamino-2-propyne (0.13 g, 1.6 mmol), bis(triphenylphosphine)palladium(II) chloride (76 mg, 0.11 mmol), and cuprous iodide (21 mg, 0.11 mmol) in N,N'-dicyclohexylmethylamine (12 mL) was stirred at 150° C. for 24 hrs. After cooling to room temperature, the mixture was diluted with water and extracted with ethyl acetate. The combined organic fractions were washed with water, dried over sodium sulfate, and concentrated under vacuum to give crude 4-(2-(difluoromethyl)-1H-benzo[d]imidazol-1-yl)—N—(1-(2(3-(dimethylamino)prop-1-yn-1-yl)phenyl)-2-methylpropan-2-yl)-6-morpholino-1,3,5-triazin-2-amine (200 mg) as yellow oil, which was used directly in the next step without further purification: MS m/z: 561 (M+1).

A mixture of the crude alkyne (120 mg, 0.21 mmol) and 10% Pd/C (40 mg) in methanol (30 mL) was stirred under hydrogen at room temperature overnight. The reaction mixture was filtered through Celite and the filtrate was concentrated under vacuum. The residue was purified by prep-HPLC to give compound A76 (20 mg, 17% yield) as a white solid: 98% purity (HPLC); MS m/z: 565.3 (M+1); $^1$H NMR (CDCl$_3$, 500 MHz) 8.41 (d, 1H), 7.90 (d, 1H), 7.69 (t, 1H), 7.42 (m, 2H), 7.20 (m, 2H), 7.13 (m, 1H), 7.05 (d, 1H), 5.31 (s, 1H), 3.95-3.75 (m, 8H), 3.26 (s, 2H), 2.80-2.24 (m, 10H), 1.88 (m, 2H), 1.51 (s, 6H) ppm.

Example I

A Luciferase-Based Luminescence Assay

PI3K catalyzes the conversion of phosphatidylinositol-4,5-bisphosphate (PIP2) and ATP to phosphatidylinositol-3,4,5-trisphosphate (PIP3) and ADP. For all assays, the reaction buffer comprised 50 mM HEPES, pH 7.5, 3 mM MgCl$_2$, 1 mM EGTA, 100 mM NaCl, 0.03% CHAPS and 2 mM DTT. Compounds for testing were dissolved and serially diluted in 100% DMSO (total of 10 concentrations), then diluted 1:25 in reaction buffer.

PI3K alpha and PI3K delta enzymatic activity was determined by measuring the amount of ATP consumed following the kinase reaction using a luciferase-based luminescence assay (Kinase Glo®, Promega Corp., Madison, Wis., USA). PI3K enzyme solutions were prepared by diluting PI3K alpha (Invitrogen Corp., Carlsbad, Calif., USA) or PI3K delta (Millipore, Billerica, Mass., USA) in reaction buffer, to 4× the final assay concentration (final concentrations of enzymes were 1.65 nM and 6.86 nM for PI3K alpha and PI3K delta, respectively). A substrate solution was prepared by mixing PIP$_2$ and ATP in reaction buffer at 2× the final assay concentration (final concentrations were 50 µM and 25 µM for PIP$_2$ and ATP respectively). 2.5 µL each of the compound and kinase mixtures were added to individual wells of white low volume 384-well assay plates and mixed by shaking The reactions were started by adding 5 µL of substrate mixture per well and shaking. The assay plates were covered and reactions were allowed to proceed for 1 hour (PI3K alpha) or 2 hours (PI3K delta), after which 10 µL of Kinase Glo® reagent was added. The plates were briefly centrifuged and incubated for 10 minutes, after which luminescence was measured using a FlexStation plate reader (Molecular Devices, Sunnyvale, Calif., USA). IC$_{50}$ values were determined by curve fitting using Graphpad Prism software (Graphpad Software, La Jolla, Calif., USA).

PI3K beta and gamma enzymatic activity was determined by measuring the amount of ADP produced following the kinase reaction using a luciferase-based luminescence assay (ADP Glo®, Promega Corp., Madison, Wis., USA). PI3K enzyme solutions were prepared by diluting PI3K beta (Millipore, Billerica, Mass., USA) or PI3K gamma (Invitrogen Corp., Carlsbad, Calif., USA) in reaction buffer, to 4× the final assay concentration (final concentrations of enzymes were 4.8 nM and 7.6 nM for PI3K beta and PI3K gamma respectively). A substrate solution was prepared by mixing PIP$_2$ and ATP in reaction buffer at 2× the final assay concentration (final concentrations were 50 µM and 25 µM for PIP$_2$ and ATP respectively). 2.5 µL each of the compound and kinase mixtures were added to individual wells of white low volume 384-well assay plates and mixed by shaking The reactions were started by adding 5 µL of substrate mixture per well and shaking. The assay plates were covered and reactions were allowed to proceed for 1 hour. Then, 5 µL of reaction mix was transferred to another white low volume 384-well plate, and 5 µL of ADP-Glo™ reagent was added. The plates were briefly centrifuged and incubated for 40 minutes, after which 10 µL of kinase detection buffer was added. The plates then were centrifuged briefly, shaken slowly and equilibrated at room temperature for 30 minutes, after which luminescence was measured using a FlexStation plate reader (Molecular Devices, Sunnyvale, Calif., USA). IC$_{50}$ values were determined by curve fitting using Graphpad Prism software (Graphpad Software, La Jolla, Calif., USA).

The biological results of inhibition of enzymatic activity of PI3Ks are summarized in Table 1, wherein A represents a value no greater than 100 nM, B represents a value greater than 100 nM but less than 200 nM, C represents a value no less than 200 nM but no greater than 500 nM, and D represents a value greater than 500 nM; and wherein A' represents a ratio of greater than 20, B' represents a ratio of no greater than 20 but no less than 10, C' represents a ratio of no greater than 10 but no less than 5, and D' represents a ratio of no greater than 5.

TABLE 1

| Compound | Biological Activity | | | | | | | | |
|---|---|---|---|---|---|---|---|---|---|
| | IC$_{50}$ | | | | | α/δ ratio | β/δ ratio | γ/δ ratio | α/β ratio |
| | p110α | p110β | p110γ | p110δ | mTOR | | | | |
| Ref. 1 | B | | | B | | D' | | | |
| A1 | D | | | A | | C' | | | |
| A2 | D | D | D | C | D | D' | A' | D' | D' |
| A3 | D | | | D | | D' | | | |
| A5 | D | D | B | C | D | C' | C' | D' | D' |
| A6 | D | | | D | | B' | | | |
| A7 | D | D | C | B | D | C' | A' | D' | D' |
| A8 | D | | | D | | C' | | | |
| A9 | D | | | D | | D' | | | |

TABLE 1-continued

Biological Activity

| Compound | IC$_{50}$ p110α | p110β | p110γ | p110δ | mTOR | α/δ ratio | β/δ ratio | γ/δ ratio | α/β ratio |
|---|---|---|---|---|---|---|---|---|---|
| A11 | C | | | A | | D' | | | |
| A12 | D | | | C | | D' | | | |
| A13 | D | | | D | | A' | | | |
| A14 | D | A | C | A | D | A' | D' | A' | A' |
| A15 | D | B | D | A | D | A' | C' | A' | D' |
| A16 | D | A | C | A | D | A' | D' | C' | A' |
| A17 | D | A | C | A | D | A' | D' | B' | A' |
| A18 | D | A | C | A | D | A' | D' | B' | A' |
| A19 | D | C | C | A | D | B' | B' | B' | D' |
| A20 | D | B | D | B | D | A' | D' | C' | A' |
| A21 | D | B | D | A | D | A' | B' | A' | C' |
| A22 | D | B | C | A | D | A' | C' | A' | C' |
| A23 | D | C | C | A | D | B' | D' | C' | D' |
| A24 | D | D | C | B | D | D' | C' | D' | D' |
| A25 | D | D | D | C | D | D' | A' | D' | D' |
| A26 | C | A | B | B | D | D' | D' | D' | C' |
| A27 | D | A | A | A | D | A' | D' | D' | B' |
| A29 | D | D | D | C | D | C' | A' | D' | D' |
| A30 | D | C | D | B | D | A' | D' | D' | B' |
| A33 | C | A | C | A | D | A' | D' | A' | B' |
| A35 | D | C | D | A | D | A' | A' | A' | B' |
| A39 | D | A | C | A | D | A' | D' | B' | A' |
| A40 | C | A | C | A | D | A' | D' | A' | B' |
| A41 | D | D | D | A | D | A' | A' | A' | D' |
| A43 | C | A | D | A | D | A' | D' | A' | A' |
| A44 | C | A | B | A | D | A' | D' | A' | A' |
| A45 | B | A | C | A | D | A' | D' | A' | A' |
| A46 | C | A | D | A | D | A' | D' | A' | A' |
| A47 | C | B | D | A | D | A' | B' | A' | D' |
| A49 | D | A | C | A | D | A' | D' | C' | A' |
| A50 | D | A | D | A | D | A' | C' | A' | B' |
| A51 | D | D | C | A | D | A' | B' | C' | D' |
| A52 | D | D | A | A | D | C' | B' | D' | D' |
| A59 | D | C | D | A | D | A' | A' | A' | C' |
| A60 | D | A | D | A | D | A' | D' | A' | A' |
| A61 | D | A | D | A | D | A' | D' | A' | A' |
| A62 | D | D | D | A | D | A' | A' | A' | D' |
| A63 | C | A | C | A | D | A' | A' | A' | D' |
| A64 | D | A | D | A | D | A' | D' | A' | A' |
| A65 | D | A | B | A | D | A' | D' | D' | A' |
| A66 | D | D | D | A | D | A' | A' | A' | D' |
| A67 | D | C | D | A | D | A' | B' | A' | D' |
| A68 | D | D | D | A | D | A' | A' | A' | D' |
| A70 | D | D | D | A | D | A' | A' | A' | C' |
| A71 | D | D | D | A | D | A' | A' | A' | D' |
| A72 | B | A | A | A | D | A' | D' | C' | A' |
| A73 | C | A | B | A | D | A' | D' | B' | A' |
| A74 | D | D | D | A | D | A' | A' | A' | D' |
| A75 | D | D | D | A | D | A' | A' | A' | D' |
| A76 | D | C | D | A | D | A' | A' | A' | C' |

In Table 1, the α/δ ratio is the ratio of the IC$_{50}$ value of a compound against PK3Kα over the IC$_{50}$ value of the same compound against PK3Kδ; and Ref 1 is N-benzyl-4-(2-(difluoromethyl)-1H-benzo[d]imidazol-1-yl)-6-morpholino-1,3,5-triazin-2-amine.

Example II

ELISA assay for PI3Kβ

Cellular PI3Kβ activity was determined by measuring the phosphorylation of AKT (Ser473) using an in-cell ELISA assay. PC-3 (prostate carcinoma) cells were obtained from ATCC (ATCC # CRL-1435). Growth medium was DMEM (CellGro # CV-10-013-CV) supplemented with 10% fetal bovine serum, 100 IU/mL penicillin, 100 μg/mL streptomycin, and 1×MEM non-essential amino acids. Phosphate buffered saline (PBS) contained 2.7 M NaCl, 54 mM KCl, 86 mM Na$_3$PO$_4$ (dibasic, anhydrous), 28 mM K$_3$PO$_4$ (monobasic, anhydrous), pH 7.2. 10× stimulation mixture contained 50 μM LPA (Cayman #62215) diluted in serum-free DMEM medium (CellGro # CV-10-013-CV). Compounds for testing were dissolved and serially diluted in 100% DMSO (total of 10 concentrations), then diluted in serum-free DMEM to 2× final assay concentration. 2× fixative solution contained 8% formaldehyde (Amresco # M134) diluted in PBS. Permeabilization solution contained PBS supplemented with 0.1% Triton X-100. Blocking buffer was obtained from LiCor (LiCor #927-40000). Wash buffer contained PBS supplemented with 0.1% Tween-20. Primary antibody solution was rabbit anti-pAKT$^{S473}$ monoclonal antibody (Cell Signaling #4060) and mouse anti-total S6 (Santa Cruz #74459) diluted 1:500 and 1:2000, respectively, in blocking buffer. Secondary antibody solution was IRDye 800CW-conjugated goat anti-rabbit IgG (LiCor #926-32211) and IRDye 680LT-conjugated goat anti-mouse IgG (LiCor #926-68020) diluted 1:2000 and 1:1000, respectively, in blocking buffer.

PC-3 cells were subcultured in growth medium and seeded into flat, clear bottom, 96-well plates (Corning #3904) at 16000 cells/well, then incubated overnight in a 37° C., 5% $CO_2$ incubator. Growth medium in plates was replaced with 100 µL/well serum-free DMEM and incubated overnight in a 37° C., 5% $CO_2$ incubator. 50 µL/well of fresh serum-free DMEM was added to plates. Compound treatment was performed by adding 50 µL/well of 2× compound mixture to plates and incubating for 2 hrs at 37° C., 5% $CO_2$, after which 11 µL/well of 10× stimulation mixture was added and plates were incubated for 10 min at 37° C., 5% $CO_2$. Fixation was performed by adding 110 µL/well of 2× fixative solution to plates and incubating for 20 min at room temperature. Permeabilization was performed by replacing fixation solution with 150 µL/well permeabilization solution and incubating for 10 min at room temperature. Permeabilization was repeated (for a total of 2 times). Permeabilization solution was replaced with 100 µL/well blocking buffer and plates were incubated for 1 hr at room temperature, after which 100 µL/well of primary antibody solution was added and plates were incubated overnight at 4° C. Plates were washed with wash buffer, after which 100 µL/well of secondary antibody solution was added to the plates and incubated in the dark for 1 hr at room temperature. Plates were washed with wash buffer, followed by a wash with PBS. After completely removing PBS, plates were scanned on the Licor Odyssey Imager. Images quantified using Licor Odyssey application software. $IC_{50}$ values were determined by curve fitting using a Collaborative Drug Discovery database (www.collaborativedrug.com).

Example III

ELISA Assay for PI3Kδ

Cellular PI3Kδ activity was determined by measuring the phosphorylation of AKT (Thr308) using a sandwich enzyme-linked immunosorbant assay (ELISA). Raji (Burkitt's Lymphoma) cells were obtained from ATCC (ATCC # CCL-86). Phosphate buffer saline (PBS) contained 2.7 M NaCl, 54 mM KCl, 86 mM $Na_3PO_4$ (dibasic, anhydrous), and 28 mM $K_3PO_4$ (monobasic, anhydrous) at pH 7.2. Wash buffer contained PBS supplemented with 0.05% Tween-20. Blocking buffer contained wash buffer supplemented with 1% BSA. A 10× stimulation mixture contained 5 µg/mL anti-Human IgM antibody (Sigma #12386) diluted in serum-free RPMI medium (CellGro # CV-10-040-CV). Compounds for testing were dissolved and serially diluted in 100% DMSO (total of 10 concentrations), and then diluted in serum-free RPMI to 5× final assay concentration.

Raji cells were subcultured in RPMI medium supplemented with 10% fetal bovine serum, 100 IU/mL penicillin, 100 µg/mL streptomycin, and 1×MEM non-essential amino acids. Sandwich ELISA plates were prepared by coating 96-well assay plates (Pierce #15042) with 100 µL/well capture antibody (Cell Signaling Technology #7142 or 7144) diluted in PBS. Plates were incubated overnight at 4° C., then washed with wash buffer, after which 200 µL/well blocking buffer was added to the plates and incubated at room temperature for at least 2 hrs. Raji cells were resuspended in serum-free RPMI medium and seeded into V-bottom, 2-mL 96-well blocks (Corning #3961) at $10^6$ cells/well, then incubated for 2 hrs in a 37° C., 5% $CO_2$ incubator. Compound treatment was performed by adding the 5× compound mixture to the cells and incubating for 2 hrs at 37° C., 5% $CO_2$, after which the 10× stimulation mixture was added to the plates and incubated for 30 min at 37° C., 5% $CO_2$. Cells were pelleted by centrifuging plates at 1500 RPM for 5 min at room temperature. Media was carefully removed and cells were lysed by adding 100 µL/well cell lysis buffer (Cell Signaling Technology #9803) supplemented with protease and phosphatase inhibitors (Thermo Fisher #78443). Plates were incubated on ice for 30 min, then the lysates (80 µL for $pAKT^{T308}$, 10 µL for total AKT) were transferred to prepared assay plates and incubated at 4° C. overnight. After washing plates with wash buffer, 100 µL/well detection antibody (Cell Signaling Technology #7142 or 7144) diluted in blocking buffer was added to the plates and incubated for 1 hr at 37° C. Plates were washed and 100 µL/well of HRP-conjugated secondary antibody (Cell Signaling Technology #7142 or 7144) diluted in blocking buffer was added to plates and incubated for 1 hr at room temperature. Plates were washed with wash buffer and 100 µL/well of luminescent substrate was added to plates. After 1 min on a plate shaker at medium speed, luminescence was read on a Wallac Victor2 plate reader. $IC_{50}$ values were determined by curve fitting using a Collaborative Drug Discovery database (www.collaborativedrug.com).

Example IV

ELISA Assay for PI3Kα

PI3K alpha (PI3Kα) activity was determined by measuring the phosphorylation of AKT (Thr308) using an in-cell ELISA assay. MDA-MB-453 (breast carcinoma) cells were obtained from ATCC (ATCC # HTB-131). Growth medium was DMEM (CellGro # CV-10-013-CV) supplemented with 10% fetal bovine serum, 100 IU/mL penicillin, 100 µg/mL streptomycin, and 1×MEM non-essential amino acids. Phosphate buffered saline (PBS) contained 2.7 M NaCl, 54 mM KCl, 86 mM $Na_3PO_4$ (dibasic, anhydrous), and 28 mM $K_3PO_4$ (monobasic, anhydrous) at pH 7.2. Stimulation mixture (10×) was 1000 ng/mL LONG® $R^3$ human IGF-1 (Sigma #11271) diluted in serum-free DMEM medium (CellGro # CV-10-013-CV). Compounds for testing were dissolved and serially diluted in 100% DMSO (total of 10 concentrations), then diluted in serum-free DMEM to 2× final assay concentration. Fixative solution (2×) was 8% formaldehyde (Amresco # M134) diluted in PBS. Permeabilization solution was PBS supplemented with 0.1% Triton X-100. Blocking buffer was obtained from LiCor (LiCor #927-40000). Wash buffer was PBS supplemented with 0.1% Tween-20. Primary antibody solution was rabbit anti-$pAKT^{T308}$ monoclonal antibody (Cell Signaling #2965) and mouse anti-total S6 (Santa Cruz #74459) diluted 1:500 and 1:2000, respectively, in the blocking buffer. Secondary antibody solution was IRDye 800CW-conjugated goat anti-rabbit IgG (LiCor #926-32211) and IRDye 680LT-conjugated goat anti-mouse IgG (LiCor #926-68020) diluted 1:1000 and 1:2000, respectively, in the blocking buffer.

MDA-MB-453 cells were subcultured in growth medium and seeded into flat, clear bottom, 96-well plates (Corning #3904) at 40000 cells/well, then incubated overnight in a 5% $CO_2$ incubator at 37° C. Growth medium in plates was replaced with 100 µL/well serum-free DMEM and incubated overnight at 37° C. in a 5% $CO_2$ incubator. Fresh serum-free DMEM (50 µL/well) was added to plates. Compound treatment was performed by adding 50 µL/well of 2× compound mixture to plates and incubating for 1 hr at 37° C. and 5% $CO_2$, after which 11 µL/well of 10× stimulation mixture was added and plates were incubated for 10 min at 37° C. and 5% $CO_2$. Fixation was performed by adding 110 µL/well of 2× fixative solution to the plates and incubating for 20 min at room temperature. Permeabilization was performed by replacing fixation solution with 150 μL/well permeabilization solution and incubating for 10 min at room temperature. Permeabilization was repeated (for a total of 2 times). Permeabilization solution was replaced with 100 μL/well blocking buffer and plates were incubated for 1 hour at room temperature, after which 100 μL/well of primary antibody solution was added and plates were incubated overnight at 4° C. Plates were washed with wash buffer, after which 100 μL/well of secondary antibody solution was added to the plates and incubated in the dark for 1 hr at room temperature. Plates were washed with wash buffer, followed by a wash with PBS. After completely removing PBS, plates were scanned on the Licor Odyssey Imager. Images were quantified using Licor Odyssey application software. $IC_{50}$ values were determined by curve fitting using a Collaborative Drug Discovery database (www.collaborativedrug.com).

Example V

ELISA Assay for PI3Kγ

PI3K gamma (PI3Kγ) activity was determined by measuring the phosphorylation of AKT (Ser473) using an in-cell ELISA assay. RAW 264.7 (mouse macrophage) cells were obtained from ATCC (ATCC # TIB-71). Growth medium was DMEM (CellGro # CV-10-013-CV) supplemented with 10% fetal bovine serum, 100 IU/mL penicillin, 100 μg/mL streptomycin, and 1×MEM non-essential amino acids. Phosphate buffered saline (PBS) contained 2.7 M NaCl, 54 mM KCl, 86 mM $Na_3PO_4$ (dibasic, anhydrous), and 28 mM $K_3PO_4$ (monobasic, anhydrous) at pH 7.2. Stimulation mixture (10×) was 500 ng/mL recombinant human complement component C5a (R&D systems #2037-05-025) diluted in serum-free DMEM medium (CellGro # CV-10-013-CV). Compounds for testing were dissolved and serially diluted in 100% DMSO (total of 10 concentrations), then diluted in serum-free DMEM to 2× final assay concentration. Fixative solution (2×) was 8% formaldehyde (Amresco # M134) diluted in PBS. Permeabilization solution was PBS supplemented with 0.1% Triton X-100. Blocking buffer was obtained from LiCor (LiCor #927-40000). Wash buffer was PBS supplemented with 0.1% Tween-20. Primary antibody solution was rabbit anti-pAKT$^{S473}$ monoclonal antibody (Cell Signaling #4060) and mouse anti-total S6 (Santa Cruz #74459) diluted 1:500 and 1:2000, respectively, in the blocking buffer. Secondary antibody solution was IRDye 800CW-conjugated goat anti-rabbit IgG (LiCor #926-32211) and IRDye 680LT-conjugated goat anti-mouse IgG (LiCor #926-68020) diluted 1:1000 and 1:2000, respectively, in the blocking buffer.

RAW 264.7 cells were subcultured in growth medium and seeded into flat, clear bottom, 96-well plates (Corning #3904) at 70000 cells/well, then incubated overnight in a 37° C., 5% $CO_2$ incubator. Growth medium in plates was replaced with 100 μL/well serum-free DMEM and incubated overnight in a 37° C., 5% $CO_2$ incubator. Fresh serum-free DMEM (50 μL/well) was added to plates. Compound treatment was performed by adding 50 μL/well of 2× compound mixture to plates and incubating for 2 hrs at 37° C., 5% $CO_2$, after which 11 μL/well of 10× stimulation mixture was added and plates were incubated for 3 min at 37° C., 5% $CO_2$. Fixation was performed by adding 110 μL/well of 2× fixative solution to plates and incubating for 20 min at room temperature. Permeabilization was performed by replacing fixation solution with 150 μL/well permeabilization solution and incubating for 10 min at room temperature. Permeabilization was repeated (for a total of 2 times). Permeabilization solution was replaced with 100 μL/well blocking buffer and plates were incubated for 1 hr at room temperature, after which 100 μL/well of primary antibody solution was added and plates were incubated overnight at 4° C. Plates were washed with wash buffer, after which 100 μL/well of secondary antibody solution was added to the plates and incubated in the dark for 1 hr at room temperature. Plates were washed with wash buffer, followed by a wash with PBS. After completely removing PBS, plates were scanned on the Licor Odyssey Imager. Images were quantified using Licor Odyssey application software. $IC_{50}$ values were determined by curve fitting using a Collaborative Drug Discovery database (www.collaborativedrug.com).

The biological results of inhibition of cellular enzymatic activity of PI3Ks are summarized in Table 2, wherein A, B, C, D, A', B', C', and D' are each as defined in Table 1.

TABLE 2

| Compound | $IC_{50}$ | | | | α/δ ratio | β/δ ratio | γ/δ ratio | α/β ratio |
|---|---|---|---|---|---|---|---|---|
| | p110α | p110β | p110γ | p110δ | | | | |
| A14 | D | A | C | A | A' | A' | A' | B' |
| A15 | D | A | C | A | A' | C' | A' | C' |
| A16 | D | A | D | A | A' | A' | A' | B' |
| A17 | C | | | A | A' | | | |
| A18 | D | A | C | A | A' | A' | A' | C' |
| A19 | | A | | A | | D' | | |
| A21 | D | B | C | A | A' | A' | A' | A' |
| A22 | D | A | C | A | A' | A' | A' | C' |
| A23 | | | | A | | | | |
| A24 | | | | A | | | | |
| A25 | | | | A | | | | |
| A27 | | A | | A | | C' | | |
| A33 | | A | | A | | A' | A' | |
| A35 | D | A | C | A | A' | A' | A' | A' |
| A39 | D | A | B | A | A' | | A' | A' |
| A40 | D | A | C | A | A' | A' | A' | A' |
| A41 | D | B | D | A | A' | A' | A' | B' |
| A43 | D | A | C | A | A' | A' | A' | C' |
| A44 | D | A | A | A | A' | A' | A' | A' |
| A45 | C | A | A | A | A' | B' | A' | A' |
| A46 | D | A | C | A | A' | B' | A' | A' |
| A49 | D | A | C | A | A' | B' | A' | B' |
| A50 | D | A | C | A | A' | A' | A' | B' |

TABLE 2-continued

| Compound | IC₅₀ | | | | α/δ ratio | β/δ ratio | γ/δ ratio | α/β ratio |
|---|---|---|---|---|---|---|---|---|
| | p110α | p110β | p110γ | p110δ | | | | |
| A51 | D | B | B | A | A' | D' | A' | C' |
| A52 | D | A | B | A | A' | D' | A' | C' |
| A59 | D | B | D | A | A' | A' | A' | A' |
| A60 | D | C | D | A | A' | A' | A' | A' |
| A61 | D | B | D | A | A' | A' | A' | A' |
| A62 | D | A | C | A | A' | A' | A' | A' |
| A63 | D | A | D | A | A' | A' | A' | A' |
| A64 | D | A | D | A | A' | A' | A' | A' |
| A65 | D | A | C | A | A' | B' | A' | A' |
| A66 | D | B | D | A | A' | A' | A' | A' |
| A67 | D | C | D | A | A' | A' | A' | A' |
| A68 | D | A | C | A | A' | A' | A' | A' |
| A70 | D | A | D | A | A' | A' | A' | A' |
| A71 | D | A | D | A | A' | A' | A' | A' |
| A72 | C | A | A | A | A' | A' | A' | A' |
| A73 | C | A | A | A | A' | C' | A' | A' |
| A74 | D | A | C | A | A' | C' | A' | A' |
| A75 | D | A | B | A | A' | B' | A' | A' |
| A76 | D | A | D | A | A' | A' | A' | A' |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula I:

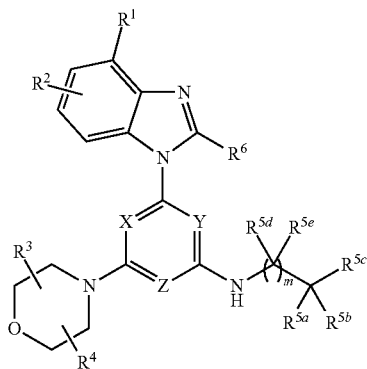

(I)

or an enantiomer, a mixture of enantiomers, a mixture of two or more diastereomers, or an isotopic variant thereof; or a pharmaceutically acceptable salt, solvate, hydrate, or prodrug thereof; wherein:

X, Y, and Z are each independently N or $CR^X$, with the proviso that at least two of X, Y, and Z are nitrogen atoms; where $R^X$ is hydrogen or $C_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^{5c}$ is —(CR$^{5f}$R$^{5g}$)$_n$—(C$_{6-14}$ aryl)

$R^{5d}$ and $R^{5e}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5f}$ and R$^{5g}$ are each independently (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$; or —S(O)$_2$NR$^{1b}$R$^{1c}$; or (d) when one occurrence of R$^{5f}$ and one occurrence of R$^{5g}$ are attached to the same carbon atom, the R$^{5f}$ and R$^{5g}$ together with the carbon atom to which they are attached form a C$_{3-10}$ cycloalkyl or heterocyclyl;

R$^6$ is hydrogen, C$_{1-6}$ alkyl, —S—C$_{1-6}$ alkyl, —S(O)—C$_{1-6}$ alkyl, or —SO$_2$—C$_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl in R$^1$, R$^2$, R$^3$, R$^4$, R$^6$, R$^X$, R$^{1a}$, R$^{1b}$, R$^{1c}$, R$^{1d}$, R$^{5a}$, R$^{5b}$, R$^{5c}$, R$^{5d}$, R$^{5e}$, R$^{5f}$, and R$^{5g}$ is optionally substituted with one or more, in one embodiment, one, two, three, or four, substituents Q, wherein each substituent Q is independently selected from (a) oxo, cyano, halo, and nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^{1'}$, R$^c$, and R$^d$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl, each of which is further optionally substituted with one or more, in one embodiment, one, two, three, or four, substituents Q$^a$; or (iii) R$^b$ and R$^c$ together with the N atom to which they are attached form heterocyclyl, which is further optionally substituted with one or more, in one embodiment, one, two, three, or four, substituents Q$^a$;

wherein each Q$^a$ is independently selected from the group consisting of (a) oxo, cyano, halo, and nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl;or (iii) R$^f$ and R$^g$ together with the N atom to which they are attached form heterocyclyl.

2. The compound of claim 1, wherein the compound is not 4-(2-(difluoromethyl)-1H-benzo[d]imidazol-1-yl)-6-morpholino-N-(2-phenyl-2-(pyrrolidin-1-yl)ethyl)-1,3,5-triazin-2-amine or 6-(2-(difluoromethyl)-1H-benzo[d]imidazol-1-yl)-N-(1-(4-((R)-3-(methoxymethyl)morpholino)phenyl)ethyl)-2-morpholinopyrimidin-4-amine.

3. The compound of claim 1, wherein R$^{5b}$ is (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, or heteroaryl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —S(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$.

4. The compound of claim 1, wherein R$^{5a}$ and R$^{5b}$ are each independently (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$.

5. The compound of claim 4, wherein R$^{5a}$ and R$^{5b}$ are each methyl, optionally substituted with one or more halo.

6. The compound of claim 1, wherein n is 1.

7. The compound of claim 1, wherein R$^{5f}$ and R$^{5g}$ are each hydrogen.

8. The compound of claim 1, wherein n is 0.

9. The compound of claim 1, wherein m is 0.

10. The compound of claim 1, having the structure of Formula Ia:

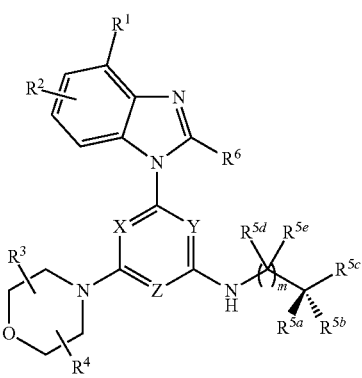

(Ia)

or an isotopic variant thereof; or a pharmaceutically acceptable salt, solvate, hydrate, or prodrug thereof.

11. The compound of claim 1, having the structure of Formula Ib:

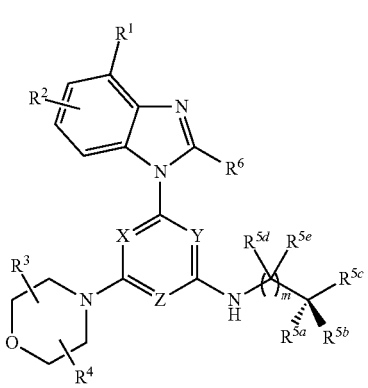

(Ib)

or an isotopic variant thereof; or a pharmaceutically acceptable salt, solvate, hydrate, or prodrug thereof.

12. The compound of claim 1, having the structure of Formula II:

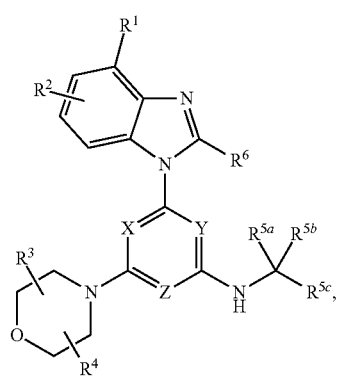

(II)

or an isotopic variant thereof; or a pharmaceutically acceptable salt, solvate, hydrate, or prodrug thereof.

13. The compound of claim 12, having the structure of Formula IIa:

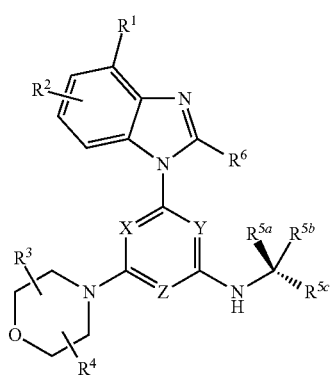

(IIa)

or an isotopic variant thereof; or a pharmaceutically acceptable salt, solvate, hydrate, or prodrug thereof.

14. The compound of claim 12, having the structure of Formula IIb:

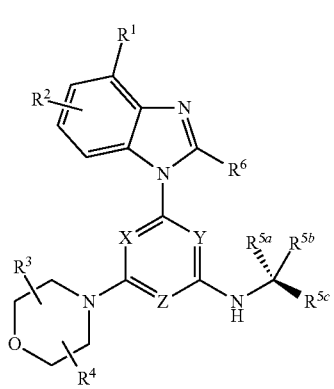

(IIb)

or an isotopic variant thereof; or a pharmaceutically acceptable salt, solvate, hydrate, or prodrug thereof.

15. The compound of claim 1, wherein $R^{5c}$ is $C_{6-14}$ aryl, optionally substituted with one or more substituents Q.

16. The compound of claim 15, wherein $R^{5c}$ is phenyl, optionally substituted with one or more substituents Q.

17. The compound of claim 15, wherein $R^{5c}$ is naphthyl, optionally substituted with one or more substituents Q.

18. The compound of claim 1, wherein $R^{5c}$ is —(CH$_2$)-phenyl, wherein the phenyl is optionally substituted with one or more substituents Q.

19. The compound of claim 1, wherein $R^{5c}$ is —(CH$_2$)-naphthyl, wherein the naphthyl is optionally substituted with one or more substituents Q.

20. The compound of claim 1, having the structure of Formula VII:

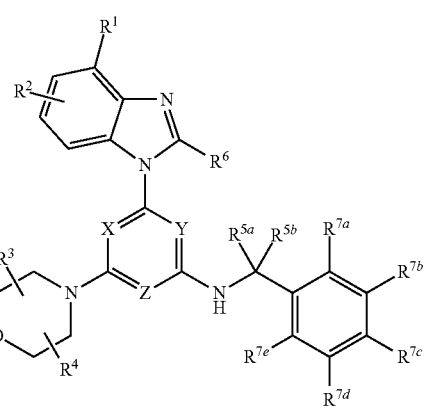

(VII)

or an enantiomer, a mixture of enantiomers, a mixture of two or more diastereomers, or an isotopic variant thereof; or a pharmaceutically acceptable salt, solvate, hydrate, or prodrug thereof; wherein:

$R^{7a}$, $R^{7b}$, $R^{7c}$, $R^{7d}$, and $R^{7e}$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)

OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; or two of R$^{7a}$, R$^{7b}$, R$^{7c}$, R$^{7d}$, and R$^{7e}$ that are adjacent to each other form C$_{3-10}$ cycloalkenyl, C$_{6-14}$ aryl, heteroaryl, or heterocyclyl, each optionally substituted with one or more substituents Q.

21. The compound of claim 20, having the structure of Formula VIIa:

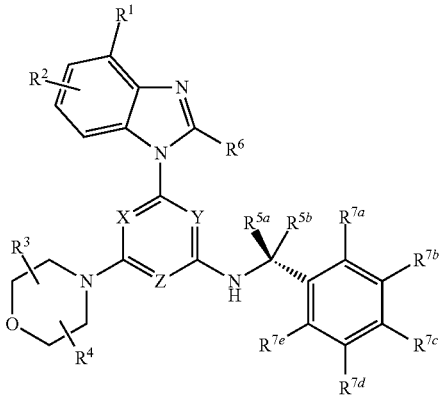

(VIIa)

or an isotopic variant thereof; or a pharmaceutically acceptable salt, solvate, hydrate, or prodrug thereof.

22. The compound of claim 20, having the structure of Formula VIIb:

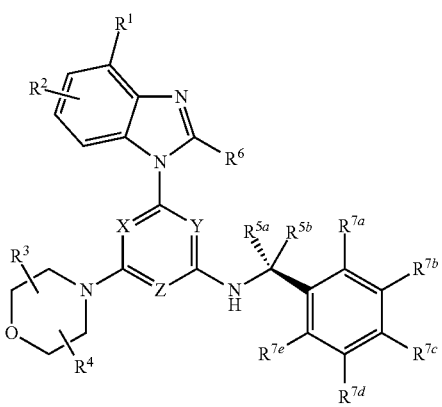

(VIIb)

or an isotopic variant thereof; or a pharmaceutically acceptable salt, solvate, hydrate, or prodrug thereof.

23. The compound of claim 1, having the structure of Formula XI:

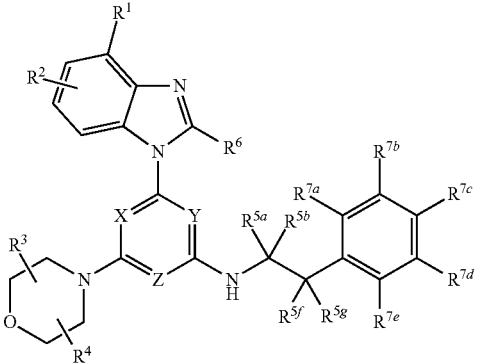

(XI)

or an enantiomer, a mixture of enantiomers, a mixture of two or more diastereomers, or an isotopic variant thereof; or a pharmaceutically acceptable salt, solvate, hydrate, or prodrug thereof; wherein:

R$^{7a}$, R$^{7b}$, R$^{7c}$, R$^{7d}$, and R$^{7e}$ are each independently (a) hydrogen, cyano, halo, or nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl, each of which is optionally substituted with one or more substituents Q; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; or two of R$^{7a}$, R$^{7b}$, R$^{7c}$, R$^{7d}$, and R$^{7e}$ that are adjacent to each other form C$_{3-10}$ cycloalkenyl, C$_{6-14}$ aryl, heteroaryl, or heterocyclyl, each optionally substituted with one or more substituents Q.

24. The compound of claim 23, having the structure of Formula XIa:

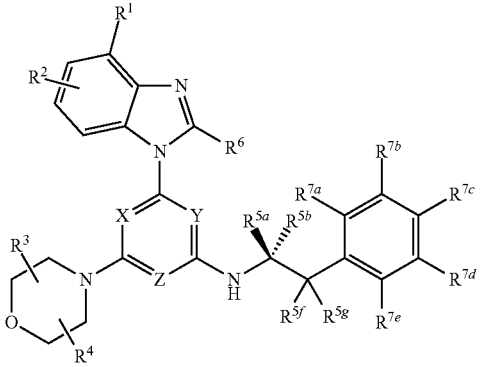

(XIa)

or an isotopic variant thereof; or a pharmaceutically acceptable salt, solvate, hydrate, or prodrug thereof.

25. The compound of claim 23, having the structure of Formula XIb:

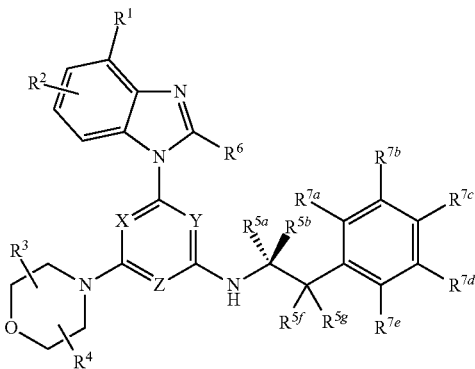

(XIb)

or an isotopic variant thereof; or a pharmaceutically acceptable salt, solvate, hydrate, or prodrug thereof.

26. The compound of claim 23, wherein $R^{7a}$ is hydrogen, halo, $C_{1-6}$ alkyl optionally substituted with one or more substituents Q, or —$OR^{1a}$.

27. The compound of claim 26, wherein $R^{7a}$ is hydrogen.

28. The compound of claim 25, wherein $R^{7a}$ is (a) cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, $OC(NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^1)NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$.

29. The compound of claim 25, wherein $R^{7a}$ is (i) halo; (ii) $C_{1-6}$ alkyl, $C_{6-14}$ aryl, $C_{7-15}$ aralkyl, heteroaryl, or heterocyclyl, each of which is optionally substituted with one or more substituents Q; or (iii) —$OR^{1a}$ or —$NR^{1b}R^{1c}$.

30. The compound of claim 23, wherein $R^{7b}$ is hydrogen, halo, $C_{1-6}$ alkyl optionally substituted with one or more substituents Q, or —$OR^{1a}$.

31. The compound of claim 30, wherein $R^{7b}$ is hydrogen.

32. The compound of claim 23, wherein $R^{7c}$ is hydrogen, halo, $C_{1-6}$ alkyl optionally substituted with one or more substituents Q, or —$OR^{1a}$.

33. The compound of claim 32, wherein $R^{7c}$ is hydrogen, halo, or —$OR^{1a}$.

34. The compound of claim 32, wherein $R^{7c}$ is chloro.

35. The compound of claim 32, wherein $R^{7c}$ is —O—$C_{1-6}$ alkyl, optionally substituted with one or more substituents Q.

36. The compound of claim 23, wherein $R^{7d}$ is hydrogen, halo, $C_{1-6}$ alkyl optionally substituted with one or more substituents Q, or —$OR^{1a}$.

37. The compound of claim 36, wherein $R^{7d}$ is hydrogen.

38. The compound of claim 23, wherein $R^{7e}$ is hydrogen, halo, $C_{1-6}$ alkyl optionally substituted with one or more substituents Q, or —$OR^{1a}$.

39. The compound of claim 38, wherein $R^{7e}$ is hydrogen.

40. The compound of claim 23, wherein two of $R^{7a}$, $R^{7b}$, $R^{7c}$, $R^{7d}$, and $R^{7e}$ that are adjacent to each other form $C_{3-10}$ cycloalkenyl, $C_{6-14}$ aryl, heteroaryl, or heterocyclyl, each optionally substituted with one or more substituents Q.

41. The compound of claim 40, wherein $R^{7a}$ and $R^{7b}$ together with the carbon atoms to which they are attached from $C_{6-14}$ aryl, optionally substituted with one or more substituents Q.

42. The compound of claim 40, wherein $R^{7b}$ and $R^{7c}$ together with the carbon atoms to which they are attached from $C_{6-14}$ aryl, optionally substituted with one or more substituents Q.

43. The compound of claim 1, wherein $R^{5a}$ is hydrogen.

44. The compound of claim 1, wherein $R^{5a}$ is $C_{1-6}$ alkyl, optionally substituted with one or more substituents Q.

45. The compound of claim 1, wherein $R^{5a}$ is hydrogen, methyl, or ethyl.

46. The compound of claim 1, wherein $R^{5b}$ is $C_{1-6}$ alkyl, optionally substituted with one or more substituents Q.

47. The compound of claim 46, wherein $R^{5b}$ is methyl, ethyl, or propyl.

48. The compound of claim 1, wherein $R^{5b}$ is —$C(O)OR^{1a}$.

49. The compound of claim 48, wherein $R^{5b}$ is —C(O)O—$C_{1-6}$ alkyl.

50. The compound of claim 48, wherein $R^{5b}$ is —$C(O)OCH_3$.

51. The compound of claim 23, having the structure of Formula XV:

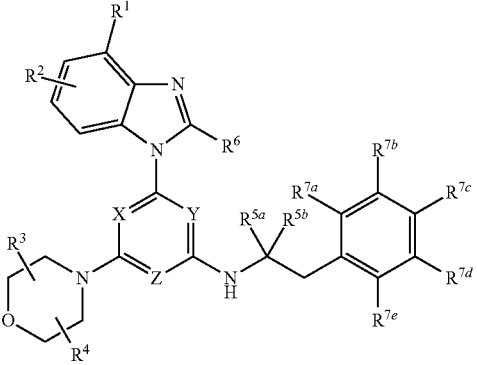

(XV)

or an enantiomer, a mixture of enantiomers, a mixture of two or more diastereomers, or an isotopic variant thereof; or a pharmaceutically acceptable salt, solvate, hydrate, or prodrug thereof.

52. The compound of claim 51, having the structure of Formula XVa:

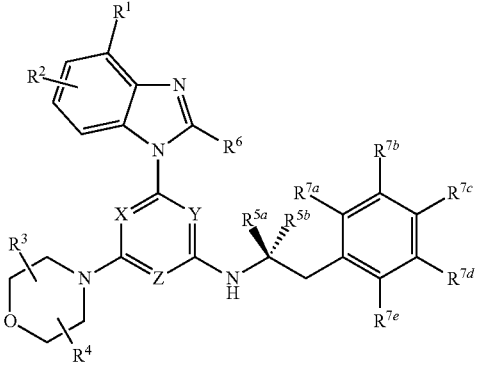

(XVa)

or an isotopic variant thereof or a pharmaceutically acceptable salt, solvate, hydrate, or prodrug thereof.

53. The compound of claim 51, having the structure of Formula XVb:

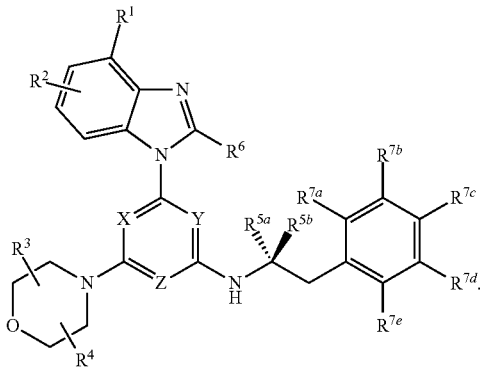

(XVb)

or an isotopic variant thereof; or a pharmaceutically acceptable salt, solvate, hydrate, or prodrug thereof.

54. The compound of claim 51, wherein $R^{5a}$ is $C_{1-6}$ alkyl, optionally substituted with one or more substituents Q.

55. The compound of claim 54, wherein $R^{5a}$ is methyl.

56. The compound of claim 51, wherein $R^{5b}$ is $C_{1-6}$ alkyl, optionally substituted with one or more substituents Q.

57. The compound of claim 56, wherein $R^{5b}$ is methyl.

58. The compound of claim 51, wherein $R^{5a}$ and $R^{5b}$ are methyl.

59. The compound of claim 51, wherein $R^{7a}$ is hydrogen, halo, $C_{1-6}$ alkyl, $C_{6-14}$ aryl, heteroaryl, or heterocyclyl, where the alkyl, aryl, heteroaryl, and heterocyclyl are each optionally substituted with one or more substituents Q.

60. The compound of claim 59, wherein $R^{7a}$ is $C_{6-14}$ aryl, optionally substituted with one or more substituents Q.

61. The compound of claim 60, wherein $R^{7a}$ is phenyl, optionally substituted with one or more substituents Q.

62. The compound of claim 60, wherein $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, or 3-morpholin-4-ylmethylphenyl.

63. The compound of claim 59, wherein $R^{7a}$ is heteroaryl, optionally substituted with one or more substituents Q.

64. The compound of claim 63, wherein $R^{7a}$ is monocyclic heteroaryl, optionally substituted with one or more substituents Q.

65. The compound of claim 63, wherein $R^{7a}$ is 5- or 6-membered heteroaryl, each optionally substituted with one or more substituents Q.

66. The compound of claim 65, wherein $R^{7a}$ is imidazolyl, pyrozolyl, pyridinyl, or pyrimidinyl, each optionally substituted with one or more substituents Q.

67. The compound of claim 65, wherein $R^{7a}$ is imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl.

68. The compound of claim 59, wherein $R^{7a}$ is heterocyclyl, optionally substituted with one or more substituents Q.

69. The compound of claim 68, wherein $R^{7a}$ is monocyclic heterocyclyl, optionally substituted with one or more substituents Q.

70. The compound of claim 68, wherein $R^{7a}$ is 5- or 6-membered heterocyclyl, each optionally substituted with one or more substituents Q.

71. The compound of claim 70, wherein $R^{7a}$ is pyrrolidinyl, piperidinyl, or piperazinyl, each optionally substituted with one or more substituents Q.

72. The compound of claim 70, wherein $R^{7a}$ is pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

73. The compound of claim 51, wherein $R^{7b}$ is hydrogen, halo, or $C_{1-6}$ alkyl optionally substituted with one or more substituents Q.

74. The compound of claim 73, wherein $R^{7b}$ is hydrogen.

75. The compound of claim 51, wherein $R^{7c}$ is hydrogen, halo, or $C_{1-6}$ alkyl optionally substituted with one or more substituents Q.

76. The compound of claim 75, wherein $R^{7c}$ is hydrogen.

77. The compound of claim 51, wherein $R^{7d}$ is hydrogen, halo, or $C_{1-6}$ alkyl optionally substituted with one or more substituents Q.

78. The compound of claim 77, wherein $R^{7d}$ is hydrogen.

79. The compound of claim 51, wherein $R^{7e}$ is hydrogen, halo, or $C_{1-6}$ alkyl optionally substituted with one or more substituents Q.

80. The compound of claim 79, wherein $R^{7e}$ is hydrogen.

81. The compound of claim 51, wherein $R^{7a}$ is $C_{6-14}$ aryl, heteroaryl, or heterocyclyl, each optionally substituted with one or more substituents Q; and $R^{7b}$, $R^{7c}$, $R^{7d}$, and $R^{7e}$ are hydrogen.

82. The compound of claim 1, wherein $R^1$ is hydrogen.

83. The compound of claim 1, wherein $R^2$ is hydrogen.

84. The compound of claim 1, wherein $R^3$ is hydrogen.

85. The compound of claim 1, wherein $R^4$ is hydrogen.

86. The compound of claim 1, wherein $R^6$ is $C_{1-6}$ alkyl, optionally substituted with one or more substituents Q.

87. The compound of claim 86, wherein $R^6$ is methyl, fluoromethyl, difluoromethyl, or trifluoromethyl.

88. The compound of claim 86, wherein $R^6$ is difluoromethyl.

89. The compound of claim 1, wherein X is N.

90. The compound of claim 1, wherein Y is N.

91. The compound of claim 1, wherein Y is $CR^X$.

92. The compound of claim 91, wherein Y is CH.

93. The compound of claim 1, wherein Z is N.

94. The compound of claim 1, wherein X, Y, and Z are N.

95. The compound of claim 1 selected from the group consisting of:

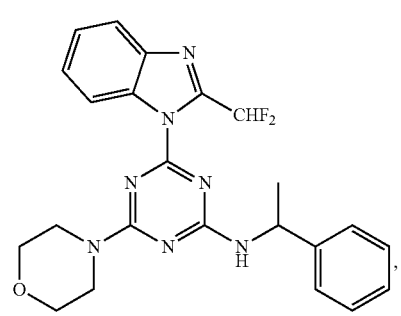

A1

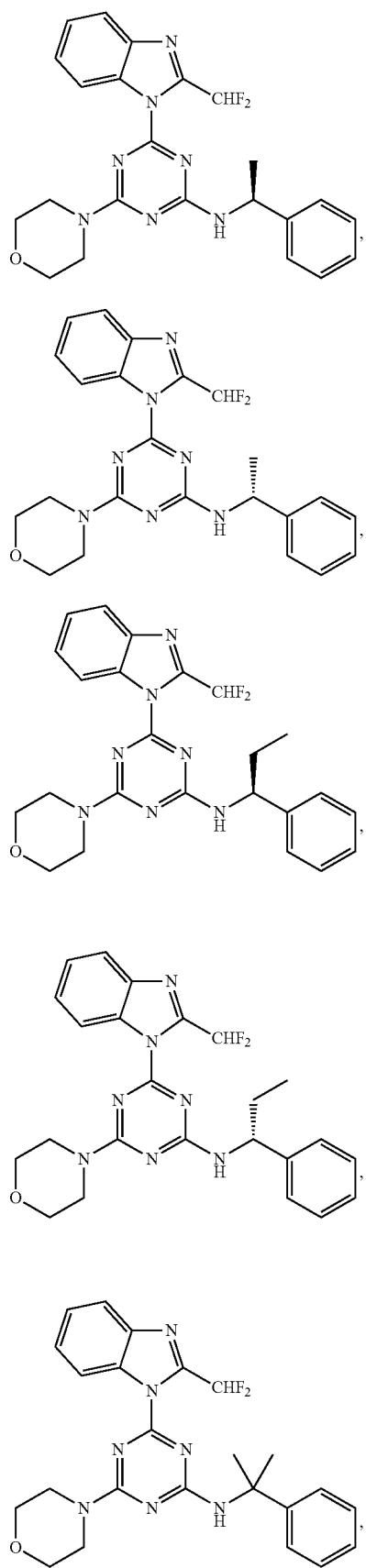
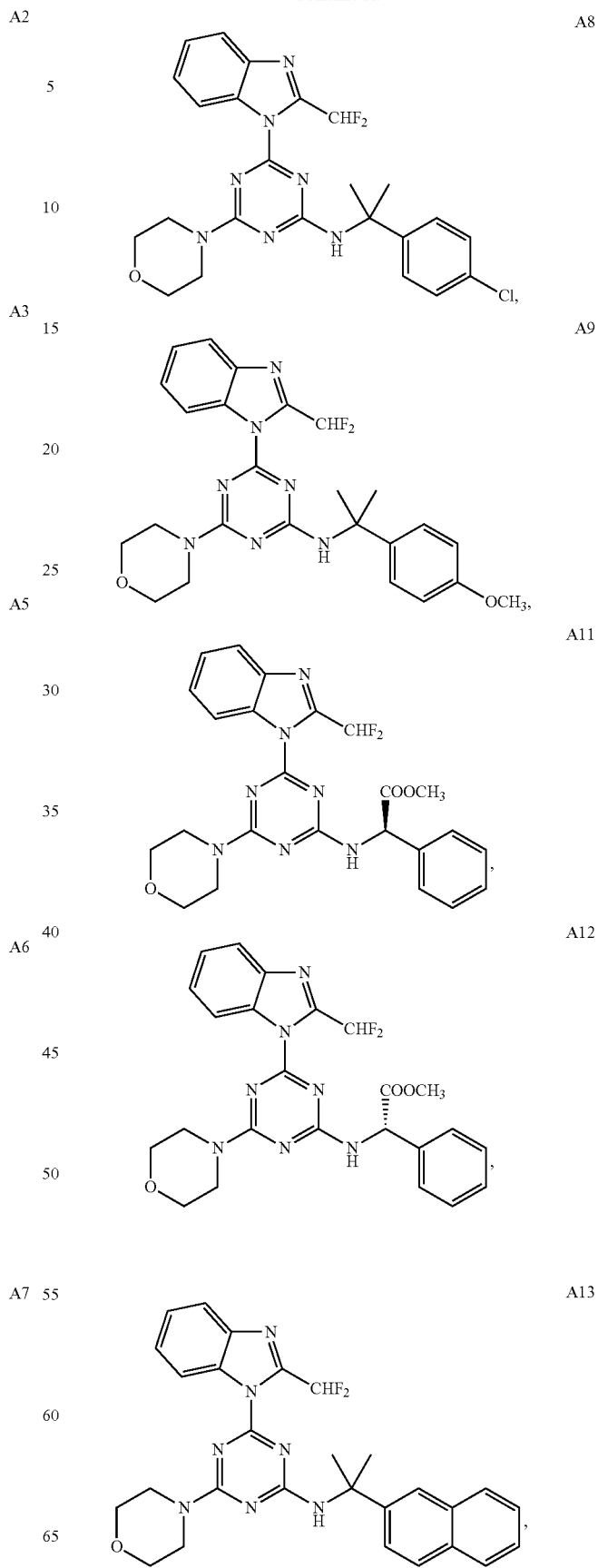

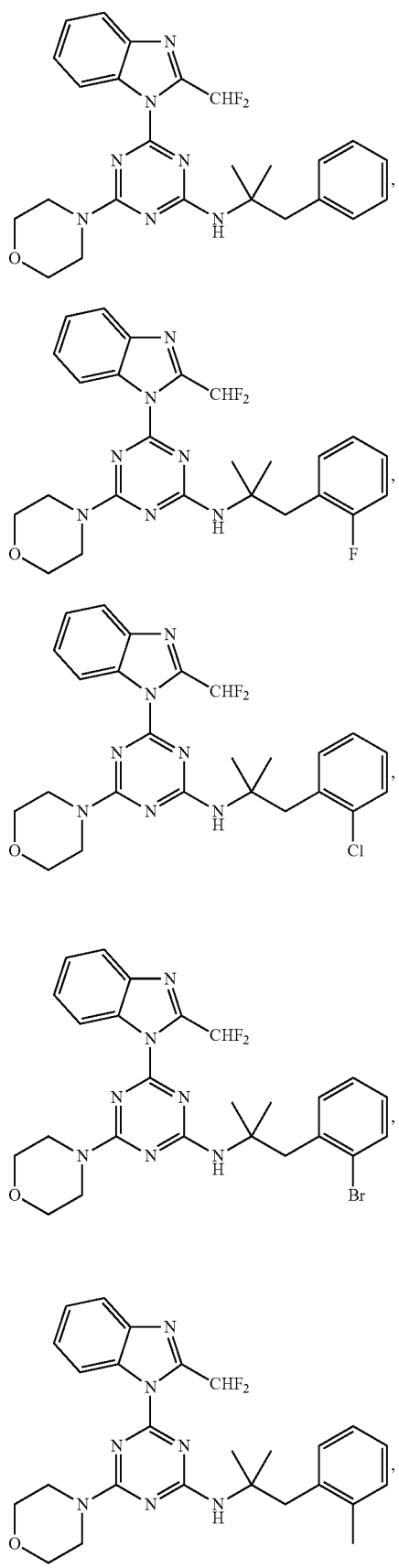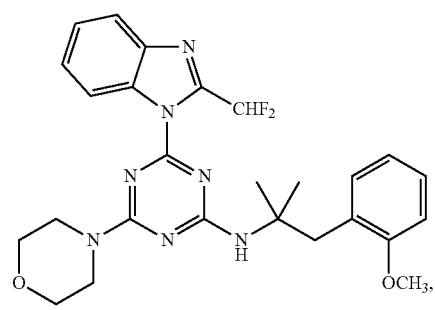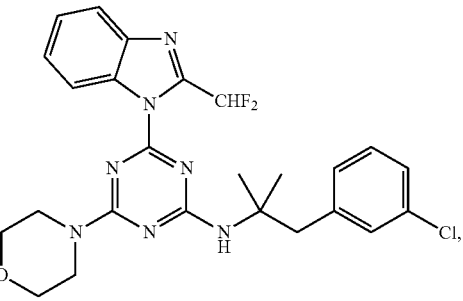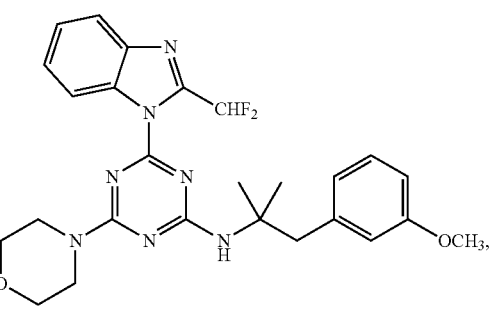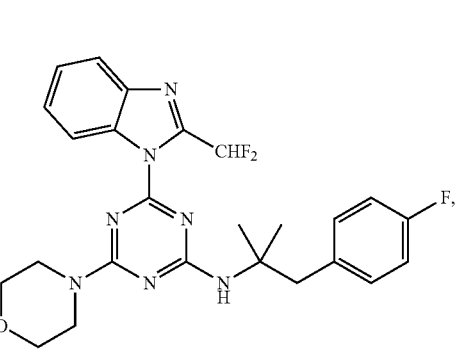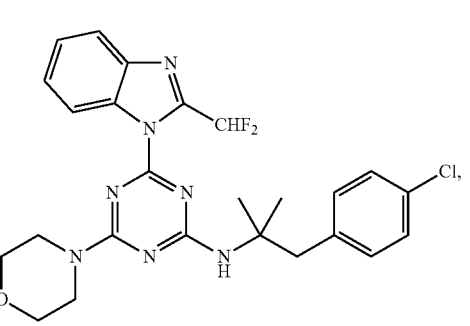

-continued
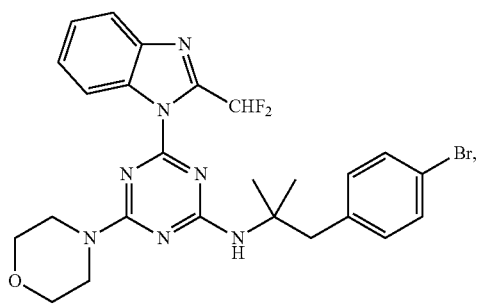
A24
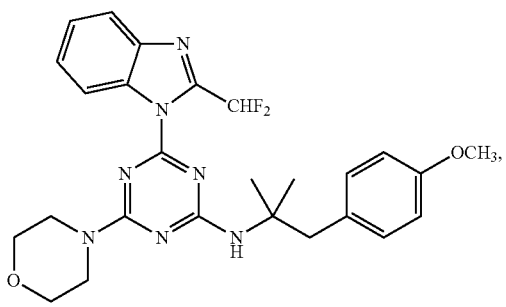
A25
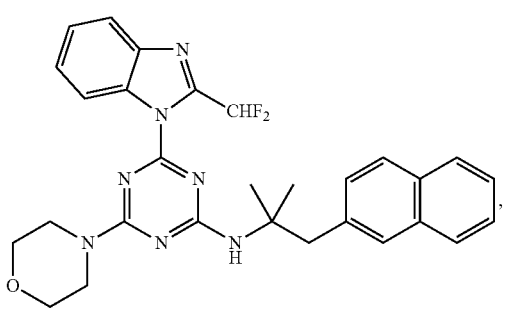
A26
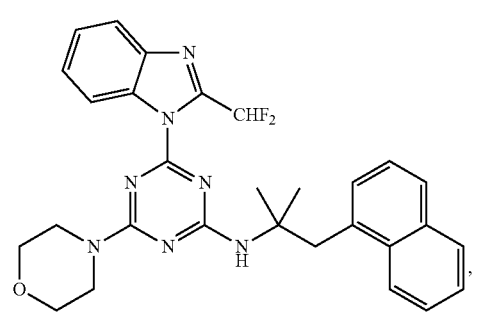
A27
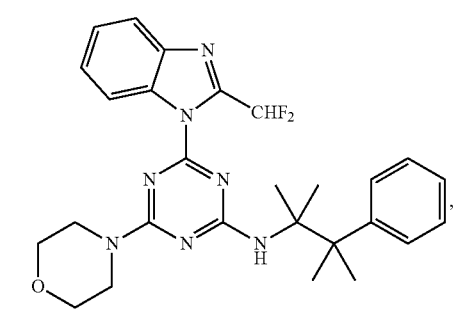
A28
-continued
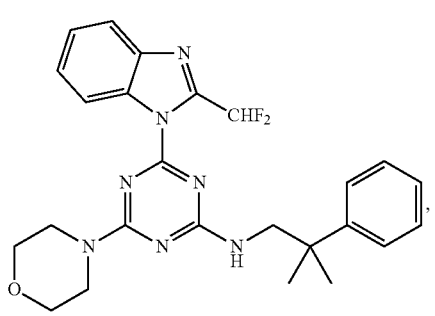
A29
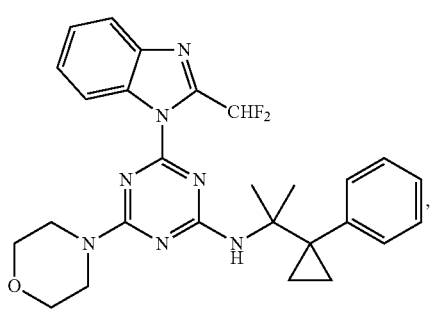
A30
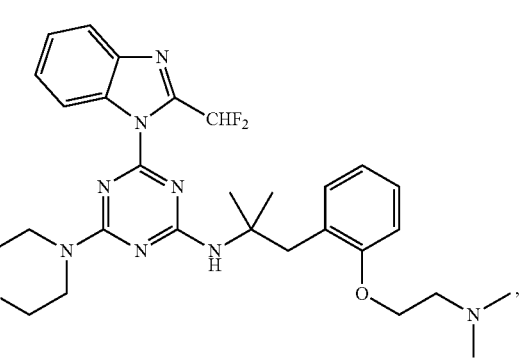
A31
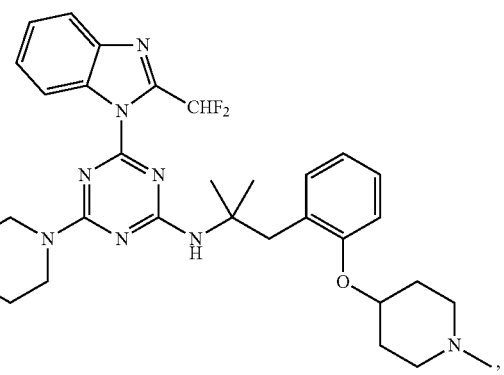
A32

A33
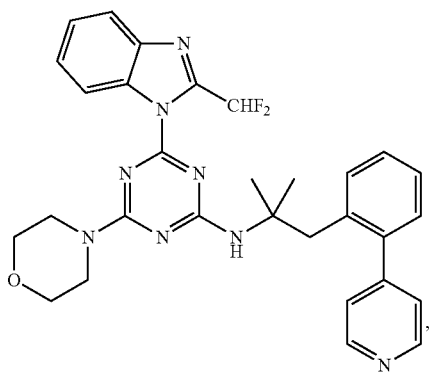
A34
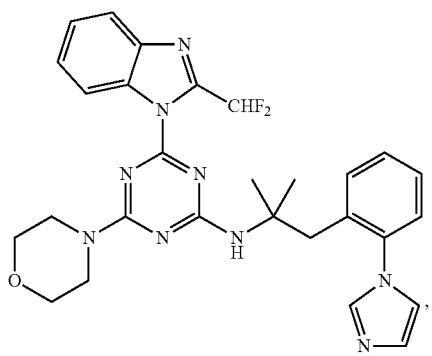
A35
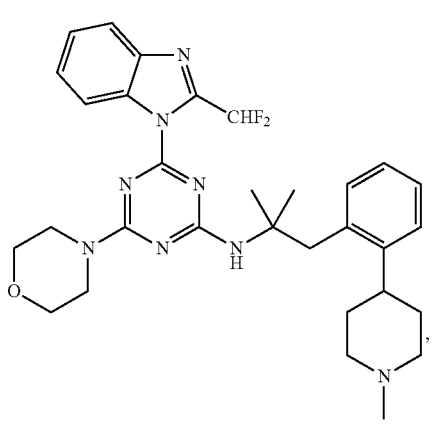
A36
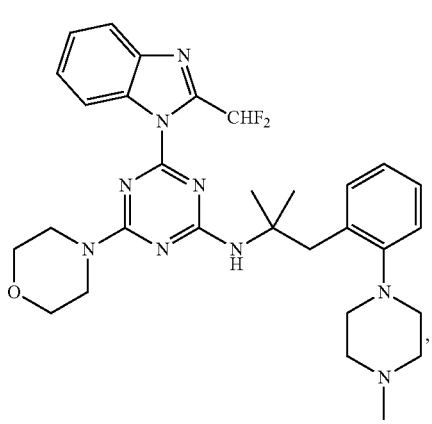
A37
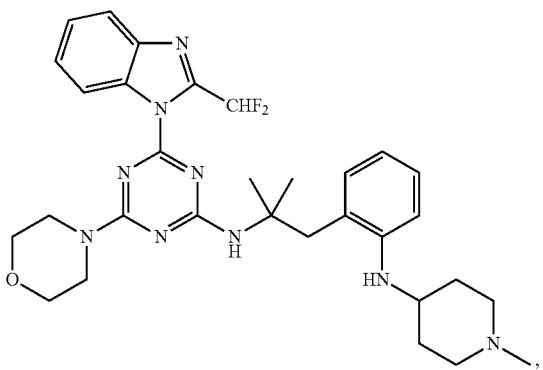
A38
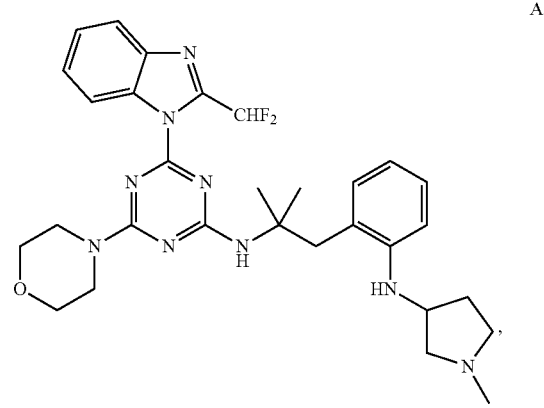
A39
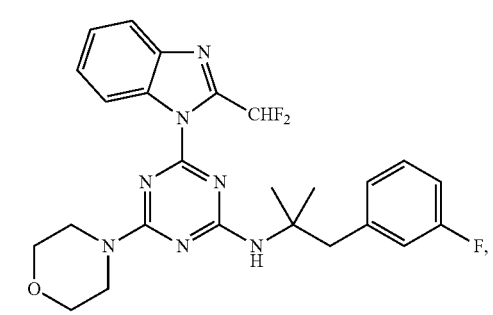
A40
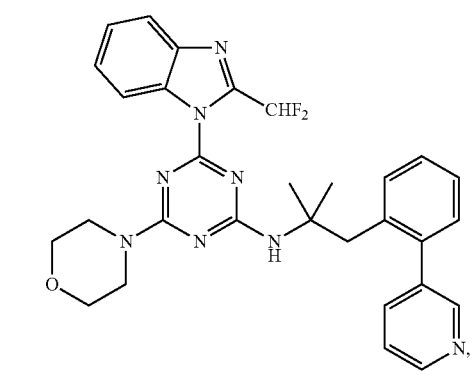

A41 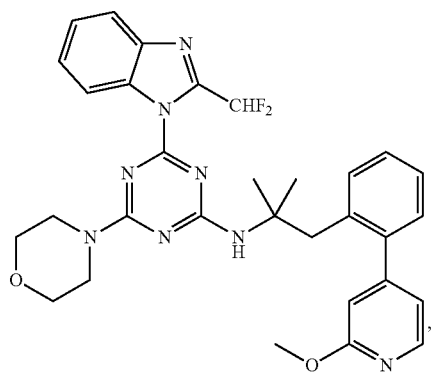
A42 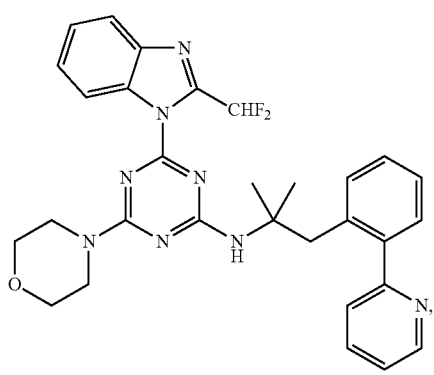
A43 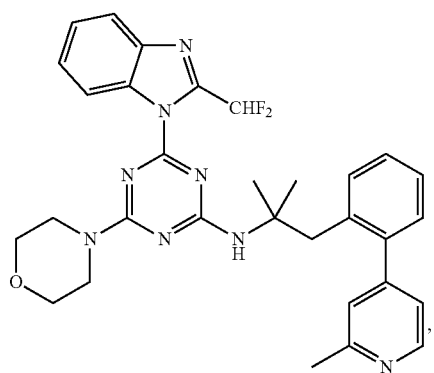
A44 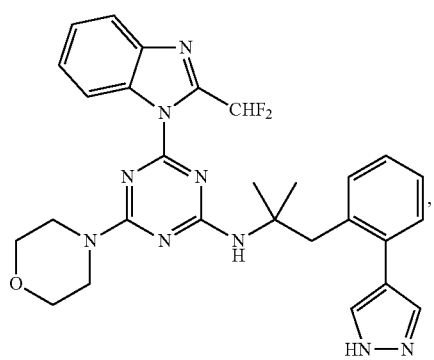
A45 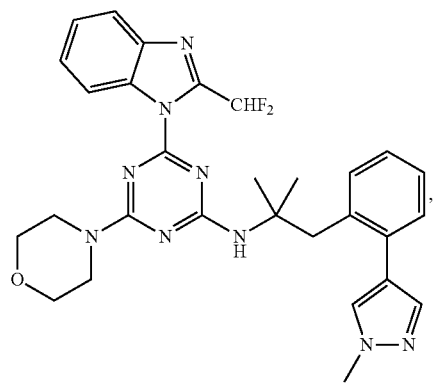
A46 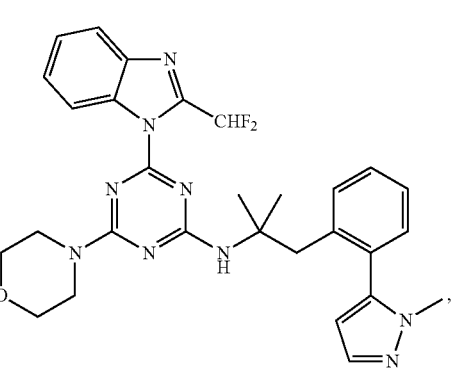
A47 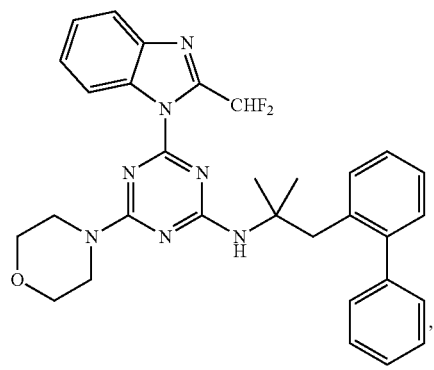
A49 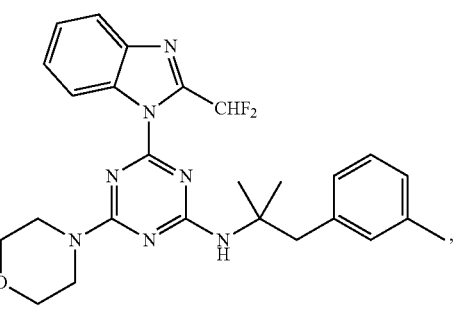

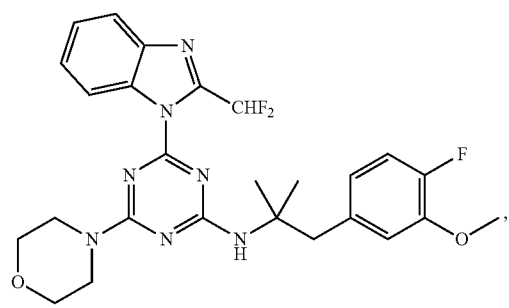
A50
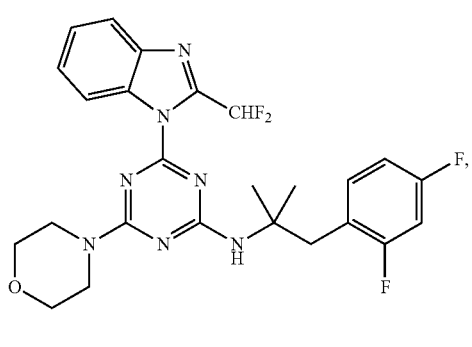
A51
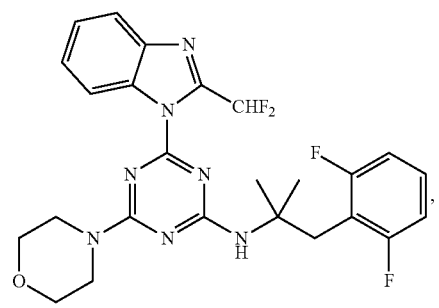
A52
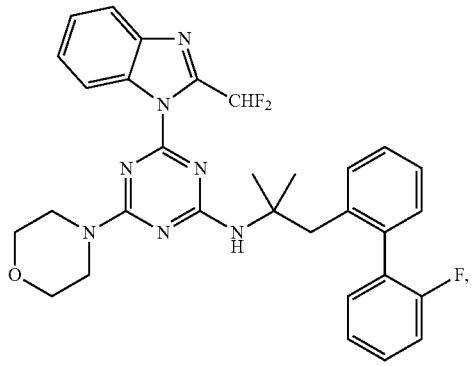
A59
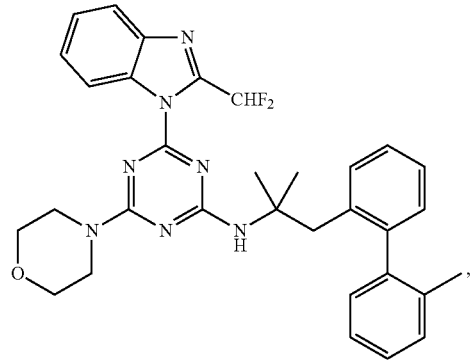
A60
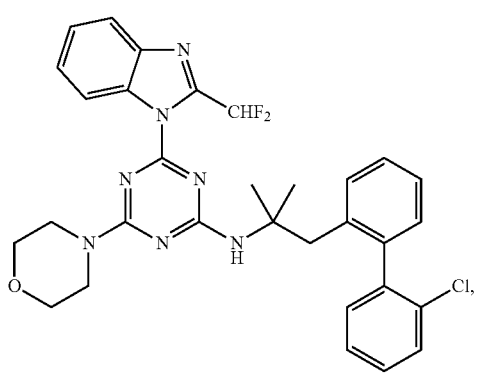
A61
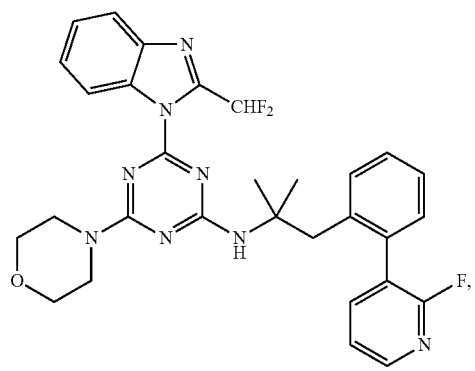
A62
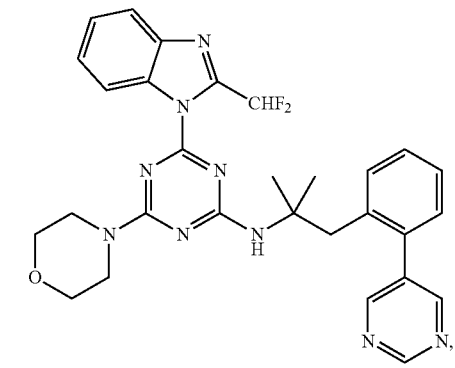
A63

205
-continued
A64
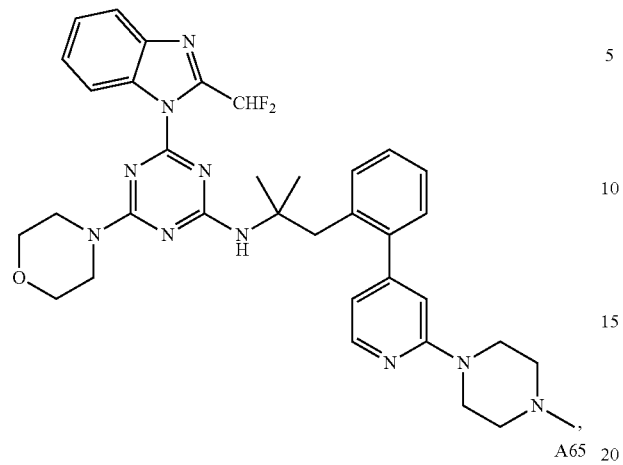
A65
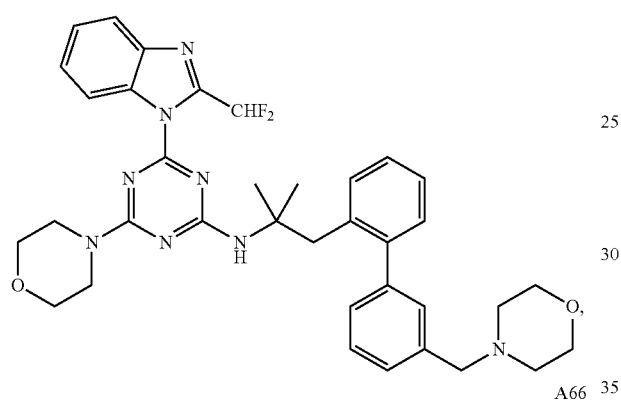
A66
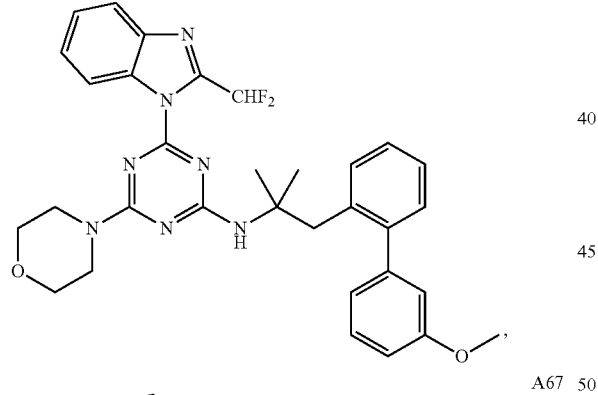
A67
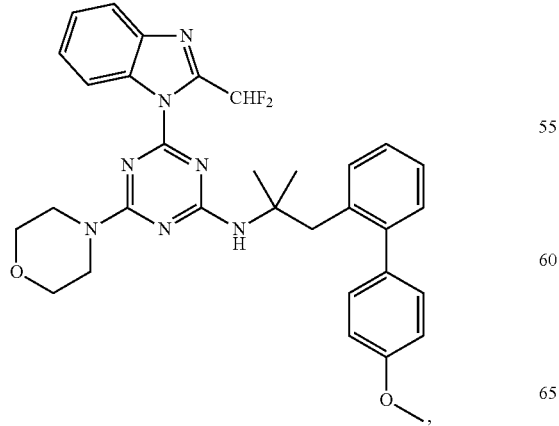
206
-continued
A68
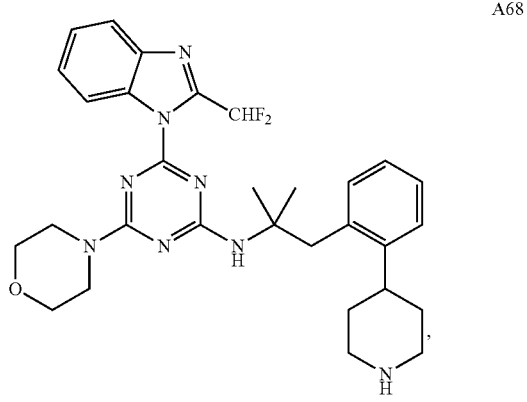 [SMILES: CC(C)(Cc1ccccc1C1CCNCC1)Nc1nc(N2CCOCC2)nc(-n2c(C(F)F)nc3ccccc32)n1]
A70
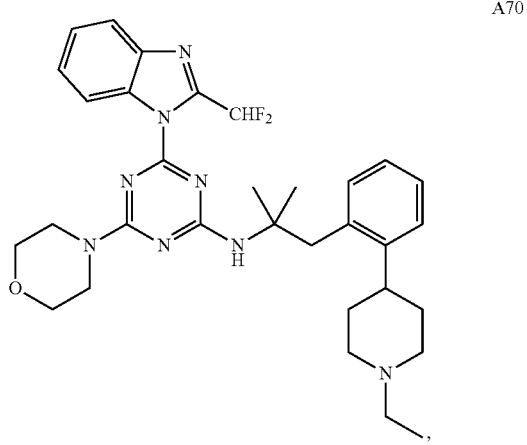 [SMILES: CC(=O)N1CCC(c2ccccc2CC(C)(C)Nc2nc(N3CCOCC3)nc(-n3c(C(F)F)nc4ccccc43)n2)CC1]
A73
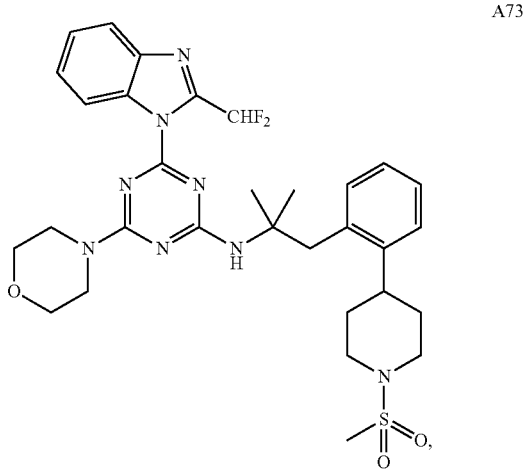
A74
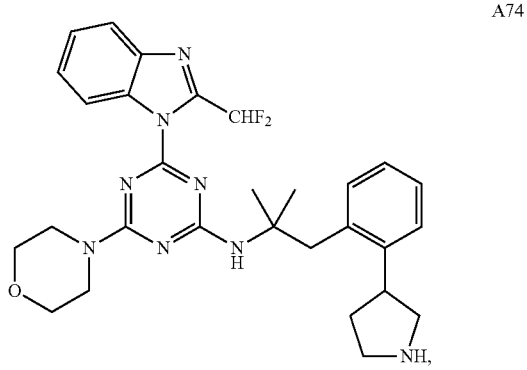

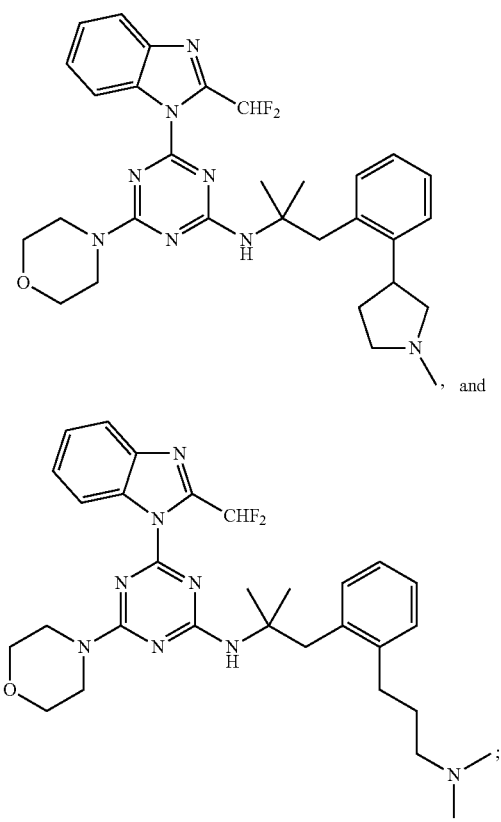

and enantiomers, mixtures of enantiomers, mixtures of two or more diastereomers, and isotopic variants thereof; and pharmaceutically acceptable salts, solvates, hydrates, and prodrugs thereof.

96. A pharmaceutical composition comprising the compound of claim 1, or an enantiomer, a mixture of enantiomers, or a mixture of two or more diastereomers thereof; or a pharmaceutically acceptable salt, solvate, hydrate, or prodrug thereof and one or more pharmaceutically acceptable excipients.

97. The pharmaceutical composition of claim 96, wherein the composition is formulated for single dose administration.

98. The pharmaceutical composition of claim 96, wherein the composition is formulated as an oral, parenteral, or intravenous dosage form.

99. The pharmaceutical composition of claim 98, wherein the composition is formulated as an oral dosage form.

100. The pharmaceutical composition of claim 99, wherein the oral dosage form is a tablet or capsule.

101. The pharmaceutical composition of claim 96, further comprising a therapeutic agent.

102. A method for the treatment, or amelioration of one or more symptoms of a PI3K-mediated disorder, disease, or condition in a subject, which comprises administering to the subject the compound of claim 1.

103. The method of claim 102, wherein the PI3K-mediated disorder, disease, or condition is an inflammatory disease.

104. The method of claim 102, wherein the compound is administered in combination with a therapeutic agent.

105. A method for inhibiting PI3K enzymatic activity, comprising contacting a PI3K enzyme with the compound of claim 1.

106. The method of claim 102, wherein the PI3K is a wild type.

107. The method of claim 102, wherein the PI3K is a PI3K variant.

108. The method of claim 102, wherein the PI3K is a Class I PI3K.

109. The method of claim 108, wherein the PI3K is p110γ.

* * * * *